US012435068B2

(12) United States Patent
Griebenow et al.

(10) Patent No.: US 12,435,068 B2
(45) Date of Patent: Oct. 7, 2025

(54) ANTHELMINTIC COMPOUNDS

(71) Applicant: Elanco Animal Health GmBh, Monheim am Rhein (DE)

(72) Inventors: Nils Griebenow, Dormagen (DE); Walter Huebsch, Wuppertal (DE); Hans-Georg Schwarz, Dorsten (DE); Wei Zhuang, Monheim am Rhein (DE); Bernd ALig, Koenigswinter (DE); Adeline Koehler, Langenfeld (DE); Daniel Kulke, Leverkusen (DE); Iring Heisler, Duesseldorf (DE); Thomas Ilg, Monheim (DE)

(73) Assignee: Elanco Animal Health GmbH, Monheim am Rhein (DE)

( * ) Notice: Subject to any disclaimer, the term of this patent is extended or adjusted under 35 U.S.C. 154(b) by 879 days.

(21) Appl. No.: 17/287,548

(22) PCT Filed: Oct. 23, 2019

(86) PCT No.: PCT/EP2019/078835
§ 371 (c)(1),
(2) Date: Apr. 22, 2021

(87) PCT Pub. No.: WO2020/083971
PCT Pub. Date: Apr. 30, 2020

(65) Prior Publication Data

US 2021/0380566 A1 Dec. 9, 2021

(30) Foreign Application Priority Data

Oct. 24, 2018 (EP) .................................... 18202419

(51) Int. Cl.
*C07D 405/14* (2006.01)
*A61P 33/10* (2006.01)
(Continued)

(52) U.S. Cl.
CPC ............ *C07D 405/14* (2013.01); *A61P 33/10* (2018.01); *C07D 241/42* (2013.01);
(Continued)

(58) Field of Classification Search
CPC .. C07D 405/14; C07D 241/42; C07D 249/18; C07D 311/58; C07D 311/68;
(Continued)

(56) References Cited

U.S. PATENT DOCUMENTS 10,604,525 B2 3/2020 Koehler et al.
10,889,573 B2 * 1/2021 Hübsch ................ C07D 413/14
(Continued)

FOREIGN PATENT DOCUMENTS

CL 2018002920 A1 2/2019
CL 2019001292 A1 9/2019
(Continued)

OTHER PUBLICATIONS

CAS Registry entry for Registry No. 1351352-38-9. (Year: 2011).*
Babulreddy et al. Synthesis, Characterization and Antimicrobial Screening of New Class of 1-Substituted-N-(1,2,3,4-Tetrahydronaphthalen-1-yl)-1hbenzo[ D][1,2,3]Triazole-5-Caboxamide Derivatives (Heteroletters, 2(3), 253-261). (Year: 2012).*
CAS Registry No. 1383704-53-7. (Year: 2012).*
(Continued)

*Primary Examiner* — Joseph K McKane
*Assistant Examiner* — Meghan C Heasley
(74) *Attorney, Agent, or Firm* — McBee Moore & Vanik IP, LLC

(57) ABSTRACT

The present invention relates to novel compounds of general formula (I):

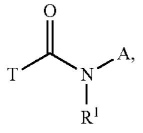

(I)

with
A being A1 or $A^2$:

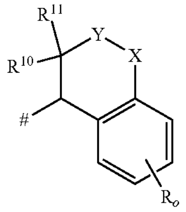

A1

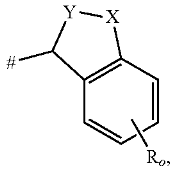

A2 and
in which T, X, Y, Ro, $R^1$, $R^{10}$ and $R^{11}$ are as defined herein, methods of preparing said compounds, intermediate compounds useful for preparing said compounds, pharmaceutical compositions and combinations comprising said compounds and the use of said compounds for the treatment, control and/or prevention of diseases, in particular of helminth infections, as a sole agent or in combination with other active ingredients.

14 Claims, No Drawings

(51) Int. Cl.

| | |
|---|---|
| ***C07D 241/42*** | (2006.01) |
| ***C07D 249/18*** | (2006.01) |
| ***C07D 311/58*** | (2006.01) |
| ***C07D 311/68*** | (2006.01) |
| ***C07D 405/12*** | (2006.01) |
| ***C07D 409/12*** | (2006.01) |
| ***C07D 471/04*** | (2006.01) |
| ***C07D 495/04*** | (2006.01) |

(52) U.S. Cl.

CPC .......... *C07D 249/18* (2013.01); *C07D 311/58* (2013.01); *C07D 311/68* (2013.01); *C07D 405/12* (2013.01); *C07D 409/12* (2013.01); *C07D 471/04* (2013.01); *C07D 495/04* (2013.01)

(58) Field of Classification Search

CPC .. C07D 405/12; C07D 409/12; C07D 471/04; C07D 495/04; C07D 407/12; A61P 33/10; A61K 31/37; A61K 31/381; A61K 31/4365; A61K 31/437

See application file for complete search history.

(56) References Cited

U.S. PATENT DOCUMENTS

| | | | | |
|---|---|---|---|---|
| 10,934,301 | B2 | 3/2021 | Goergens et al. | |
| 11,001,590 | B2 | 5/2021 | Schwarz et al. | |
| 11,254,661 | B2 | 2/2022 | Griebenow et al. | |
| 11,505,545 | B2 * | 11/2022 | Hübsch ................ | C07D 215/54 |
| 2007/0129359 | A1 | 6/2007 | Huwe et al. | |
| 2008/0242695 | A1 | 10/2008 | Morgan et al. | |
| 2011/0034441 | A1 * | 2/2011 | Hood ................... | C07D 231/56 514/228.2 |
| 2014/0235612 | A1 | 8/2014 | Chappie et al. | |
| 2014/0275503 | A1 | 9/2014 | Giampietro et al. | |
| 2019/0071447 | A1 | 3/2019 | Kohler et al. | |
| 2020/0024264 | A1 | 1/2020 | Hubsch et al. | |
| 2020/0239482 | A1 | 7/2020 | Gorgens et al. | |
| 2020/0299299 | A1 | 9/2020 | Schwarz et al. | |
| 2020/0377486 | A1 | 12/2020 | Griebenow et al. | |
| 2021/0115026 | A1 | 4/2021 | Huebsch et al. | |
| 2021/0380566 | A1 | 12/2021 | Griebenow et al. | |

FOREIGN PATENT DOCUMENTS

| | | | | |
|---|---|---|---|---|
| CL | 2020000301 | A1 | 7/2020 | |
| CL | 2020002919 | A1 | 4/2021 | |
| CL | 2021000646 | A1 | 9/2021 | |
| CL | 2021000994 | A1 | 9/2021 | |
| CL | 2021001057 | A1 | 9/2021 | |
| CL | 2021001040 | A1 | 10/2021 | |
| CL | 2021001025 | A1 | 11/2021 | |
| CN | 101337937 | A | 1/2009 | |
| CN | 101337940 | A | 1/2009 | |
| CN | 101715774 | A | 6/2010 | |
| CN | 103109816 | A | 5/2013 | |
| CN | 103232431 | A | 8/2013 | |
| CN | 103265527 | A | 8/2013 | |
| CN | 103524422 | A | 1/2014 | |
| CN | 104884453 | A | 9/2015 | |
| CN | 106536518 | A | 3/2017 | |
| DE | 3639877 | A1 | 5/1988 | |
| EP | 2647626 | A1 | 10/2013 | |
| JP | 2010018586 | A | 1/2010 | |
| RU | 2543374 | C2 | 2/2015 | |
| WO | 02/32856 | A2 | 4/2002 | |
| WO | 2002/070509 | A2 | 9/2002 | |
| WO | 03106457 | A1 | 12/2003 | |
| WO | 2004099160 | A1 | 11/2004 | |
| WO | 2005/012283 | A1 | 2/2005 | |
| WO | 2006003494 | A2 | 1/2006 | |
| WO | 2006043635 | A1 | 4/2006 | |
| WO | 2007040280 | A1 | 4/2007 | |
| WO | 2007040282 | A1 | 4/2007 | |
| WO | 2007/092403 | A1 | 8/2007 | |
| WO | 2009/100250 | A1 | 8/2009 | |
| WO | 2009/155388 | A1 | 12/2009 | |
| WO | 2010051926 | A2 | 5/2010 | |
| WO | 2010052161 | A2 | 5/2010 | |
| WO | 2010066780 | A1 | 6/2010 | |
| WO | 2011085575 | A1 | 7/2011 | |
| WO | 2011105506 | A1 | 9/2011 | |
| WO | 2011151146 | A1 | 12/2011 | |
| WO | 2012087861 | A1 | 6/2012 | |
| WO | 2012/106472 | A1 | 8/2012 | |
| WO | 2012112363 | A1 | 8/2012 | |
| WO | 2013050317 | A1 | 4/2013 | |
| WO | 2013162715 | A2 | 10/2013 | |
| WO | 2013162716 | A2 | 10/2013 | |
| WO | 2014081697 | A2 | 5/2014 | |
| WO | 2014187846 | A1 | 11/2014 | |
| WO | 2015058021 | A1 | 4/2015 | |
| WO | 2015058028 | A1 | 4/2015 | |
| WO | 2015179414 | A1 | 11/2015 | |
| WO | 2016005276 | A1 | 1/2016 | |
| WO | 2016/123392 | A2 | 8/2016 | |
| WO | 2016133011 | A1 | 8/2016 | |
| WO | 2017143041 | A1 | 8/2017 | |
| WO | 2017178416 | A1 | 10/2017 | |
| WO | WO-2018087036 | A1 * | 5/2018 | ............. A61K 31/47 |
| WO | 2019025341 | A1 | 2/2019 | |
| WO | 2020014068 | A1 | 1/2020 | |
| WO | 2020061150 | A1 | 3/2020 | |
| WO | 2020083733 | A1 | 4/2020 | |
| WO | 2020084492 | A1 | 4/2020 | |
| WO | 2020085219 | A1 | 4/2020 | |
| WO | 2020086844 | A1 | 4/2020 | |
| WO | 2019222112 | A1 | 11/2020 | |

OTHER PUBLICATIONS

Wojnarowska et al., "On the kinetics of tautomerism in drugs:New application of broadband dielectricspectroscopy", J. Chem. Phys. (2010), vol. 133, No. 9, 094507.

Kier et al., "Bioisosterism: Quantitation of Structure and Property Eff ects", Chemistry & Biodiversity (2004), vol. 1, Issue 1, pp. 138-151.

Babulreddy et al., "Synthesis, Characterization and Antimicrobial Screening of New Class of 1-Substituted-N-(1,2,3,4-Tetrahydronapthalen-1-YL)-1Hbenzo[D][1,2,3]Triazole-5-Caboxamide Derivatives", Heterocyclic Letters, 2012, 2(3), p. 253-261.

International Search Report of International Patent Application No. PCT/EP2019/078835 dated May 8, 2020.

European Search Report of International Patent Application No. PCT/EP2019/078835 dated Mar. 26, 2019.

Uray, G. et al., "Diphenylethanediamine derivatives as chiral selectors", Journal of Chromatography A, Apr. 1994, pp. 41-53, vol. 666, No. 1-2, 22, Elsevier, Amsterdam, NL.

Maddirala, Amarendar Reddy et al., "Synthesis of 3-Substituted 2-Indolinones by a Multicomponent Coupling Isocyanide-Dependent Microwave-Assisted Intramolecular Transamidation Process", European Journal of Organic Chemistry, Jan. 1, 2016, pp. 196-209, vol. 2016, No. 1.

Azizoglu, Murat et al., "A series of novel [beta]-hydroxyamide based catalysts for borane-mediated enantioselective reductions of prochiral ketone", Tetrahedron: Asymmetry, Pergamon Press Ltd, Jun. 10, 2016, pp. 614-622, vol. 27, No. 14, Oxford, GB.

Ashwood, Valerie A. et al., "Synthesis and Antihypertensive Activity of 4-(Substituted-carbonylamino)-2H-1-benzopyrans", Journal of Medicinal Chemistry, American Chemical Society, Jan. 1, 1990, pp. 2667-2672, vol. 33, No. 9, US.

Folkes, Adrian et al., "Design, Synthesis and In Vitro Evaluation of Potent, Novel, Small Molecule Inhibitors of Plasminogen Activator Inhibitor-1", Bioorganic & Medicinal Chemistry Letters, May 2002, pp. 1063-1066, vol. 12.

Naumchuk et al., "Study of inhibitory activity of imidazolone derivatives and their non-cyclic precursors in relation to human SC2

(56) References Cited

OTHER PUBLICATIONS protein kinase", Ukrainica Bioorganica Acta 1, 2015, pp. 32-38, vol. 13(1)—(machine translation provided).
C. L. Perrin et al., "Secondary Deuterium Isotope Effects on the Acidity of Carboxylic Acids and Phenols", J. Am. Chem. Soc., vol. 129, 2007 (Abstract), pp. 4490.
C. MacBean, "The Pesticide Manual", 2012, British Crop Protection Council (First page).
T.W. Greenep.G.M. Wuts: "Protective Groups in Organic Synthesis", 1999, Wiley.
Pure Appl Chem, vol. 45, 1976, pp. 11-30.
S. M. Berge et al.: "Pharmaceutical Salts", J. Pharm. Sci., vol. 66, 1977, pp. 1-19.
B. Testa et al., Int. J. Pharm., vol. 19, No. 3, 1984, pp. 271.
F. Schneider et al., "Enhanced plasma concentration by selective deuteration of rofecoxib in rats", Arzneim. Forsch. / Drug. Res., vol. 56, 2006, pp. 295.
F. Maltais et al., "In vitro and in vivo isotope effects with hepatitis C protease inhibitors: enhanced plasma exposure of deuterated telaprevir versus telaprevir in rats", J. Med. Chem., vol. 52, 2009, pp. 7993.
Mehlhorn et al., "Encyclopedic Reference of Parasitology", 4th edition (ISBN 978-3-662-43978-4), 2016.
C. J. Wenthur et al., "Discovery of (R)-(2-Fluoro-4-((-4-methoxyphenyl)ethynyl)phenyl) (3-Hydroxypiperidin-1-yl) methanone (ML337), An mGlu3 Selective and CNS Penetrant Negative Allosteric Modulator (Nam)", J. Med. Chem., vol. 56, 2013, pp. 5208.
C. L. Perrin et al., "Stereochemistry of β-deuterium isotope effects on amine basicity", J. Am. Chem. Soc., vol. 127, 2005, pp. 9641.
KJR Rosman et al., "Isotopic Compositions of the Elements 1997", Pure Appl. Chem., vol. 70, No. 1, 1998, pp. 217-235.
A. M. Sharma et al., "Nevirapine bioactivation and covalent binding in the skin", Chem. Res. Toxicol., vol. 26, 2013, pp. 410.
A. E. Mutlib et al., "The species-dependent metabolism of efavirenz produces a nephrotoxic glutathione conjugate in rats", Toxicol. Appl. Pharmacol., vol. 169, 2000, pp. 102.

* cited by examiner

ANTHELMINTIC COMPOUNDS

CROSS-REFERENCE TO RELATED APPLICATIONS

This application is the National Stage entry of International Application No. PCT/EP2019/078835, filed 23 Oct. 2019, which claims priority to European Patent Application No. 18202419.0, filed 24 Oct. 2018.

BACKGROUND

Field

The present invention covers new compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the control, treatment and/or prevention of diseases, in particular for the control, treatment and/or prevention of infections with helminths, more particularly of infections with gastro-intestinal and extra-intestinal nematodes, in animals and humans, formulations containing such compounds and methods for the control, treatment and/or prevention of infections with helminths, more particularly of infections with gastro-intestinal and extra-intestinal nematodes, in animals and humans as a sole agent or in combination with other active ingredients.

Description of Related Art

The occurrence of resistances against all commercial anthelmintics seems to be a growing problem in the area of veterinary medicine. The extensive utilisation of anthelmintics to manage the control of nematodes resulted in significant selection of highly resistant worm populations. Therefore, the spread of resistance against all anthelmintic drug classes threatens effective worm control in cattle, goats, sheep and horses.

Furthermore, successful prevention of heartworm disease in dogs, which currently solely relies on the utilisation of macrocyclic lactones, is in danger as loss of efficacy for multiple macrocyclic lactones has been described for some regions of the United States of America—especially in those areas where the heartworm challenge for infection is high. Finally, experimental infection studies with *Dirofilaria immitis* larvae from suspected field loss of efficacy cases in the Lower Mississippi Delta provided in vivo confirmation of the existence of macrocyclic lactone resistance.

Although resistance of human helminths against anthelmintics seems currently to be rare, the spread of anthelmintic resistance in the veterinary field as mentioned before needs to be considered in the treatment of human helminthosis as well. Persistent underdosed treatments against filariosis may lead to highly resistant genotypes and resistances have already been described for certain anthelmintics (e.g. praziquantel, benzimidazole and niclosamide).

Therefore, resistance-breaking anthelmintics with new molecular modes of action are urgently required.

It is an object of the present invention to provide compounds which can be used as anthelmintics in the medical, especially veterinary, field with a satisfactory or improved anthelmintic activity against a broad spectrum of helminths, particularly at relatively low dosages, for the control, treatment and/or prevention of infections with helminths in animals and humans, preferably without any adverse toxic effects to the treated organism.

WO 2005012283 describes the preparation of certain benzothiophene carboxamides as IKK kinase inhibitors for the treatment of inflammation, cancer and autoimmune diseases. New azabenzimidazole compounds are described in US 20140235612 as PDE4 inhibitors. Imidazopyridine and imidazopyrazine compounds are disclosed as kinase inhibitors in WO 2009155388. WO 2016123392 describes pyrazolopyrimidines as inhibitors of glucocorticoid receptor translocation and their preparation. Novel N-phenylbenzotriazoles as c-Kit inhibitors are disclosed in WO 2007092403. Naumchuk et al. described the inhibitory activity of imidazolone derivatives and their precursors toward human protein kinase CK2 (Ukrainica Bioorganica Acta 2015, 13(1), 32-38). US 20080242695 discloses the preparation of 1H-imidazo[4,5-b]pyridin-2-ol derivatives which modulate skeletal muscle. Naphthyridine derivatives as inhibitors of hypoxia inducible factor (HIF) hydroxylase and their preparation and use for the treatment of HIF-mediated diseases are described in WO 2012106472. Furthermore, WO 2009100250 outlines chromen-3-ylamide derivatives as hypoxia inducible factor hydroxylase inhibitors. 2-Oxo-1,2-dihydroquinoline-3-carboxamides are disclosed (Bioorganic & Medicinal Chemistry Letters (2002), 12(7), 1063-1066) as potent and novel small molecule inhibitors of plasminogen activator inhibitor-1. WO 2009100250 discloses chromen-3-ylamide derivatives as hypoxia inducible factor hydroxylase inhibitors. Furthermore, benzodioxanes, quinoxalines, benzoxazines, and related compounds as antagonists of MCP-1 for treatment of inflammatory and autoimmune disease are described in WO 2002070509.

WO 2017178416 describes new pyrazolopyrimidine derivatives and their anthelminitic activity.

WO 2018087036 describes new quinoline-3-carboxamide derivatives ant their anthelmintic activity.

However, the state of the art does not describe the new compounds of general formula (I) of the present invention as described and defined herein.

SUMMARY

It has now been found, and this constitutes the basis of the present invention, that the compounds of the present invention have surprising and advantageous properties.

In particular, the compounds of the present invention have surprisingly been found to effectively interact with Slo-1 of nematodes. This interaction is characterized by achieving paralysis/inhibition in particular of gastro-intestinal nematodes, of free-living nematodes, and of filariae, for which data are given in the biological experimental section. Therefore the compounds of the present invention may be used as anthelmintics for the control, treatment and/or prevention of gastro-intestinal and extra-intestinal helminth infections, in particular gastro-intestinal and extra-intestinal infections with nematodes, including filariae.

DESCRIPTION OF THE INVENTION

In accordance with a first aspect, the present invention covers compounds of general formula (I):

(I)

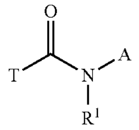

wherein:

A is A1 or A2,

A1

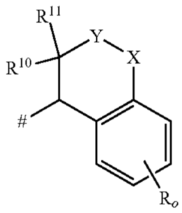

A2

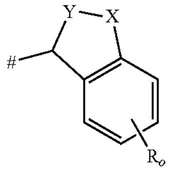

o is 0, 1, 2, 3 or 4;

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms;

X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—;

T is selected from the groups consisting of 10-membered aryl and 8- to 10-membered heteroaryl, each of which is optionally partially saturated and optionally substituted by 1, 2, 3, 4, 5 or 6 substituents selected from $R^2$, $R^3$, $R^4$, $R^5$, $R^6$ and Q, or T is selected from $T^1$, $T^2$, $T^3$, $T^4$, $T^5$, $T^6$, $T^7$, $T^{8a}$, $T^{8b}$ and $T^9$:

$T^1$

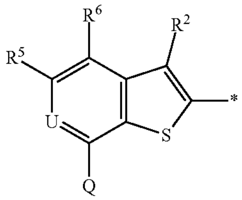

-continued $T^2$

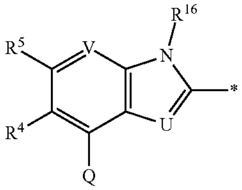

$T^3$

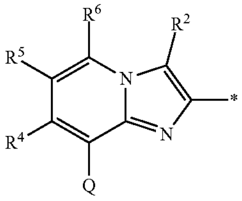

$T^4$

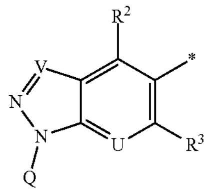

$T^5$

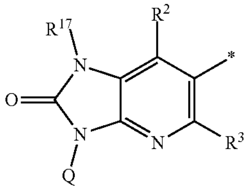

$T^6$

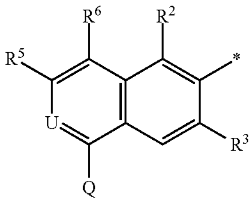

$T^7$

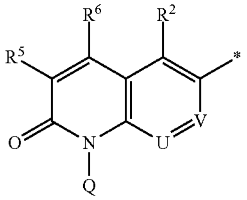

$T^{8a}$

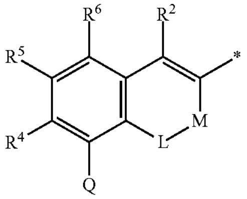

-continued

T8b

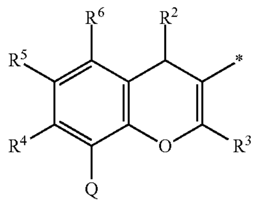

T9

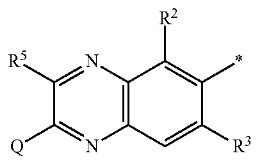

L is selected from the group consisting of O and $NR^9$;

M is selected from the group consisting of C═O and $CR^7R^8$;

U is selected from the group consisting of $CR^7$ and N;

V is selected from the group consisting of $CR^7$ and N;

$R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;

- phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$- $C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
- heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$- $C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of

- hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;
- —$NR^{12}R^{13}$;
- —$OR^{14}$;
- —$SR^{15}$, —S(O)$R^{15}$, —$SO_2R^{15}$;
- $C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
- heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, and wherein the heterocyclyl substituent and/or the $C_1$-$C_4$-alkyl-group is optionally substituted by 1, 2 or 3 substituents independently selected from the group consisting of halogen, —OH, —$NO_2$, cyano, —COOH, $C_1$-$C_4$-alkyl-C(O)—, $C_1$-$C_4$-alkoxy-C(O)—, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
- phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; or
- a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and 4- to 10-membered heterocycloalkyl;

$R^3$ is selected from the group consisting of hydrogen, halogen or $C_1$-$C_4$-alkyl;

$R^4$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S—$C_1$-$C_4$-halogenoalkyl having 1 to 5 halogen atoms, —S(O)—$C_1$-$C_4$-alkyl, —$SO_2$—$C_1$-$C_4$-alkyl;

$R^5$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl;

$R^6$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S—$C_1$-$C_4$-halogenoalkyl having 1 to 5 halogen atoms, —S(O)—$C_1$-$C_4$-alkyl, —$SO_2$—$C_1$-$C_4$-alkyl;

$R^7$ is selected from the group consisting of hydrogen, —OH, halogen, $C_1$-$C_4$-alkyl and $C_1$-$C_4$-alkoxy;

$R^8$ is selected from the group consisting of hydrogen, —OH, halogen, $C_1$-$C_4$-alkyl and $C_1$-$C_4$-alkoxy;

or $R^7$ and $R^8$ form, together with the carbon atom to which they are attached, a 3- to 6-membered ring selected from the group consisting of $C_3$-$C_6$-cycloalkyl and 3- to 6-membered heterocycloalkyl;

$R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy;

$R^{10}$ is selected from the group consisting of hydrogen, —OH, $C_1$-$C_4$-alkyl and $C_1$-$C_4$-alkoxy;

$R^{11}$ is selected from the group consisting of hydrogen, $C_1$-$C_4$-alkyl and $C_1$-$C_4$-alkoxy;

or $R^{10}$ and $R^{11}$ form, together with the carbon atom to which they are attached, a 3- to 6-membered ring selected from the group consisting of $C_3$-$C_6$-cycloalkyl and 3- to 6-membered heterocycloalkyl, $R^{12}$ and $R^{13}$ are independently selected from the group consisting of hydrogen, —OH, —$NH_2$, —NH($C_1$-$C_4$-alkyl), —N($C_1$-$C_4$-alkyl)$_2$, —NH(—C(O)—$C_1$-$C_4$-alkyl), —N($C_1$-$C_4$-alkyl)(—C(O)—$C_1$-$C_4$-alkyl), $C_1$-$C_4$-alkoxy, $C_1$-$C_4$-alkoxy-C(O)—;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(═O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, benzo-$C_5$-$C_6$-cycloalkyl, each of which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{14}$ is selected from the group consisting of —$NH_2$, —NH($C_1$-$C_4$-alkyl), —N($C_1$-$C_4$-alkyl)$_2$;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{16}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

$R^{17}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

Q is selected from the group consisting of 6- to 10-membered aryl and 5- to 10-membered heteroaryl, each of which is optionally substituted by 1, 2, 3, 4 or 5 substituents selected from the group consisting of halogen, $SF_5$, cyano, —CHO, nitro, oxo, $C_1$-$C_4$-alkyl, $C_1$-$C_4$-hydroxyalkyl, $C_1$-$C_4$-halogenoalkyl having 1 to 5 halogen atoms, —OH, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$- $C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms;

wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH;

and stereoisomers, tautomers, N-oxides, hydrates, solvates, and salts thereof, and mixtures of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule.

Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

As used herein, the position via which a respective substituent is connected to the rest of the molecule may in a drawn structure be depicted by a hash sign (#) or a dashed line in said substituent.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom, more particularly chlorine or fluorine.

The term "$C_1$-$C_6$-alkyl" means a linear or branched, saturated, monovalent hydrocarbon group having 1, 2, 3, 4, 5 or 6 carbon atoms. The term "$C_1$-$C_4$-alkyl" means a linear or branched, saturated, monovalent hydrocarbon group having 1, 2, 3, or 4 carbon atoms, e.g. a methyl, ethyl, n-propyl, isopropyl, n-butyl, sec-butyl, isobutyl or a tert-butyl group etc., or an isomer thereof. Particularly, said group has 1, 2 or 3 carbon atoms ("$C_1$-$C_3$-alkyl"), e.g. a methyl, ethyl, n-propyl or isopropyl group.

The term "$C_1$-$C_4$-hydroxyalkyl" means a linear or branched, saturated, monovalent hydrocarbon group in which the term "$C_1$-$C_4$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "—NH($C_1$-$C_4$-alkyl)" or "—N($C_1$-$C_4$-alkyl)$_2$" means a linear or branched, saturated, monovalent group in which the term "$C_1$-$C_4$-alkyl" is as defined supra, e.g. a methylamino, ethylamino, n-propylamino, isopropylamino, N,N-dimethylamino, N-methyl-N-ethylamino or N,N-diethylamino group.

The term "—S—$C_1$-$C_4$-alkyl", "—S(O)—$C_1$-$C_4$-alkyl" or "—$SO_2$—$C_1$-$C_4$-alkyl" means a linear or branched, saturated group in which the term "$C_1$-$C_4$-alkyl" is as defined supra, e.g. a methylsulfanyl, ethylsulfanyl, n-propylsulfanyl, isopropylsulfanyl, n-butylsulfanyl, sec-butylsulfanyl, isobutylsulfanyl or tert-butylsulfanyl group, a methylsulfinyl, ethylsulfinyl, n-propylsulfinyl, isopropylsulfinyl, n-butylsulfinyl, sec-butylsulfinyl, isobutylsulfinyl or tert-butylsulfinyl group, or a methylsulfonyl, ethylsulfonyl, n-propylsulfonyl, isopropylsulfonyl, n-butylsulfonyl, sec-butylsulfonyl, isobutylsulfonyl or tert-butylsulfonyl group.

The term "S—$C_1$-$C_4$-halogenoalkyl" means a linear or branched group in which the term "$C_1$-$C_4$-halogenoalkyl" is as defined infra, and in which one or more of the hydrogen atoms are replaced, identically or differently, with a halogen atom. Particularly, said halogen atom is a fluorine atom. More particularly, all said halogen atoms are fluorine atoms ("$C_1$-$C_4$-fluoroalkyl"). Said $C_1$-$C_4$-halogenoalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl, wherein a trifluoromethyl-group is particularly preferred.

The term "$C_1$-$C_4$-halogenoalkyl" means a linear or branched, saturated, monovalent hydrocarbon group in which the term "$C_1$-$C_4$-alkyl" is as defined supra, and in which one or more of the hydrogen atoms are replaced, identically or differently, with a halogen atom. Particularly, said halogen atom is a fluorine atom. More particularly, all said halogen atoms are fluorine atoms ("$C_1$-$C_4$-fluoroalkyl"). Said $C_1$-$C_4$-halogenoalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl, wherein a trifluoromethyl-group is particularly preferred.

The term "$C_1$-$C_4$-alkoxy" means a linear or branched, saturated, monovalent group of formula ($C_1$-$C_4$-alkyl)-O—, in which the term "$C_1$-$C_4$-alkyl" is as defined supra, e.g. a methoxy, ethoxy, n-propoxy, isopropoxy, n-butoxy, sec-butoxy, isobutoxy or tert-butoxy group, or an isomer thereof, with a methoxy-group being particularly preferred.

The term "$C_1$-$C_4$-halogenoalkoxy" means a linear or branched, saturated, monovalent $C_1$-$C_4$-alkoxy group, as defined supra, in which one or more of the hydrogen atoms is replaced, identically or differently, with a halogen atom. Particularly, said halogen atom is a fluorine atom. Said $C_1$-$C_4$-halogenoalkoxy group is, for example, fluoromethoxy, difluoromethoxy, trifluoromethoxy, 2,2,2-trifluoroethoxy or pentafluoroethoxy.

The term "$C_2$-$C_4$-alkenyl" means a linear or branched, monovalent hydrocarbon group, which contains one double bond, and which has 2, 3 or 4 carbon atoms. Said $C_2$-$C_4$-alkenyl group is, for example, an ethenyl (or "vinyl"), a prop-2-en-1-yl (or "allyl"), prop-1-en-1-yl, but-3-enyl, but-2-enyl, but-1-enyl, prop-1-en-2-yl (or "isopropenyl"), 2-methylprop-2-enyl, 1-methylprop-2-enyl, 2-methylprop-1-enyl or a 1-methylprop-1-enyl, group. Particularly, said group is allyl.

The term "$C_2$-$C_4$-alkynyl" means a linear monovalent hydrocarbon group which contains one triple bond, and which contains 2, 3 or 4 carbon atoms. Said $C_2$-$C_4$-alkynyl group is, for example, an ethynyl, a prop-1-ynyl, prop-2-ynyl (or "propargyl"), but-1-ynyl, but-2-ynyl, but-3-ynyl or 1-methylprop-2-ynyl, group. Particularly, said alkynyl group is prop-1-ynyl or prop-2-ynyl.

The term "$C_3$-$C_6$-cycloalkyl" means a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl group.

The term "$C_3$-$C_6$-halogenocycloalkyl" means a saturated, monovalent, monocyclic hydrocarbon ring in which the term "$C_3$-$C_6$-cycloalkyl" is as defined supra, and in which one or more of the hydrogen atoms are replaced, identically or differently, with a halogen atom. Particularly, said halogen atom is a fluorine or chlorine atom. Said $C_3$-$C_6$-halogenocycloalkyl group is for example, a monocyclic hydrocarbon ring substituted with one or two fluorine or chlorine atoms, e.g. a 1-fluoro-cyclopropyl, 2-fluorocyclopropyl, 2,2-difluorocyclopropyl, 2,3-difluorocyclopropyl, 1-chlorocyclopropyl, 2-chlorocyclopropyl, 2,2-dichlorocyclopropyl, 2,3-dichlorocyclopropyl, 2-fluoro-2-chlorocyclopropyl and 2-fluoro-3-chlorocyclopropyl group.

The term "heterocyclyl-$C_1$-$C_4$-alkyl" means a linear or branched, saturated, monovalent group in which the term "$C_1$-$C_4$-alkyl" is as defined supra, and in which 1 or 2 hydrogen atoms are replaced with a heterocyclyl-group as defines infra.

The term "—NH($C_3$-$C_6$-cycloalkyl)" or "—N($C_1$-$C_4$-alkyl)($C_3$-$C_6$-cycloalkyl)" means a linear or branched, saturated, monovalent group in which the term "$C_1$-$C_4$-alkyl" and the term "$C_3$-$C_6$-cycloalkyl" each is as defined supra, e.g. a cyclopropylamino, cyclobutylamino, cyclopentylamino, cyclohexylamino, N-methyl-N-cyclopropylamino, N-ethyl-N-cyclopropylamino, N-methyl-N-cyclobutylamino, N-ethyl-N-cyclobutylamino, N-methyl-N-cyclopentylamino, N-ethyl-N-cyclopentylamino, N-methyl-N-cyclohexylamino, or N-ethyl-N-cyclohexylamino group.

The term "benzo-$C_5$-$C_6$-cycloalkyl" means a monovalent, bicyclic hydrocarbon ring wherein a saturated, monovalent, monocyclic hydrocarbon ring which contains 5 or 6 carbon atoms ("$C_5$-$C_6$-cycloalkyl") is annelated to a phenyl ring. Said benzo-$C_5$-$C_6$-cycloalkyl group is for example, a bicyclic hydrocarbon ring, e.g. an indane (i.e. 2,3-dihydro-1H-indene) or tetraline (i.e. 1,2,3,4-tetrahydronaphthalene) group.

The term "spirocycloalkyl" means a saturated, monovalent bicyclic hydrocarbon group in which the two rings share one common ring carbon atom, and wherein said bicyclic hydrocarbon group contains 5, 6, 7, 8, 9, 10 or 11 carbon atoms, it being possible for said spirocycloalkyl group to be attached to the rest of the molecule via any one of the carbon atoms except the spiro carbon atom. Said spirocycloalkyl group is, for example, spiro[2.2]pentyl, spiro[2.3]hexyl, spiro[2.4]heptyl, spiro[2.5]octyl, spiro[2.6]nonyl, spiro[3.3]heptyl, spiro[3.4]octyl, spiro[3.5]nonyl, spiro[3.6]decyl, spiro[4.4]nonyl, spiro[4.5]decyl, spiro[4.6]undecyl or spiro[5.5]undecyl.

The term "heterocycloalkyl" means a monocyclic or bicyclic, saturated or partially saturated heterocycle with 4, 5, 6, 7, 8, 9 or 10 ring atoms in total (a "4- to 10-membered heterocycloalkyl" group), particularly 4, 5 or 6 ring atoms (a "4- to 6-membered heterocycloalkyl" group), which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl, 1,3-thiazolidinyl or 1,2,4-triazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example; or a 7-membered ring, such as azepanyl, 1,4-diazepanyl or 1,4-oxazepanyl, for example; or a bicyclic 7-membered ring, such as 6-oxa-3-azabicyclo[3.1.1]heptan, for example; or a bicyclic 8-membered ring, such as 5,6-dihydro-4H-furo[2,3-c]pyrrole or 8-oxa-3-azabicyclo[3.2.1]octan, for example; or a bicyclic 9-membered ring, such as octahydro-1H-pyrrolo[3,4-b]pyridine, 1,3-dihydro-isoindol, 2,3-dihydro-indol or 3,9-dioxa-7-azabicyclo[3.3.1]nonan, for example; or a bicyclic 10-membered ring, such as decahydroquinoline or 3,4-dihydroisoquinolin, for example.

The term "heterospirocycloalkyl" means a bicyclic, saturated heterocycle with 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, oxaazaspiro[2.5]octyl, azaspiro[4.5]decyl, oxazaspiro[5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "6- to 10-membered aryl" means a monovalent, monocyclic or bicyclic aromatic ring having 6 to 10 carbon ring atoms, comprising in particular a phenyl and naphthyl group.

The term "heteroaryl" means a monovalent, monocyclic, bicyclic or tricyclic aromatic ring having 5, 6, 9 or 10 ring atoms (a "5- to 10-membered heteroaryl" group), particularly 5 or 6 ring atoms (a "5- to 6-membered heteroaryl" group), which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl.

The term "heterocyclyl" means a heterocycle selected from the group consisting of heterocycloalkyl and heteroaryl. Particularly, the term "4- to 6-membered heterocyclyl" means a heterocycle selected from the group consisting of 4- to 6-membered heterocycloalkyl and 5- to 6-membered heteroaryl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_4$", as used in the present text, e.g. in the context of the definition of "$C_1$-$C_4$-alkyl", "$C_1$-$C_4$-halogenoalkyl", "$C_1$-$C_4$-hydroxyalkyl", "$C_1$-$C_4$-alkoxy" or "$C_1$-$C_4$-halogenoalkoxy" means an alkyl group having a finite number of carbon atoms of 1 to 4, i.e. 1, 2, 3 or 4 carbon atoms.

Further, as used herein, the term "$C_3$-$C_6$", as used in the present text, e.g. in the context of the definition of "$C_3$-$C_6$-cycloalkyl" or $C_3$-$C_6$-halogenocycloalkyl, means a cycloalkyl group having a finite number of carbon atoms of 3 to 6, i.e. 3, 4, 5 or 6 carbon atoms.

When a range of values is given, said range encompasses each value and sub-range within said range.

For example:

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$- $C_6$, $C_3$-$C_5$, $C_3$-$C_4$, $C_4$-$C_6$, $C_4$-$C_5$, and $C_5$-$C_6$;

"$C_3$-$C_4$" encompasses $C_3$, $C_4$, and $C_3$-$C_4$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_5$, $C_6$-$C_7$, $C_7$-$C_{10}$, $C_7$-$C_9$, $C_7$-$C_8$, $C_5$-$C_{10}$, $C_5$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_6$, $C_5$-$C_7$, $C_5$-$C_6$, $C_6$-$C_5$, $C_6$-$C_7$ and $C_7$-$C_5$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_6$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$- $C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_5$, $C_5$-$C_{10}$, $C_6$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_5$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

An oxo substituent in the context of the invention means an oxygen atom, which is bound to a carbon atom via a double bond.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^4C$, $^{15}N$, $^{17}O$, $^{18}O$, $^{32}P$, $^{33}P$, $^{33}S$, $^{34}S$, $^{35}S$, $^{36}S$, $^{18}F$, $^{36}C$, $^{82}Br$, $^{123}I$, $^{124}I$, $^{125}I$, $^{129}I$ and $^{131}I$ respectively.

With respect to the treatment and/or prevention of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers.

Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains a substitution pattern resulting in α-CH-moiety at the azaquinoline that has an increased C—H-acidity can exist as a tautomer, or even a mixture in any amount of the two tautomers.

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with a second embodiment of the first aspect, the present invention covers compounds of general formula (I), supra, in which:

A is A1 or A2,

A1

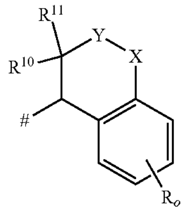

A2

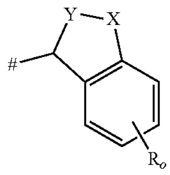

o is 0, 1, 2, 3 or 4;

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms;

X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—;

T is selected from $T^1$, $T^2$, $T^3$, $T^4$, $T^5$, $T^6$, $T^7$, $T^{8a}$, $T^{8b}$ and $T^9$ as defined supra;

$R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$- $C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$- $C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;

—$NR^{12}R^{13}$;

—$OR^{14}$;

—$SR^{15}$, —S(O)$R^{15}$, —$SO_2R^{15}$;

$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$- $C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and 4- to 10-membered heterocycloalkyl;

$R^3$ is selected from the group consisting of hydrogen, halogen or $C_1$-$C_4$-alkyl;

$R^4$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^5$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy;

$R^6$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^7$ is selected from the group consisting of hydrogen, —OH, halogen, $C_1$-$C_4$-alkyl and $C_1$-$C_4$-alkoxy;

$R^8$ is selected from the group consisting of hydrogen, —OH, halogen, $C_1$-$C_4$-alkyl and $C_1$-$C_4$-alkoxy;

$R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy;

$R^{10}$ is selected from the group consisting of hydrogen, —OH, $C_1$-$C_4$-alkyl and $C_1$-$C_4$-alkoxy;

$R^{11}$ is selected from the group consisting of hydrogen, $C_1$-$C_4$-alkyl and $C_1$-$C_4$-alkoxy;

$R^{12}$ and $R^{13}$ are independently selected from the group consisting of hydrogen, —OH, —$NH_2$, —NH($C_1$-$C_4$-alkyl), —N($C_1$-$C_4$-alkyl)$_2$, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, benzo-$C_5$-$C_6$-cycloalkyl, each of which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{14}$ is selected from the group consisting of —$NH_2$, —NH($C_1$-$C_4$-alkyl), —N($C_1$-$C_4$-alkyl)$_2$;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-

$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substitutent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$- halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{16}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

$R^{17}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

Q is selected from the group consisting of 6-membered aryl and 5- to 6-membered heteroaryl, each of which is optionally substituted by 1, 2, 3, 4 or 5 substituents selected from the group consisting of halogen, SFs, cyano, —CHO, nitro, oxo, $C_1$-$C_4$-alkyl, $C_1$-$C_4$-hydroxyalkyl, $C_1$-$C_4$-halogenoalkyl having 1 to 5 halogen atoms, —OH, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl$)_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), NHCO($C_1$-$C_4$-halogenoalkyl) having 1 to 5 halogen atoms;

wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH;

and stereoisomers, tautomers, N-oxides, hydrates, solvates, and salts thereof, and mixtures of same.

In accordance with a third embodiment of the first aspect, the present invention covers compounds of general formula (I), supra, in which:

A is A1 or A2,

A1

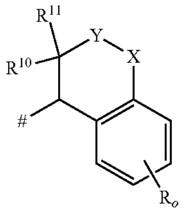

A2

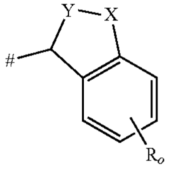

o is 0, 1 or 2;

R is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy;

X, Y are independently selected from the group consisting of $CR^7R^8$, O, S, and N—$R^9$, wherein at least one of X and Y is $CR^7R^8$;

T is selected from $T^1$, $T^2$, $T^3$, $T^4$, $T^5$, $T^6$, $T^7$, $T^{8a}$, $T^{8b}$ and $T^9$ as defined supra;

$R^1$ is selected from the group consisting of hydrogen, $C_1$-$C_4$-alkyl, $C_1$-$C_4$-halogenoalkyl having 1 to 5 halogen atoms, $C_1$-$C_4$-alkoxy;

$R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl$)_2$;

—$NR^{12}R^{13}$;

—$OR^{14}$;

—$SR^{15}$, —$S(O)R^{15}$, —$SO_2R^{15}$;

$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl$)_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl$)_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl$)_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl$)_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and 4- to 10-membered heterocycloalkyl;

$R^3$ is selected from the group consisting of hydrogen, halogen or $C_1$-$C_4$-alkyl;

$R^4$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^5$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy;

$R^6$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^7$ is selected from the group consisting of hydrogen, halogen, $C_1$-$C_4$-alkyl;

$R^8$ is selected from the group consisting of hydrogen, halogen, $C_1$-$C_4$-alkyl;

$R^9$ is selected from the group consisting of hydrogen, $C_1$-$C_4$-alkyl;

$R^{10}$ is selected from the group consisting of hydrogen, —OH, $C_1$-$C_4$-alkyl and $C_1$-$C_4$-alkoxy;

$R^{11}$ is selected from the group consisting of hydrogen;

$R^{12}$ and $R^{13}$ are independently selected from the group consisting of hydrogen;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl$)_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(═O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

phenyl, benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, —OH, oxo, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms;

$R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{15}$ is selected from the group consisting of $C_1$-$C_4$-alkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{16}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

$R^{17}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

Q is selected from the group consisting of 6-membered aryl and 5- to 6-membered heteroaryl, each of which is optionally substituted by 1, 2, 3, 4 or 5 substituents selected from the group consisting of halogen, cyano, $C_1$-$C_4$-alkyl, $C_1$-$C_4$-hydroxyalkyl, $C_1$-$C_4$-halogenoalkyl having 1 to 5 halogen atoms, —OH, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, 4- to 6-membered heterocyclyl, which is optionally substituted with 1 or 2 substituents selected from the group consisting of fluorine, chlorine, bromine, methyl and cyano;

wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH;

and stereoisomers, tautomers, N-oxides, hydrates, solvates, and salts thereof, and mixtures of same.

In accordance with a fourth embodiment of the first aspect, the present invention covers compounds of general formula (I), supra, in which:

A is A1 or A2,

A1

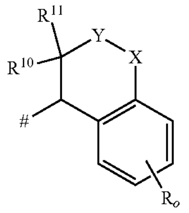

A2

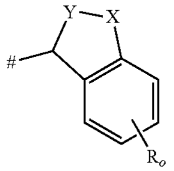

o is 0 or 1;

R is selected from the group consisting of hydrogen, halogen, $C_1$-$C_4$-alkyl, $C_1$-$C_4$-halogenoalkyl having 1 to 5 halogen atoms, $C_1$-$C_4$-alkoxy;

X is selected from the group consisting of $CR^7R^8$, O, S, and N—$R^9$,

Y is $CR^7R^8$;

T is selected from $T^1$, $T^2$, $T^3$, $T^4$, $T^5$, $T^6$, $T^7$, $T^{8a}$, $T^{8b}$ and $T^9$ as defined supra;

$R^1$ is selected from the group consisting of hydrogen and $C_1$-$C_4$-alkyl;

$R^2$ is selected from the group consisting of hydrogen, halogen;

$NR^{12}R^{13}$;

—$OR^{14}$;

$SR^{15}$, —S(O)$R^{15}$, —$SO_2R^{15}$;

$C_1$-$C_6$-alkyl or $C_3$-$C_6$-cycloalkyl, each of which is optionally substituted by 1, 2, 3, 4 or 5 substituents independently selected from the group consisting of halogen, cyano, $C_1$-$C_4$-alkyl;

a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, —OH, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms;

$R^3$ is selected from the group consisting of hydrogen, halogen or $C_1$-$C_4$-alkyl;

$R^4$ is selected from the group consisting of hydrogen, halogen, $C_1$-$C_4$-alkyl, $C_1$-$C_4$-halogenoalkyl having 1 to 5 halogen atoms;

$R^5$ is selected from the group consisting of hydrogen, halogen, $C_1$-$C_4$-alkyl, $C_1$-$C_4$-halogenoalkyl having 1 to 5 halogen atoms;

$R^6$ is selected from the group consisting of hydrogen, halogen, $C_1$-$C_4$-alkyl, $C_1$-$C_4$-halogenoalkyl having 1 to 5 halogen atoms;

$R^7$ is selected from the group consisting of hydrogen, halogen, $C_1$-$C_4$-alkyl;

$R^8$ is selected from the group consisting of hydrogen, halogen, $C_1$-$C_4$-alkyl;

$R^9$ is selected from the group consisting of hydrogen, $C_1$-$C_4$-alkyl;

$R^{10}$ is selected from the group consisting of hydrogen, $C_1$-$C_4$-alkyl;

$R^{11}$ is selected from the group consisting of hydrogen;

$R^{12}$ and $R^{13}$ are independently selected from the group consisting of hydrogen;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl;

heterocyclyl-$C_1$-$C_4$-alkyl, wherein the heterocyclyl substituent is selected from the group consisting of 4- to 10-membered heterocycloalkyl, which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

phenyl, which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

heterocyclyl-$C_1$-$C_4$-alkyl, wherein the heterocyclyl substitutent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{15}$ is selected from the group consisting of $C_1$-$C_4$-alkyl, phenyl-$C_1$-$C_4$-alkyl, each of which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{16}$ is selected from the group consisting of hydrogen, $C_1$-$C_4$-alkyl, $C_1$-$C_4$-halogenoalkyl having 1 to 5 halogen atoms;

$R^{17}$ is selected from the group consisting of hydrogen, $C_1$-$C_4$-alkyl, $C_1$-$C_4$-halogenoalkyl having 1 to 5 halogen atoms;

Q is selected from the group consisting of 6-membered aryl and 5- to 6-membered heteroaryl, each of which is optionally substituted by 1, 2, 3, 4 or 5 substituents selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH;

and stereoisomers, tautomers, N-oxides, hydrates, solvates, and salts thereof, and mixtures of same.

In accordance with a fifth embodiment of the first aspect, the present invention covers compounds of general formula (I), as defined in any of the first to fourth embodiments supra, in which:

Q is a substituted phenyl ring of the formula (Q1)

(Q1)

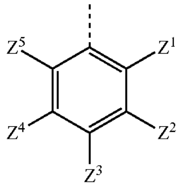

in which:

$Z^1$, $Z^2$, $Z^3$, $Z^4$, and $Z^5$ are independently selected from the group consisting of hydrogen, halogen, $SF_5$, cyano, —CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or $Z^1$ and $Z^2$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substitutents selected from the group consisting of methyl, fluorine and oxo, and $Z^3$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-alkoxy-C(O)—, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substitutents selected from the group consisting of methyl, fluorine and oxo, and $Z^1$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or Q is a pyridine ring of the formula (Q2)

(Q2)

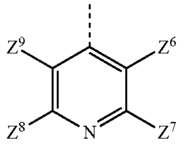

in which:

$Z^6$, $Z^7$, $Z^8$ and $Z^9$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, $NH_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyrimidine ring of the formula (Q3)

(Q3)

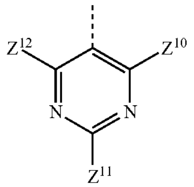

in which:

$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyridine ring of the formula (Q4)

(Q4)

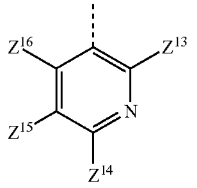

in which:

$Z^1$, $Z^{14}$, $Z^{15}$ and $Z^{16}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyridine ring of the formula (Q5)

(Q5)

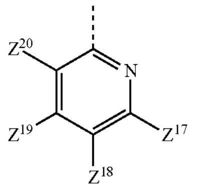

in which:

$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a 5-membered aromatic heterocycle of the formula (Q6)

(Q6)

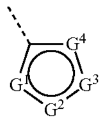

in which:

$G^1$-4 are independently selected from the group consisting of N, O, S, C—$Z^{21}$ and N—$Z^{22}$, wherein not more than one of $G^1$-$G^4$ is O, not more than one of $G^1$-$G^4$ is S, not more than one of $G^1$-$G^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

(Q7)

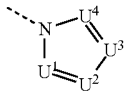

in which:

$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and stereoisomers, tautomers, N-oxides, hydrates, solvates, and salts thereof, and mixtures of same.

Therein, a 5-membered aromatic heterocycle of the formula (Q6) may preferably be selected from the group consisting of:

(Q6-1)

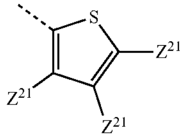

(Q6-2)

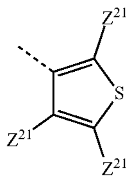

(Q6-3)

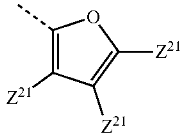

(Q6-4)

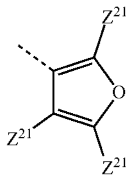

(Q6-5)

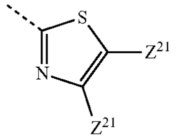

(Q6-6)

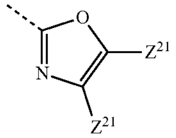

-continued
(Q6-7)
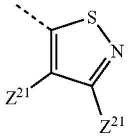
(Q6-8)
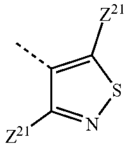
(Q6-9)
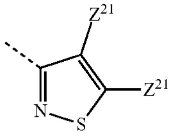
(Q6-10)
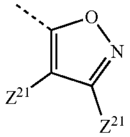
(Q6-11)
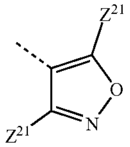
(Q6-12)
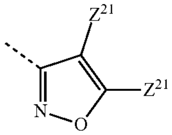
(Q6-13)
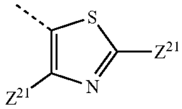
(Q6-14)
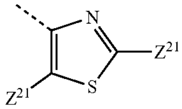
(Q6-15)
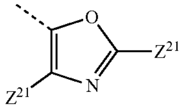
(Q6-16)
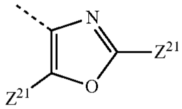
(Q6-17)
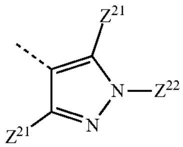
-continued
(Q6-18)
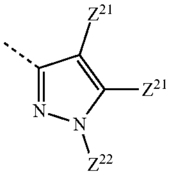
(Q6-19)
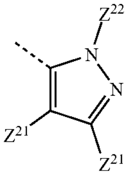
(Q6-20)
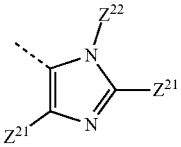
(Q6-21)
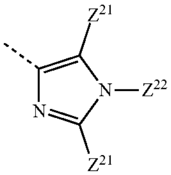
(Q6-22)
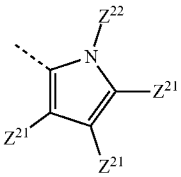
(Q6-23)
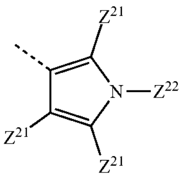
(Q6-24)
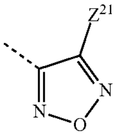
(Q6-25)
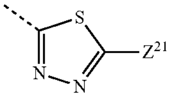
(Q6-26)
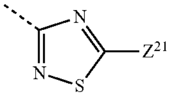
(Q6-27)
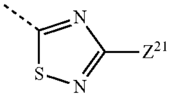

-continued
(Q6-28)
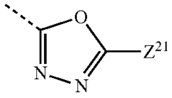
(Q6-29)
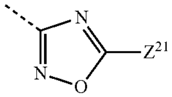
(Q6-30)
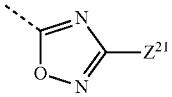
(Q6-31)
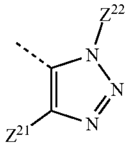
(Q6-32)
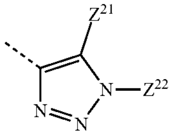
(Q6-33)
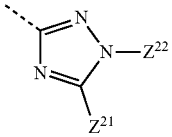
(Q6-34)
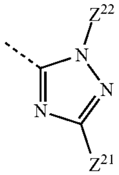
(Q6-35)
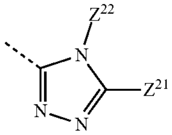
(Q6-36)
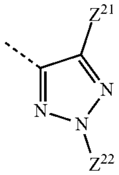
(Q6-37)
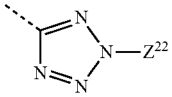
(Q6-38)
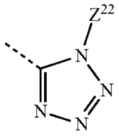
or
-continued
(Q6-39)
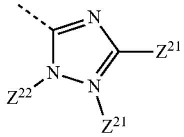
in which:
each $Z^{21}$ is independently selected from the group consisting of hydrogen, fluorine, chlorine, cyano, methyl, trifluoromethyl, methoxy and
$Z^{22}$ is hydrogen, methyl, or
a 5-membered aromatic heterocycle of the formula (Q7) may preferably be selected from the group consisting of:
(Q7-1)
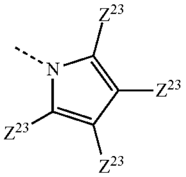
(Q7-2)
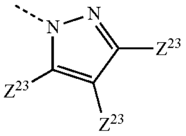
(Q7-3)
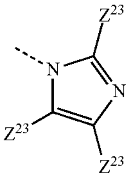
(Q7-4)
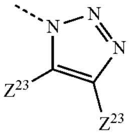
(Q7-5)
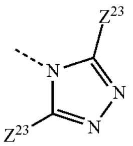
(Q7-6)
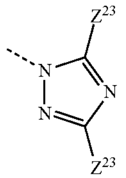
(Q7-7)
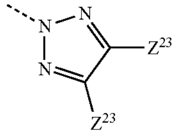

-continued (Q7-8)

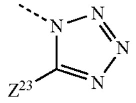

(Q7-9)

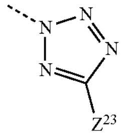

in which:

each $Z^{23}$ is independently selected from the group consisting of hydrogen, fluorine, chlorine, cyano, methyl, trifluoromethyl, methoxy, or Q may be selected from the group consisting of:

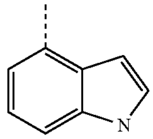
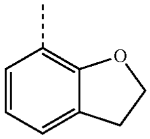
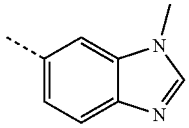
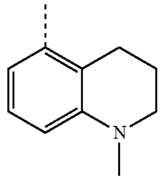
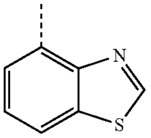
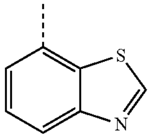
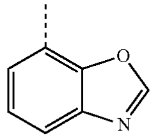
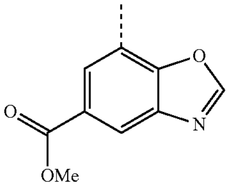.

In accordance with a sixth embodiment of the first aspect, the present invention covers compounds of general formula (I), supra, in which:

A is selected from the group consisting of

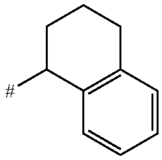
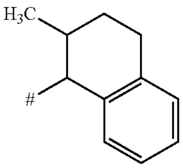
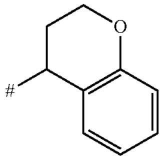
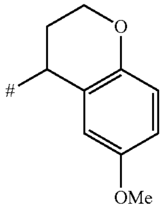

-continued

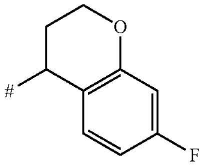
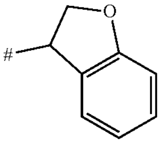
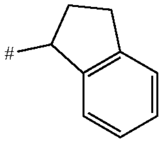
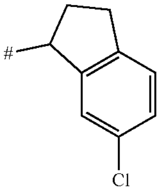
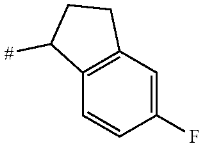
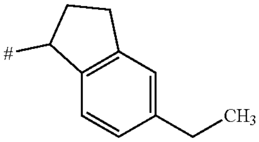
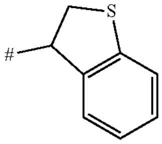
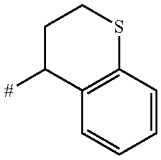
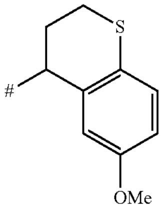
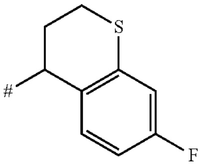
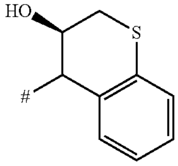
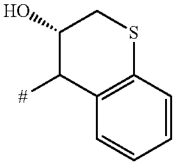
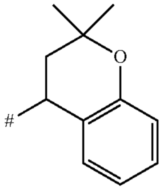
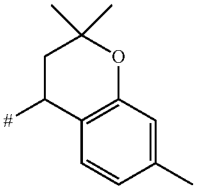
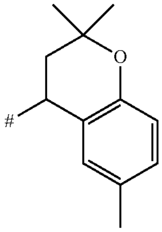
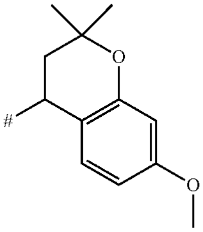
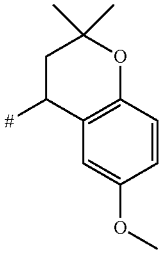
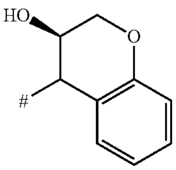

-continued

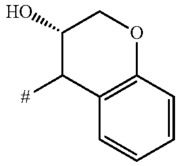

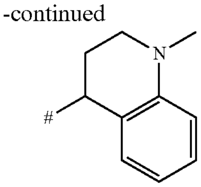
,

T is selected from $T^1$, $T^2$, $T^3$, $T^4$, T, $T^6$, $T^7$, $T^{8a}$, $T^{8b}$ and $T^9$ as defined supra;

$R^1$ is selected from the group consisting of hydrogen or methyl;

$R^2$ is selected from the group consisting of hydrogen, chlorine, fluorine, bromine;

$NR^{12}R^{13}$;

—$OR^{14}$;

methyl, ethyl, propyl, isopropyl, cyclopropyl, cyclohexyl, each of which is optionally substituted by 1 of 2 substituents independently selected from the group consisting of fluorine, chlorine, cyano, methyl, ethyl, propyl, and isopropyl;

a monocyclic or a bicyclic heterocycle selected from the group consisting of azetidine, pyrrolidine, pyrazolidine, imidazolidine, 1,2,4-triazolidine, piperidine, piperazine, tetrahydropyridine, dihydro-2H-pyrane, tetrahydropyrane, 1,2-oxazolidine, 1,2-oxazine, morpholine, thiomorpholine, 3,4-dihydroisoquinoline, 2,3-dihydro-indole, 1,3-dihydro-isoindole, 3,9-dioxa-7-azabicyclo[3.3.1]nonane, 6-oxa-3-azabicyclo[3.1.1]heptane, 8-oxa-3-azabicyclo[3.2.1]octane, imidazole, pyrazole, 1,2,4-triazole, 1,2,3-triazole, 4-oxa-7-azaspiro[2.5]octane, each of which is optionally substituted by 1, 2, 3 or 4 substituents independently selected from the group consisting of fluorine, chlorine, —OH, methyl, trifluoromethyl, methoxymethyl, trifluoromethoxymethyl;

$R^3$ is selected from the group consisting of hydrogen, chlorine or methyl;

$R^4$ is selected from the group consisting of hydrogen, fluorine, chlorine, methyl, methoxy, trifluoromethyl, trifluoromethoxy;

$R^5$ is selected from the group consisting of hydrogen, fluorine, chlorine, methyl, trifluoromethyl;

$R^6$ is selected from the group consisting of hydrogen, fluorine, chlorine, methyl, methoxy, trifluoromethyl, trifluoromethoxy;

$R^7$ is selected from the group consisting of hydrogen, fluorine, chlorine, methyl;

$R^8$ is selected from the group consisting of hydrogen, fluorine, chlorine, methyl;

$R^9$ is selected from the group consisting of hydrogen, methyl;

$R^{10}$ is selected from the group consisting of hydrogen, methyl;

$R^{11}$ is selected from the group consisting of hydrogen;

$R^{12}$ and $R^{13}$ are independently selected from the group consisting of hydrogen and methyl;

$R^{14}$ is methyl;

$R^{16}$ is selected from the group consisting of hydrogen, methyl, ethyl, propyl, isopropyl, trifluoromethyl;

$R^{17}$ is selected from the group consisting of hydrogen, methyl, ethyl, propyl, isopropyl, trifluoromethyl;

Q is a phenyl ring of the formula (Q1)

(Q1)

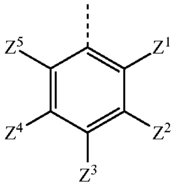

wherein:

$Z^1$ to $Z^5$ are independently selected from the group consisting of hydrogen, fluorine, chlorine, methyl and trifluoromethyl;

or

Q is a phenyl ring of the formula (Q2)

(Q2)

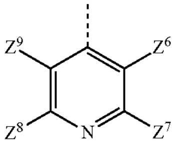

wherein:

$Z^6$ to $Z^9$ are independently selected from the group consisting of hydrogen, fluorine, chlorine, methyl and trifluoromethyl;

and stereoisomers, tautomers, N-oxides, hydrates, solvates, and salts thereof, and mixtures of same.

In accordance with a seventh embodiment of the first aspect, the present invention covers compounds of general formula (I), as defined in any of the first to sixth embodiments supra, in which:

Q is a phenyl ring of the formula (Q1)

(Q1)

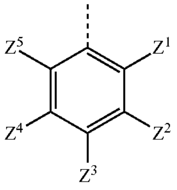

wherein:

$Z^1$, $Z^3$ and $Z^5$ are independently selected from the group consisting of hydrogen, fluorine and chlorine;

$Z^2$ and $Z^4$ are independently selected from the group consisting of hydrogen, fluorine, chlorine and trifluoromethyl;

or

Q is a phenyl ring of the formula (Q2)

(Q2)

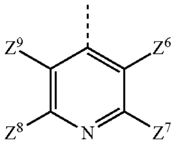

wherein:

$Z^6$ to $Z^9$ are independently selected from the group consisting of hydrogen, fluorine and chlorine; and stereoisomers, tautomers, N-oxides, hydrates, solvates, and salts thereof, and mixtures of same.

In accordance with an eighth embodiment of the first aspect, the present invention covers compounds of general formula (I), as defined in any of the first to seventh embodiments supra, in which:

A is selected from the group consisting of

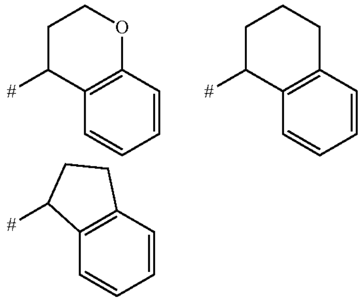

and stereoisomers, tautomers, N-oxides, hydrates, solvates, and salts thereof, and mixtures of same.

In accordance with a ninth embodiment of the first aspect, the present invention covers compounds of general formula (I), supra, in which:

A is selected from the group consisting of

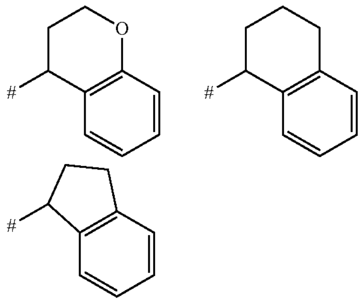

T is selected from $T^1$, $T^2$, $T^3$, $T^4$, $T^5$, $T^6$, $T^7$, $T^{8a}$, $T^{8b}$ and $T^9$ as defined supra;

$R^1$ is hydrogen;

$R^2$ is selected from hydrogen, chlorine;

—$NR^{12}R^{13}$;

—$OR^{14}$;

methyl, isopropyl;

morpholine;

$R^3$ is hydrogen or methyl;

$R^4$ is hydrogen or fluorine;

$R^5$ is hydrogen or methyl;

$R^6$ is hydrogen or fluorine;

$R^7$ is hydrogen or methyl;

$R^8$ is hydrogen;

$R^9$ is hydrogen;

$R^{10}$ is hydrogen;

$R^{11}$ is hydrogen;

$R^{12}$ and $R^{13}$ are independently selected from the group consisting of hydrogen and methyl;

$R^{14}$ is methyl;

$R^{16}$ is methyl or isopropyl;

$R^{17}$ is methyl;

Q is a phenyl ring of the formula (Q1)

(Q1)

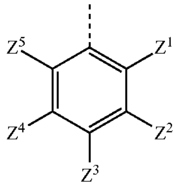

wherein:

$Z^1$, $Z^3$ and $Z^5$ are independently selected from the group consisting of hydrogen, fluorine and chlorine;

$Z^2$ and $Z^4$ are independently selected from the group consisting of hydrogen, fluorine, chlorine and trifluoromethyl;

or

Q is a phenyl ring of the formula (Q2)

(Q2)

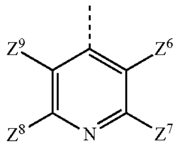

wherein:

$Z^6$ to $Z^9$ are independently selected from hydrogen and chlorine;

and stereoisomers, tautomers, N-oxides, hydrates, solvates, and salts thereof, and mixtures of same.

In accordance with a tenth embodiment of the first aspect, the present invention covers compounds of general formula (I), as defined in any of the first to ninth embodiments supra, wherein:

A is selected from the group consisting of:

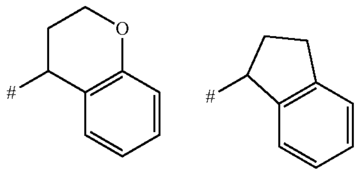

, preferably A is

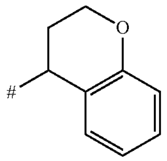

;

and stereoisomers, tautomers, N-oxides, hydrates, solvates, and salts thereof, and mixtures of same.

In accordance with a further particular embodiment of the first aspect, the present invention covers compounds of general formula (I), as defined in any of the first to tenth embodiments supra, in which:

T is $T^1$ as defined supra:

$T^1$

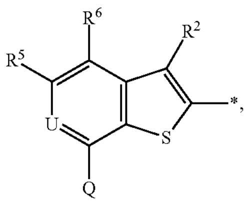

and

A, U, Q and $R^1$ to $R^{15}$ have the meaning as defined for any of the embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I), as defined in any of the first to tenth embodiments supra, in which:

T is $T^2$ as defined supra:

$T^2$

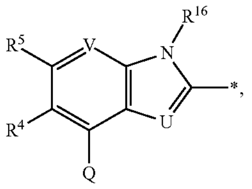

and

A, U, V, Q and $R^1$ to $R^{16}$ have the meaning as defined for any of the embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I), as defined in any of the first to tenth embodiments supra, in which: T is $T^3$ as defined supra:

$T^3$

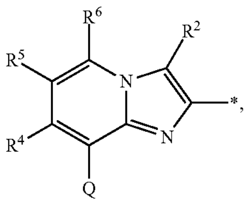

and

A, Q and $R^1$ to $R^{15}$ have the meaning as defined for any of the embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I), as defined in any of the first to tenth embodiments supra, in which:

T is $T^4$ as defined supra:

$T^4$

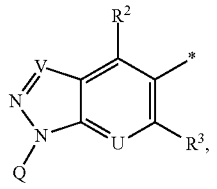

and

A, U, V, Q and $R^1$ to $R^{15}$ have the meaning as defined for any of the embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I), as defined in any of the first to tenth embodiments supra, in which:

T is $T^5$ as defined supra:

$T^5$

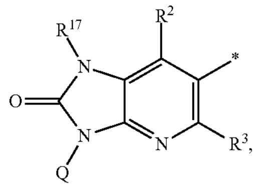

and

A, Q and $R^1$ to $R^{17}$ have the meaning as defined for any of the embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I), as defined in any of the first to tenth embodiments supra, in which:

T is $T^6$ as defined supra:

$T^6$

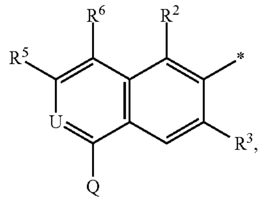

and

A, U, Q and $R^1$ to $R^{15}$ have the meaning as defined for any of the embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I), as defined in any of the first to tenth embodiments supra, in which:

T is $T^7$ as defined supra:

$T^7$

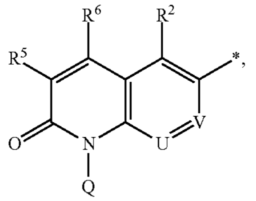

and

A, U, V, Q and $R^1$ to $R^{15}$ have the meaning as defined for any of the embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I), as defined in any of the first to tenth embodiments supra, in which:

T is $T^{8a}$ as defined supra:

$T^{8a}$

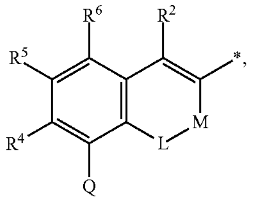

and

A, L, M, Q and $R^1$ to $R^{15}$ have the meaning as defined for any of the embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I), as defined in any of the first to tenth embodiments supra, in which:

T is $T^{8b}$ as defined supra:

$T^{8b}$

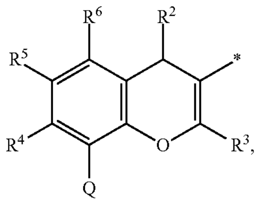

and

A, Q and $R^1$ to $R^{15}$ have the meaning as defined for any of the embodiments of the first aspect supra, and stereoisomers, tautomers, N-oxides, hydrates, solvates, and salts thereof, and mixtures of same.

In accordance with a further particular embodiment of the first aspect, the present invention covers compounds of general formula (I), as defined in any of the first to tenth embodiments supra, in which:

T is $T^9$ as defined supra:

$T^9$

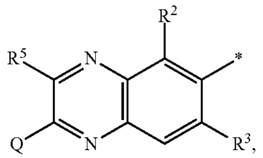

and

A, Q and $R^1$ to $R^{15}$ have the meaning as defined for any of the embodiments of the first aspect supra, and stereoisomers, tautomers, N-oxides, hydrates, solvates, and salts thereof, and mixtures of same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers the compounds of general formula (I) which are disclosed in the Example Section of this text, infra. Such as in particular Example Compounds S1-1, S1-2, S1-3, S1-4, S1-5, S1-6, S1-7, S1-8, S1-9, S1-10, S1-11, S1-12, S1-13, S1-14, S1-15, S1-16, S1- 17, S1-18, S2-1, S2-2, S2-3, S2-4, S2-5, S2-6, S2-7, S3-1, S4-1, S4-2, S4-3, S4-4, S4-5, S4-6, S4- 7, S4-8, S4-9, S4-10, S5-1, S6-1, S6-2, S7-1, S7-2, S8a-1, S8a-2, S8a-3, S8a-4, S8a-5, S8a-6, S8b-1, S8b-2, S8b-3, S9-1, S9-2, S9-3, S9-4, S9-5, S9-6.

The compounds according to the invention of general formula (I) can be prepared according to the schemes 1 to 10 as shown in the Experimental Section to the present invention (General Synthesis Scheme). The schemes and procedures described illustrate synthetic routes to the compounds of general formula (I) of the invention and are not intended to be limiting. It is clear to the person skilled in the art that the order of transformations as exemplified in schemes 1 to 10 can be modified in various ways. The order of transformations exemplified in these schemes is therefore not intended to be limiting. In addition, interconversion of any of the substituents, T, Q, A, $R^1$, $R^2$, $R^3$, $R^4$, $R^5$ or $R^6$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3rd edition, Wiley 1999). Specific examples are described in the subsequent paragraphs.

In the following, several routes for the preparation of compounds of general formula (I) are described in schemes 1 to 10.

In accordance with a second aspect, the present invention covers methods of preparing compounds of general formula (I) as defined supra, said methods comprising the step of allowing an intermediate compound of general formula Int-I-T1, Int-I-T2, Int-I-T3, Int-I-T4, Int-I-T5, Int-I-T6, Int-I-T7, Int-I-T8a, Int-I-T8b or Int-I-T9:

Int-I-T1

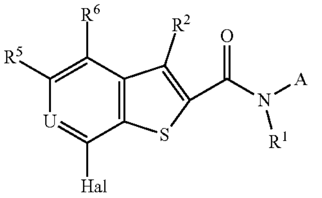

Int-I-T2

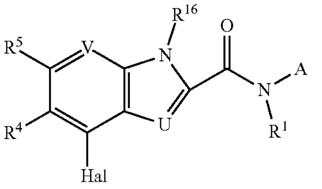

Int-I-T3

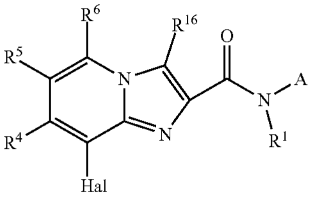

Int-I-T4

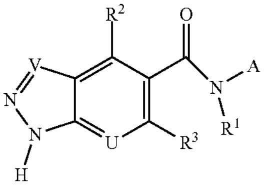

Int-I-T5

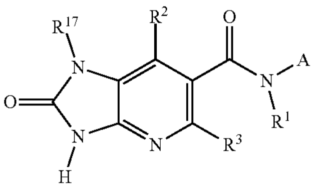

Int-I-T6

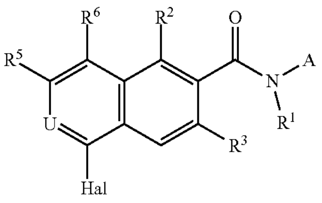

Int-I-T7

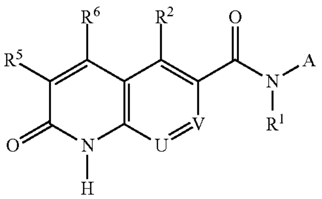

Int-I-T8a

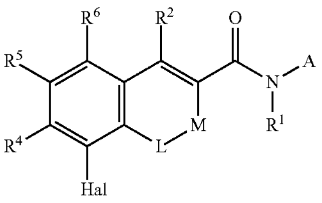

-continued

Int-I-T8b

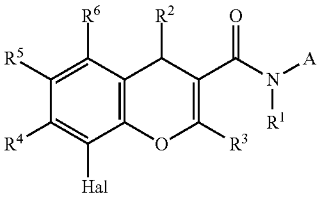

Int-I-T9

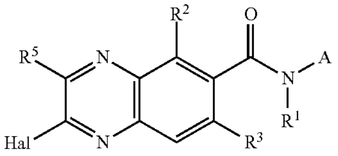

in which L, M, U, V, A, $R^1$, $R^2$, $R^3$, $R^4$, $R^5$ and $R^6$ are as defined for the compound of general formula (I) as defined supra, and in which Hal is halogen, particularly chlorine, bromine or iodine, to react with a compound of general formula 1H:

$Q\text{-}B(OR)_2$ 1H, in which Q is as defined for the compound of general formula (I) as defined supra, and each R may be individually H or Me or both R are pinacolate, thereby giving a compound of general formula (I)

(I)

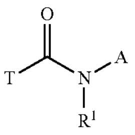

in which T, L, M, U, V, A, $R^1$, $R^2$, $R^3$, $R^4$, R, $R^6$, and Q are as defined supra.

In accordance with an alternative embodiment of the second aspect, the present invention covers methods of preparing compounds of general formula (I) as defined supra, said methods comprising the step of allowing an intermediate compound of general formula Int-II-T1, Int-II-T2, Int-II-T3, Int-II-T4, Int-II-T5, Int-II-T6, Int-II-T7, Int-II-T8a, Int-II-T8b or Int-II-T9:

Int-II-T1

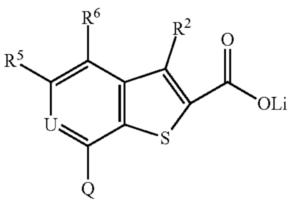

Int-II-T2

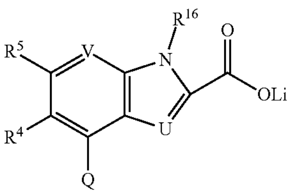

-continued

Int-II-T3

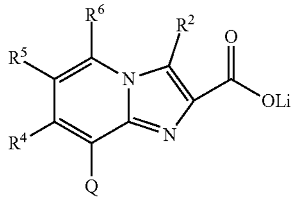

Int-II-T4

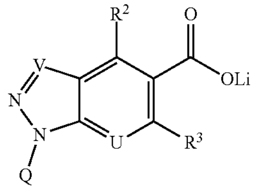

Int-II-T5

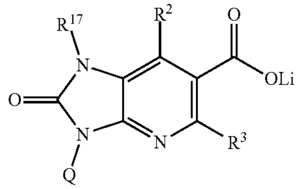

Int-II-T6

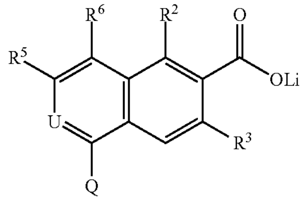

Int-II-T7

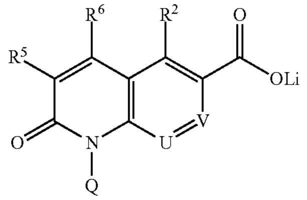

Int-II-T8a

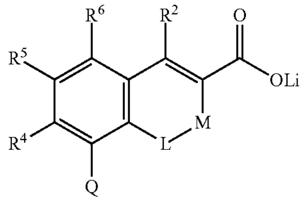

Int-II-T8b

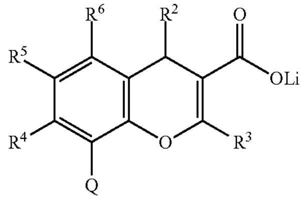

Int-II-T9

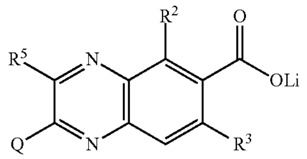

in which L, M, U, V, Q, $R^2$, $R^3$, $R^4$, $R^5$ and $R^6$ are as defined for the compound of general formula (I) as defined supra, to react with a compound of general formula 1V:

1V

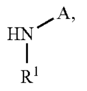

in which $R^1$ and A are as defined for the compound of general formula (I) as defined supra, thereby giving a compound of general formula (I)

(I)

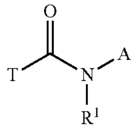

in which T, A and $R^1$ are as defined supra.

In accordance with a third aspect, the present invention covers methods of preparing compounds of general formula (I) as defined supra, said methods comprising the steps of preparing the intermediate compounds as described supra, and then converting the resulting compound into solvates, salts and/or solvates thereof using the corresponding (i) solvents and/or (ii) bases or acids.

The present invention covers methods of preparing compounds of the present invention of general formula (I), said methods comprising the steps as described in the Experimental Section infra.

In accordance with a fourth aspect, the present invention covers intermediate compounds which are useful for the preparation of the compounds of general formula (I), supra.

Particularly, the inventions covers the intermediate compounds of general formulae Int-I-T1

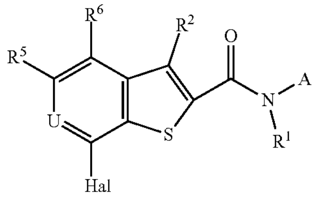

Int-I-T2

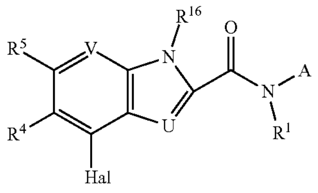

Int-I-T3

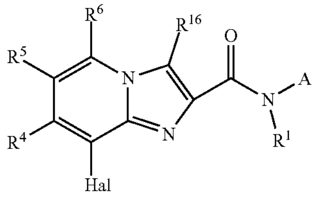

-continued

Int-I-T4

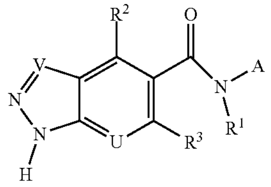

Int-I-T5

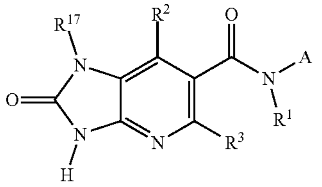

Int-I-T6

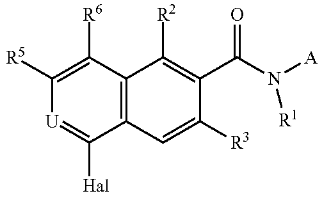

Int-I-T7

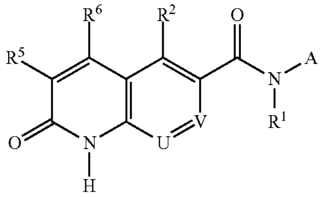

Int-I-T8a

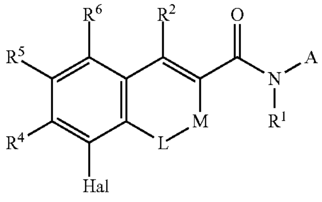

Int-I-T8b

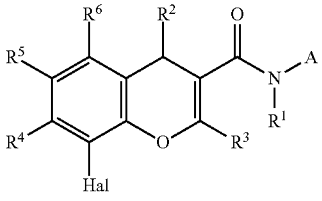

Int-I-T9

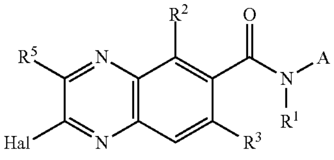

in which L, M, U, V, A, $R^1$, $R^2$, $R^3$, $R^4$, $R^5$ and $R^6$ are as defined for the compound of general formula (I) supra, and Hal is halogen, and stereoisomers, tautomers, N-oxides, hydrates, solvates, and salts thereof, and mixtures of same.

Further, the inventions covers the intermediate compounds of general formulae

Int-II-T1

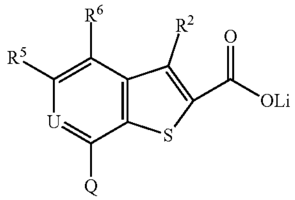

Int-II-T2

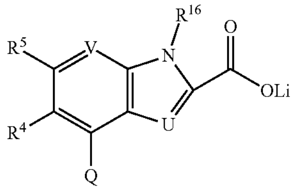

Int-II-T3

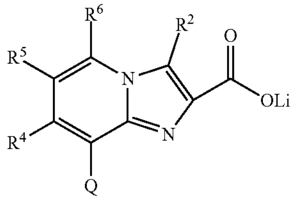

Int-II-T4

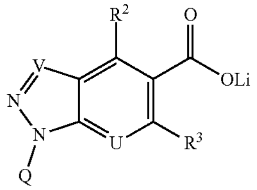

Int-II-T5

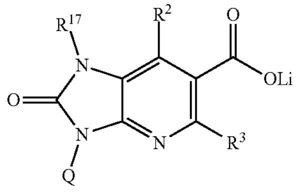

Int-II-T6

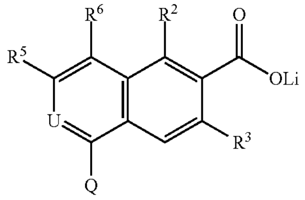

Int-II-T7

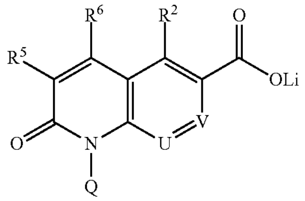

-continued

Int-II-T8a

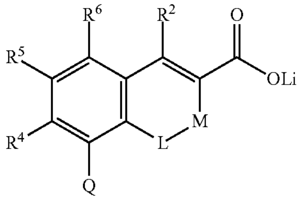

Int-II-T8b

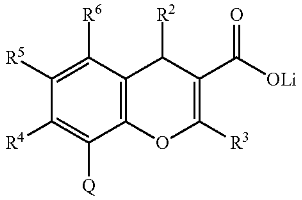

Int-II-T9

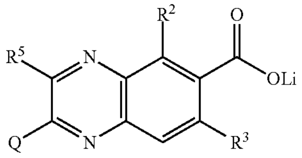

in which L, M, U, V, Q, $R^2$, $R^3$, $R^4$, $R^5$ and $R^6$ are as defined for the compound of general formula (I) as defined supra, and stereoisomers, tautomers, N-oxides, hydrates, solvates, and salts thereof, and mixtures of same.

The present invention covers in particular the intermediate compounds which are disclosed in the Example Section of this text, infra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively interact with Slo-1 and it is possible therefore that said compounds be used for the treatment or prevention of diseases, preferably helminthic infections, particularly of gastro-intestinal and extra-intestinal helminth infections, more particularly of gastro-intestinal and extra-intestinal infections with nematodes in humans and animals.

Compounds of the present invention can be utilized to control, treat and/or prevent helminth infections, in particular gastro-intestinal and extra-intestinal helminth infections. This method comprises administering to a mammal in need thereof an amount of a compound of this invention, or a pharmaceutically acceptable salt, isomer, polymorph, metabolite, hydrate, solvate or ester thereof; which is effective to treat the disorder.

In an alternative aspect, this method comprises administering to birds, namely cage birds or in particular poultry, in need thereof an amount of a compound of this invention, or a pharmaceutically acceptable salt, isomer, polymorph, metabolite, hydrate, solvate or ester thereof; which is effective to treat the disorder.

Specifically in the field of veterinary medicine, compounds of the the present invention are suitable, with favourable toxicity in warm blooded animals, for controlling parasites, in particular helminths, which occur in animal breeding and animal husbandry in livestock, breeding, zoo, laboratory, experimental and domestic animals. They are active against all or specific stages of development of the parasites, in particular of the helminths.

Agricultural livestock include, for example, mammals, such as, sheep, goats, horses, donkeys, camels, buffaloes, rabbits, reindeers, fallow deers, and in particular cattle and pigs; or poultry, such as turkeys, ducks, geese, and in particular chickens; or fish or crustaceans, e.g. in aquaculture.

Domestic animals include, for example, mammals, such as hamsters, guinea pigs, rats, mice, chinchillas, ferrets or in particular dogs, cats; cage birds; reptiles; amphibians or aquarium fish.

The present invention also provides methods of treating helminth infections, particularly gastro-intestinal and extra-intestinal helminth infections, more particularly gastro-intestinal and extra-intestinal infections with nematodes.

These disorders have been well characterized in animals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as a nematode infection. In particular, and particularly in the animal health or veterinary field, the term "treating" or "treatment" includes prophylactic, metaphylactic or therapeutical treatment Helminths pathogenic for humans or animals include, for example, acanthocephala, nematodes, pentastoma and platyhelmintha (e.g. monogenea, cestodes and trematodes).

Exemplary helminths include, without any limitation:

Monogenea: e.g.: *Dactylogyrus* spp., *Gyrodactylus* spp., *Microbothrium* spp., *Polystoma* spp., *Troglocephalus* spp.

Cestodes: from the order of the Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp. from the order of the Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of the Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of the Trichinellida, for example: *Capillaria* spp., *Eucoleus* spp., *Paracapillaria* spp., *Trichinella* spp., *Trichomosoides* spp., *Trichuris* spp.

from the order of the Tylenchida, for example: *Micronema* spp., *Parastrongyloides* spp., *Strongyloides* spp.

from the order of the Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

from the order of the Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acantocephala: from the order of the Oligacanthorhynchida, for example: *Macracanthorhynchus* spp., *Prosthenorchis* spp.; from the order of the Moniliformida, for example: *Moniliformis* spp.

from the order of the Polymorphida, for example: *Filicollis* spp.; from the order of the Echinorhynchida, for example: *Acanthocephalus* spp., *Echinorhynchus* spp., *Leptorhynchoides* spp.

Pentastoma: from the order of the Porocephalida, for example: *Linguatula* spp.

The compounds of the present invention can be used in particular in therapy and prevention, i.e. prophylaxis, of helminth infections, particularly gastro-intestinal and extra-intestinal helminth infections, more particularly gastro-intestinal and extra-intestinal infections with nematodes.

By using the compounds of the present invention to control animal parasites, in particular helminths, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling", as used herein with regard to the animal health field, means that the compounds of the present invention are effective in reducing the incidence of the respective parasite in an animal infected with such parasites to innocuous levels. More specifically, "controlling", as used herein, means that the compounds of the present invention are effective in killing the respective parasite, inhibiting its growth, or inhibiting its proliferation.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prevention of diseases, in particular of helminth infections, particularly of gastro-intestinal and extra-intestinal helminth infections, more particularly of gastro-intestinal and extra-intestinal infections with nematodes.

The pharmaceutical activity of the compounds according to the invention can be explained by their interaction with the Slo-1 ion channel.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prevention or treatment of diseases, in particular of helminth infections, particularly of gastro-intestinal and extra-intestinal helminth infections, more particularly of gastro-intestinal and extra-intestinal infections with nematodes.

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as an antiendoparasitical agent.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use as a anthelmintic agent, in particular for use as a nematicidal agent, a platyhelminthicidal agent, an acanthocephalicidal agent, or a pentastomicidal agent.

In accordance with a further aspect, the present invention covers pharmaceutical compositions, in particular a veterinary formulation, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

In accordance with a further aspect, the present invention covers a method for preparing a pharmaceutical composition, in particular a veterinary formulation, comprising the step of mixing a compound of general formula (I), as described supra, or a stereoisomer, a tautomer, an N-oxide, a hydrate, a solvate, a salt thereof, particularly a pharmaceutically acceptable salt, or a mixture of same, with one or more excipients), in particular one or more pharmaceutically acceptable excipient(s).

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using a pharmaceutical composition, in particular a veterinary formulation, comprising an effective amount of a compound of general formula (I), as described supra, or stereoisomers, tautomers, N-oxides, hydrates, solvates, and salts thereof, particularly pharmaceutically acceptable salts thereof, or mixtures of same.

Accordingly, the present invention covers a method for controlling helminth infections in humans and/or animals by administering an anthelminthically effective amount of at least one compound of general formula (I) supra to a human or an animal in need thereof.

The present invention furthermore covers pharmaceutical compositions, in particular veterinary formulations, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent. Such administration can be carried out prophylactically, metaphylactically or therapeutically.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, chewables (for example soft chewables), powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, spot-ons, dusting powders, implants or stents.

The compounds according to the invention can be incorporated into the stated administration forms. This can be effected in a manner known per se by mixing with pharmaceutically suitable excipients. Pharmaceutically suitable excipients include, inter alia,

- fillers and carriers (for example cellulose, microcrystalline cellulose (such as, for example, Avicel®), lactose, mannitol, starch, calcium phosphate (such as, for example, D1-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, isopropanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
- buffers, acids and bases (for example phosphates, carbonates, citric acid, acetic acid, hydrochloric acid, sodium hydroxide solution, ammonium carbonate, trometamol, triethanolamine),
- isotonicity agents (for example glucose, sodium chloride),
- adsorbents (for example highly-disperse silicas),
- viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine),
- disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and block copolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prevention of an endo- and/or ectoparasiticidal infection.

The term "endoparasite" in the present invention is used as known to persons skilled in the art, and refers in particular to helminths. The term "ectoparasite" in the present invention is used as known to persons skilled in the art, and refers in particular to arthropods, particularly insects or acarids.

Particularly, the present invention covers a pharmaceutical combination, in particular a veterinary combination, which comprises:

one or more first active ingredients, in particular compounds of general formula (I) as defined supra, and one or more further active ingredients, in particular one or more endo- and/or ectoparasiticides.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known ectoparasiticides and/or endoparasiticides.

The other or further active ingredients specified herein by their common names are known and described, for example, in the Pesticide Manual ("The Pesticide Manual" 16th Ed., British Crop Protection Council 2012) or can be searched in the internet (e.g. http://www.alanwood.net/pesticides). The classification is based on the current IRAC Mode of Action Classification Scheme at the time of filing of this patent application.

Examples of ectoparasiticides and/or endoparasiticides are insecticides, acaricides and nematicides, and include in particular:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCl) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(9) Modulators of Chordotonal Organs, such as, for example pymetrozine or flonicamid.

(10) Mite growth inhibitors, such as, for example clofentezine, hexythiazox and diflovidazin or etoxazole.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide, further active ingredients such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tioxazafen, Thiofluoximate, Triflumezopyrim and iodomethane; furthermore preparations based on Bacillus-firmus (I-1582, BioNeem, Votivo), and also the following compounds: 1-{2-fluoro-4-methyl-5-[(2,2,2-trifluoroethyl) sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro [indol-3,4'-piperidin]-1(2H)-yl}(2-chloropyridin-4-yl) methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl) benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)—N-[3-chloro-1-(3-pyridinyl)-1H-pyrazol-4-yl]-N-ethyl-3-[(3,3,3-trifluoropropyl)sulfinyl]-propanamide and (−)—N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl) phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy) phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-aza-bicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8) and N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1,8-diazaspiro[4.5]dec-3-en-4-yl-carbonic acid ethyl ester (known from WO 2010/066780 A1, WO 2011151146 A1) (CAS 1229023-00-0), N-[1-[(6-chloro-3-pyridinyl) methyl]-2(1H)-pyridinylidene]-2,2,2-trifluoro-acetamide (known from DE 3639877 A1, WO 2012029672 A1) (CAS 1363400-41-2), [N(E)]—N-[1-[(6-chloro-3-pyridinyl) methyl]-2(1H)-pyridinylidene]-2,2,2-trifluoro-acetamide, (known from WO 2016005276 A1) (CAS 1689566-03-7), [N(Z)]—N-[1-[(6-chloro-3-pyridinyl)methyl]-2(1H)-pyridinylidene]-2,2,2-trifluoro-acetamide, (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1] nonane (known from WO 2011/105506 A1, WO 2016/133011 A1) (CAS 1332838-17-1).

Active ingredients with unknown or non-specific mode of action, e.g., fentrifanil, fenoxacrim, cycloprene, chlorobenzilate, chlordimeform, flubenzimine, dicyclanil, amidoflumet, quinomethionate, triarathene, clothiazoben, tetrasul, potassium oleate, petroleum, metoxadiazone, gossyplure, flutenzin, bromopropylate, cryolite;

Active ingredients from other classes, e.g. butacarb, dimetilan, cloethocarb, phosphocarb, pirimiphos (-ethyl), parathion (-ethyl), methacrifos, isopropyl o-salicylate, trichlorfon, sulprofos, propaphos, sebufos, pyridathion, prothoate, dichlofenthion, demeton-S-methylsulphone, isazofos, cyanofenphos, dialifos, carbophenothion, autathiofos, aromfenvinfos (-methyl), azinphos (-ethyl), chlorpyrifos (-ethyl), fosmethilan, iodofenphos, dioxabenzofos, formothion, fonofos, flupyrazofos, fensulfothion, etrimfos; organochlorines, e.g. camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner; pyrethroids, e.g. (cis-, trans-), metofluthrin, profluthrin, flufenprox, flubrocythrinate, fubfenprox, fenfluthrin, protrifenbute, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated carbonhydrogen compounds (HCHs);

neonicotinoids, e.g. nithiazine;

dicloromezotiaz, triflumezopyrim;

macrocyclic lactones, e.g. nemadectin, ivermectin, latidectin, moxidectin, selamectin, eprinomectin, doramectin, emamectin benzoate; milbemycin oxime;

triprene, epofenonane, diofenolan; Biologicals, hormones or pheromones, for example natural products, e.g. thuringiensin, codlemone or neem components;

dinitrophenols, e.g. dinocap, dinobuton, binapacryl;

benzoylureas, e.g. fluazuron, penfluron;

amidine derivatives, e.g. chlormebuform, cymiazole, demiditraz;

Bee hive *varroa* acaricides, for example organic acids, e.g. formic acid, oxalic acid.

Non-limiting examples of insecticides and acaricides of particular interest for use in animal health are and include in particular [i.e. Mehlhorn et al Encyclpaedic Reference of Parasitology 4$^{th}$ edition (ISBN 978-3-662-43978-4)]:

Effectors at arthropod ligand gated chloride channels: chlordane, heptachlor, endoculfan. Dieldrin, bromocyclen, toxaphene, lindane, fipronil, pyriprole, sisapronil, afoxolaner, fluralaner, sarolaner, lotilaner, fluxametamide, broflanilide, avermectin, doramectin, eprinomectin, ivermectin, milbemycin, moxidectin, selamectin;

Modulators of arthropod octopaminergic receptors: amitraz, BTS27271, cymiazole, demiditraz;

Effectors at arthropod voltage-gated sodium channels: DDT, methoxychlor, metaflumizone, indoxacarb, cinerin I, cinerin II, jasmolin I, jasmolin II, pyrethrin I, pyrethrin II, allethrin, alphacypermethrin, bioallethrin, betacyfluthrin, cyfluthrin, cyhalothrin, cypermethrin, deltamethrin, etofenprox, fenvalerate, flucythrinate, flumethrin, halfenprox, permethrin, phenothrin, resmethrin, tau-fluvalinate, tetramethrin;

Effectors at arthropod nicotinic cholinergic synapses (acetylcholine esterase, acetylcholine receptors): bromoprypylate, bendiocarb, carbaryl, methomyl, promacyl, propoxur, azamethiphos, chlorfenvinphos, chlorpyrifos, coumaphos, cythioate, diazinon, diclorvos, dicrotophos, dimethoate, ethion, famphur, fenitrothion, fenthion, heptenophos, malathion, naled, phosmet, phoxim, phtalofos, propetamphos, temephos, tetrachlorvinphos, trichlorfon, imidacloprid, nitenpyram, dinotefuran, spinosad, spinetoram; Effectors on arthropod development processes: cyromazine, dicyclanil, diflubenzuron, fluazuron, lufenuron, triflumuron, fenoxycarb, hydroprene, methoprene, pyriproxyfen, fenoxycarb, hydroprene, S-methoprene, pyriproxyfen.

Exemplary active ingredients from the group of endoparasiticides, as a further or other active ingredient in the present invention, include, without limitation, anthelmintically active compounds and antiprotozoal active compounds.

Anthelmintically active compounds, including, without limitation, the following nematicidally, trematicidally and/or cestocidally active compounds:

from the class of macrocyclic lactones, for example: eprinomectin, abamectin, nemadectin, moxidectin, doramectin, selamectin, lepimectin, latidectin, milbemectin, ivermectin, emamectin, milbemycin;

from the class of benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole-sulphoxide, albendazole, flubendazole;

from the class of depsipeptides, preferably cyclic depsipetides, in particular 24-membered cyclic depsipeptides, for example: emodepside, PF1022A;

from the class of tetrahydropyrimidines, for example: morantel, pyrantel, oxantel;

from the class of imidazothiazoles, for example: butamisole, levamisole, tetramisole;

from the class of aminophenylamidines, for example: amidantel, deacylated amidantel (dAMD), tribendimidine;

from the class of aminoacetonitriles, for example: monepantel;

from the class of paraherquamides, for example: paraherquamide, derquantel;

from the class of salicylanilides, for example: tribromsalan, bromoxanide, brotianide, clioxanide, closantel, niclosamide, oxyclozanide, rafoxanide;

from the class of substituted phenols, for example: nitroxynil, bithionol, disophenol, hexachlorophene, niclofolan, meniclopholan;

from the class of organophosphates, for example: trichlorfon, naphthalofos, dichlorvos/DDVP, crufomate, coumaphos, haloxon;

from the class of piperazinones/quinolines, for example: praziquantel, epsiprantel;

from the class of piperazines, for example: piperazine, hydroxyzine;

from the class of tetracyclines, for example: tetracyclin, chlorotetracycline, doxycyclin, oxytetracyclin, rolitetracyclin;

from diverse other classes, for example: bunamidine, niridazole, resorantel, omphalotin, oltipraz, nitroscanate, nitroxynile, oxamniquine, mirasan, miracil, lucanthone, hycanthone, hetolin, emetine, diethylcarbamazine, dichlorophen, diamfenetide, clonazepam, bephenium, amoscanate, clorsulon.

Antiprotozoal active ingredients in the present invention, including, without limitation, the following active ingredients:

from the class of triazines, for example: diclazuril, ponazuril, letrazuril, toltrazuril;

from the class of polylether ionophore, for example: monensin, salinomycin, maduramicin, narasin;

from the class of macrocyclic lactones, for example: milbemycin, erythromycin;

from the class of quinolones, for example: enrofloxacin, pradofloxacin;

from the class of quinines, for example: chloroquine;

from the class of pyrimidines, for example: pyrimethamine;

from the class of sulfonamides, for example: sulfaquinoxaline, trimethoprim, sulfaclozin;

from the class of thiamines, for example: amprolium;

from the class of lincosamides, for example: clindamycin;

from the class of carbanilides, for example: imidocarb;

from the class of nitrofuranes, for example: nifurtimox;

from the class of quinazolinone alkaloids, for example: halofuginon;

from diverse other classes, for example: oxamniquin, paromomycin;

from the class of vaccines or antigenes from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All named other or further active ingredients in the present invention can, if their functional groups enable this, optionally form salts with suitable bases or acids.

Based upon standard laboratory techniques known to evaluate compounds useful for the treatment of helminth infections, by standard toxicity tests and by standard pharmacological assays for the determination of treatment of the conditions identified above in animals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the subject treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a subject is not dosed with a drug for a certain period of time, to be beneficial to the overall balance between pharmacological effect and tolerability. Furthermore, it is possible to have long-acting treatments, wherein the subject gets treated once for more than four weeks. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each subject will vary according to the nature and severity of the condition as determined by the attending diagnostician, the activity of the specific compound employed, the age and general condition of the subject, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

The various aspects of the invention described in this application are illustrated by the following examples which are not meant to limit the invention in any way.

The example testing experiments described herein serve to illustrate the present invention and the invention is not limited to the examples given.

Abbreviations and Acronyms atm standard atmosphere
DAD diode array detector
DMSO dimethyl sulfoxide
DME 1,2-Dimethoxyethane
ELSD evaporative light scattering detector
ESI electrospray ionization
h hour(s)
LC-MS liquid chromatography-coupled mass spectrometry
min minute(s)
NMR nuclear magnetic resonance spectrometry
$R_t$ retention time
TLC thin layer chromatography

EXPERIMENTAL SECTION—GENERAL PART

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP—NH© in combination with a Biotage autopurifier system (SP4® or Isolera Four®) and eluents such as gradients of hexane/ethyl acetate or dichloromethane/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Analytical Methods

Analytical Liquid Chromatography

Analytical (UP)LC-MS was performed by means of different equipments as described below. The masses (m/z) are reported from the positive mode electrospray ionisation unless the negative mode is indicated (ESI−).

LC-MS Methods

Method 1:

MS instrument type: Agilent Technologies 6130 Quadrupole LC-MS; HPLC instrument type: Agilent Technologies 1260 Infinity; column: Waters XSelect (C18, 30×2.1 mm, 3.5μ); flow: 1 mL/min; column temp: 35° C.; eluent A: 0.1% formic acid in acetonitrile; eluent B: 0.1% formic acid in water; lin. gradient: t=0 min 5% A, t=1.6 min 98% A, t=3 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method 2:

MS instrument type: Agilent Technologies 6130 Quadrupole LC-MS; HPLC instrument type: Agilent Technologies 1260 Infinity; column: Waters XSelect (C18, 50×2.1 mm, 3.5μ); flow: 0.8 mL/min; column temp: 35° C.; eluent A: 0.1% formic acid in acetonitrile; eluent B: 0.1% formic acid in water; lin. gradient: t=0 min 5% A, t=3.5 min 98% A, t=6 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method 3:

MS instrument type: Agilent Technologies LC/MSD SL; HPLC instrument type: Agilent Technologies 1100 Series; column: Waters XSelect (C18, 30×2.1 mm, 3.5μ); flow: 1 mL/min; column temp: 25° C., eluent A: 95% acetonitrile+5% 10 mM ammoniumbicarbonate in water, eluent B: 10 mM ammoniumbicarbonate in water pH=9.0; lin. gradient: t=0 min 5% A, t=1.6 min 98% A, t=3 min 98% A; detection: DAD (220-320 nm); detection: MSD (ESI pos/neg) mass range: 100-800.

Method 4:

MS instrument type: Agilent Technologies LC/MSD SL; HPLC instrument type: Agilent Technologies 1100 Series; column: Waters XSelect (C18, 50×2.1 mm, 3.5μ; flow: 0.8 mL/min; column temp: 25° C.; eluent A: 95% acetonitrile+5% 10 mM ammoniumbicarbonate in water; eluent B: 10 mM ammoniumbicarbonate in water pH=9.0; lin. gradient: t=0 min 5% A, t=3.5 min 98% A, t=6 min 98% A; detection: DAD (220-320 nm); detection: MSD (ESI pos/neg) mass range: 100-800.

Method 5:

instrument type: Reveleris™ Flash Chromatography System; columns: Reveleris™ C18 Flash Cartridge; 4 g, flow 18 mL/min; 12 g, flow 30 ml/min; 40 g, flow 40 mL/min; 80 g, flow 60 mL/min; 120 g, flow 80 mL/min; eluent A: 0.1% formic acid in acetonitrile; eluent B: 0.1% formic acid in water; gradient: t=0 min 5% A, t=1 min 5% A, t=13 min 100% A, t=16 min 100% A; detection: UV (200-360 nm), ELSD.

Method 6:

instrument type: Reveleris™ Flash Chromatography System; columns: GraceResolv™ Silica Cartridge; 4 g, flow 15 ml/min; 12 g, flow 28 mL/min; 24 g, flow 30 mL/min; 40 g, flow 40 ml/min; 80 g, flow 55 mL/min; 120 g, flow 80 mL/min and Davisil™ Chromatographic Silica Media (LC60A 20-45 micron); 300 g, flow 70 mL/min; 500 g, flow 70 ml/min; eluents: see experiment; detection: UV (200-360 nm), ELSD.

Method 7:

instrument type: Büchi Pump Manager C-615, Büchi Pump Module C-601; columns: GraceResolv™ Silica Cartridge; 4 g, flow 15 mL/min; 12 g, flow 28 mL/min; 24 g, flow 30 mL/min; 40 g, flow 40 mL/min; 80 g, flow 55 mL/min; 120 g, flow 80 mL/min and Davisil™ Chromatographic Silica Media (LC60A 20-45 micron); 300 g, flow 70 mL/min; 500 g, flow 70 mL/min; eluents: see experiment; detection: TLC plates; TLC Silica gel 60 F254 (Merck).

Method 8:

MS instrument type: Agilent Technologies 6130 Quadrupole LC-MS; HPLC instrument type: Agilent Technologies 1260 Infinity; column: Waters XSelect (C18, 50×2.1 mm, 3.5μ); flow: 0.8 mL/min; column temp: 35° C.; eluent A: 0.1% formic acid in acetonitrile; eluent B: 0.1% formic acid in water; lin. gradient: t=0 min 5% A, t=3.5 min 98% A, t=8 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method 9:

MS instrument type: Agilent Technologies G1956B Quadrupole LC-MS; HPLC instrument type: Agilent Technologies 1200 preparative LC; column: Waters Sunfire (C18, 150×19 mm, 5μ); flow: 25 ml/min; column temp: RT; eluent A: 0.1% formic acid in acetonitrile; eluent B: 0.1% formic acid in water; detection: DAD (220-320 nm); detection: MSD (ESI pos/neg) mass range: 100-800; fraction collection based on MS and DAD, or MS instrument type: ACQ-SQD2; HPLC instrument type: Waters Modular Preparative HPLC System; column: Waters XSelect (C18, 150×19 mm, 10 μm); flow: 24 ml/min prep pump, 1 mL/min loading pump; column temp: RT; eluent A: 0.1% formic acid in acetonitrile; eluent B: 0.1% formic acid in water; detection: DAD (220-320 nm); detection: MSD (ESI pos/neg) mass range: 100-800; fraction collection based on MS and DAD.

Method 10:

MS instrument type: Agilent Technologies G1956B Quadrupole LC-MS; HPLC instrument type: Agilent Technologies 1200 preparative LC; column: Waters XSelect (C18, 150×19 mm, 5μ); flow: 25 ml/min; column temp: RT; eluent A: 99% acetonitrile+1% 10 mM ammonium bicarbonate in water pH=9.0, eluent B: 10 mM ammonium bicarbonate in water pH=9.0; detection: DAD (220-320 nm); detection: MSD (ESI pos/neg) mass range: 100-800; fraction collection based on MS and DAD, or MS instrument type: ACQ-SQD2; HPLC instrument type: Waters Modular Preparative HPLC System; column: Waters XSelect (C18, 150×19 mm, 10 μm); flow: 24 ml/min prep pump, 1 mL/min loading pump; column temp: RT; eluent A: 99% acetonitrile+1% 10 mM ammonium bicarbonate in water pH=9.5, eluent B: 10 mM ammonium bicarbonate in water pH=9.5; detection: DAD (220-320 nm); detection: MSD (ESI pos/neg) mass range: 100-800; fraction collection based on MS and DAD.

Method 11:

instrument type: Reveleris Prep; detection: UV (220-360 nm), ELSD; column: XSelect™ CSH C18, 145×25 mm, 10μ or GEMINI™ C18, 185×25 mm, 10μ flow: 40 mL/min; eluent A: 10 mM ammoniumbicarbonate in water (pH=9.0), eluent B: 99% acetonitrile+1% 10 mM ammoniumbicarbonate in water in acetonitrile or eluent A: 250 mM ammonia in water, eluent B: 250 mM ammonia in acetonitrile.

Method 12:

MS instrument type: Agilent Technologies LC/MSD SL; HPLC instrument type: Agilent Technologies 1100 Series; column: Phenomenex Gemini NX (C18, 50×2.0 mm, 3.0μ; flow: 0.8 mL/min; column temp: 25° C.; eluent A: 95% acetonitrile+5% 10 mM ammoniumbicarbonate in water pH=9.0; eluent B: 10 mM ammoniumbicarbonate in water pH=9.0; lin. gradient: t=0 min 5% A, t=3.5 min 98% A, t=6 min 98% A; detection: DAD (220-320 nm); detection: MSD (ESI pos/neg) mass range: 100-800.

Method 13:

The determination of $[M+H]^+$ or $M^-$ by LC-MS under acidic chromatographic conditions was done with 1 ml formic acid per liter acetonitrile and 0.9 ml formic acid per liter Millipore water as eluents. The column Zorbax Eclipse Plus C18 50 mm*2.1 mm was used. The temperature of the column oven was 55° C.

Instrument: Agilent 1290 LC, Agilent MSD, HTS PAL autosampler. Linear gradient 0.0 to 1.80 minutes from 10% acetonitrile to 95% acetonitrile, from 1.80 to 2.50 minutes constant 95% acetonitrile, flow 1.0 ml/min.

Retention time indices were calculated in all cases according to a homologous series of straight chain alkan-2-ones with 3 to 16 carbons where the index of the first alkanone was set to 300, the last alkanone to 1600, the ones between correspondingly by use of a linear interpolation between successive alkanones.

Method 14:

The determination of $[M+H]^+$ or $M^-$ by LC-MS under acidic chromatographic conditions was done with 1 ml formic acid per liter acetonitrile and 0.9 ml formic acid per liter Millipore water as eluents. The column Zorbax Eclipse Plus C18 50 mm*2.1 mm was used. The temperature of the column oven was 55° C.

The determination of $[M+H]^+$ by LC-MS under neutral chromatographic conditions was done with acetonitrile and Millipore water containing 79 mg/l ammonia carbonate as eluents.

Instruments:

LC-MS3:

Waters UPLC with SQD2 mass spectrometer and Sample Manager autosampler. Linear gradient 0.0 to 1.70 minutes from 10% acetonitrile to 95% acetonitrile, from 1.70 to 2.40 minutes constant 95% acetonitrile, flow 0.85 ml/min.

LC-MS5:

Agilent 1100 LC system with MSD mass spectrometer and HTS PAL autosampler (column: Zorbax XDB C18 1.8 µm 50 mm*4.6 mm, oven temperature 55° C.). Linear gradient 0.0 to 4.25 minutes from 10% acetonitrile to 95% acetonitrile, from 4.25 to 5.80 minutes constant 95% acetonitrile, flow 2.0 ml/min.

Retention time indices were calculated in all cases according to a homologous series of straight chain alkan-2-ones with 3 to 16 carbons where the index of the first alkanone was set to 300, the last alkanone to 1600, the ones between correspondingly by use of a linear interpolation between successive alkanones.

Method 15: MCW-SQ-HSST3

Instrument: Waters ACQUITY SQD UPLC System; column: Waters Acquity UPLC HSS T3 1.8 µm 50×1 mm; eluent A: 1 µl water+0.25 ml 99% formic acid, eluent B: 1 l acetonitril+0.25 ml 99% formic acid; gradient: 0.0 min 90% A→1.2 min 5% A→2.0 min 5% A oven: 50° C.; flow: 0.40 ml/min; UV-detection: 210 nm.

[NG1]

GC-MS Methods

Instrument: GC: Agilent 6890N, FID: Det. temp: 300° C. and MS: 5973 MSD, EI-positive, Det.temp.: 280° C. Mass range: 50-550; Column: RXi-5MS 20 m, ID 180 µm, df 0.18 µm; Average velocity: 50 cm/s; Injection vol: 1 µl; Injector temp: 250° C.; Split ratio: 20/1; Carrier gas: He.

Method S:

Initial temp: 60° C.; Initial time: 1.0 min; Solvent delay: 1.3 min; Rate 50° C./min; Final temp 250° C.; Final time 3.5 min.

Method A:

Initial temp: 100° C.; Initial time: 1.5 min; Solvent delay: 1.3 min; Rate 75° C./min; Final temp 250° C.; Final time 2.5 min.

Method C:

Initial temp: 100° C.; Initial time: 1.0 min; Solvent delay: 1.3 min; Rate 75° C./min; Final temp 280° C.; Final time 2.6 min.

Method U:

Initial temp: 100° C.; Initial time: 1.0 min; Solvent delay: 1.3 min; Rate 120° C./min; Final temp 280° C.; Final time 6.5 min.

Ion Exchange Chromatography

Anion exchange chromatography: ISOLUTE™ SAX; chemical description: quaternary amine (non-endcapped) functionalized silica. manufactured using a trifunctional silane; sorbent type: strong anion exchange; average particle size: 50 µm; pore diameter: 60 A; exchange capacity: 0.6 meq/g.

Microwave

Biotage™ Initiator, Microwave Synthesizer; temperature range: 40° C.-250° C.; pressure range: 0-20 bar; power range: 0-400 W.

Nuclear Magnetic Resonance Spectroscopy $^1H$—and $^{13}C$-NMR instrument types: Bruker DMX300 ($^1H$ NMR: 300 MHz; $^{13}C$ NMR: 75 MHz), Bruker Avance III 400 ($^1H$ NMR: 400 MHz; $^{13}C$ NMR: 100 MHz) or Bruker 400 Ultrashield ($^1H$ NMR: 400 MHz; $^{13}C$ NMR: 100 MHz); internal standard: tetramethylsilane; chemical shifts (6) are displayed in parts per million [ppm]; the following abbreviations are used: s=singlet, d=doublet, t=triplet, q=quartet, m=multiplet, br.=broad; coupling constants are displayed in Hertz [Hz].

Alternatively, the determination of the $^1H$-NMR data was done with a Bruker Avance III 400 MHz spectrometer equipped with a 1.7 mm TCI probehead, with tetramethylsilane as reference (0.00 ppm) and the measurements were usually recorded from solutions in the solvents $CD_3CN$, $CDCl_3$ or $d_6$-DMSO. Alternatively a Bruker Avance III 600 MHz instrument equipped with a 5 mm CPNMP probehead or a Bruker Avance NEO 600 MHz instrument equipped with a 5 mm TCI probehead were used for the measurements. Usually the measurements were carried out with a probehead temperature of 298 K. Other measurement temperatures are explicitly noticed.

EXPERIMENTAL SECTION—GENERAL PROCEDURES

The synthesis of the compounds of the formula (I) can be performed according to or in analogy to the following schemes (Scheme 1-10).

Therein and in the overall context of the present invention crossed bonds indicate cis/trans mixtures.

General Reaction Scheme—1 (S1): Example Compounds S1-1 to S1-4

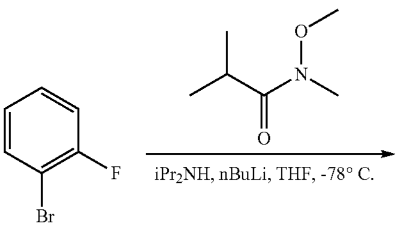

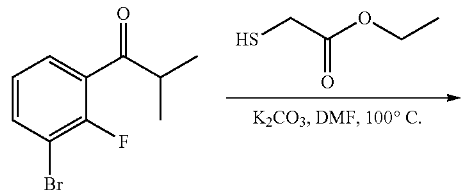

S1-1A

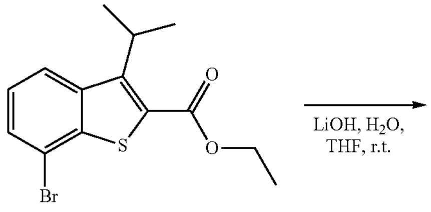

S1-1B

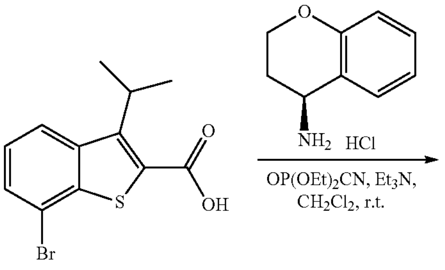

S1-1C

-continued
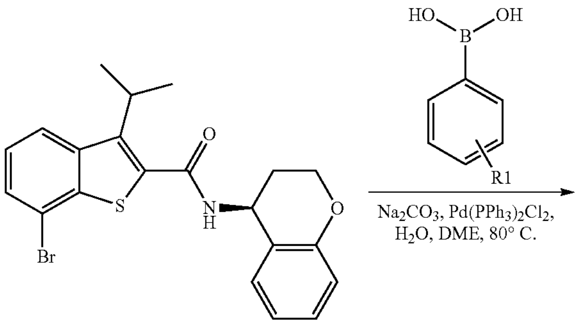
S1-1D
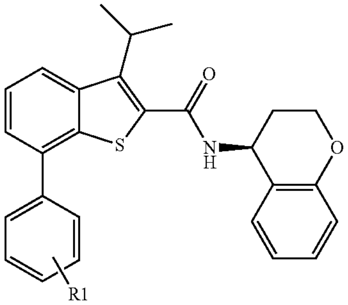
S1-1 to S1-4
General Reaction Scheme—2 (S1): Example Compounds S1-5 to S1-8
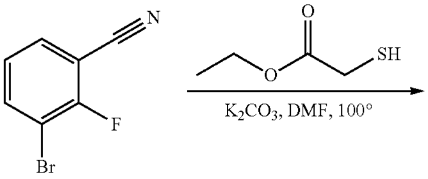
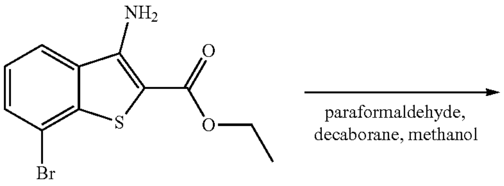
S1-2A
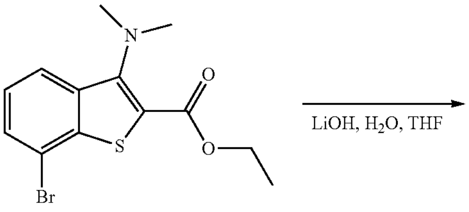
S1-2B
-continued
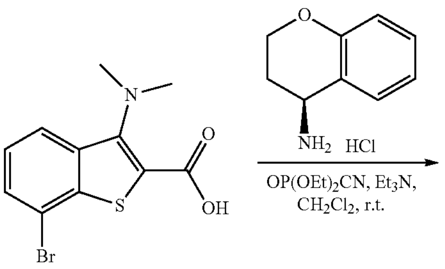
S1-2C
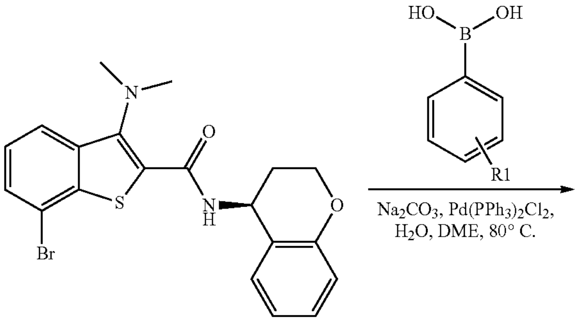
S1-2D
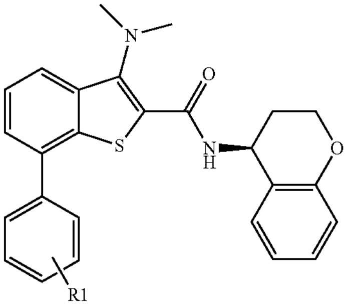
S1-5 to S1-8
General Reaction Scheme—3 (S1): Example Compounds S1-9 to S1-11
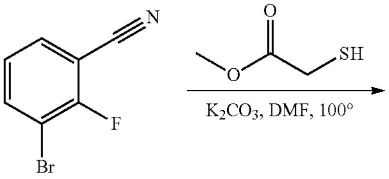
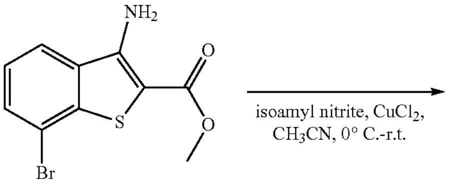
S1-3A -continued
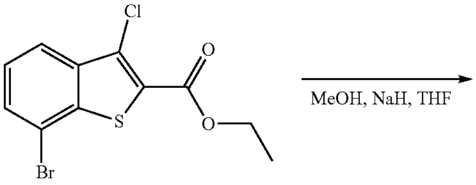
S1-3B
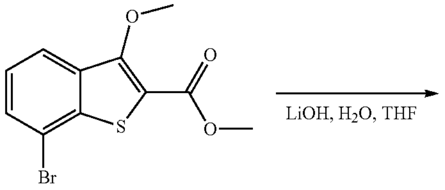
S1-3C
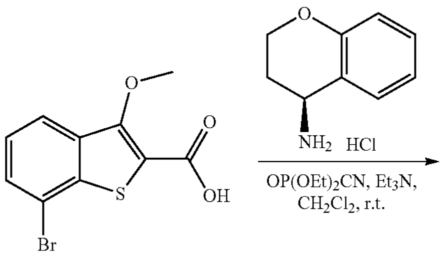
S1-3D
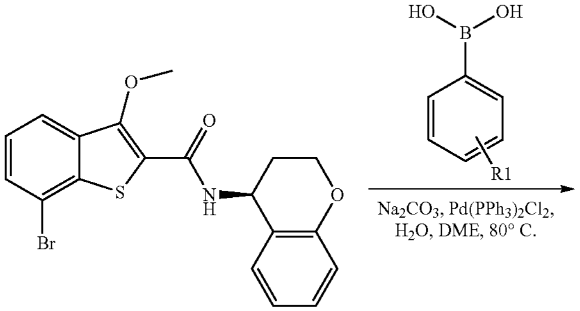
S1-3E
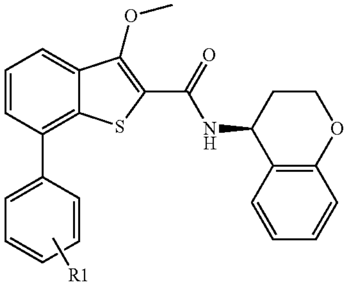
S1-9 to S1-11
General Synthesis Scheme—4 (S1): Example Compound S1-12
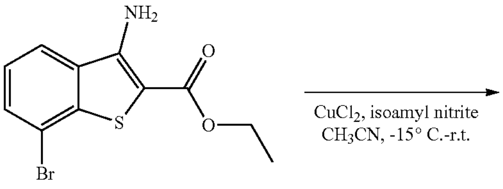
S1-2A
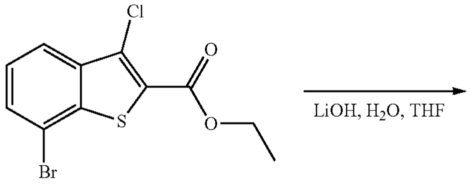
S1-4A
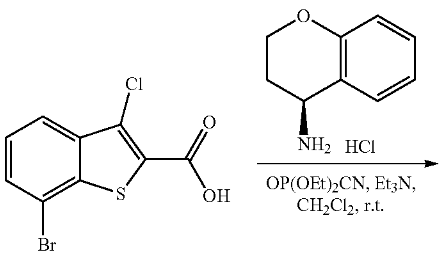
S1-4B
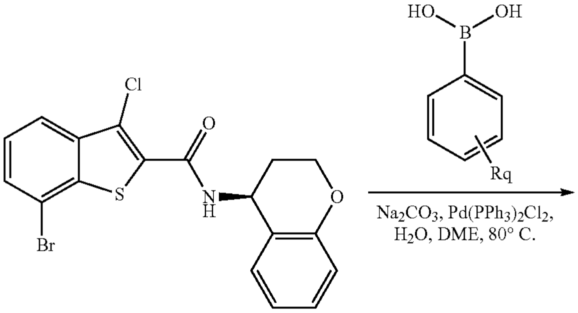
S1-4C
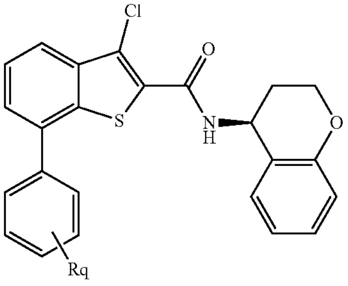
S1-12
wherein Rq indicates one or more substituents of Q as defined for the compound of general formula (I) supra.

General Synthesis Scheme—5 (S1): Example Compound S1-13
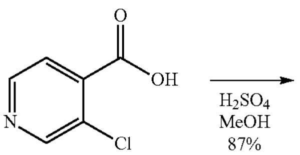
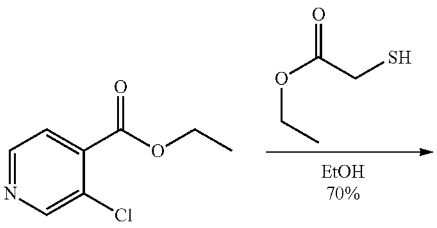
S1-1F
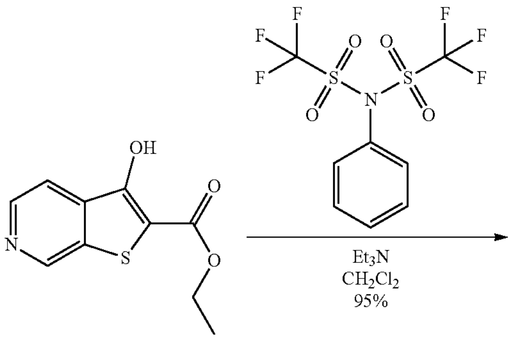
S1-2F
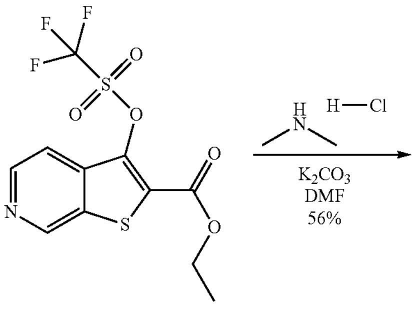
S1-3F
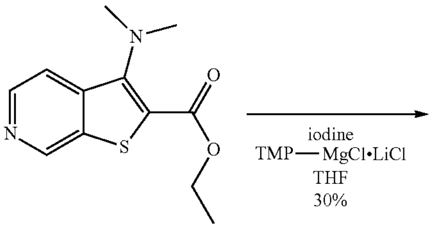
S1-4F
-continued
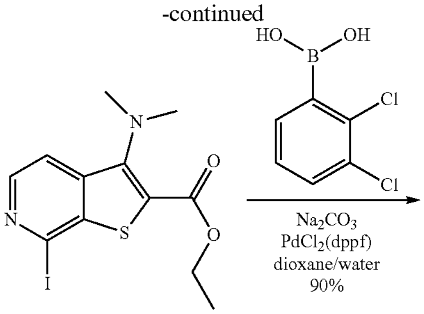
S1-5F
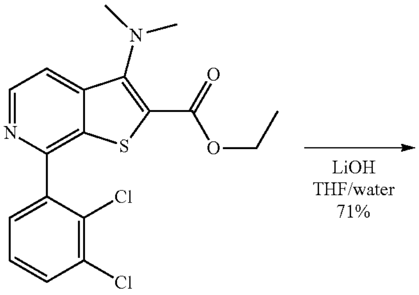
S1-6F
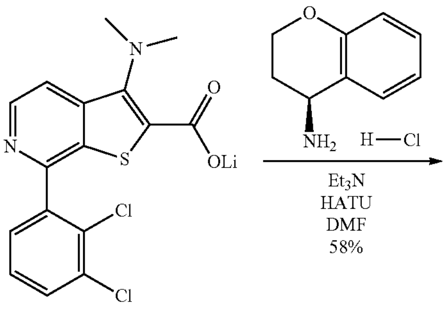
S1-7F
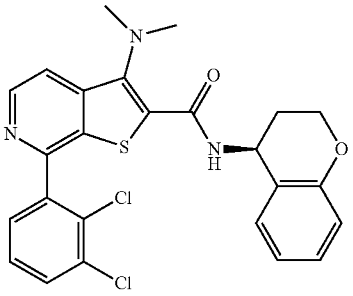
S1-13
General Synthesis Scheme—6 (S1): Example Compounds S1-14 to S1-6
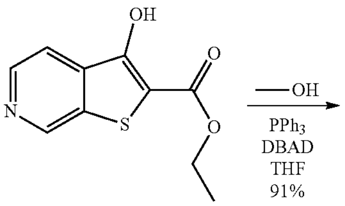
S1-2F -continued
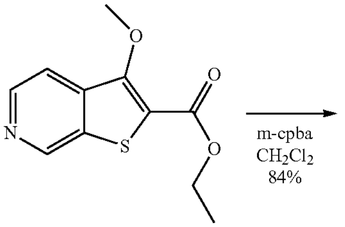
S1-8F
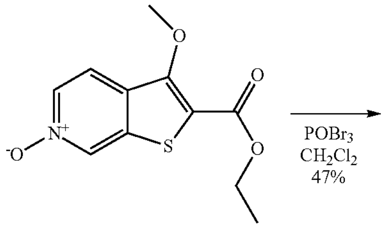
S1-9F
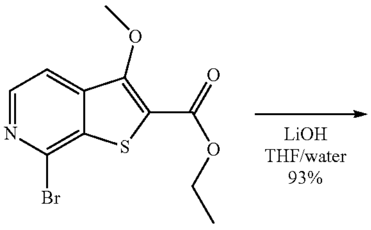
S1-10F
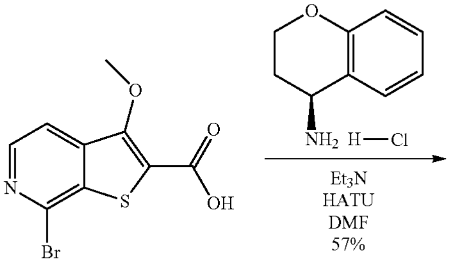
1S1-1F
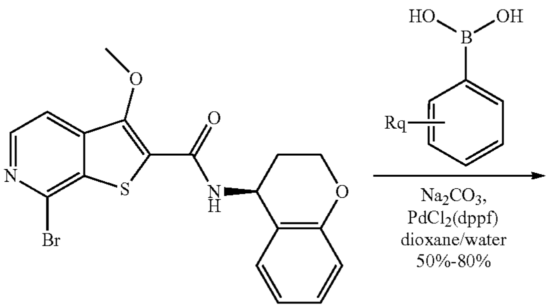
S1-12F
-continued
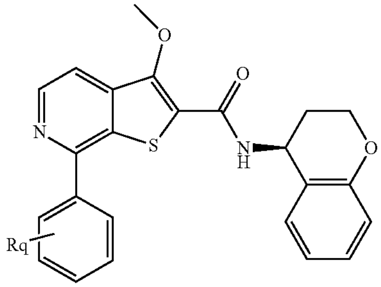
S1-14 to S1-16
wherein Rq indicates one or more substituents of Q as defined for the compound of general formula (I) supra.
General Synthesis Scheme—7 (S4): Example Compound S4-1
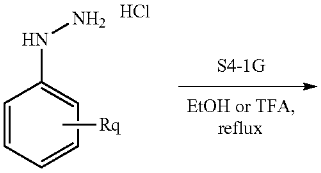
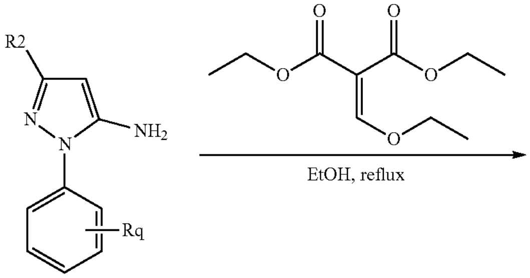
S4-2G to S4-5G
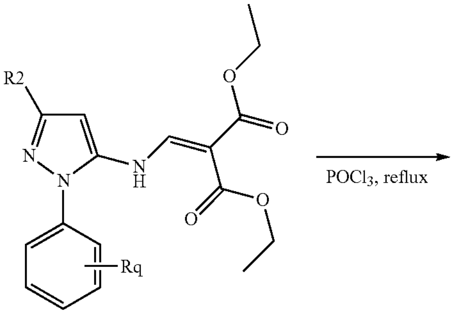
S4-6G to S4-9G
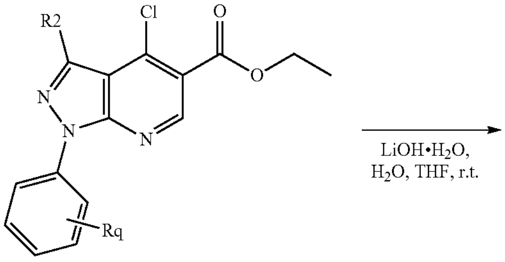
S4-10G to S4-13G -continued
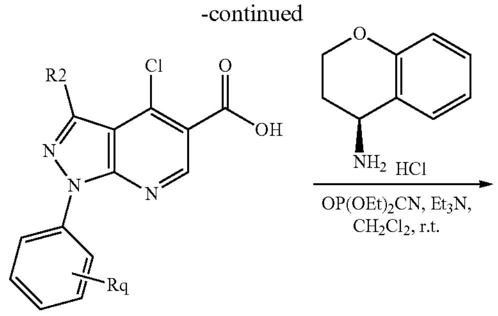
S4-14G to S4-17G
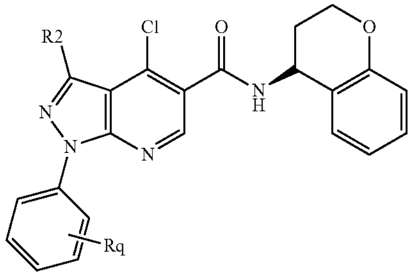
S4-1
wherein Rq indicates one or more substituents of Q as defined for the compound of general formula (I) supra.
General Synthesis Scheme—8 (S4)
S4-14G to S4-17G
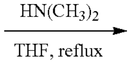
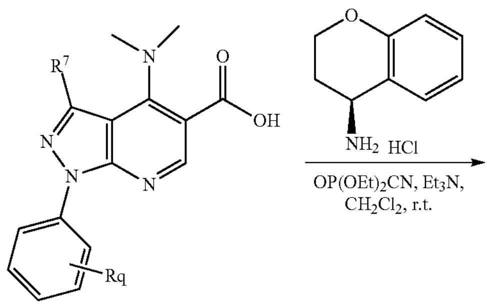
S4-18G to S4-21G
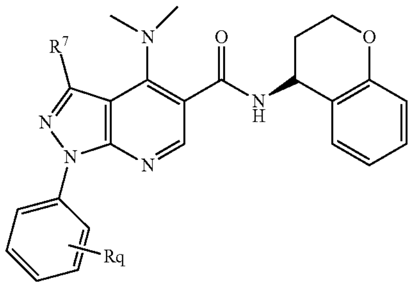
wherein $R^7$ has the meaning as defined for the compound of general formula (I) supra.
General Synthesis Scheme—9 (S8a): Example Compound S8a-1
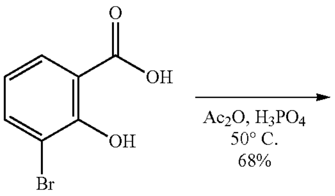
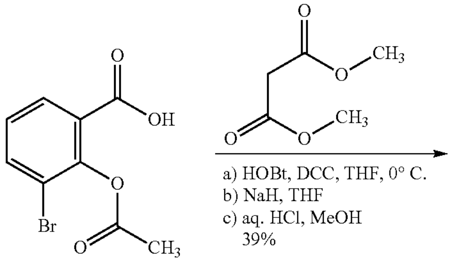
S8a-1A
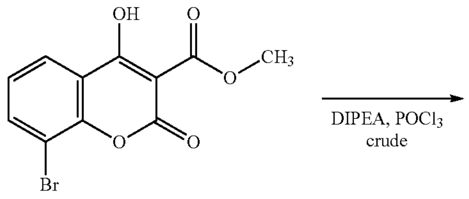
S8a-2A
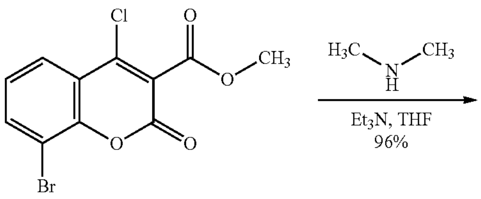
S8a-4A
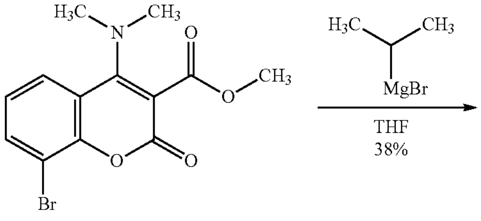
S8a-5A
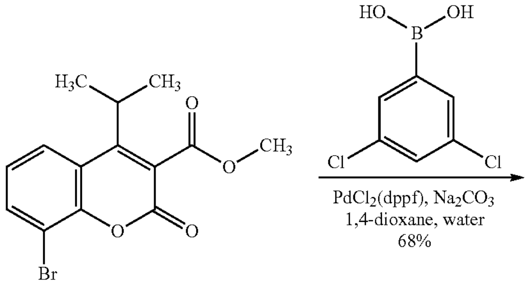
S8a-6A -continued
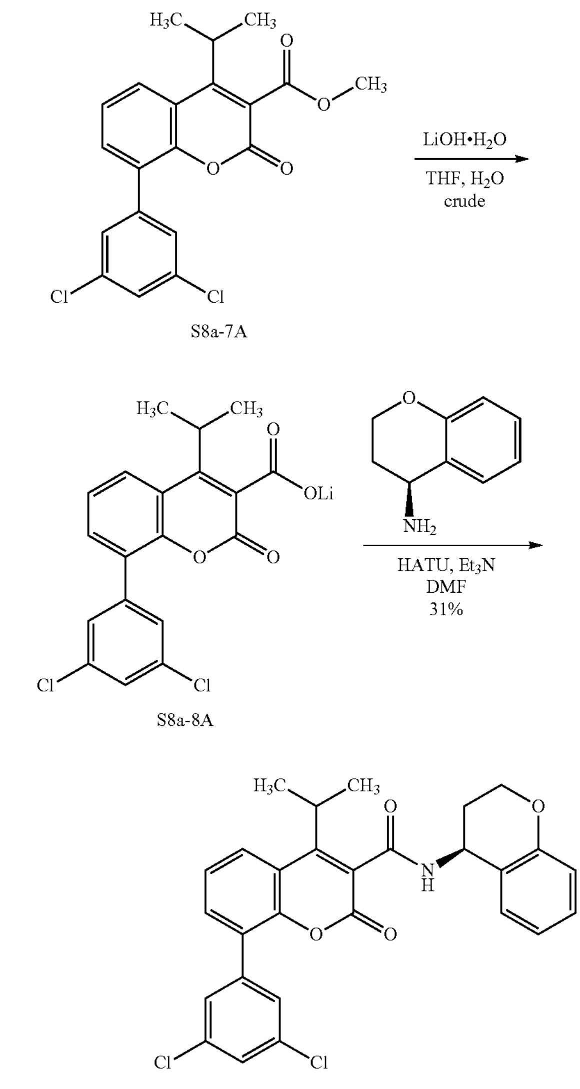
S8a-7A
S8a-8A
S8a-1
General Synthesis Scheme—10 (S8b): Example Compound S8b-1
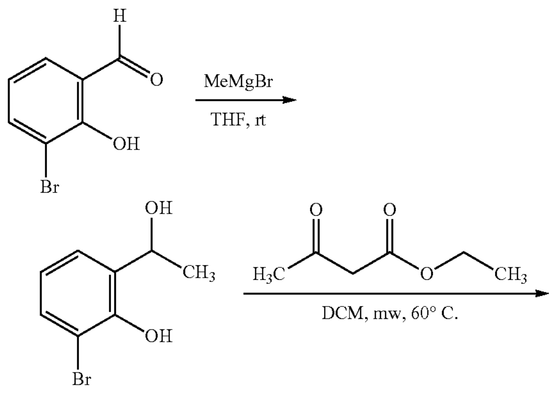
S8b-1A
-continued
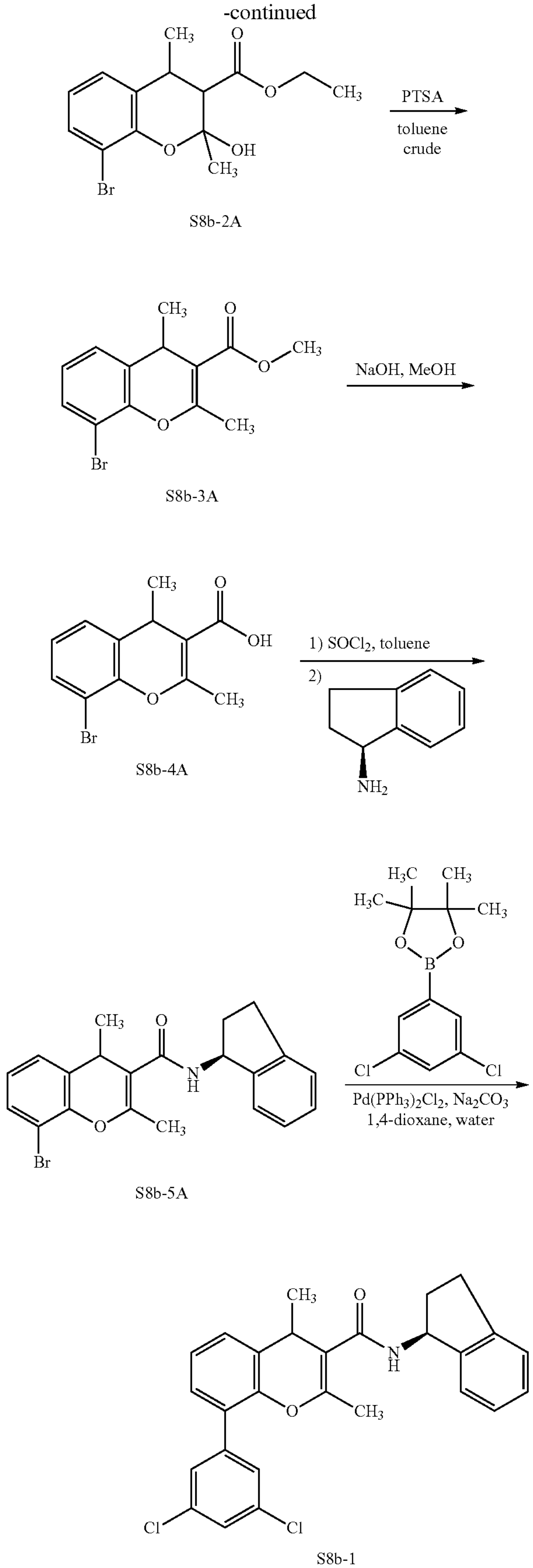
S8b-2A
S8b-3A
S8b-4A
S8b-5A
S8b-1

EXPERIMENTAL SECTION—EXAMPLES

Intermediates (S1)

Example S1-1A 1-(3-Bromo-2-fluorophenyl)-2-methylpropan-1-one

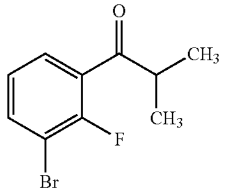

Diisopropylamine (740 mg, 7.31 mmol, 1.04 mL) was dissolved in tetrahydrofuran (2 mL). The solution was cooled with an ice bath. n-Butyllithium (2.5 M in hexanes; 7.31 mmol, 2.93 mL) was slowly added. After 30 min the mixture was cooled with a dry ice/acetone bath. A solution of 1-bromo-2-fluorobenzene (800 mg, 4.57 mmol) in tetrahydrofuran (8 mL) was slowly added. After 3 h N-methoxy-N-methylisobutyramide (600 mg, 4.57 mmol) was slowly added. After 40 min the dry ice/acetone bath was removed. Saturated aqueous ammonium chloride, water and diethyl ether were added. The organic layer was separated and the aqueous layer was extracted with diethyl ether. The combined organic layers were dried with sodium sulfate. The solvent was removed in vacuo to afford 852 mg (3.48 mmol, 76% of theory) of the title compound.

GC-MS (Method S): $R_t$=4.46 min; m/z=244/246 $M^+$

Example S1-1B

Ethyl 7-bromo-3-isopropyl-1-benzothiophene-2-carboxylate

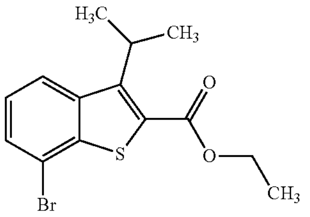 [SMILES: CCOC(=O)c1sc2c(Br)cccc2c1C(C)C]

Ethyl 2-mercaptoacetate (478 mg, 3.98 mmol, 0.44 mL) was added to a mixture of 1-(3-bromo-2-fluorophenyl)-2-methylpropan-1-one (848 mg, 3.46 mmol) and potassium carbonate (1435 mg, 10.38 mmol) in N,N-dimethylformamide (8 mL). The mixture was heated to 100° C. for 10 h and was allowed to cool to room temperature. Ethyl acetate and water were added. Hydrochloric acid (1 N) was added until an acidic pH-value was obtained. The organic phase was separated and the aqueous phase was extracted with ethyl acetate. The combined organic layers were washed with water and brine. After drying with sodium sulfate the solvent was removed in vacuo to afford 861 mg (2.63 mmol, 76% of theory) of the title compound.

LC-MS (Method 1): $R_t$=2.27 min; m/z=297/299 $(M-C2H5)^-$

Example S1-1C

7-Bromo-3-isopropyl-1-benzothiophene-2-carboxylic acid

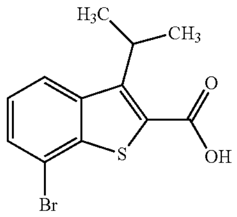 [SMILES: CC(C)c1c(C(=O)O)sc2c(Br)cccc12]

Ethyl 7-bromo-3-isopropyl-1-benzothiophene-2-carboxylate (861 mg, 2.63 mmol) was dissolved in tetrahydrofuran (8 mL). Aqueous lithium hydroxide monohydrate (1 N; 7.89 mmol, 7.89 mL) was added. After 20 h hydrochloric acid (1 N) was added until an acidic pH-value was obtained. Ethyl acetate was added. The organic phase was separated and the aqueous phase was extracted with ethyl acetate. The combined organic layers were dried with sodium sulfate. The solvent was removed in vacuo to afford 718 mg (2.40 mmol, 91% of theory) of the title compound.

LC-MS (Method 1): $R_t$=2.28 min; m/z=297/299 $(M-H)^-$

Example S1-1D

7-Bromo-N-[(4S)-3,4-dihydro-2H-chromen-4-yl]-3-isopropyl-1-benzothiophene-2-carboxamide

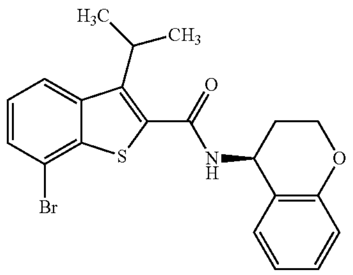 [SMILES: CC(C)c1c(C(=O)N[C@H]2CCOc3ccccc32)sc2c(Br)cccc12]

Triethylamine (729 mg, 7.20 mmol, 1.00 mL) was added to a mixture of 7-bromo-3-isopropylbenzo[b]thiophene-2-carboxylic acid (718 mg, 2.40 mmol) and (S)-chroman-4-amine hydrochloride (535 mg, 2.88 mmol) in dichloromethane (20 mL). Diethyl cyanophosphonate (783 mg, 4.80 mmol) was added. After 75 min the volatiles were removed in vacuo. Purification by flash column chromatography (Method 7; 80 g; heptane, 2%-20% ethyl acetate) afforded 442 mg (1.03 mmol, 42% of theory) of the title compound.

LC-MS (Method 1): $R_t$=2.32 min; m/z=430/432 $(M+H)^+$

Example S1-2A

Ethyl 3-amino-7-bromo-1-benzothiophene-2-carboxylate

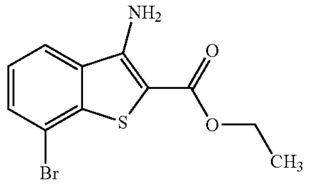 [SMILES: CCOC(=O)c1sc2c(Br)cccc2c1N]

Ethyl-2-mercaptoacetate (0.721 g, 6.00 mmol, 0.66 mL) was added to a mixture of 3-bromo-2-fluorobenzonitrile (1.000 g, 5.00 mmol) and potassium carbonate (2.073 g, 15.00 mmol) in dry N,N-dimethylformamide (4 mL). The reaction mixture was stirred at 100° C. for 16 h, was allowed to cool to room temperature and was concentrated in vacuo. Water (50 mL) was added until a precipitate formed. The solid was filtered off and dried on air. 1.470 g (4.90 mmol, 98% of theory) of the title compound were obtained.

LC-MS (Method 1): $R_t$=2.24 min; m/z=300/302 $(M+H)^+$

1H NMR (400 MHz, DMSO-d6) δ=8.21 (d, J=8.1 Hz, 1H), 7.78 (d, J=7.6 Hz, 1H), 7.39 (t, J=7.9 Hz, 1H), 7.24 (s, 2H), 4.28 (q, J=7.1 Hz, 2H), 1.30 (t, J=7.1 Hz, 3H).

Example S1-2B

Ethyl 7-bromo-3-(dimethylamino)-1-benzothiophene-2-carboxylate

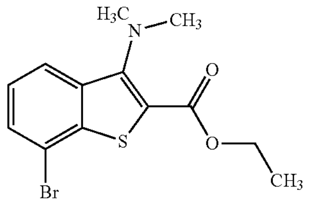

Decaborane (0.36 g, 2.94 mmol) was added to a solution of ethyl 3-amino-7-bromo-1-benzothiophene-2-carboxylate (1.47 g, 4.90 mmol) and paraformaldehyde (0.59 g, 19.59 mmol) in methanol (20 mL). The reaction mixture was stirred for 4 h. Decaborane (0.15 g, 1.23 mmol) was added. After 16 h the reaction mixture was concentrated in vacuo. Purification by flash column chromatography (Method 6; 80 g; heptane, 0%-50% ethyl acetate) afforded 1.05 g (3.20 mmol, 65% of theory) of the title compound.

LC-MS (Method 1): $R_t$=2.42 min; m/z=328/330 $(M+H)^+$

1H NMR (400 MHz, DMSO-d6) δ=8.05 (d, J=8.2 Hz, 1H), 7.78 (d, J=7.6 Hz, 1H), 7.40 (t, J=7.9 Hz, 1H), 4.29 (q, J=7.1 Hz, 2H), 3.08 (s, 6H), 1.32 (t, J=7.1 Hz, 3H).

Example S1-2C

7-Bromo-3-(dimethylamino)-1-benzothiophene-2-carboxylic acid

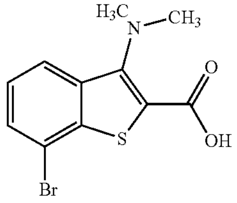

Lithium hydroxide monohydrate (0.81 g, 19.19 mmol) was added to a suspension of ethyl 7-bromo-3-(dimethylamino)-1-benzothiophene-2-carboxylate (1.05 g, 3.20 mmol) in a mixture of water (20 mL) and tetrahydrofuran (20 mL). The mixture was stirred at room temperature for 16 h. Lithium hydroxide monohydrate (0.81 g, 19.19 mmol) was added and the reaction mixture was stirred at room temperature for 1 h and at 70° C. for 16 h. The reaction mixture was allowed to cool to room temperature and was acidified with hydrochloric acid (2 M) until a precipitate formed. The solid was filtered off, washed with water and dried on air. 0.93 g (3.10 mmol, 97% of theory) of the title compound were obtained.

LC-MS (Method 1): $R_t$=1.78 min; m/z=300/302 $(M+H)^+$

1H NMR (400 MHz, DMSO-d6) δ=13.83 (s, 1H), 8.09 (d, J=8.1 Hz, 1H), 7.79 (d, J=7.6 Hz, 1H), 7.42 (t, J=7.9 Hz, 1H), 3.06 (s, 6H).

Example S1-2D

7-Bromo-N-[(4S)-3,4-dihydro-2H-chromen-4-yl]-3-(dimethylamino)-1-benzothiophene-2-carboxamide

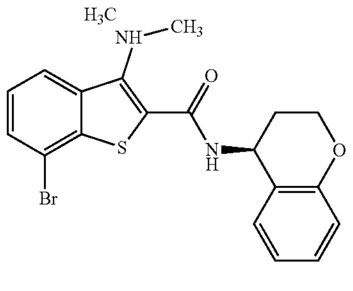

Diethyl cyanophosphonate (657 mg, 4.03 mmol, 0.6 mL) was added to a solution of 7-bromo-3-(dimethylamino)-1-benzothiophene-2-carboxylic acid (930 mg, 3.10 mmol), (S)-chroman-4-amine hydrochloride (690 mg, 3.72 mmol) and triethylamine (941 mg, 9.29 mmol, 1.3 mL) in dichloromethane (20 mL). The mixture was stirred at room temperature for 16 h. Purification by flash column chromatography (Method 6; 80 g; heptane, 0%-50% ethyl acetate) afforded 1080 mg (2.50 mmol, 81% of theory) of the title compound.

LC-MS (Method 1): $R_t$=2.36 min; m/z=431/433 $(M+H)^+$

1H NMR (400 MHz, DMSO-d6) δ=9.91 (d, J=8.0 Hz, 1H), 8.13 (d, J=8.1 Hz, 1H), 7.75 (d, J=7.6 Hz, 1H), 7.41 (t, J=7.9 Hz, 1H), 7.31 (d, J=7.4 Hz, 1H), 7.24-7.14 (m, 1H), 6.97-6.88 (m, 1H), 6.83 (d, J=8.2 Hz, 1H), 5.24 (q, J=6.7 Hz,

1H), 4.32 (ddd, J=10.7, 7.5, 2.9 Hz, 1H), 4.21 (ddd, J=11.0, 7.5, 3.0 Hz, 1H), 2.88 (s, 6H), 2.24 (ddt, J=13.1, 8.1, 3.9 Hz, 1H), 2.11 (dtd, J=14.0, 7.3, 3.0 Hz, 1H).

Example S1-3A

Methyl 3-amino-7-bromo-1-benzothiophene-2-carboxylate

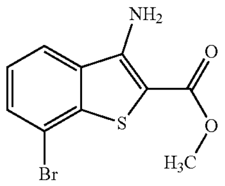

Methyl 2-mercaptoacetate (2.37 g, 22.33 mmol, 2.0 mL) was added to a mixture of 3-bromo-2-fluorobenzonitrile (3.72 g, 18.61 mmol) and potassium carbonate (7.71 g, 55.80 mmol) in N,N-dimethylformamide (20 mL). The reaction mixture was stirred at 100° C. for 16 h and was allowed to cool to room temperature. The mixture was poured out into water. The resulting precipitate was filtered off and dried on air to afford 5.16 g (18.02 mmol, 97% of theory) of the title compound.

LC-MS (Method 1): $R_t$=2.12 min; m/z=286/288 $(M+H)^+$

Example S1-3B

Methyl 7-bromo-3-chloro-1-benzothiophene-2-carboxylate

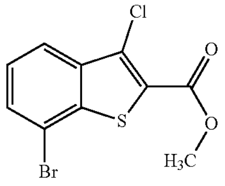

Copper(II) chloride (1.489 g, 11.07 mmol) was suspended in acetonitrile (100 mL). Isoamyl nitrite (1.621 g, 13.84 mmol, 1.86 mL) was added and the mixture was cooled with an ice bath. Methyl 3-amino-7-bromo-1-benzothiophene-2-carboxylate (2.640 g, 9.23 mmol) was added in portions. The mixture was allowed to warm to room temperature. After 16 h the volatiles were removed in vacuo. Water and diethyl ether were added to the residue. The mixture was filtered through a layer of Kieselguhr. The organic layer of the filtrate was separated and the aqueous layer was extracted with diethyl ether. The combined organic layers were dried with sodium sulfate and the solvent was removed in vacuo. The residue was suspended in dimethylsulfoxide. Solids were removed by filtration. The filtrate was purified by flash column chromatography (Method 5; 120 g). 0.569 g (1.86 mmol, 20% of theory) of the title compound were obtained.

LC-MS (Method 1): $R_t$=2.30 min; m/z=305/307 $(M+H)^+$

Example S1-3C

Methyl 7-bromo-3-methoxy-1-benzothiophene-2-carboxylate

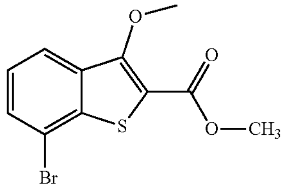 [SMILES: COC(=O)c1sc2c(Br)cccc2c1OC]

Sodium hydride (60% in mineral oil; 223 mg, 5.59 mmol) was suspended in dry tetrahydrofuran (4 mL). Methanol (179 mg, 5.59 mmol, 0.23 mL) was added. The reaction mixture was stirred for 30 min. A solution of methyl 7-bromo-3-chloro-1-benzothiophene-2-carboxylate (569 mg, 1.86 mmol) in dry tetrahydrofuran (5 mL) was added. After 20 h the mixture was added to hydrochloric acid (1 N). This mixture was extracted with ethyl acetate. The combined organic extracts were dried with sodium sulfate and the solvents were removed in vacuo. The residue was coated on hydromatrix. Purification by flash column chromatography (Method 7; 24 g; heptane, 5%-40% ethyl acetate containing 1% acetic acid) afforded 158 mg (0.53 mmol, 28% of theory) of the title compound.

LC-MS (Method 1): $R_t$=2.23 min; m/z=301/303 $(M+H)^+$

Example S1-3D

7-Bromo-3-methoxy-1-benzothiophene-2-carboxylic acid

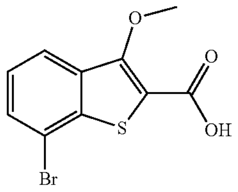

Aqueous lithium hydroxide monohydrate (1 N; 1.574 mmol, 1.574 mL) was added to a solution of methyl 7-bromo-3-methoxy-1-benzothiophene-2-carboxylate (158 mg, 0.525 mmol) in tetrahydrofuran (2 mL). The reaction mixture was stirred for 4 h and hydrochloric acid (1 N) was added until an acidic pH-value was obtained. Ethyl acetate and water were added. The organic phase was separated and the aqueous phase was extracted with ethyl acetate. The combined organic layers were dried with sodium sulfate and the solvent was removed in vacuo. 147 mg (0.512 mmol, 98% of theory) of the title compound were obtained.

LC-MS (Method 1): $R_t$=2.07 min; m/z=287/289 $(M+H)^+$

Example S1-3E

7-Bromo-N-[(4S)-3,4-dihydro-2H-chromen-4-yl]-3-methoxy-1-benzothiophene-2-carboxamide

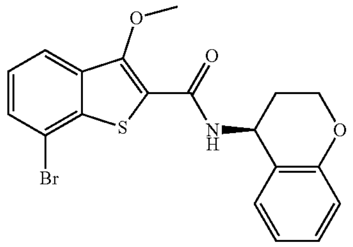 [SMILES: COc1c(C(=O)N[C@H]2CCOc3ccccc32)sc2c(Br)cccc12]

7-Bromo-3-methoxy-1-benzothiophene-2-carboxylic acid (295 mg, 1.03 mmol) was dissolved in dry N,N-dimethylformamide (3 mL). Triethylamine (260 mg, 2.57 mmol, 0.36 mL) and (1-[bis(dimethylamino)methylene]-1H-1,2,3-triazolo[4,5-b]pyridinium 3-oxid hexafluorophosphate) (391 mg, 1.03 mmol) were added. The reaction mixture was stirred for 30 min and (S)-chroman-4-amine hydrochloride (191 mg, 1.03 mmol) was added. Stirring was continued for 16 h. Ethyl acetate and water were added. The organic phase was separated and the aqueous phase was extracted with ethyl acetate. The combined organic layers were washed with water and dried with sodium sulfate. Solvents were removed in vacuo to afford 398 mg (0.951 mmol, 93% of theory) of the title compound.

LC-MS (Method 1): $R_t$=2.270 min; m/z=418/420 $(M+H)^+$

Example S1-4A

Ethyl 7-bromo-3-chlorobenzothiophene-2-carboxylate

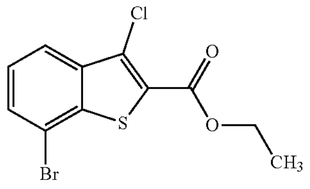 [SMILES: CCOC(=O)c1sc2c(Br)cccc2c1Cl]

Copper(II) chloride (1.114 g, 8.28 mmol) was suspended in acetonitrile (80 mL). Isoamyl nitrite (1.213 g, 10.35 mmol, 1.39 mL) was added and the mixture was cooled with an ice bath. Ethyl 3-amino-7-bromobenzothiophene-2-carboxylate (2.072 g, 6.90 mmol) was added in portions. The mixture was allowed to warm to room temperature. After 16 h diethyl ether and water were added. The organic layer was separated and the aqueous layer was extracted with diethyl ether. The combined organic layers were washed with brine and dried with sodium sulfate. Solvents were removed in vacuo. The residue was purified by flash column chromatography (Method 5; 120 g). 0.860 g (2.69 mmol, 39% of theory) of the title compound were obtained.

LC-MS (Method 1): $R_t$=2.41 min; m/z=319/321 $(M+H)^+$

Example S1-4B

7-Bromo-3-chloro-1-benzothiophene-2-carboxylic acid

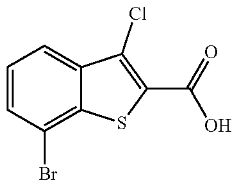 [SMILES: O=C(O)c1sc2c(Br)cccc2c1Cl]

At 0° C. aqueous lithium hydroxide monohydrate (1 N; 1.891 mmol, 1.891 mL) was added to a solution of ethyl 7-bromo-3-chlorobenzothiophene-2-carboxylate (403 mg, 1.261 mmol) in tetrahydrofuran (12 mL). After 0.5 h the reaction mixture was allowed to warm to room temperature. Stirring was continued for 64 h and hydrochloric acid (1 N) was added until an acidic pH-value was obtained. The formed precipitate was filtered off and dried on air to afford 351 mg (1.204 mmol, 95% of theory) of the title compound.

LC-MS (Method 1): $R_t$=2.23 min; m/z=245/247 $(M-COO—H)^-$

Example S1-4C

7-Bromo-3-chloro-N-[(4S)-3,4-dihydro-2H-chromen-4-yl]-1-benzothiophene-2-carboxamide

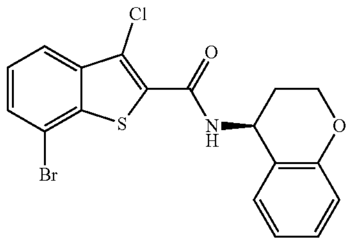 [SMILES: O=C(N[C@H]1CCOc2ccccc21)c1sc2c(Br)cccc2c1Cl]

Triethylamine (451 mg, 4.46 mmol, 0.62 mL) was added to a mixture of 7-bromo-3-chloro-1-benzothiophene-2-carboxylic acid (433 mg, 1.49 mmol) and (S)-chroman-4-amine hydrochloride (331 mg, 1.78 mmol) in dichloromethane (10 mL). To the resulting solution diethyl cyanophosphonate (242 mg, 1.49 mmol, 0.23 mL) was added. The reaction mixture was stirred for 16 h. Diethyl cyanophosphonate (242 mg, 1.49 mmol, 0.23 mL) was added. After 20 h the volatiles were removed in vacuo. The residue was purified by flash column chromatography (Method 7; 40 g; heptane, 2%-20% ethyl acetate). 254 mg (0.60 mmol, 40% of theory) of the title compound were obtained.

LC-MS (Method 1): $R_t$=2.33 min; m/z=422/424 $(M+H)^+$

Example S1-1F

Ethyl 3-chloroisonicotinate

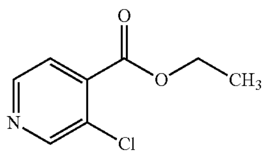

3-Chloroisonicotinic acid (5.00 g, 32 mmol) was suspended in ethanol (200 mL). Sulfuric acid (9.34 g, 95 mmol, 5.07 mL) was added and the mixture was stirred at reflux temperature for 64 h. Most of the solvent was removed in vacuo. The residue was partitioned between saturated aqueous sodium hydrogencarbonate (200 mL) and ethyl acetate (100 mL). The organic phase was separated and the aqueous phase was extracted with ethyl acetate (2×50 mL). The combined organic layers were dried with sodium sulfate and concentrated in vacuo to afford 5.15 g (28 mmol, 87% of theory) of the title compound.

LC-MS (Method 1): $R_t$=1.79 min; m/z=186 $(M+1)^+$

Example S1-2F

Ethyl 3-hydroxythieno[2,3-c]pyridine-2-carboxylate

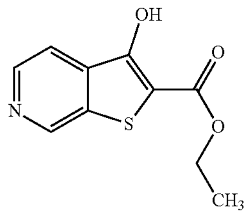

Ethyl 3-chloroisonicotinate (4.95 g, 27 mmol) was dissolved in N,N-dimethylformamide (50 mL). Ethyl 2-mercaptoacetate (6.40 g, 53 mmol, 5.84 mL) was added and the resulting mixture was cooled with an ice bath. Sodium hydride (2.66 g, 67 mmol; 60% in mineral oil) was added in portions and the resulting mixture was stirred under ice-bath cooling for 45 min. Stirring was continued at room temperature for 2.5 h. Water (500 mL) was added and the mixture was acidified to pH 3 with acetic acid. The resulting mixture was extracted with ethyl acetate (3×100 mL). The combined organic layers were washed with saturated aqueous sodium hydrogencarbonate (100 mL), water (3×100 mL) and brine. The organic layers were dried with sodium sulfate and the solvent was removed in vacuo. Purification by trituration in diisopropyl ether (100 mL) afforded 4.17 g (19 mmol, 70% of theory) of the title compound.

LC-MS (Method 1): $R_t$=1.65 min; m/z=224 $(M+1)^+$

1H NMR (400 MHz, Chloroform-d) δ 10.07 (s, 1H), 9.09 (s, 1H), 8.58 (d, J=5.4 Hz, 1H), 7.80 (dd, J=5.5, 0.9 Hz, 1H), 4.46 (q, J=7.1 Hz, 2H), 1.44 (t, J=7.1 Hz, 3H).

Example S1-3F

Ethyl 3-(((trifluoromethyl)sulfonyl)oxy)thieno[2,3-c]pyridine-2-carboxylate

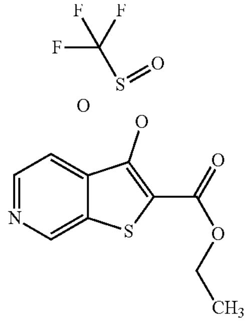

Under nitrogen atmosphere at room temperature to a stirred solution of ethyl 3-hydroxythieno[2,3-c]pyridine-2-carboxylate (1.00 g, 4.5 mmol) and N-phenyltrifluoromethane-sulfonimide (1.68 g, 4.7 mmol) in dichloromethane (20 mL) was added triethylamine (1.13 g, 11.2 mmol, 1.56 mL). The resulting mixture was stirred at room temperature for 16 h. N-phenyltrifluoromethanesulfonimide (0.40 g, 1.1 mmol) and triethylamine (0.23 mg, 2.2 mmol, 0.31 mL) were added and stirring was continued for 2 h. The reaction mixture was concentrated in vacuo. Purification by flash column chromatography (Method 6, 40 g; heptane, 5%-100% ethyl acetate) afforded 1.51 g (4.3 mmol, 95% of theory) of the title compound.

LC-MS (Method 1): $R_t$=2.13 min; m/z=356 $(M+1)^+$

1H NMR (400 MHz, Chloroform-d) δ 9.21 (d, J=0.9 Hz, 1H), 8.69 (d, J=5.7 Hz, 1H), 7.70 (d, J=5.7 Hz, 1H), 4.51 (q, J=7.1 Hz, 2H), 1.46 (t, J=7.1 Hz, 3H).

Example S1-4F

Ethyl 3-(dimethylamino)thieno[2,3-c]pyridine-2-carboxylate

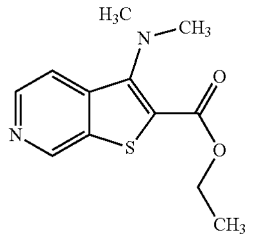

A mixture of ethyl 3-(((trifluoromethyl)sulfonyl)oxy)thieno[2,3-c]pyridine-2-carboxylate (0.50 g, 1.4 mmol), potassium carbonate (1.17 g, 8.4 mmol) and dimethylamine hydrochloride (0.34 g, 4.2 mmol) in N,N-dimethylformamide (5 mL) was stirred at 90° C. for 1 h. The reaction mixture was cooled to room temperature and was filtered. The filter cake was washed with ethyl acetate (2×10 mL). The filtrate was concentrated in vacuo. Purification by flash column chromatography (Method 6, 40 g; heptane, 5%-100% ethyl acetate) afforded 0.20 g (0.8 mmol, 56% of theory) of the title compound.

LC-MS (Method 1): $R_t$=1.73 min; m/z=251 $(M+1)^+$

1H NMR (400 MHz, Chloroform-d) δ 9.03 (d, J=1.0 Hz, 1H), 8.49 (d, J=5.7 Hz, 1H), 7.78 (dd, J=5.7, 1.1 Hz, 1H), 4.37 (q, J=7.1 Hz, 2H), 3.14 (s, 6H), 1.41 (t, J=7.1 Hz, 3H).

Example S1-5F

Ethyl 3-(dimethylamino)-7-iodothieno[2,3-c]pyridine-2-carboxylate

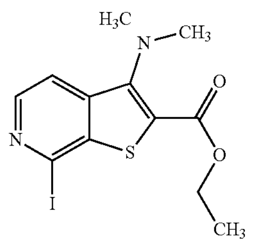

At −78° C. to a stirred solution of ethyl 3-(dimethylamino)thieno[2,3-c]pyridine-2-carboxylate (50 mg, 0.200 mmol) in tetrahydrofuran (1.00 mL) was added dropwise 2,2,6,6-tetramethyl-piperidinylmagnesium chloride lithium chloride complex (1 M; 0.80 mmol, 0.80 mL). The resulting solution was stirred for 15 min while warming up to room temperature. The solution was cooled back to −78° C. and a solution of iodine (253 mg, 1.00 mmol) in tetrahydrofuran (1.00 mL) was added. The resulting mixture was stirred at −78° C. for 15 min. The reaction mixture was quenched in aqueous sodium thiosulfate (1 M, 10 mL) and extracted with ethyl acetate (2×5 mL). The combined organic extracts were dried with sodium sulfate and concentrated in vacuo. Purification by flash column chromatography (Method 6, 40 g; heptane, 5%-50% ethyl acetate) afforded 23 mg (0.06 mmol, 30% of theory) of the title compound.

LC-MS (Method 1): $R_t$=2.25 min; m/z=377 $(M+1)^+$

1H NMR (400 MHz, Chloroform-d) δ 8.24 (d, J=5.5 Hz, 1H), 7.78 (d, J=5.5 Hz, 1H), 4.38 (q, J=7.1 Hz, 2H), 3.12 (s, 6H), 1.42 (t, J=7.1 Hz, 3H).

Example S1-6F

Ethyl 7-(2,3-dichlorophenyl)-3-(dimethylamino)thieno[2,3-c]pyridine-2-carboxylate

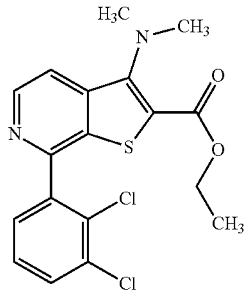

A stirred mixture of ethyl 3-(dimethylamino)-7-iodothieno[2,3-c]pyridine-2-carboxylate (40 mg, 0.11 mmol), sodium carbonate (23 mg, 0.21 mmol) in 1,4-dioxane (1.00 mL) and water (0.15 mL) was flushed with nitrogen. 1,1'-bis-(diphenylphosphino)-ferrocene) palladium dichloride (5 mg, 0.01 mmol) was added and the resulting mixture was stirred under nitrogen atmosphere at 60° C. for 8 h in a closed vial. After cooling to room temperate (2,3-dichlorophenyl)boronic acid (21 mg, 0.11 mmol) and sodium carbonate (11 mg, 0.11 mmol) were added. The resulting mixture was flushed with nitrogen. 1,1'-bis-(diphenylphosphino)-ferrocene) palladium dichloride (5 mg, 0.01 mmol) was added and the reaction mixture was stirred at 60° C. for 4 h under nitrogen in a closed vial. The reaction mixture was cooled to room temperature, was diluted with ethyl acetate (1 mL) and filtered. The filter cake was washed with ethyl acetate (1 mL). The filtrate was concentrated in vacuo. Purification by flash column chromatography (Method 6, 4 g; heptane, 5%-100% ethyl acetate) afforded 38 mg (0.10 mmol, 90% of theory) of the title compound.

LC-MS (Method 1): $R_t$=2.34 min; m/z=395/397 $(M+1)^+$

1H NMR (400 MHz, DMSO-d6) δ 8.64 (d, J=5.7 Hz, 1H), 8.05 (d, J=5.7 Hz, 1H), 7.86 (dd, J=6.3, 3.3 Hz, 1H), 7.63-7.49 (m, 2H), 4.25 (q, J=7.1 Hz, 2H), 3.13 (s, 6H), 1.26 (t, J=7.1 Hz, 3H).

Example S1-7F

Lithium 7-(2,3-dichlorophenyl)-3-(dimethylamino)thieno[2,3-c]pyridine-2-carboxylate

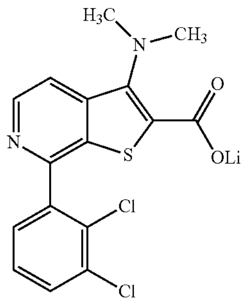

At room temperature to a stirred solution of ethyl 7-(2,3-dichlorophenyl)-3-(dimethylamino)thieno[2,3-c]pyridine-2-carboxylate (34 mg, 0.09 mmol) in tetrahydrofuran (0.20 mL) was added aqueous lithium hydroxide monohydrate (1 M; 0.13 mmol, 0.13 ml). The resulting mixture was stirred at 60° C. for 16 h. The reaction mixture was cooled to room temperature, diluted with brine (5 mL) and extracted with tetrahydrofuran (3×2 mL). Combined organic extracts were concentrated in vacuo to afford 23 mg (0.06 mmol, 71% of theory) of the title compound.

LC-MS (Method 1): $R_t$=1.81 min; m/z=365/367 $(M-H)^-$ [free acid]

Example S1-8F

Ethyl 3-methoxythieno[2,3-c]pyridine-2-carboxylate

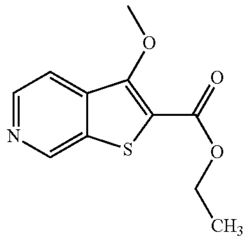 [SMILES: CCOC(=O)c1sc2cnccc2c1OC]

Ethyl 3-hydroxythieno[2,3-c]pyridine-2-carboxylate (2.00 g, 9.0 mmol) was dissolved in tetrahydrofuran (40 mL). To the resulting solution were added triphenylphosphine (2.82 g, 10.8 mmol) and methanol (0.32 mg, 9.9 mmol, 0.40 mL). A solution of di-tert-butylazodicarboxylate (2.48 g, 10.8 mmol) in tetrahydrofuran (10 mL) was slowly added under ice-bath cooling. Stirring was continued for 10 min under ice-bath cooling. The reaction was continued for 1.5 h while warming up to room temperature. The reaction mixture was concentrated in vacuo. Ethyl acetate (100 mL) and an aqueous sodium hydroxide (1 M; 100 mL) were added under stirring. The organic phase was separated and the aqueous phase was extracted with ethyl acetate (2×50 mL). The combined organic layers were washed with brine, dried with sodium sulfate and concentrated in vacuo. Purification by flash column chromatography (Method 6, 120 g; heptane, 7%-60% ethyl acetate) afforded 1.94 g (8.2 mmol, 91% of theory) of the title compound.

LC-MS (Method 1): $R_t$=1.66 min; m/z=238 $(M+1)^+$

Example S1-9F 2-(Ethoxycarbonyl)-3-methoxythieno[2,3-c]pyridine 6-oxide

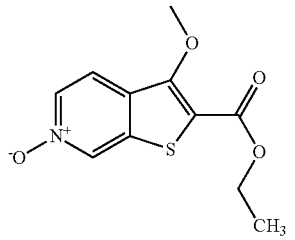

At 0° C. to a stirred solution of ethyl 3-methoxythieno[2,3-c]pyridine-2-carboxylate (200 mg, 0.84 mmol) in dichloromethane (5 mL) was added m-chloroperbenzoic acid (249 mg, 1.01 mmol; 70%). The resulting mixture was stirred for 16 h while warming up to room temperature. The reaction mixture was diluted with dichloromethane (20 mL), washed with saturated aqueous sodium hydrogencarbonate (2×10 mL), was dried with sodium sulfate and concentrated in vacuo to afford 180 mg (0.71 mmol, 84% of theory) of the title compound.

LC-MS (Method 1): $R_t$=1.62 min; m/z=254 $(M+1)^+$

Example S1-10F

Ethyl 7-bromo-3-methoxythieno[2,3-c]pyridine-2-carboxylate

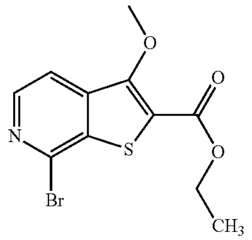 [SMILES: CCOC(=O)c1sc2c(Br)nccc2c1OC]

At 0° C. to a stirred solution of 2-(ethoxycarbonyl)-3-methoxythieno[2,3-c]pyridine 6-oxide (209 mg, 0.83 mmol) in dichloromethane (5 mL) was added phosphorus oxybromide (473 mg, 1.65 mmol) in one portion. The resulting mixture was stirred while warming up to room temperature for 16 h. The reaction mixture was slowly poured out into saturated aqueous sodium hydrogencarbonate (20 mL). After stirring for 15 min the layers were separated and the aqueous layer was extracted with dichloromethane (20 mL). Combined organic layers were dried with sodium sulfate and concentrated in vacuo. Purification by flash column chromatography (Method 6, 12 g; heptane, 5%-50% ethyl acetate) afforded 122 mg (0.39 mmol, 47% of theory) of the title compound.

LC-MS (Method 1): $R_t$=2.16 min; m/z=316/318 $(M+1)^+$

1H NMR (400 MHz, Chloroform-d) δ 8.32 (d, J=5.4 Hz, 1H), 7.72 (d, J=5.4 Hz, 1H), 4.43 (q, J=7.1 Hz, 2H), 4.18 (s, 3H), 1.44 (t, J=7.1 Hz, 3H).

Example S1-11F

7-Bromo-3-methoxythieno[2,3-c]pyridine-2-carboxylic acid

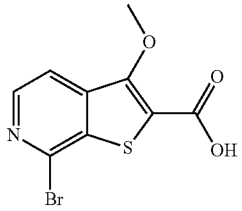

At room temperature to a stirred solution of ethyl 7-bromo-3-methoxythieno[2,3-c]pyridine-2-carboxylate (123 mg, 0.28 mmol) in tetrahydrofuran (3 mL) was added aqueous lithium hydroxide monohydrate (1 M; 0.59 mmol, 0.59 mL). The resulting mixture was stirred for 16 h. The reaction mixture was acidified with hydrochloric acid (1 M; 5 mL). The resulting precipitate was filtered off and dried on air to afford 104 mg (0.36 mmol, 93% of theory) of the title compound.

LC-MS (Method 1): $R_t$=1.90 min; m/z=288/290 $(M+1)^+$

1H NMR (400 MHz, DMSO-d6) δ 13.98 (s, 1H), 8.39 (d, J=5.4 Hz, 1H), 7.93 (d, J=5.4 Hz, 1H), 4.12 (s, 3H).

Example S1-12F

7-Bromo-N-[(4S)-3,4-dihydro-2H-chromen-4-yl]-3-methoxythieno[2,3-c]pyridine-2-carboxamide

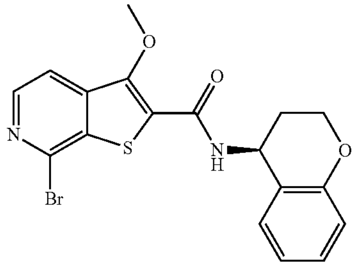 [SMILES: COc1c(C(=O)N[C@H]2CCOc3ccccc32)sc2c(Br)nccc12]

To a stirred suspension of 7-bromo-3-methoxythieno[2,3-c]pyridine-2-carboxylic acid (100 mg, 0.35 mmol) in N,N-dimethylformamide (2 mL) was added triethyl amine (105 mg, 1.04 mmol, 0.15 mL). To the resulting clear solution were added O-(7-azabenzotriazol-1-yl)-N,N,N',N'-tetramethyluronium hexafluorophosphate (139 mg, 0.36 mmol) and (S)-chroman-4-amine hydrochloride (71 mg, 0.38 mmol). The mixture was stirred room temperature in a closed vial for 72 h. The reaction mixture was concentrated in vacuo. The residue was partitioned between dichloromethane (2 mL) and water (3 mL). Layers were separated and the aqueous layer was extracted with dichloromethane (1 mL). Combined organic layers were purified by flash column chromatography (Method 6, 12 g; heptane, 5%-100% ethyl acetate) to afford 83 mg (0.20 mmol, 57% of theory) of the title compound.

LC-MS (Method 1): $R_t$=2.16 min; m/z=419/421 $(M+1)^+$

1H NMR (400 MHz, DMSO-d6) δ 8.55 (d, J=8.2 Hz, 1H), 8.38 (d, J=5.5 Hz, 1H), 8.02 (d, J=5.5 Hz, 1H), 7.27 (d, J=7.5

Hz, 1H), 7.23-7.15 (m, 1H), 6.95-6.88 (m, 1H), 6.82 (dd, J=8.2, 1.1 Hz, 1H), 5.29 (q, J=6.5 Hz, 1H), 4.27 (dd, J=6.3, 4.3 Hz, 2H), 4.12 (s, 3H), 2.22-2.14 (m, 2H).

Intermediates (S4)

Example S4-1G

Sodium 1-cyanoprop-1-en-2-olate

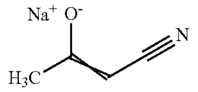

At 0° C. to a solution of sodium methoxide (5.4 M in methanol; 320 mmol, 59 mL) in dry methanol (250 mL) was dropwise added 5-methyl-isoxazole (25.5 g, 291 mmol, 25 mL). The resulting mixture was stirred at room temperature for 2 h. The solvents were removed in vacuo. The solid residue was triturated in diethylether for 30 min. The solid was filtered off and dried on air. 24.2 g (230 mmol, 79% of theory) of the title compound were obtained as a mixture of E/Z-isomers.

1H NMR (400 MHz, DMSO-d6) δ 3.12 (s, 0.5H), 2.92 (s, 0.5H), 1.70 (s, 1.5H), 1.48 (s, 1.5H).

Example S4-2G 1-(3,5-Dichlorophenyl)-3-methyl-1H-pyrazol-5-amine

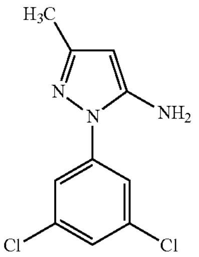

A mixture of sodium 1-cyanoprop-1-en-2-olate (0.98 g, 9.4 mmol) and 3,5-dichlorophenyl-hydrazine hydrochloride (2.00 g, 9.4 mmol) in ethanol (50 mL) was stirred at reflux for 16 h. The reaction mixture was cooled to room temperature and was concentrated in vacuo. The residue was poured out into water (200 mL). The precipitate was filtered off and dried on air. 1.56 g (6.44 mmol, 68% of theory) of the title compound were obtained.

LC-MS (Method 1): $R_t$=1.91 min; m/z=242/244 $(M+H)^+$

1H NMR (400 MHz, DMSO-d6) δ 7.67 (d, J=1.8 Hz, 2H), 7.47 (t, J=1.8 Hz, 1H), 5.54 (s, 2H), 5.37 (s, 1H), 2.06 (s, 3H).

Example S4-3G 1-(2,6-Difluorophenyl)-3-methyl-1H-pyrazol-5-amine

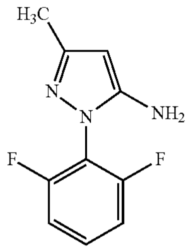

A mixture of sodium 1-cyanoprop-1-en-2-olate (1.4 g, 13.3 mmol) and 2,6-difluorophenyl-hydrazine hydrochloride (2.0 g, 11.1 mmol) in trifluoroacetic acid (20 mL) was stirred at 100° C. for 1 h. The volatiles were removed in vacuo and the residue was dissolved in ethyl acetate (50 mL). The solution was washed with saturated aqueous sodium carbonate and brine. The organic layer was dried with sodium sulfate and solvents were removed in vacuo. The crude product was coated on hydromatrix and purified by flash column chromatography (Method 6; 120 g; heptane, 0%-50% ethyl acetate). 1.97 g (9.4 mmol, 85% of theory) of the title compound were obtained.

LC-MS (Method 1): $R_t$=1.96 min; m/z=210 $(M+H)^+$

Example S4-4G 1-(3,5-Dichlorophenyl)-1H-pyrazol-5-amine

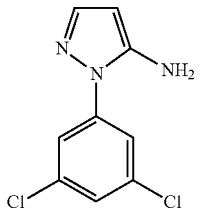 [SMILES: Nc1ccnn1-c1cc(Cl)cc(Cl)c1]

3-Methoxyacrylonitrile (0.93 g, 11.2 mmol, 0.94 mL) was added to a suspension of 3,5-dichlorophenylhydrazine hydrochloride (2.00 g, 9.4 mmol) in trifluoroacetic acid (50 mL). The reaction mixture was stirred at 100° C. for 1 h. The solvent was removed in vacuo and the residue was dissolved in ethyl acetate (50 mL). The solution was washed with saturated aqueous sodium carbonate. Layers were separated and the organic layer was washed with brine, dried with sodium sulfate and concentrated in vacuo. The crude product was coated on hydromatrix and purified by flash column chromatography (Method 6; 80 g; heptane, 0%-40% ethyl acetate). 1.60 g (4.98 mmol, 53% of theory; purity 71%) of the title compound were obtained.

LC-MS (Method 1): $R_t$=1.93 min; m/z=228/230 $(M+H)^+$

Example S4-5G 1-(2,6-Difluorophenyl)-1H-pyrazol-5-amine

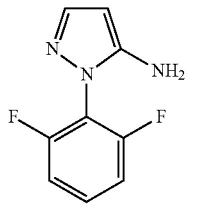 [SMILES: Nc1ccnn1-c1c(F)cccc1F]

3-Methoxyacrylonitrile (1.1 g, 13.3 mmol, 1.12 mL) was added to a suspension of 2,6-difluorophenyihydrazine hydrochloride (2.0 g, 11.1 mmol) in trifluoroacetic acid (50 mL). The reaction mixture was stirred at 100° C. for 1 h. The solvent was removed in vacuo and the residue was dissolved in ethyl acetate (50 mL). The solution was washed with saturated aqueous sodium carbonate. Layers were separated and the organic layer was washed with brine, dried with sodium sulfate and concentrated in vacuo. The crude product was purified by flash column chromatography (Method 6; 80 g; heptane, 0%-50% ethyl acetate) and (Method 6; 120 g; heptane, 0%-30% ethyl acetate). 1.1 g (5.4 mmol, 48% of theory) of the title compound were obtained LC-MS (Method 3): $R_t$=1.60 min; m/z=196 $(M+H)^+$ 1H NMR (400 MHz, DMSO-d6) δ 7.59 (tt, J=8.5, 6.4 Hz, 1H), 7.35-7.23 (m, 3H), 5.38 (d, J=1.8 Hz, 1H), 5.35 (s, 2H).

Example S4-6G

Diethyl 2-(((1-(3,5-dichlorophenyl)-3-methyl-1H-pyrazol-5-yl)amino)methylene)malonate

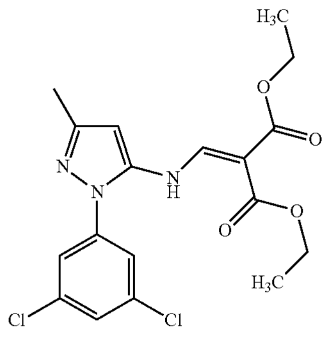 [SMILES: CCOC(=O)C(=CNc1cc(C)nn1-c1cc(Cl)cc(Cl)c1)C(=O)OCC]

Diethyl ethoxymethylenemalonate (2.29 g, 10.6 mmol, 2.1 mL) was added to a solution of 1-(3,5-dichlorophenyl)-3-methyl-1H-pyrazol-5-amine (1.28 g, 5.3 mmol) in ethanol (50 mL). The mixture was stirred at reflux for 16 h and was cooled to room temperature. A precipitate formed, was collected by filtration, washed with ethanol and dried on air. 1.32 g (3.2 mmol, 60% of theory) of the title compound were obtained.

LC-MS (Method 1): $R_t$=2.31 min; m/z=412/414 $(M+H)^+$

Example S4-7G

Diethyl 2-(((1-(2,6-difluorophenyl)-3-methyl-1H-pyrazol-5-yl)amino)methylene)malonate

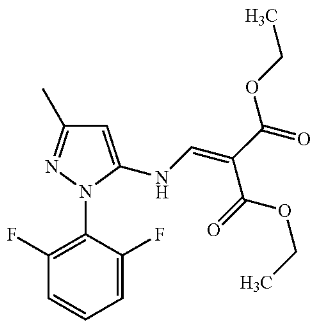 [SMILES: CCOC(=O)C(=CNc1cc(C)nn1-c1c(F)cccc1F)C(=O)OCC]

Diethyl ethoxymethylenemalonate (1.2 g, 5.7 mmol, 1.2 mL) was added to a solution of 1-(2,6-difluorophenyl)-3-methyl-1H-pyrazol-5-amine (1.0 g, 4.8 mmol) in ethanol (20 mL). The mixture was stirred at reflux for 16 h and was cooled to room temperature. Volatiles were removed in vacuo. The crude product was purified by flash column chromatography (Method 6; 80 g; heptane, 0%-50% ethyl acetate). 1.6 g (4.2 mmol, 88% of theory) of the title compound were obtained.

LC-MS (Method 1): $R_t$=2.17 min; m/z=380 $(M+H)^+$

1H NMR (400 MHz, DMSO-d6) δ 10.47 (d, J=13.0 Hz, 1H), 8.04 (d, J=13.0 Hz, 1H), 7.68 (ddd, J=14.8, 8.3, 6.6 Hz, 1H), 7.42 (t, J=8.5 Hz, 2H), 6.42 (s, 1H), 4.08 (p, J=6.9 Hz, 4H), 2.21 (s, 3H), 1.17 (dt, J=29.7, 7.1 Hz, 6H).

Example S4-8G

Diethyl 2-(((1-(3,5-dichlorophenyl)-1H-pyrazol-5-yl)amino)methylene)malonate

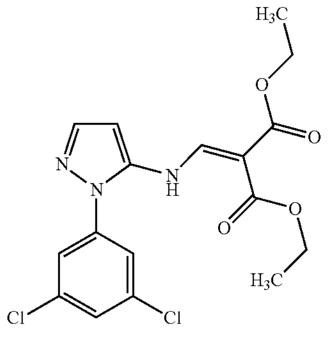 [SMILES: CCOC(=O)C(=CNc1ccnn1-c1cc(Cl)cc(Cl)c1)C(=O)OCC]

Diethyl ethoxymethylenemalonate (1.3 g, 6 mmol, 1.2 mL) was added to a solution of 1-(3,5-dichlorophenyl)-1H-pyrazol-5-amine (1.6 g, 5 mmol; purity 71%) in ethanol (20 mL). The mixture was stirred at reflux for three days and was cooled to room temperature. A precipitate formed, was filtered off, washed with cold ethanol and dried on air. 1.2 g (3 mmol, 60% of theory) of the title compound were obtained.

LC-MS (Method 1): $R_t$=2.25 min; m/z=398/400 $(M+H)^+$

1H NMR (400 MHz, DMSO-d6) δ 10.61 (d, J=11.6 Hz, 1H), 8.04 (d, J=12.7 Hz, 1H), 7.72 (s, 4H), 6.60 (s, 1H), 4.12 (dt, J=13.9, 7.1 Hz, 4H), 1.21 (t, J=7.1 Hz, 6H).

Example S4-9G

Diethyl 2-(((1-(2,6-difluorophenyl)-1H-pyrazol-5-yl)amino)methylene)malonate

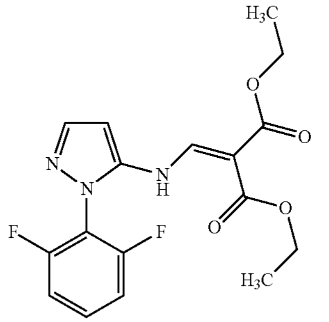 [SMILES: CCOC(=O)C(=CNc1ccnn1-c1c(F)cccc1F)C(=O)OCC]

Diethyl ethoxymethylenemalonate (1.4 g, 6.4 mmol, 1.3 mL) was added to a solution of 1-(2,6-difluorophenyl)-1H-pyrazol-5-amine (1.1 g, 5.4 mmol) in ethanol (20 mL). The mixture was stirred at reflux for 16 h and was cooled to room temperature. Volatiles were removed in vacuo. The crude product was purified by flash column chromatography (Method 6; 80 g; heptane, 0%-50% ethyl acetate). 1.7 g (4.7 mmol, 88% of theory) of the title compound were obtained.

LC-MS (Method 1): $R_t$=2.04 min; m/z=366 $(M+H)^+$

1H NMR (400 MHz, DMSO-d6) δ 10.51 (d, J=12.9 Hz, 1H), 8.07 (d, J=13.0 Hz, 1H), 7.78 (d, J=1.8 Hz, 1H), 7.71 (ddd, J=14.9, 8.5, 6.4 Hz, 1H), 7.45 (t, J=8.4 Hz, 2H), 6.68-6.53 (m, 1H), 4.09 (p, J=7.0 Hz, 4H), 1.18 (dt, J=28.7, 7.1 Hz, 6H).

Example S4-10G

Ethyl 4-chloro-1-(3,5-dichlorophenyl)-3-methyl-1H-pyrazolo[3,4-b]pyridine-5-carboxylate

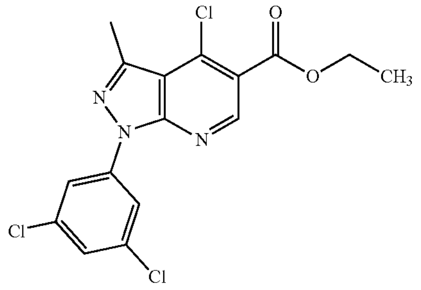 [SMILES: CCOC(=O)c1cnc2c(c(C)nn2-c2cc(Cl)cc(Cl)c2)c1Cl]

A solution of diethyl 2-(((1-(3,5-dichlorophenyl)-3-methyl-1H-pyrazol-5-yl)amino)methylene)malonate (1.1 g, 2.7 mmol) in phosphorus oxychloride (32.9 g, 215 mmol, 20 mL) was stirred at reflux for 16 h. Volatiles were removed in vacuo. The residue was poured out onto ice. The mixture was allowed to warm to room temperature and was extracted with ethyl acetate (2×50 mL). The combined organic layers were washed with brine and dried with sodium sulfate. Solvents were removed in vacuo. 0.9 g (2.3 mmol, 88% of theory) of the title compound were obtained.

LC-MS (Method 1): $R_t$=2.82 min; no mass was detected

1H NMR (400 MHz, DMSO-d6) δ 9.08 (s, 1H), 8.34 (d, J=1.9 Hz, 2H), 7.65 (t, J=1.8 Hz, 1H), 4.40 (q, J=7.1 Hz, 2H), 2.79 (s, 3H), 1.37 (t, J=7.1 Hz, 3H).

Example S4-11G

Ethyl 4-chloro-1-(2,6-difluorophenyl)-3-methyl-1H-pyrazolo[3,4-b]pyridine-5-carboxylate

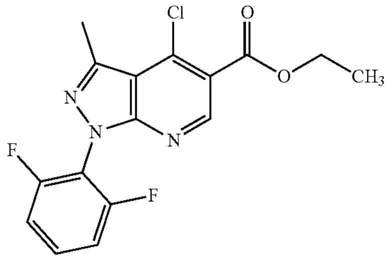 [SMILES: CCOC(=O)c1cnc2c(c(C)nn2-c2c(F)cccc2F)c1Cl]

A solution of diethyl 2-(((1-(2,6-difluorophenyl)-3-methyl-1H-pyrazol-5-yl)amino)methylene)malonate (1.6 g, 4.1 mmol) in phosphorus oxychloride (82.0 g, 536 mmol, 50 mL) was stirred at reflux for 16 h. Volatiles were removed in vacuo. The residue was dissolved in ethyl acetate (50 mL) and was washed with water (50 mL). The organic layer was washed with brine and dried with sodium sulfate. Solvents were removed in vacuo. 1.2 g (3.4 mmol, 82% of theory) of the title compound were obtained.

LC-MS (Method 1): $R_t$=2.23 min; m/z=352 $(M+H)^+$

1H NMR (400 MHz, DMSO-d6) δ 8.93 (s, 1H), 7.76 (tt, J=8.5, 6.4 Hz, 1H), 7.47 (t, J=8.4 Hz, 2H), 4.39 (q, J=7.1 Hz, 2H), 2.78 (s, 3H), 1.36 (t, J=7.1 Hz, 3H).

Example S4-12G

Ethyl 4-chloro-1-(3,5-dichlorophenyl)-1H-pyrazolo[3,4-b]pyridine-5-carboxylate

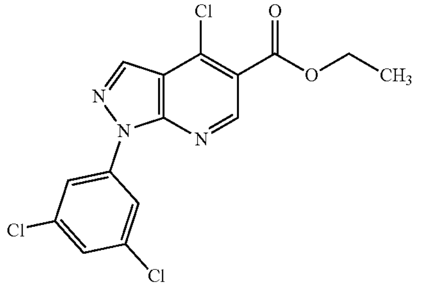 [SMILES: CCOC(=O)c1cnc2c(cnn2-c2cc(Cl)cc(Cl)c2)c1Cl]

A solution of diethyl 2-(((1-(3,5-dichlorophenyl)-1H-pyrazol-5-yl)amino)methylene)malonate (1.2 g, 3.01 mmol) in phosphorus oxychloride (82.0 g, 536 mmol, 50 mL) was stirred at reflux for 16 h. Volatiles were removed in vacuo. The residue was dissolved in ethyl acetate (50 mL) and was washed with water (50 mL). The organic layer was washed with brine and dried with sodium sulfate. Solvents were removed in vacuo. 1.1 g (2.97 mmol, 98% of theory) of the title compound were obtained.

LC-MS (Method 1): $R_t$=2.65 min; no mass detected

1H NMR (400 MHz, DMSO-d6) δ 9.16 (s, 1H), 8.83 (s, 1H), 8.36 (s, 2H), 7.70 (s, 1H), 4.42 (q, J=7.1 Hz, 2H), 1.38 (t, J=7.1 Hz, 3H).

Example S4-13G

Ethyl 4-chloro-1-(2,6-difluorophenyl)-1H-pyrazolo[3,4-b]pyridine-5-carboxylate

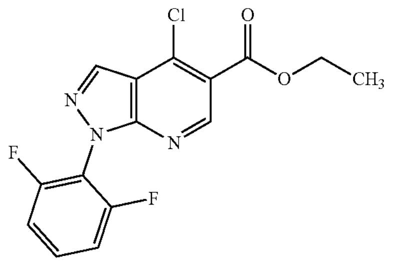 [SMILES: CCOC(=O)c1cnc2c(cnn2-c2c(F)cccc2F)c1Cl]

A solution of diethyl 2-(((1-(2,6-difluorophenyl)-1H-pyrazol-5-yl)amino)methylene)malonate (1.7 g, 4.7 mmol) in phosphorus oxychloride (82.0 g, 536 mmol, 50 mL) was stirred at reflux for 16 h. Volatiles were removed in vacuo. The residue was dissolved in ethyl acetate (50 mL) and was washed with water (50 mL). The organic layer was washed with brine and dried with sodium sulfate. Solvents were removed in vacuo. 1.4 g (4.0 mmol, 85% of theory) of the title compound were obtained.

LC-MS (Method 1): $R_t$=2.18 min; m/z=338 $(M+H)^+$

1H NMR (400 MHz, DMSO-d6) δ 9.02 (s, 1H), 8.85 (s, 1H), 7.79 (ddd, J=15.0, 8.6, 6.4 Hz, 1H), 7.50 (t, J=8.4 Hz, 2H), 4.41 (d, J=7.1 Hz, 2H), 1.37 (t, J=7.1 Hz, 3H).

Example S4-14G

4-Chloro-1-(3,5-dichlorophenyl)-3-methyl-1H-pyrazolo[3,4-b]pyridine-5-carboxylic acid

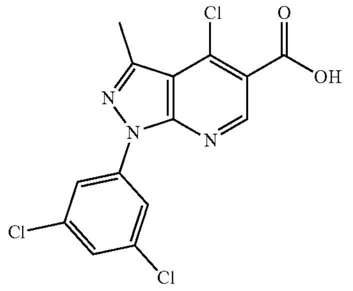

To a suspension of ethyl 4-chloro-1-(3,5-dichlorophenyl)-3-methyl-1H-pyrazolo[3,4-b]pyridine-5-carboxylate (700 mg, 1.82 mmol) in a mixture of tetrahydrofuran (20 mL) and water (20 mL) was added lithium hydroxide monohydrate (458 mg, 10.92 mmol). The mixture was stirred for 16 h at room temperature. Hydrochloric acid (2 M) was added until a white precipitate formed. The solid was filtered off, washed with water and dried on air. 636 mg (1.78 mmol, 98% of theory) of the title compound were obtained.

LC-MS (Method 1): $R_t$=2.77 min; m/z=354/356 $(M-H)^-$

1H NMR (400 MHz, DMSO-d6) δ 13.83 (s, 1H), 9.05 (s, 1H), 8.31 (d, J=1.8 Hz, 2H), 7.61 (t, J=1.8 Hz, 1H), 2.77 (s, 3H).

Example S4-15G

4-Chloro-1-(2,6-difluorophenyl)-3-methyl-1H-pyrazolo[3,4-b]pyridine-5-carboxylic acid

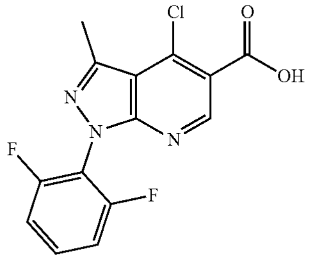 [SMILES: Cc1nn(-c2c(F)cccc2F)c2ncc(C(=O)O)c(Cl)c12]

To a suspension of ethyl 4-chloro-1-(2,6-difluorophenyl)-3-methyl-1H-pyrazolo[3,4-b]pyridine-5-carboxylate (1.20 g, 3.4 mmol) in a mixture of tetrahydrofuran (20 mL) and water (20 mL) was added lithium hydroxide monohydrate (0.86 g, 20.5 mmol). The mixture was stirred for 16 h at room temperature and was concentrated in vacuo. The aqueous residue was acidified by the addition of hydrochloric acid (1 M) until a white precipitate formed. The solid was filtered off, washed with water and dried on air. 1.06 g (3.2 mmol, 96% of theory) of the title compound were obtained.

LC-MS (Method 1): $R_t$=2.04 min; m/z=324 $(M+H)^+$

1H NMR (400 MHz, DMSO-d6) δ 13.77 (s, 1H), 8.94 (s, 1H), 7.81-7.70 (m, 1H), 7.47 (t, J=8.3 Hz, 2H), 2.78 (s, 3H).

Example S4-16G

4-Chloro-1-(3,5-dichlorophenyl)-1H-pyrazolo[3,4-b]pyridine-5-carboxylic acid

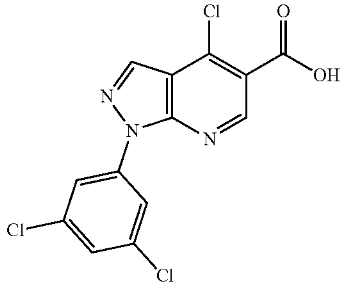 [SMILES: O=C(O)c1cnc2c(cnn2-c2cc(Cl)cc(Cl)c2)c1Cl]

To a suspension of ethyl 4-chloro-1-(3,5-dichlorophenyl)-1H-pyrazolo[3,4-b]pyridine-5-carboxylate (1.10 g, 3.0 mmol) in a mixture of tetrahydrofuran (20 mL) and water (20 mL) was added lithium hydroxide monohydrate (0.75 g, 17.8 mmol). The mixture was stirred for 16 h at room temperature and was concentrated in vacuo. The aqueous residue was acidified by the addition of hydrochloric acid (1 M) until a white precipitate formed. The solid was filtered off, washed with water and dried on air. 0.87 g (2.5 mmol, 86% of theory) of the title compound were obtained.

LC-MS (Method 1): $R_t$=2.58 min; m/z=340/342 $(M-H)^-$

1H NMR (400 MHz, DMSO-d6) δ 13.89 (s, 1H), 9.15 (s, 1H), 8.79 (s, 1H), 8.36 (d, J=1.8 Hz, 2H), 7.69 (s, 1H).

Example S4-17G

4-Chloro-1-(2,6-difluorophenyl)-1H-pyrazolo[3,4-b]pyridine-5-carboxylic acid

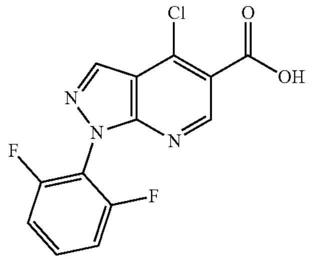 [SMILES: O=C(O)c1cnc2c(cnn2-c2c(F)cccc2F)c1Cl]

To a solution of ethyl 4-chloro-1-(2,6-difluorophenyl)-1H-pyrazolo[3,4-b]pyridine-5-carboxylate (1.35 g, 4.0 mmol) in a mixture of tetrahydrofuran (20 mL) and water (20 mL) was added lithium hydroxide monohydrate (1.00 g, 24.0 mmol). The mixture was stirred for 16 h at room temperature. Hydrochloric acid (1 M) was added until a white precipitate formed. The solid was filtered off, washed with water and dried on air. 0.97 g (3.1 mmol, 78% of theory) of the title compound were obtained.

LC-MS (Method 1): $R_t$=2.02 min; m/z=310 $(M+H)^+$

1H NMR (400 MHz, DMSO-d6) δ 13.86 (s, 1H), 9.03 (s, 1H), 8.83 (s, 1H), 7.78 (ddd, J=14.9, 8.5, 6.4 Hz, 1H), 7.50 (t, J=8.4 Hz, 2H).

Example S4-18G 1-(3,5-Dichlorophenyl)-4-(dimethylamino)-3-methyl-1H-pyrazolo[3,4-b]pyridine-5-carboxylic acid

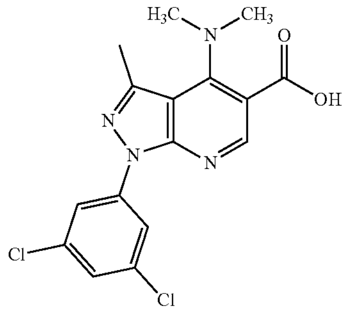 [SMILES: Cc1nn(-c2cc(Cl)cc(Cl)c2)c2ncc(C(=O)O)c(N(C)C)c12]

A suspension of 4-chloro-1-(3,5-dichlorophenyl)-3-methyl-1H-pyrazolo[3,4-b]pyridine-5-carboxylic acid (0.20 g, 0.56 mmol) in a solution of dimethylamine in tetrahydrofuran (2.0 M; 1.78 g, 4.00 mmol, 2.0 mL) was stirred at 80° C. for 16 h. The reaction mixture was cooled to room temperature and hydrochloric acid (1 M) was added until a white precipitate formed. The solid was filtered off, washed with water and dried on air. 0.20 g (0.54 mmol, 98% of theory) of the title compound were obtained.

LC-MS (Method 1): $R_t$=2.51 min; m/z=365/367 $(M+H)^+$

1H NMR (400 MHz, DMSO-d6) δ 8.36 (d, J=21.0 Hz, 3H), 7.46 (s, 1H), 3.01 (s, 6H), 2.64 (s, 3H) [acidic proton was not detected].

Example S4-19G 1-(2,6-Difluorophenyl)-4-(dimethylamino)-3-methyl-1H-pyrazolo[3,4-b]pyridine-5-carboxylic acid

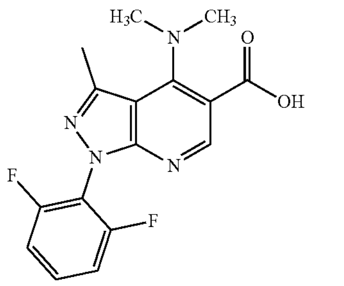 [SMILES: Cc1nn(-c2c(F)cccc2F)c2ncc(C(=O)O)c(N(C)C)c12]

A solution of 4-chloro-1-(2,6-difluorophenyl)-3-methyl-1H-pyrazolo[3,4-b]pyridine-5-carboxylic acid (0.20 g, 0.62 mmol) in a solution of dimethylamine in tetrahydrofuran (2.0 M; 1.78 g, 4.00 mmol, 2.0 mL) was stirred at 80° C. for 1 h. The reaction mixture was cooled to room temperature and hydrochloric acid (1 M) was added until a white precipitate formed. The solid was filtered off, washed with water and dried on air. 0.14 g (0.43 mmol, 70% of theory) of the title compound were obtained.

LC-MS (Method 1): $R_t$=1.93 min; m/z=333 $(M+H)^+$

Example S4-20G 1-(3,5-Dichlorophenyl)-4-(dimethylamino)-1H-pyrazolo[3,4-b]pyridine-5-carboxylic acid

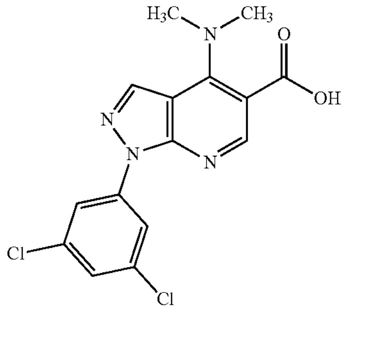 [SMILES: CN(C)c1c(C(=O)O)cnc2c1cnn2-c1cc(Cl)cc(Cl)c1]

A suspension of 4-chloro-1-(3,5-dichlorophenyl)-1H-pyrazolo[3,4-b]pyridine-5-carboxylic acid (0.20 g, 0.58 mmol) in a solution of dimethylamine in tetrahydrofuran (2.0 M; 1.78 g, 4.00 mmol, 2.0 mL) was stirred at 80° C. for 1 h. The reaction mixture was cooled to room temperature and hydrochloric acid (1 M) was added until a white precipitate formed. The solid was filtered off, washed with water and dried on air. 0.17 g (0.48 mmol, 83% of theory) of the title compound were obtained.

LC-MS (Method 1): $R_t$=2.23 min; m/z=351/353 $(M+H)^+$

1H NMR (400 MHz, DMSO-d6) δ 12.83 (s, 1H), 8.66 (s, 1H), 8.58 (s, 1H), 8.42 (d, J=1.8 Hz, 2H), 7.58 (s, 1H), 3.25 (s, 6H).

Example S4-21G 1-(2,6-Difluorophenyl)-4-(dimethylamino)-1H-pyrazolo[3,4-b]pyridine-5-carboxylic acid

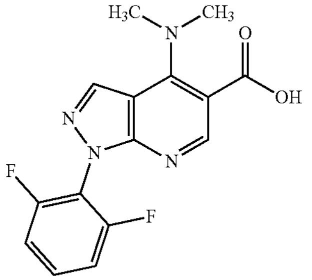 [SMILES: CN(C)c1c(C(=O)O)cnc2c1cnn2-c1c(F)cccc1F]

A solution of 4-chloro-1-(2,6-difluorophenyl)-1H-pyrazolo[3,4-b]pyridine-5-carboxylic acid (0.20 g, 0.65 mmol) in a solution of dimethylamine in tetrahydrofuran (2.0 M; 1.78 g, 4.00 mmol, 2.0 mL) was stirred at 80° C. for 1 h. The reaction mixture was cooled to room temperature and hydrochloric acid (1 M) was added until a white precipitate formed. The solid was filtered off, washed with water and dried on air. 0.12 g (0.37 mmol, 57% of theory) of the title compound were obtained.

LC-MS (Method 1): $R_t$=1.71 min; m/z=319 $(M+H)^+$

Intermediates (S8)

Example S8a-1A

2-Acetoxy-3-bromobenzoic acid

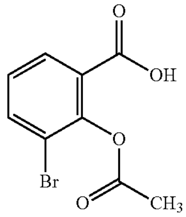

A mixture of 3-bromo-2-hydroxybenzoic acid (10 g, 46 mmol) and phosphoric acid (0.2 mL, 4 mmol) in acetic anhydride (50.0 mL, 530 mmol) was stirred at 50° C. for 18 h. The reaction mixture was cooled to room temperature and water (120 mL) was added. The resulting mixture was stirred at 50° C. for 1 h and was cooled in an ice-water bath. Solids were filtered off. The filtrate was again stirred at 50° C. for 1 h. A clear solution was obtained. After cooling in an ice-water bath, a precipitate formed. The precipitate was filtered off, washed with water and dried on air. 8 g (31 mmol; 68% of theory) of the title compound were obtained.

LC-MS (Method 1): $R_t$=1.80 min; m/z=257/259 $(M-H)^-$.

1H NMR (400 MHz, Chloroform-d) δ 10.65 (s, 1H), 8.06 (m, 1H), 7.86 (m, 1H), 7.29-7.19 (m, 1H), 2.40 (s, 3H).

Example S8a-2A

Methyl 8-bromo-4-hydroxy-2-oxo-2H-chromene-3-carboxylate

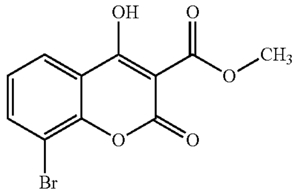 [SMILES: COC(=O)c1c(O)c2cccc(Br)c2oc1=O]

At 0° C. to a solution of 2-acetoxy-3-bromobenzoic acid (8.1 g, 31.3 mmol) and 1-hydroxy-benzotriazole hydrate (4.8 g, 31.3 mmol) in tetrahydrofuran (120 mL) was added N,N'-dicyclohexylcarbodiimide (6.5 g, 31.7 mmol). After stirring for 5 min a suspension was obtained. The reaction mixture was stored at 5° C. for 20 h. Solids were filtered off and the filtrate was used in the subsequent step (see below).

To a stirring solution of dimethyl malonate (3.6 mL, 31.3 mmol) in tetrahydrofuran (240 mL) was added sodium hydride (60% in mineral oil; 2.6 g, 65.7 mmol). The filtrate obtained from the preceding step (see above) was added. After 2 h, the reaction mixture was concentrated in vacuo. A mixture of hydrochloric acid (10% (v/v); 120 mL, 390 mmol) and methanol (120 mL) was added to the residue. The mixture was stirred for four days. The precipitate was filtered off, washed with methanol (120 mL) and dried on air. 3.6 g (12.3 mmol; 39% of theory) of the title compound were obtained.

LC-MS (Method 1): $R_t$=1.92 min; m/z=299/301 $(M+H)^+$

1H NMR (400 MHz, Chloroform-d) δ 14.66 (s, 1H), 7.99 (m, 1H), 7.91 (m, 1H), 7.23 (t, J=7.9 Hz, 1H), 4.05 (s, 3H).

Example S8a-3A (S)-8-Bromo-N-(chroman-4-yl)-4-hydroxy-2-oxo-2H-chromene-3-carboxamide

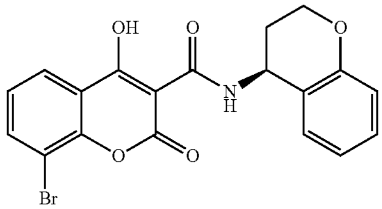 [SMILES: O=C(N[C@H]1CCOc2ccccc21)c1c(O)c2cccc(Br)c2oc1=O]

A mixture of (S)-chroman-4-amine hydrochloride (0.248 g, 1.337 mmol) and sodium methoxide (0.072 g, 1.337 mmol) in methanol (3 mL) was stirred for 1 h. Volatiles were removed in vacuo. A mixture of methyl 8-bromo-4-hydroxy-2-oxo-2H-chromene-3-carboxylate (0.100 g, 0.334 mmol) in tetrahydrofuran (3 mL) was added and the suspension was stirred at 60° C. for 72 h. The reaction mixture was allowed to cool to room temperature. Volatiles were removed in vacuo. The residue was triturated in methanol. The solid was filtered off, washed with methanol and was dried on air. 0.068 g of the title compound were obtained. The filtrate was concentrated in vacuo. The residue was triturated in diisopropyl ether. The solid was filtered off, washed with diisopropyl ether and water and was dried on air. 0.077 g of the title compound were obtained. In total 0.145 g (0.317 mmol; 94% of theory) of the title compound with a purity of >90% according to LC-MS were obtained.

LC-MS (Method 1): $R_t$=2.32 min; m/z=414/416 $(M-H)^-$

1H NMR (400 MHz, DMSO-d6) δ 9.46 (s, 1H), 8.10 (d, J=7.5 Hz, 1H), 8.00 (d, J=7.6 Hz, 1H), 7.39 (t, J=7.8 Hz, 1H), 7.24 (dd, J=20.5, 7.5 Hz, 2H), 6.92 (t, J=7.3 Hz, 1H), 6.84 (d, J=8.1 Hz, 1H), 5.30 (d, J=6.3 Hz, 1H), 4.29 (d, J=7.3 Hz, 1H), 4.20 (d, J=7.5 Hz, 1H), 2.29-2.11 (m, 2H). [signal for OH is not detected]

Example S8a-4A

Methyl 8-bromo-4-chloro-2-oxo-2H-chromene-3-carboxylate

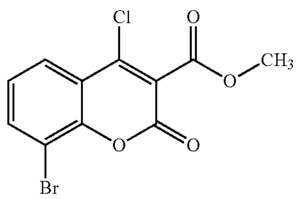 [SMILES: COC(=O)c1c(Cl)c2cccc(Br)c2oc1=O]

A mixture of methyl 8-bromo-4-hydroxy-2-oxo-2H-chromene-3-carboxylate (3.64 g, 12.17 mmol), N,N-diisopropylethylamine (2.1 mL, 12.17 mmol) and phosphorus oxychloride (12.48 mL, 134 mmol) was stirred at 110° C. for 1.5 h The reaction mixture was concentrated in vacuo, aerated with argon and was used as such in the next step.

Example S8a-5A

Methyl 8-bromo-4-(dimethylamino)-2-oxo-2H-chromene-3-carboxylate

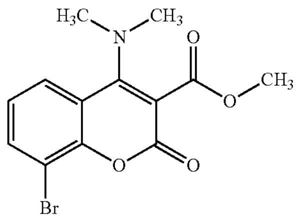 [SMILES: COC(=O)c1c(N(C)C)c2cccc(Br)c2oc1=O]

Under argon atmosphere, to a solution of crude methyl 8-bromo-4-chloro-2-oxo-2H-chromene-3-carboxylate (3.86 g, 12.2 mmol) in dry tetrahydrofuran (25 mL) were added triethylamine (5.1 mL, 36.5 mmol) and dimethylamine (2 M in tetrahydrofuran; 30.4 mL, 60.9 mmol). The resulting suspension was stirred at room temperature for 1 h. Solids were filtered off. The filtrate was concentrated in vacuo. The residue was dissolved in ethyl acetate (120 mL). The solution was washed with water (2×100 mL) and brine (50 mL), was dried with sodium sulfate and concentrated in vacuo. 3.85 g (11.6 mmol; 96% of theory over two steps) of the title compound were obtained.

LC-MS (Method 1): $R_t$=1.84 min; m/z=326/328 $(M+H)^+$

1H NMR (400 MHz, Chloroform-d) δ 7.76 (dd, J=7.8, 1.2 Hz, 1H), 7.70 (dd, J=8.2, 1.2 Hz, 1H), 7.14 (t, J=8.0 Hz, 1H), 3.95 (s, 3H), 3.08 (s, 6H).

Example S8a-6A

Methyl 8-bromo-4-isopropyl-2-oxo-2H-chromene-3-carboxylate

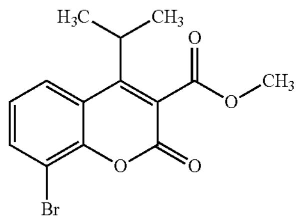 [SMILES: COC(=O)c1c(C(C)C)c2cccc(Br)c2oc1=O]

Under nitrogen atmosphere at 0° C., isopropylmagnesium bromide (1 M in tetrahydrofuran; 3.2 mL, 3.24 mmol) was added dropwise to a solution of methyl 8-bromo-4-(dimethylamino)-2-oxo-2H-chromene-3-carboxylate (0.96 g, 2.94 mmol) in dry tetrahydrofuran (50 mL). The reaction mixture was stirred at 0° C. for 30 min. Aqueous saturated ammonium chloride (30 mL) and brine (30 mL) were added. The mixture was allowed to warm to room temperature. Layers were separated. Aqueous layer was extracted with ethyl acetate (30 mL). Combined organic layers were dried with sodium sulfate. Solvents were removed in vacuo. Purification by flash column chromatography (Method 6; 40 g; heptane, 3%-25% ethyl acetate) afforded 0.38 g (1.12 mmol; 38% of theory) of the title compound.

LC-MS (Method 1): $R_t$=2.06 min; m/z=325/327 $(M+H)^+$

1H NMR (400 MHz, Chloroform-d) δ 7.81 (t, J=8.7 Hz, 2H), 7.20 (t, J=8.0 Hz, 1H), 3.95 (s, 3H), 3.43-3.23 (m, 1H), 1.44 (d, J=7.1 Hz, 6H).

Example S8a-7A

Methyl 8-(3,5-dichlorophenyl)-4-isopropyl-2-oxo-2H-chromene-3-carboxylate

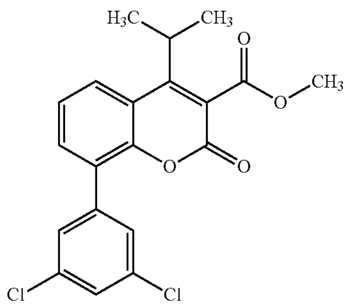 [SMILES: COC(=O)c1c(C(C)C)c2cccc(-c3cc(Cl)cc(Cl)c3)c2oc1=O]

A mixture of methyl 8-bromo-4-isopropyl-2-oxo-2H-chromene-3-carboxylate (330 mg, 1.02 mmol), (3,5-dichlorophenyl)boronic acid (194 mg, 1.02 mmol) and sodium carbonate (323 mg, 3.04 mmol) in a mixture of 1,4-dioxane (9.0 mL) and water (1.5 mL) was purged with argon. 1,1'-Bis(diphenylphosphino)ferrocenepalladium(II) dichloride (74 mg, 0.10 mmol) was added. The reaction mixture was stirred at 100° C. for 1.5 h and was allowed to cool to room temperature. The reaction mixture was combined with crude material obtained from the same reaction starting from 50 mg (0.15 mmol) of methyl 8-bromo-4-isopropyl-2-oxo-2H-chromene-3-carboxylate. The resulting mixture was diluted with dichloromethane (20 mL). The layers were separated via a phase separator. The organic layer was concentrated in vacuo. Purification by flash column chromatography (Method 6; 24 g; heptane; 2%-20% ethyl acetate) afforded 31 mg (0.79 mmol; 68% of theory based on 1.17 mmol) of the title compound.

LC-MS (Method 1): $R_t$=2.33 min; m/z=391/393 $(M+H)^+$

1H NMR (400 MHz, Chloroform-d) δ 7.91 (dd, J=8.3, 1.6 Hz, 1H), 7.53 (dd, J=7.6, 1.5 Hz, 1H), 7.40 (d, J=6.4 Hz, 4H), 3.95 (s, 3H), 3.38 (p, J=7.2 Hz, 1H), 1.48 (d, J=7.1 Hz, 6H).

Example S8a-8A

Lithium 8-(3,5-dichlorophenyl)-4-isopropyl-2-oxo-2H-chromene-3-carboxylate

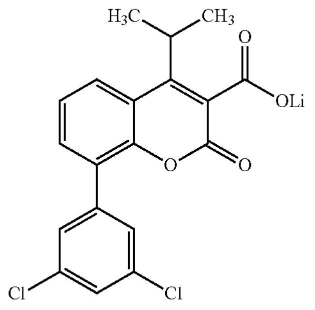

To a solution of methyl 8-(3,5-dichlorophenyl)-4-isopropyl-2-oxo-2H-chromene-3-carboxylate (310 mg, 0.792 mmol) in a mixture of tetrahydrofuran (5 mL) and water (5 mL) was added lithium hydroxide monohydrate (100 mg, 2.377 mmol). The reaction mixture was stirred at room temperature for 25 min and was concentrated in vacuo. The crude product was used as such.

LC-MS (Method 1): $R_t$=2.19 min; m/z=377/379 $(M+H)^+$ [free acid]

(Target) Example Compounds (S1)

Example Compound S1-1

7-(3,5-Dichlorophenyl)-N-[(4S)-3,4-dihydro-2H-chromen-4-yl]-3-isopropyl-1-benzothiophene-2-carboxamide

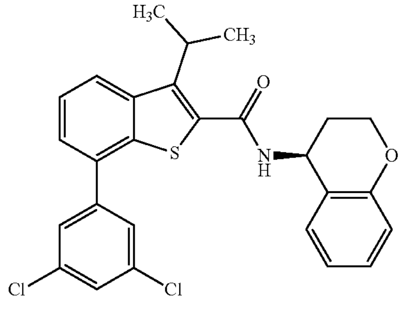 [SMILES: CC(C)c1c(C(=O)N[C@H]2CCOc3ccccc32)sc2c(-c3cc(Cl)cc(Cl)c3)cccc12]

To a mixture of 7-bromo-N-[(4S)-3,4-dihydro-2H-chromen-4-yl]-3-isopropyl-1-benzothiophene-2-carboxamide (88 mg, 0.204 mmol), (3,5-dichlorophenyl)boronic acid (43 mg, 0.225 mmol) and sodium carbonate (65 mg, 0.613 mmol) in a degassed mixture of 1,2-dimethoxyethane (4 mL) and water (1 mL) was added bis(triphenylphosphine) palladium(II) chloride (7 mg, 0.010 mmol). The mixture was stirred at 100° C. for 16 h. Water and dichloromethane were added. The mixture was passed through a phase separator and the organic layer was passed through a layer of sodium sulfate. The solvent was removed in vacuo. Purification of the residue by flash column chromatography (Method 7; 4 g; heptane, 2%-20% ethyl acetate) afforded 58 mg (0.111 mmol, 54% of theory) of the title compound.

LC-MS (Method 2): $R_t$=4.65 min; m/z=496/498 $(M+H)^+$

1H NMR (400 MHz, chloroform-d) δ=8.06 (dd, J=8.3, 1.0 Hz, 1H), 7.54-7.45 (m, 3H), 7.42 (t, J=1.9 Hz, 1H), 7.36 (dd, J=7.3, 1.0 Hz, 1H), 7.31-7.26 (m, 1H), 7.24-7.16 (m, 1H), 6.98-6.90 (m, 1H), 6.86 (dd, J=8.2, 1.2 Hz, 1H), 6.20 (d, J=7.2 Hz, 1H), 5.33 (q, J=5.6 Hz, 1H), 4.37-4.27 (m, 1H), 4.26-4.16 (m, 1H), 4.16-4.03 (m, 1H), 2.42-2.27 (m, 1H), 2.26-2.13 (m, 1H), 1.66-1.48 (m, 6H).

Example Compound S1-2

7-(3-Chlorophenyl)-N-[(4S)-3,4-dihydro-2H-chromen-4-yl]-3-isopropyl-1-benzothiophene-2-carboxamide

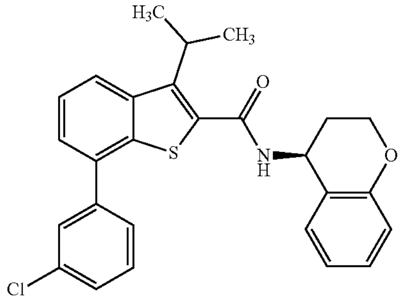 [SMILES: CC(C)c1c(C(=O)N[C@H]2CCOc3ccccc32)sc2c(-c3cccc(Cl)c3)cccc12]

To a mixture of 7-bromo-N-[(4S)-3,4-dihydro-2H-chromen-4-yl]-3-isopropyl-1-benzothiophene-2-carboxamide (88 mg, 0.204 mmol), 3-chlorophenyl)boronic acid (35 mg, 0.225 mmol) and sodium carbonate (65 mg, 0.613 mmol) in a degassed mixture of 1,2-dimethoxyethane (4 mL) and water (1 mL) was added bis(triphenylphosphine) palladium(II) chloride (7 mg, 0.010 mmol). The mixture was stirred at 100° C. for 16 h. Water and dichloromethane were added. The mixture was passed through a phase separator and the organic layer was passed through a layer of sodium sulfate. The solvent was removed in vacuo. Purification of the residue by flash column chromatography (Method 7; 4 g; heptane, 2%-20% ethyl acetate) afforded 74 mg (0.155 mmol, 76% of theory) of the title compound.

LC-MS (Method 2): $R_t$=4.45 min; m/z=462/463 $(M+H)^+$

1H NMR (400 MHz, chloroform-d) δ=8.10-7.95 (m, 1H), 7.63-7.57 (m, 1H), 7.57-7.45 (m, 2H), 7.45-7.34 (m, 3H), 7.27 (d, J=6.9 Hz, 1H), 7.23-7.15 (m, 1H), 6.96-6.89 (m, 1H), 6.89-6.82 (m, 1H), 6.19 (d, J=7.6 Hz, 1H), 5.41-5.20 (m, 1H), 4.37-4.25 (m, 1H), 4.25-4.03 (m, 2H), 2.40-2.26 (m, 1H), 2.26-2.13 (m, 1H), 1.62-1.47 (m, 6H).

Example Compound S1-3

7-(2,3-Dichlorophenyl)-N-[(4S)-3,4-dihydro-2H-chromen-4-yl]-3-isopropyl-1-benzothiophene-2-carboxamide

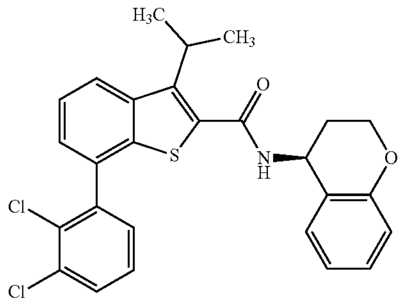 [SMILES: CC(C)c1c(C(=O)N[C@H]2CCOc3ccccc32)sc2c(-c3cccc(Cl)c3Cl)cccc12]

To a mixture of 7-bromo-N-[(4S)-3,4-dihydro-2H-chromen-4-yl]-3-isopropyl-1-benzothiophene-2-carboxamide (88 mg, 0.204 mmol), (2,3-dichlorophenyl)boronic acid (43 mg, 0.225 mmol) and sodium carbonate (65 mg, 0.613 mmol) in a degassed mixture of 1,2-dimethoxyethane (4 mL) and water (1 mL) was added bis(triphenylphosphine) palladium(II) chloride (7 mg, 0.010 mmol). The mixture was stirred at 100° C. for 16 h. Water and dichloromethane were added. The mixture was passed through a phase separator and the organic layer was passed through a layer of sodium sulfate. The solvent was removed in vacuo. Purification of the residue by flash column chromatography (Method 7; 4 g; heptane, 2%-20% ethyl acetate) afforded 32 mg (0.061 mmol, 30% of theory) of the title compound.

LC-MS (Method 2): $R_t$=4.45 min; m/z=496/498 $(M+H)^+$

1H NMR (400 MHz, chloroform-d) δ=8.13-8.04 (m, 1H), 7.58-7.52 (m, 1H), 7.52-7.45 (m, 1H), 7.36-7.28 (m, 2H), 7.26 (s, 2H), 7.22-7.14 (m, 1H), 6.91 (t, J=7.5 Hz, 1H), 6.87-6.80 (m, 1H), 6.14 (d, J=7.4 Hz, 1H), 5.35-5.21 (m, 1H), 4.35-4.24 (m, 1H), 4.23-4.06 (m, 2H), 2.37-2.24 (m, 1H), 2.24-2.08 (m, 1H), 1.65-1.47 (m, 6H).

Example Compound S1-4

7-(3,4-Difluorophenyl)-N-[(4S)-3,4-dihydro-2H-chromen-4-yl]-3-isopropyl-1-benzothiophene-2-carboxamide

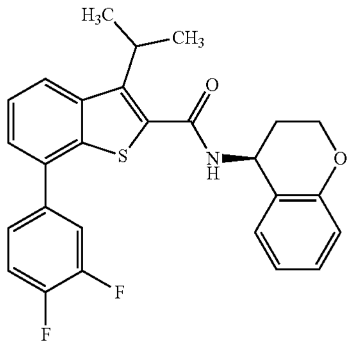 [SMILES: CC(C)c1c(C(=O)N[C@H]2CCOc3ccccc32)sc2c(-c3ccc(F)c(F)c3)cccc12]

To a mixture of 7-bromo-N-[(4S)-3,4-dihydro-2H-chromen-4-yl]-3-isopropyl-1-benzothiophene-2-carboxamide (88 mg, 0.204 mmol), (3,4-difluorophenyl)boronic acid (36 mg, 0.225 mmol) and sodium carbonate (65 mg, 0.613 mmol) in a degassed mixture of 1,2-dimethoxyethane (4 mL) and water (1 mL) was added bis(triphenylphosphine) palladium(II) chloride (7 mg, 0.010 mmol). The mixture was stirred at 100° C. for 16 h. Water and dichloromethane were added. The mixture was passed through a phase separator and the organic layer was passed through a layer of sodium sulfate. The solvent was removed in vacuo. Purification of the residue by flash column chromatography (Method 7; 4 g; heptane, 2%-20% ethyl acetate) afforded 68 mg (0.144 mmol, 70% of theory) of the title compound.

LC-MS (Method 2): $R_t$=4.33 min; m/z=464 $(M+H)^+$

1H NMR (400 MHz, chloroform-d) δ=8.08-7.99 (m, 1H), 7.53-7.47 (m, 1H), 7.47-7.40 (m, 1H), 7.39-7.33 (m, 2H), 7.32-7.25 (m, 2H), 7.25-7.17 (m, 1H), 6.98-6.90 (m, 1H), 6.90-6.82 (m, 1H), 6.18 (d, J=7.0 Hz, 1H), 5.37-5.25 (m, 1H), 4.37-4.27 (m, 1H), 4.26-4.03 (m, 2H), 2.40-2.27 (m, 1H), 2.26-2.13 (m, 1H), 1.63-1.46 (m, 6H).

Example Compound S1-5

7-(3,5-Dichlorophenyl)-N-[(4S)-3,4-dihydro-2H-chromen-4-yl]-3-(dimethylamino)-1-benzothiophene-2-carboxamide

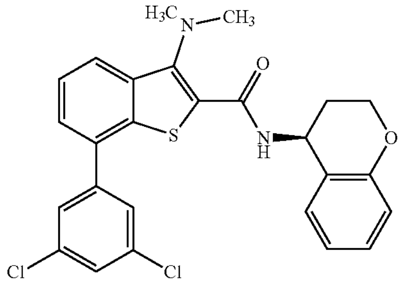

A mixture of 3,5-dichlorophenylboronic acid (44 mg, 0.232 mmol), 7-bromo-N-[(4S)-3,4-dihydro-2H-chromen-4-yl]-3-(dimethylamino)-1-benzothiophene-2-carboxamide (100 mg, 0.232 mmol) and saturated aqueous sodium carbonate (0.34 mL) in 1,2-dimethoxyethane (4 mL) was flushed with argon for 5 min. Tetrakis(triphenylphosphine) palladium(0) (13 mg, 0.012 mmol) was added and the mixture was stirred at 100° C. for 1 h. Dichloromethane (2 mL) was added and layers were separated with a phase separator. The organic layer was dried with sodium sulfate and solvents were removed in vacuo. The crude product was purified by flash column chromatography (Method 6; 24 g; heptane, 0%-50% ethyl acetate) and by reversed phase flash column chromatography (Method 10; 24 g). 72 mg (0.14 mmol, 62% of theory) of the title compound were obtained.

LC-MS (Method 2): $R_t$=4.66 min; m/z=497/499 $(M+H)^+$

1H NMR (400 MHz, DMSO-d6) δ=9.96 (d, J=8.0 Hz, 1H), 8.14 (dd, J=6.6, 2.6 Hz, 1H), 7.76 (dd, J=9.7, 1.8 Hz, 3H), 7.64-7.49 (m, 2H), 7.29 (d, J=7.5 Hz, 1H), 7.25-7.12 (m, 1H), 6.92 (t, J=7.4 Hz, 1H), 6.83 (d, J=8.2 Hz, 1H), 5.23 (q, J=6.8 Hz, 1H), 4.31 (ddd, J=10.6, 7.5, 2.8 Hz, 1H), 4.21 (ddd, J=11.0, 7.5, 3.0 Hz, 1H), 2.90 (s, 6H), 2.24 (ddd, J=12.9, 9.0, 4.1 Hz, 1H), 2.09 (dtd, J=13.9, 7.2, 2.9 Hz, 1H).

Example Compound S1-6

7-(3-Chlorophenyl)-N-[(4S)-3,4-dihydro-2H-chromen-4-yl]-3-(dimethylamino)-1-benzothiophene-2-carboxamide

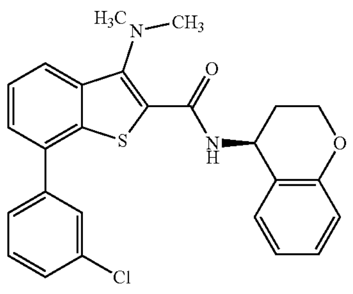

A mixture of 3-chlorophenylboronic acid (36 mg, 0.232 mmol), 7-bromo-N-[(4S)-3,4-dihydro-2H-chromen-4-yl]-3-(dimethylamino)-1-benzothiophene-2-carboxamide (100 mg, 0.232 mmol) and saturated aqueous sodium carbonate (0.34 mL) in 1,2-dimethoxyethane (4 mL) was flushed with argon for 5 min. Tetrakis(triphenylphosphine)palladium(0) (13 mg, 0.012 mmol) was added and the mixture was stirred at 100° C. for 1 h. Dichloromethane (2 mL) was added and layers were separated with a phase separator. The organic layer was dried with sodium sulfate and solvents were removed in vacuo. The crude product was purified by flash column chromatography (Method 6; 24 g; heptane, 0%-50% ethyl acetate). 98 mg (0.21 mmol, 91% of theory) of the title compound were obtained.

LC-MS (Method 2): $R_t$=4.43 min; m/z=463 $(M+H)^+$

1H NMR (400 MHz, DMSO-d6) δ=9.97 (d, J=8.0 Hz, 1H), 8.11 (dd, J=7.1, 2.0 Hz, 1H), 7.75-7.52 (m, 6H), 7.29 (d, J=7.4 Hz, 1H), 7.22-7.15 (m, 1H), 6.95-6.88 (m, 1H), 6.83 (d, J=8.2 Hz, 1H), 5.22 (q, J=6.7 Hz, 1H), 4.31 (ddd, J=10.6, 7.5, 2.9 Hz, 1H), 4.21 (ddd, J=11.0, 7.5, 3.0 Hz, 1H), 2.91 (s, 6H), 2.20 (s, 1H), 2.09 (dtd, J=13.8, 7.2, 2.9 Hz, 1H).

Example Compound S1-7

7-(2,3-Dichlorophenyl)-N-[(4S)-3,4-dihydro-2H-chromen-4-yl]-3-(dimethylamino)-1-benzothiophene-2-carboxamide

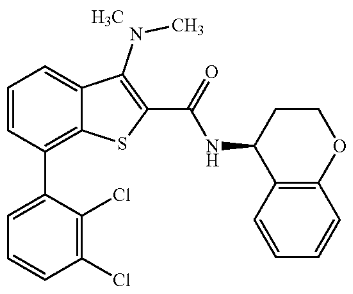

A mixture of 2,3-dichlorophenylboronic acid (44 mg, 0.232 mmol), 7-bromo-N-[(4S)-3,4-dihydro-2H-chromen-4-yl]-3-(dimethylamino)-1-benzothiophene-2-carboxamide (100 mg, 0.232 mmol) and saturated aqueous sodium carbonate (0.34 mL) in 1,2-dimethoxyethane (4 mL) was flushed with argon for 5 min. Tetrakis(triphenylphosphine) palladium(0) (13 mg, 0.012 mmol) was added and the mixture was stirred at 100° C. for 1 h. Dichloromethane (2 mL) was added and layers were separated with a phase separator. The organic layer was dried with sodium sulfate and solvents were removed in vacuo. The crude product was purified by flash column chromatography (Method 6; 24 g; heptane, 0%-50% ethyl acetate) and by reversed phase flash column chromatography (Method 10; 24 g). 61 mg (0.12 mmol, 52% of theory) of the title compound were obtained.

LC-MS (Method 2): $R_t$=4.42 min; m/z=497/499 $(M+H)^+$

1H NMR (400 MHz, DMSO-d6) δ=9.92 (d, J=7.8 Hz, 1H), 8.14 (d, J=8.1 Hz, 1H), 7.81 (dd, J=7.8, 1.7 Hz, 1H), 7.61-7.41 (m, 4H), 7.27 (d, J=7.5 Hz, 1H), 7.22-7.14 (m, 1H), 6.94-6.87 (m, 1H), 6.82 (d, J=8.2 Hz, 1H), 5.20 (q, J=6.5 Hz, 1H), 4.30 (ddd, J=10.6, 7.4, 2.9 Hz, 1H), 4.20 (ddd, J=10.9, 7.4, 2.9 Hz, 1H), 2.92 (s, 6H), 2.21 (ddd, J=13.3, 8.1, 3.1 Hz, 1H), 2.12-2.02 (m, 1H).

Example Compound S1-8

7-(3,4-Difluorophenyl)-N-[(4S)-3,4-dihydro-2H-chromen-4-yl]-3-(dimethylamino)-1-benzothiophene-2-carboxamide

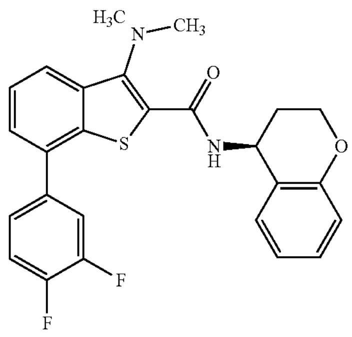

A mixture of 3,4-difluorophenylboronic acid (37 mg, 0.232 mmol 7-bromo-N-[(4S)-3,4-dihydro-2H-chromen-4-yl]-3-(dimethylamino)-1-benzothiophene-2-carboxamide (100 mg, 0.232 mmol) and saturated aqueous sodium carbonate (0.34 mL) in 1,2-dimethoxyethane (4 mL) was flushed with argon for 5 min. Tetrakis(triphenylphosphine) palladium(0) (13 mg, 0.012 mmol) was added and the mixture was stirred at 100° C. for 1 h. Dichloromethane (2 mL) was added and layers were separated with a phase separator. The organic layer was dried with sodium sulfate and solvents were removed in vacuo. The crude product was purified by flash column chromatography (Method 6; 24 g; heptane, 0%-50% ethyl acetate). 104 mg (0.22 mmol, 97% of theory) of the title compound were obtained.

LC-MS (Method 2): $R_t$=4.30 min; m/z=465 $(M+H)^+$

1H NMR (400 MHz, DMSO-d6) δ=9.97 (d, J=8.0 Hz, 1H), 8.14-8.07 (m, 1H), 7.78 (ddd, J=11.3, 7.7, 2.0 Hz, 1H), 7.70-7.48 (m, 4H), 7.29 (d, J=7.5 Hz, 1H), 7.23-7.14 (m, 1H), 6.95-6.87 (m, 1H), 6.83 (d, J=8.1 Hz, 1H), 5.22 (q, J=6.6 Hz, 1H), 4.31 (td, J=7.9, 3.7 Hz, 1H), 4.25-4.16 (m, 1H), 2.90 (s, 6H), 2.23 (dt, J=10.1, 5.4 Hz, 1H), 2.11-2.03 (m, 1H).

Example Compound S1-9

7-(3,5-Dichlorophenyl)-N-[(4S)-3,4-dihydro-2H-chromen-4-yl]-3-methoxy-1-benzothiophene-2-carboxamide

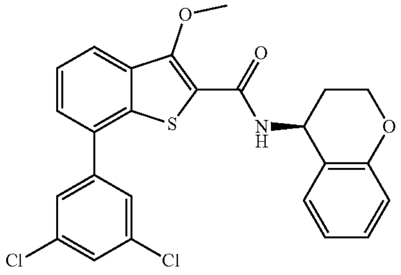 [SMILES: COc1c(C(=O)N[C@H]2CCOc3ccccc32)sc2c(-c3cc(Cl)cc(Cl)c3)cccc12]

To a mixture of 7-bromo-N-[(4S)-3,4-dihydro-2H-chromen-4-yl]-3-methoxy-1-benzothiophene-2-carboxamide (100 mg, 0.239 mmol), (3,5-dichlorophenyl)boronic acid (50 mg, 0.263 mmol) and sodium carbonate (76 mg, 0.717 mmol) in a degassed mixture of 1,2-dimethoxyethane (4 mL) and water (1 mL) was added bis(triphenylphosphine) palladium(II) chloride (8 mg, 0.012 mmol). The mixture was stirred at 100° C. for 16 h. Water and dichloromethane were added. Layers were separated using a phase separator. The aqueous layer was extracted with ethyl acetate. The combined organic extracts were dried with sodium sulfate and the solvents were removed in vacuo. The crude product was purified by flash column chromatography (Method 7; 4 g; heptane, 2%-20% ethyl acetate). 72 mg (0.146 mmol, 60% of theory) of the title compound were obtained.

LC-MS (Method 2): $R_t$=4.57 min; m/z=484/486 $(M+H)^+$

1H NMR (400 MHz, chloroform-d) δ=7.80 (dd, J=8.0, 1.1 Hz, 1H), 7.72 (d, J=7.7 Hz, 1H), 7.57 (dd, J=1.9, 0.7 Hz, 2H), 7.54-7.47 (m, 1H), 7.47-7.39 (m, 2H), 7.35-7.29 (m, 1H), 7.22 (td, J=8.2, 1.6 Hz, 1H), 6.98-6.83 (m, 2H), 5.44-5.35 (m, 1H), 4.38-4.29 (m, 1H), 4.29-4.19 (m, 1H), 4.03 (s, 3H), 2.44-2.31 (m, 1H), 2.26-2.14 (m, 1H).

Example Compound S1-10

7-(3-Chlorophenyl)-N-[(4S)-3,4-dihydro-2H-chromen-4-yl]-3-methoxy-1-benzothiophene-2-carboxamide

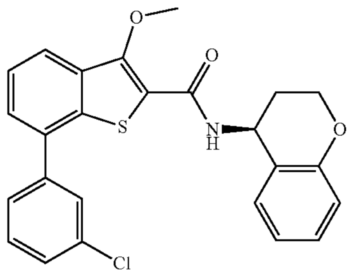 [SMILES: COc1c(C(=O)N[C@H]2CCOc3ccccc32)sc2c(-c3cccc(Cl)c3)cccc12]

To a mixture of 7-bromo-N-[(4S)-3,4-dihydro-2H-chromen-4-yl]-3-methoxy-1-benzothiophene-2-carboxamide (100 mg, 0.239 mmol), (3-chlorophenyl)boronic acid (41 mg, 0.263 mmol) and sodium carbonate (76 mg, 0.717 mmol) in a degassed mixture of 1,2-dimethoxyethane (4 mL) and water (1 mL) was added bis(triphenylphosphine) palladium(II) chloride (8 mg, 0.012 mmol). The mixture was stirred at 100° C. for 16 h. Water and dichloromethane were added. Layers were separated using a phase separator. The aqueous layer was extracted with ethyl acetate. The combined organic extracts were dried with sodium sulfate and the solvents were removed in vacuo. The crude product was purified by flash column chromatography (Method 7; 4 g; heptane, 2%-20% ethyl acetate). 57 mg (0.123 mmol, 51% of theory) of the title compound were obtained.

LC-MS (Method 2): $R_t$=4.36 min; m/z=450 $(M+H)^+$

1H NMR (400 MHz, chloroform-d) δ=7.78 (dd, J=7.9, 1.2 Hz, 1H), 7.73 (d, J=7.8 Hz, 1H), 7.65 (dt, J=1.7, 1.1 Hz, 1H), 7.61 (dt, J=6.9, 1.9 Hz, 1H), 7.53-7.47 (m, 1H), 7.47-7.40 (m, 3H), 7.35-7.29 (m, 1H), 7.21 (dd, J=8.1, 1.0 Hz, 1H), 6.93 (td, J=7.5, 1.2 Hz, 1H), 6.89 (dd, J=8.3, 1.2 Hz, 1H), 5.45-5.33 (m, 1H), 4.39-4.29 (m, 1H), 4.29-4.19 (m, 1H), 4.03 (s, 3H), 2.43-2.30 (m, 1H), 2.26-2.13 (m, 1H).

Example Compound S1-11

7-(2,3-Dichlorophenyl)-N-[(4S)-3,4-dihydro-2H-chromen-4-yl]-3-methoxy-1-benzothiophene-2-carboxamide

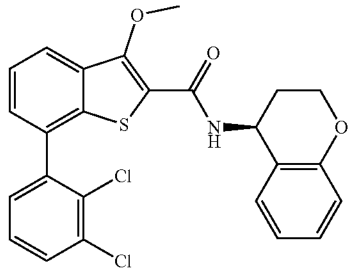 [SMILES: COc1c(C(=O)N[C@H]2CCOc3ccccc32)sc2c(-c3cccc(Cl)c3Cl)cccc12]

To a mixture of 7-bromo-N-[(4S)-3,4-dihydro-2H-chromen-4-yl]-3-methoxy-1-benzothiophene-2-carboxamide (100 mg, 0.239 mmol), (2,3-dichlorophenyl)boronic acid (68 mg, 0.359 mmol) and sodium carbonate (76 mg, 0.717 mmol) in a degassed mixture of 1,2-dimethoxyethane (4 mL) and water (1 mL) was added bis(triphenylphosphine) palladium(II) chloride (8 mg, 0.012 mmol). The mixture was stirred at 100° C. for 16 h. Ethyl acetate and water were added. Layers were separated and the aqueous phase was extracted with ethyl acetate. The combined organic layers were dried with sodium sulfate. Solvents were removed in vacuo. The crude product was purified by flash column chromatography (Method 7; 4 g; heptane, 2%-20% ethyl acetate). 73 mg (0.143 mmol, 60% of theory) of the title compound were obtained.

LC-MS (Method 2): $R_t$=4.37 min; m/z=484/486 $(M+H)^+$

1H NMR (400 MHz, chloroform-d) δ=7.83 (dd, J=8.1, 1.1 Hz, 1H), 7.72 (d, J=7.7 Hz, 1H), 7.58 (dd, J=7.5, 2.1 Hz, 1H), 7.51 (dd, J=8.1, 7.3 Hz, 1H), 7.39 (dd, J=7.3, 1.1 Hz, 1H), 7.37-7.28 (m, 3H), 7.24-7.18 (m, 1H), 6.97-6.90 (m, 1H), 6.88 (dd, J=8.3, 1.0 Hz, 1H), 5.43-5.31 (m, 1H), 4.38-4.28 (m, 1H), 4.28-4.17 (m, 1H), 4.06 (s, 3H), 2.41-2.29 (m, 1H), 2.25-2.11 (m, 1H).

Example Compound S1-12

3-Chloro-7-(2,3-dichlorophenyl)-N-[(4S)-3,4-dihydro-2H-chromen-4-yl]-1-benzothiophene-2-carboxamide

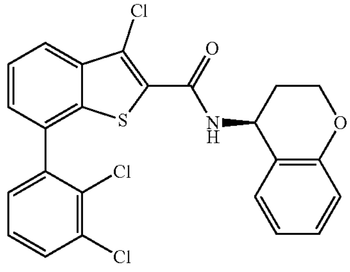 [SMILES: O=C(N[C@H]1CCOc2ccccc21)c1sc2c(-c3cccc(Cl)c3Cl)cccc2c1Cl]

To a mixture of 7-bromo-3-chloro-N-[(4S)-3,4-dihydro-2H-chromen-4-yl]-1-benzothiophene-2-carboxamide (70 mg, 0.166 mmol), (2,3-dichlorophenyl)boronic acid (47 mg, 0.248 mmol) and sodium carbonate (53 mg, 0.497 mmol) in a degassed mixture of 1,2-dimethoxyethane (2 mL) and water (1 mL) was added bis(triphenylphosphine)palladium (II) chloride (6 mg, 0.008 mmol). The mixture was stirred at 100° C. for 16 h. Water and dichloromethane were added. Layers were separated and the aqueous layer was extracted with dichloromethane. The combined organic extracts were dried with sodium sulfate and the solvents were removed in vacuo. The crude product was purified by flash column chromatography (Method 7; 4 g; heptane, 2%-20% ethyl acetate). 43 mg (0.084 mmol, 51% of theory) of the title compound were obtained.

LC-MS (Method 2): $R_t$=4.52 min; m/z=488/490 $(M+H)^+$

1H NMR (400 MHz, chloroform-d) δ=7.92 (dd, J=8.2, 0.9 Hz, 1H), 7.68-7.55 (m, 2H), 7.45 (dd, J=7.3, 0.9 Hz, 1H), 7.42-7.29 (m, 4H), 7.26-7.18 (m, 1H), 7.00-6.82 (m, 2H), 5.38 (q, J=5.7 Hz, 1H), 4.40-4.19 (m, 2H), 2.45-2.31 (m, 1H), 2.29-2.15 (m, 1H).

Example Compound S1-13

7-(2,3-Dichlorophenyl)-N-[(4S)-3,4-dihydro-2H-chromen-4-yl]-3-(dimethylamino)thieno[2,3-c]pyridine-2-carboxamide

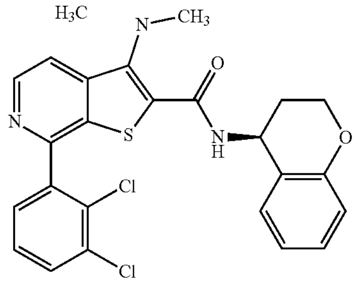

To a stirred suspension of lithium 7-(2,3-dichlorophenyl)-3-(dimethylamino)thieno[2,3-c]pyridine-2-carboxylate (23 mg, 0.06 mmol) in N,N-dimethylformamide (1.00 mL) was added triethyl amine (19 mg, 0.19 mmol, 0.03 mL). To the resulting clear solution were added O-(7-Azabenzotriazol-1-yl)-N,N,N',N'-tetramethyluronium hexafluorophosphate (35 mg, 0.09 mmol) and (S)-chroman-4-amine hydrochloride (17 mg, 0.09 mmol). The mixture was stirred at room temperature under nitrogen atmosphere in a closed vessel for 16 hours. The reaction mixture was partitioned between ethyl acetate (5 mL) and water (10 mL). Layers were separated and the aqueous layer was extracted with ethyl acetate (2×5 mL). Combined organic extracts were washed brine (3×5 mL), dried with sodium sulfate and concentrated in vacuo. Purification by flash column chromatography (Method 6, 4 g; heptane, 5%-100% ethyl acetate) afforded 18 mg (0.04 mmol, 58% of theory) of the title compound.

LC-MS (Method 4): $R_t$=4.16 min; m/z=498/500 $(M+1)^+$

1H NMR (400 MHz, DMSO-d6) δ 9.81 (d, J=8.1 Hz, 1H), 8.64 (d, J=5.6 Hz, 1H), 8.09 (d, J=5.6 Hz, 1H), 7.90-7.83 (m, 1H), 7.61-7.54 (m, 2H), 7.26 (d, J=7.6 Hz, 1H), 7.23-7.15 (m, 1H), 6.94-6.86 (m, 1H), 6.81 (dd, J=8.2, 1.1 Hz, 1H), 5.21 (q, J=6.5 Hz, 1H), 4.33-4.16 (m, 2H), 2.93 (s, 6H), 2.27-2.15 (m, 1H), 2.14-2.02 (m, 1H).

Example Compound S1-14

7-(3,5-Dichlorophenyl)-N-[(4S)-3,4-dihydro-2H-chromen-4-yl]-3-methoxythieno[2,3-c]pyridine-2-carboxamide

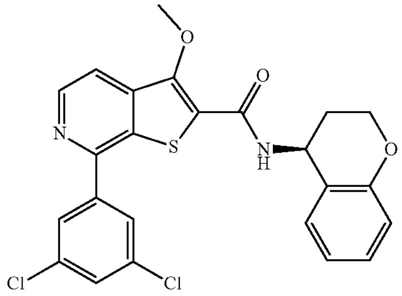 [SMILES: COc1c(C(=O)N[C@H]2CCOc3ccccc32)sc2c(-c3cc(Cl)cc(Cl)c3)nccc12]

A stirred mixture of 7-bromo-N-[(4S)-3,4-dihydro-2H-chromen-4-yl]-3-methoxythieno[2,3-c]pyridine-2-carboxamide (40 mg, 0.10 mmol), (3,5-dichlorophenyl)boronic acid (20 mg, 0.11 mmol) and sodium carbonate (20 mg, 0.19 mmol) in 1,4-dioxane (1.00 mL) and water (0.15 mL) was flushed with nitrogen. 1,1'-Bis(diphenylphosphino)ferrocene palladium dichloride (4 mg, 0.01 mmol) was added and the resulting mixture was stirred at 60° C. for 4 h under nitrogen atmosphere in a closed vessel. The reaction mixture was cooled to room temperature, diluted with ethyl acetate (1 mL) and filtered. The filter cake was rinsed with ethyl acetate (1 mL) and the filtrate was concentrated in vacuo. Purification by flash column chromatography (Method 6, 12 g; heptane, 5%-100% ethyl acetate) afforded 37 mg (0.08 mmol, 80% of theory) of the title compound.

LC-MS (Method 2): $R_t$=4.43 min; m/z=485/487 $(M+1)^+$

1H NMR (400 MHz, DMSO-d6) δ 8.72 (d, J=5.5 Hz, 1H), 8.60 (d, J=8.2 Hz, 1H), 8.03-7.95 (m, 3H), 7.86 (t, J=1.9 Hz, 1H), 7.27 (d, J=7.6 Hz, 1H), 7.23-7.15 (m, 1H), 6.96-6.87 (m, 1H), 6.82 (dd, J=8.2, 1.0 Hz, 1H), 5.30 (q, J=6.5 Hz, 1H), 4.27 (dd, J=6.3, 4.4 Hz, 2H), 4.12 (s, 3H), 2.18 (q, J=6.4 Hz, 2H).

Example Compound S1-15

7-(3-Chlorophenyl)-N-[(4S)-3,4-dihydro-2H-chromen-4-yl]-3-methoxythieno[2,3-c]pyridine-2-carboxamide

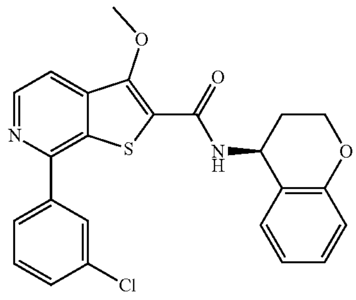 [SMILES: COc1c(C(=O)N[C@H]2CCOc3ccccc32)sc2c(-c3cccc(Cl)c3)nccc12]

A stirred mixture of 7-bromo-N-[(4S)-3,4-dihydro-2H-chromen-4-yl]-3-methoxythieno[2,3-c]pyridine-2-carboxamide (40 mg, 0.10 mmol), (3-chlorophenyl)boronic acid (16 mg, 0.11 mmol) and sodium carbonate (20 mg, 0.19 mmol) in 1,4-dioxane (1.00 mL) and water (0.15 mL) was flushed with nitrogen. 1,1'-Bis(diphenylphosphino)ferrocene palladium dichloride (4 mg, 0.01 mmol) was added and the resulting mixture was stirred at 60° C. for 4 h under nitrogen atmosphere in a closed vessel. The reaction mixture was cooled to room temperature, diluted with ethyl acetate (1 mL) and was filtered. The filter cake was rinsed with ethyl acetate (1 mL) and the filtrate was concentrated in vacuo. Purification by flash column chromatography (Method 6, 12 g; heptane, 5%-100% ethyl acetate), preparative HPLC (Method 11) and trituration in diisopropyl ether afforded 23 mg (0.05 mmol, 53% of theory) of the title compound.

LC-MS (Method 2): $R_t$=4.20 min; m/z=451/453 $(M+1)^+$

1H NMR (400 MHz, DMSO-d6) δ 8.71 (d, J=5.4 Hz, 1H), 8.57 (d, J=8.2 Hz, 1H), 8.04-7.98 (m, 2H), 7.94 (d, J=5.5 Hz, 1H), 7.70-7.63 (m, 2H), 7.27 (d, J=7.6 Hz, 1H), 7.23-7.15 (m, 1H), 6.95-6.88 (m, 1H), 6.82 (dd, J=8.2, 1.0 Hz, 1H), 5.29 (q, J=6.4 Hz, 1H), 4.27 (dd, J=6.4, 4.4 Hz, 2H), 4.12 (s, 3H), 2.18 (q, J=6.2 Hz, 2H).

Example Compound S1-16

7-(2,3-Dichlorophenyl)-N-[(4S)-3,4-dihydro-2H-chromen-4-yl]-3-methoxythieno[2,3-c]pyridine-2-carboxamide

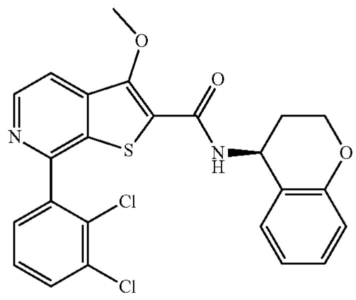 [SMILES: COc1c(C(=O)N[C@H]2CCOc3ccccc32)sc2c(-c3cccc(Cl)c3Cl)nccc12]

A stirred mixture of 7-bromo-N-[(4S)-3,4-dihydro-2H-chromen-4-yl]-3-methoxythieno[2,3-c]pyridine-2-carboxamide (80 mg, 0.19 mmol), (2,3-dichlorophenyl)boronic acid (40 mg, 0.21 mmol) and sodium carbonate (40 mg, 0.38 mmol) in 1,4-dioxane (2.0 mL) and water (0.3 mL) was flushed with nitrogen. 1,1'-Bis(diphenylphosphino)ferrocene palladium dichloride (9 mg, 0.01 mmol) was added and the resulting mixture was stirred at 70° C. for 4 h under nitrogen atmosphere in a closed vessel. The reaction mixture was cooled to room temperature, diluted with ethyl acetate (1 mL) and filtered. The filter cake was rinsed with ethyl acetate (1 mL) and the filtrate was concentrated in vacuo. Purification by flash column chromatography (Method 6, 12 g; toluene, 5%-100% diisopropyl ether) afforded 68 mg (0.14 mmol, 73% of theory) of the title compound.

LC-MS (Method 4): $R_t$=4.08 min; m/z=485/487 $(M+1)^+$

1H NMR (400 MHz, DMSO-d6) δ 8.69 (d, J=5.6 Hz, 1H), 8.54 (d, J=8.3 Hz, 1H), 8.01 (d, J=5.6 Hz, 1H), 7.91-7.83 (m, 1H), 7.61-7.55 (m, 2H), 7.24 (d, J=7.5 Hz, 1H), 7.21-7.14 (m, 1H), 6.93-6.86 (m, 1H), 6.84-6.76 (m, 1H), 5.26 (q, J=6.6 Hz, 1H), 4.25 (dd, J=6.1, 4.5 Hz, 2H), 4.15 (s, 3H), 2.15 (q, J=6.2 Hz, 2H).

Example Compound S1-17

7-(2,3-Dichlorophenyl)-N-[(4S)-3,4-dihydro-2H-chromen-4-yl]-4-fluoro-3-(morpholin-4-yl)-1-benzothiophene-2-carboxamide

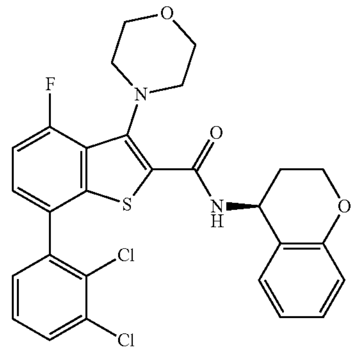 [SMILES: O=C(N[C@H]1CCOc2ccccc21)c1sc2c(-c3cccc(Cl)c3Cl)ccc(F)c2c1N1CCOCC1]

LC-MS (Method 15): $R_t$=1.41 min; MS (ESIpos): m/z=557 [M+H]+

1H NMR (peaklist): (400 MHz, DMSO-d6) δ[ppm]: −0.149 (1.79), −0.008 (16.00), 0.008 (14.78), 0.146 (1.88), 1.235 (0.66), 2.162 (7.53), 2.323 (1.88), 2.327 (2.64), 2.332 (1.88), 2.366 (2.35), 2.524 (8.85), 2.665 (2.35), 2.670 (3.01), 2.674 (2.26), 2.710 (2.64), 3.032 (3.48), 4.158 (3.01), 4.173 (2.45), 4.302 (4.61), 4.312 (2.82), 4.330 (3.48), 5.099 (4.71), 5.115 (4.61), 5.754 (11.76), 6.879 (7.91), 6.899 (8.94), 6.915 (4.71), 6.933 (9.51), 6.952 (5.55), 7.234 (4.14), 7.238 (4.71), 7.255 (7.25), 7.273 (3.58), 7.276 (3.67), 7.324 (2.82), 7.341 (5.08), 7.360 (2.64), 7.441 (5.08), 7.462 (9.32), 7.469 (5.27), 7.478 (4.89), 7.490 (12.24), 7.506 (8.00), 7.518 (8.28), 7.527 (10.92), 7.538 (4.42), 7.547 (10.54), 7.566 (4.52), 7.816 (9.60), 7.820 (9.79), 7.836 (8.38), 7.840 (8.19), 10.427 (4.14), 10.440 (4.14).

Example Compound S1-18

7-(3,5-Dichlorophenyl)-N-[(4S)-3,4-dihydro-2H-chromen-4-yl]-4-fluoro-3-(morpholin-4-yl)-1-benzothiophene-2-carboxamide

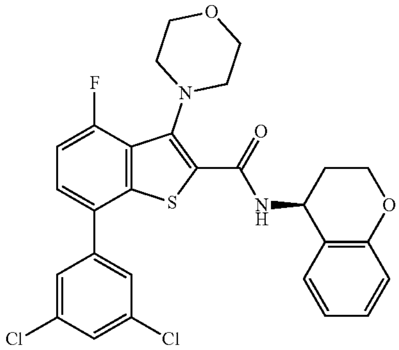 [SMILES: O=C(N[C@H]1CCOc2ccccc21)c1sc2c(-c3cc(Cl)cc(Cl)c3)ccc(F)c2c1N1CCOCC1]

LC-MS (Method 15): $R_t$=1.50 min; MS (ESIpos): m/z=557 $[M+H]^+$

1H NMR (peaklist): (600 MHz, DMSO-d6) δ[ppm]: −0.023 (1.36), 0.005 (2.27), 1.232 (2.59), 2.157 (0.49), 2.164 (0.68), 2.173 (1.33), 2.181 (3.20), 2.187 (3.62), 2.195 (2.36), 2.203 (1.61), 2.210 (1.16), 2.219 (0.42), 2.227 (0.41), 2.387 (0.51), 2.518 (1.40), 2.521 (1.43), 2.524 (1.13), 2.615 (0.66), 3.016 (0.53), 4.139 (1.01), 4.145 (1.07), 4.158 (1.76), 4.174 (1.43), 4.180 (1.11), 4.317 (1.11), 4.324 (1.98), 4.331 (1.28), 4.336 (1.10), 4.343 (1.70), 4.350 (0.87), 5.120 (1.02), 5.127 (2.16), 5.138 (2.09), 5.146 (0.92), 5.761 (7.62), 6.892 (3.87), 6.905 (4.13), 6.931 (2.03), 6.943 (3.96), 6.956 (2.20), 7.249 (1.87), 7.252 (1.92), 7.264 (3.16), 7.275 (1.61), 7.278 (1.66), 7.344 (3.26), 7.357 (3.11), 7.461 (2.42), 7.474 (3.01), 7.480 (2.46), 7.493 (2.72), 7.630 (2.85), 7.638 (2.92), 7.644 (2.69), 7.651 (2.44), 7.722 (15.12), 7.725 (16.00), 7.785 (4.30), 7.788 (7.12), 7.791 (3.39), 10.462 (3.29), 10.473 (3.14).

(Target) Example Compounds (S2)

Example Compound S2-1

7-(2,3-Dichlorophenyl)-N-[(4S)-3,4-dihydro-2H-chromen-4-yl]-3-methyl-3H-imidazo[4,5-b]pyridine-2-carboxamide

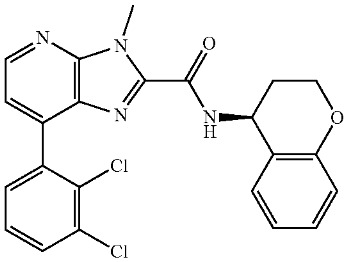 [SMILES: Cn1c(C(=O)N[C@H]2CCOc3ccccc32)nc2c(-c3cccc(Cl)c3Cl)ccnc21]

Step 1: Ethyl 7-(2,3-dichlorophenyl)-3-methyl-3H-imidazo[4,5-b]pyridine-2-carboxylate

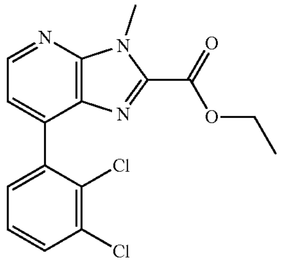 [SMILES: CCOC(=O)c1nc2c(-c3cccc(Cl)c3Cl)ccnc2n1C]

Ethyl 7-bromo-3-methyl-3H-imidazo[4,5-b]pyridine-2-carboxylate [CAS 2090992-55-3] (1 g, 3.52 mmol), 2,3-dichlorophenyl boronic acid (1 g, 5.28 mmol) and potassium fluoride (0.61 g, 10.5 mmol) were mixed with 50 mL tetrahydrofurane and 4 mL water. The mixture was degassed with argon for 5 minutes. Tris(dibenzylideneacetone)dipalladium(0) (0.32 g, 0.35 mmol) and tri-tert-butylphosphine tetrafluoroborate (0.2 g, 0.7 mmol) were added. The mixture was heated to 60° C. for 4 hours. After cooling to room temperature, the mixture was diluted with water (10 mL) and extracted twice with dichloromethane. The combined organic layers were dried over sodium sulfate, filtered and evaporated in vacuo. The remaining residue was purified by silica gel chromatography with an ethyl acetate/cyclohexane gradient to yield 0.96 g (72.8%) ethyl 7-(2,3-dichlorophenyl)-3-methyl-3H-imidazo[4,5-b]pyridine-2-carboxylate as a yellow oil.

LC-MS (Method 13): retention index 932; m/z=350.1; 352.0 $(M+H)^+$ $^1$H-NMR (400 MHz, DMSO-d6) δ 8.68-8.67 (d, 1H), 7.84-7.82 (d, 1H), 7.58-7.50 (m, 2H), 7.47-7.45 (d, 1H), 4.44-4.39 (q, 2H), 1.37-1.31 (t, 3H).

Step 2: 7-(2,3-Dichlorophenyl)-3-methyl-3H-imidazo[4,5-b]pyridine-2-carboxylic acid

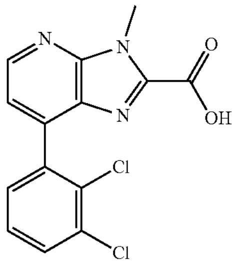 [SMILES: Cn1c(C(=O)O)nc2c(-c3cccc(Cl)c3Cl)ccnc21]

Ethyl 7-(2,3-dichlorophenyl)-3-methyl-3H-imidazo[4,5-b]pyridine-2-carboxylate from step 1 (0.45 g, 1.28 mmol) was dissolved in 21 mL dichloromethane. Boron tribromide (6.42 mL, 1M in dichloromethane) was added dropwise at −10° C. and kept for 1 hour at −10° C. The reaction mixture was allowed to warm to room temperature overnight and was quenched slowly with 20 mL water. The organic layer was separated and the solvent was evaporated under reduced pressure. The crude product contains some decarboxylation impurities and was used as such in the next step.

LC-MS (Method 13): retention index 923; m/z=322.0; 324.0 $(M+H)^+$

Step 3: 7-(2,3-Dichlorophenyl)-N-[(4S)-3,4-dihydro-2H-chromen-4-yl]-3-methyl-3H-imidazo-[4,5-b]pyridine-2-carboxamide

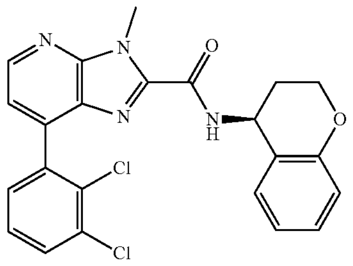 [SMILES: Cn1c(C(=O)N[C@H]2CCOc3ccccc32)nc2c(-c3cccc(Cl)c3Cl)ccnc21]

To a stirred mixture of 7-(2,3-dichlorophenyl)-3-methyl-3H-imidazo[4,5-b]pyridine-2-carboxylic acid (crude material 122 mg, 0.34 mmol), (S)-chroman-4-amine hydrochloride (71 mg, 0.38 mmol) and N,N-diisopropylethylamine (135 mg, 1.04 mmol) in dichlormethane (7.5 mL) were added N-(3-dimethylaminopropyl)-N'-ethylcarbodiimide hydrochloride (67 mg, 0.34 mmol), 1-hydroxy-1H-benzotriazole (24 mg, 0.17 mmol) and 4-N,N-dimethylamino pyridine (21 mg, 0.17 mmol) at room temperature. The resulting mixture was stirred overnight. The reaction mixture was mixed with water (10 mL) and the dichloromethane phase was separated. The aqueous phase was extracted again with dichloromethane. The combined organic layers were dried via a sodium sulfate/silica gel cartridge and concentrated in vacuo. Purification by flash chromatography with an ethyl acetate/cyclohexane gradient afforded 46 mg (27.1%) of the title compound.

LC-MS (Method 13): retention index: 1089; m/z=453.1; 455.1 $(M+H)^+$ $^1$H-NMR (400 MHz, DMSO-d6) δ 9.24 (d, 1H, NH), 8.61 (d, 1H), 7.75 (d, 1H), 7.53-7.46 (m, 2H), 7.41 (d, 1H), 7.17-7.12 (m, 2H), 6.86-6.83 (t, 1H), 6.77 (d, 1H), 5.33-5.28 (q, 1H), 4.32-4.28 (m, 1H), 4.20-4.16 (m+s, 1H+3H), 2.23-2.18 (m, 1H), 2.09-2.06 (m, 1H).

Example Compound S2-2

7-(2,3-Dichlorophenyl)-N-[(1S)-2,3-dihydro-1H-inden-1-yl]-3-methyl-3H-imidazo[4,5-b]pyridine-2-carboxamide

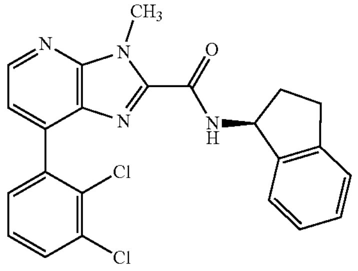 [SMILES: Cn1c(C(=O)N[C@H]2CCc3ccccc32)nc2c(-c3cccc(Cl)c3Cl)ccnc21]

This example was prepared analogously to Example S2-1.

LC-MS (Method 13): retention index: 1163; m/z=437.1; 439.1 $(M+H)^+$ $^1$H-NMR (400 MHz, DMSO-d6) δ 9.13 (d, 1H, NH), 8.61 (d, 1H), 7.76 (d, 1H), 7.54-7.47 (m, 2H), 7.41 (d, 1H), 7.26-7.15 (m, 4H), 5.59-5.52 (q, 1H), 4.19 (s, 3H), 3.02-2.95 (m, 1H), 2.86-2.78 (m, 1H), 2.42-2.36 (m, 1H), 2.15-2.10 (m, 1H).

Example Compound S2-3

4-(2,6-Dichloropyridin-4-yl)-N-[(4S)-3,4-dihydro-2H-chromen-4-yl]-1-(propan-2-yl)-1H-indole-2-carboxamide

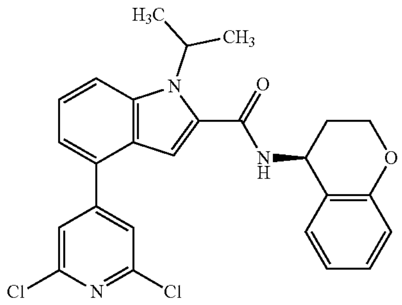 [SMILES: CC(C)n1c(C(=O)N[C@H]2CCOc3ccccc32)cc2c(-c3cc(Cl)nc(Cl)c3)cccc21]

This example was prepared analogously to Example S2-1.

Example Compound S2-4

N-[(4S)-3,4-Dihydro-2H-chromen-4-yl]-1-(propan-2-yl)-4-(2,3,5-trichlorophenyl)-1H-indole-2-carboxamide

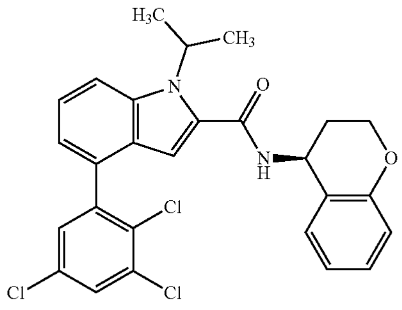 [SMILES: CC(C)n1c(C(=O)N[C@H]2CCOc3ccccc32)cc2c(-c3cc(Cl)cc(Cl)c3Cl)cccc21]

This example was prepared analogously to Example S2-1.

Example Compound S2-5

4-(3,5-Dichlorophenyl)-N-[(4S)-3,4-dihydro-2H-chromen-4-yl]-1-(propan-2-yl)-1H-indole-2-carboxamide

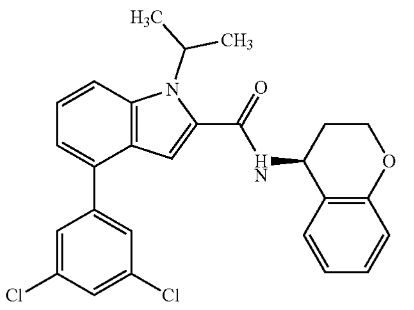 [SMILES: CC(C)n1c(C(=O)N[C@H]2CCOc3ccccc32)cc2c(-c3cc(Cl)cc(Cl)c3)cccc21]

This example was prepared analogously to Example S2-1.

Example Compound S2-6

N-[(4S)-3,4-Dihydro-2H-chromen-4-yl]-1-(propan-2-yl)-4-(2,3,5-trifluorophenyl)-1H-indole-2-carboxamide

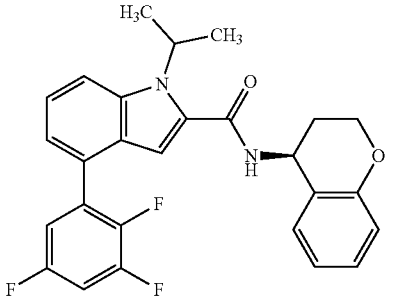 [SMILES: CC(C)n1c(C(=O)N[C@H]2CCOc3ccccc32)cc2c(-c3cc(F)cc(F)c3F)cccc21]

This example was prepared analogously to Example S2-1.

Example Compound S2-7

4-(2,3-Dichlorophenyl)-N-[(4S)-3,4-dihydro-2H-chromen-4-yl]-1-(propan-2-yl)-1H-indole-2-carboxamide

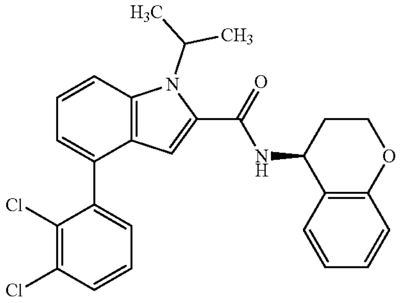 [SMILES: CC(C)n1c(C(=O)N[C@H]2CCOc3ccccc32)cc2c(-c3cccc(Cl)c3Cl)cccc21]

This example was prepared analogously to Example S2-1.

(Target) Example Compounds (S3)

Example Compound S3-1

8-(2,3-Dichlorophenyl)-N-[(4S)-3,4-dihydro-2H-chromen-4-yl]-3-(propan-2-yl)imidazo[1,2-a]pyridine-2-carboxamide

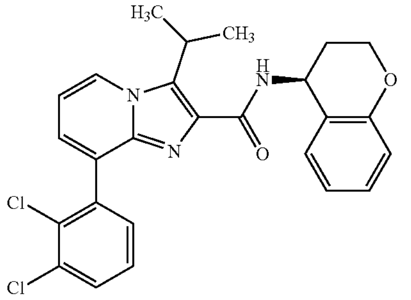 [SMILES: CC(C)c1c(C(=O)N[C@H]2CCOc3ccccc32)nc2c(-c3cccc(Cl)c3Cl)cccn12]

(Target) Example Compounds (S4)

Example Compound S4-1

4-Chloro-1-(2,6-difluorophenyl)-N-[(4S)-3,4-dihydro-2H-chromen-4-yl]-1H-pyrazolo[3,4-b]pyridine-5-carboxamide

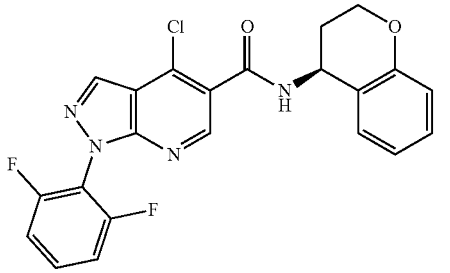 [SMILES: O=C(N[C@H]1CCOc2ccccc21)c1cnc2c(cnn2-c2c(F)cccc2F)c1Cl]

Diethyl cyanophosphonate (69 mg, 0.42 mmol, 0.06 mL) was added to a solution of (S)-chroman-4-amine hydrochloride (72 mg, 0.39 mmol), 4-chloro-1-(2,6-difluorophenyl)-1H-pyrazolo[3,4-b]pyridine-5-carboxylic acid (100 mg, 0.32 mmol) and triethylamine (98 mg, 0.97 mmol, 0.14 mL) in dichloromethane (4.0 mL). The mixture was stirred at room temperature for 16 h. Volatiles were removed in vacuo. Purification by flash column chromatography (Method 6; 24 g; heptane, 0%-50% ethyl acetate) afforded 110 mg (0.25 mmol, 77% of theory) of the title compound.

LC-MS (Method 4): $R_t$=3.92 min; m/z=441 $(M+H)^+$

1H NMR (400 MHz, DMSO-d6) δ 9.21 (d, J=8.1 Hz, 1H), 8.78 (s, 1H), 8.69 (s, 1H), 7.77 (ddd, J=14.9, 8.5, 6.4 Hz, 1H), 7.49 (t, J=8.4 Hz, 2H), 7.36 (d, J=7.2 Hz, 1H), 7.21-7.13 (m, 1H), 6.97-6.88 (m, 1H), 6.80 (d, J=8.1 Hz, 1H), 5.32-5.17 (m, 1H), 4.36-4.16 (m, 2H), 2.21 (ddt, J=13.5, 8.4, 4.3 Hz, 1H), 2.06 (dtd, J=13.5, 6.5, 3.0 Hz, 1H).

Example Compound S4-2

1-(3,5-Dichlorophenyl)-N-[(4S)-3,4-dihydro-2H-chromen-4-yl]-4-(dimethylamino)-3-methyl-1H-pyrazolo[3,4-b]pyridine-5-carboxamide

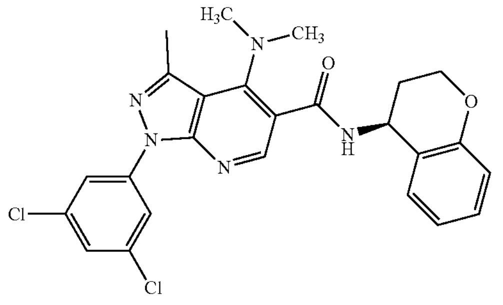 [SMILES: Cc1nn(-c2cc(Cl)cc(Cl)c2)c2ncc(C(=O)N[C@H]3CCOc4ccccc43)c(N(C)C)c12]

Diethyl cyanophosphonate (58 mg, 0.36 mmol, 0.05 mL) was added to a solution of 1-(3,5-dichlorophenyl)-4-(dimethylamino)-3-methyl-1H-pyrazolo[3,4-b]pyridine-5-carboxylic acid (100 mg, 0.27 mmol), triethylamine (83 mg, 0.82 mmol, 0.11 mL) and (S)-chroman-4-amine hydrochloride (61 mg, 0.33 mmol) in dichloromethane (4.0 mL). The mixture was stirred at room temperature for 16 h. A precipitate had formed. The solid was filtered off and dried. 45 mg (0.09 mmol, 33% of theory) of the title compound were obtained.

LC-MS (Method 4): $R_t$=4.58 min; m/z=496/498 $(M+H)^+$

1H NMR (400 MHz, DMSO-d6) δ 9.06 (d, J=8.2 Hz, 1H), 8.42 (d, J=1.8 Hz, 2H), 8.37 (s, 1H), 7.53 (t, J=1.8 Hz, 1H), 7.36 (d, J=7.4 Hz, 1H), 7.23-7.12 (m, 1H), 6.93 (t, J=7.0 Hz, 1H), 6.80 (d, J=8.2 Hz, 1H), 5.21 (q, J=6.1 Hz, 1H), 4.33-4.18 (m, 2H), 3.05 (s, 6H), 2.68 (s, 3H), 2.18 (dd, J=8.9, 4.5 Hz, 1H), 2.03 (dd, J=14.0, 3.3 Hz, 1H).

Example Compound S4-3

1-(2,6-Difluorophenyl)-N-[(4S)-3,4-dihydro-2H-chromen-4-yl]-4-(dimethylamino)-3-methyl-1H-pyrazolo[3,4-b]pyridine-5-carboxamide

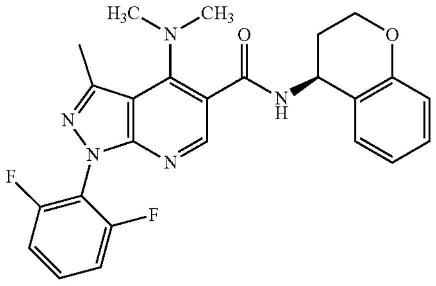 [SMILES: Cc1nn(-c2c(F)cccc2F)c2ncc(C(=O)N[C@H]3CCOc4ccccc43)c(N(C)C)c12]

Diethyl cyanophosphonate (82 mg, 0.50 mmol, 0.08 mL) was added to a solution of (S)-chroman-4-amine hydrochloride (86 mg, 0.46 mmol), 1-(2,6-difluorophenyl)-4-(dimethylamino)-3-methyl-1H-pyrazolo[3,4-b]pyridine-5-carboxylic acid (144 mg, 0.39 mmol; purity 89%) and triethylamine (117 mg, 1.16 mmol, 0.16 mL) in dichloromethane (4.0 mL). The mixture was stirred at room temperature for 16 h and was concentrated in vacuo. Purification by flash column chromatography (Method 6; 24 g; heptane, 0%-50% ethyl acetate) afforded 78 mg (0.16 mmol, 43% of theory of the title compound.

LC-MS (Method 4): $R_t$=3.75 min; m/z=464 $(M+H)^+$

1H NMR (400 MHz, DMSO-d6) δ 8.99 (d, J=8.2 Hz, 1H), 8.16 (s, 1H), 7.67 (ddd, J=14.8, 8.5, 6.4 Hz, 1H), 7.39 (t, J=8.6 Hz, 2H), 7.32 (d, J=7.4 Hz, 1H), 7.19-7.13 (m, 1H), 6.91 (t, J=7.1 Hz, 1H), 6.79 (d, J=8.1 Hz, 1H), 5.25-5.14 (m, 1H), 4.24 (qd, J=12.4, 11.1, 5.3 Hz, 2H), 3.07 (s, 6H), 2.66 (s, 3H), 2.17 (dq, J=9.6, 4.6 Hz, 1H), 2.09-1.93 (m, 1H).

Example Compound S4-4

1-(3,5-Dichlorophenyl)-N-[(4S)-3,4-dihydro-2H-chromen-4-yl]-4-(dimethylamino)-1H-pyrazolo[3,4-b]pyridine-5-carboxamide

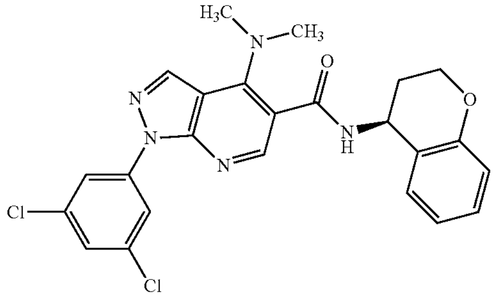 [SMILES: CN(C)c1c(C(=O)N[C@H]2CCOc3ccccc32)cnc2c1cnn2-c1cc(Cl)cc(Cl)c1]

Diethyl cyanophosphonate (103 mg, 0.63 mmol, 0.10 mL) was added to a solution of (S)-chroman-4-amine hydrochloride (108 mg, 0.58 mmol), 1-(3,5-dichlorophenyl)-4-(dimethylamino)-1H-pyrazolo[3,4-b]pyridine-5-carboxylic acid (170 mg, 0.48 mmol) and triethylamine (147 mg, 1.45 mmol, 0.20 mL) in dichloromethane (4.0 mL). The mixture was stirred at room temperature for 16 h and was concentrated in vacuo. The residue was triturated in dichloromethane. The solid was filtered off and dried. 145 mg (0.30 mmol, 62% of theory) of the title compound were obtained.

LC-MS (Method 4): $R_t$=4.54 min; m/z=482/484 $(M+H)^+$

1H NMR (400 MHz, DMSO-d6) δ 8.98 (d, J=8.2 Hz, 1H), 8.62 (s, 1H), 8.46 (d, J=1.9 Hz, 2H), 8.28 (s, 1H), 7.54 (t, J=1.9 Hz, 1H), 7.33 (d, J=7.3 Hz, 1H), 7.22-7.11 (m, 1H), 6.96-6.87 (m, 1H), 6.80 (d, J=8.2 Hz, 1H), 5.25-5.14 (m, 1H), 4.25 (q, J=7.9, 6.2 Hz, 2H), 3.27 (s, 6H), 2.24-2.10 (m, 1H), 2.02 (dq, J=13.8, 5.3, 4.8 Hz, 1H).

Example Compound S4-5

1-(2,6-Difluorophenyl)-N-[(4S)-3,4-dihydro-2H-chromen-4-yl]-4-(dimethylamino)-1H-pyrazolo [3,4-b]pyridine-5-carboxamide

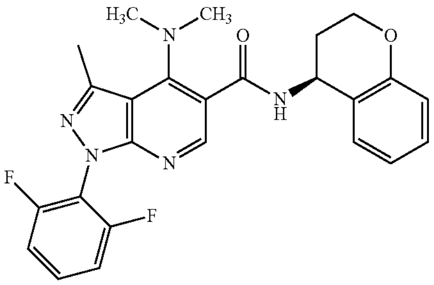 [SMILES: Cc1nn(-c2c(F)cccc2F)c2ncc(C(=O)N[C@H]3CCOc4ccccc43)c(N(C)C)c12]

Diethyl cyanophosphonate (79 mg, 0.48 mmol, 0.07 mL) was added to a solution of (S)-chroman-4-amine hydrochloride (83 mg, 0.45 mmol), 1-(2,6-difluorophenyl)-4-(dimethylamino)-1H-pyrazolo[3,4-b]pyridine-5-carboxylic acid (118 mg, 0.37 mmol) and triethylamine (113 mg, 1.11 mmol, 0.16 mL) in dichloromethane (4.0 mL). The mixture was stirred for 16 h at room temperature and was concentrated in vacuo. Purification by flash column chromatography (Method 6; 24 g; heptane, 0%-50% ethyl acetate) and preparative HPLC (Method 10) afforded 45 mg (0.10 mmol, 27% of theory) of the title compound.

LC-MS (Method 4): $R_t$=3.60 min; m/z=450 $(M+H)^+$

Example Compound S4-6

1-(4-Chlorophenyl)-N-[(1S)-2,3-dihydro-1H-inden-1-yl]-4-(propan-2-yl)-1H-benzotriazole-5-carboxamide

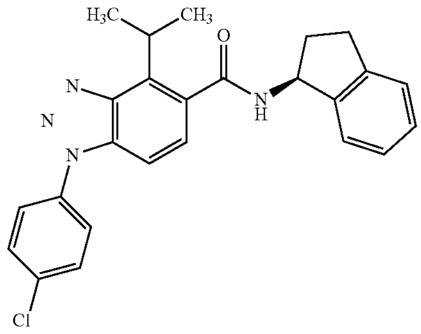

Example Compound S4-7

N-[(1S)-2,3-Dihydro-1H-inden-1-yl]-1-phenyl-4-(propan-2-yl)-1H-benzotriazole-5-carboxamide

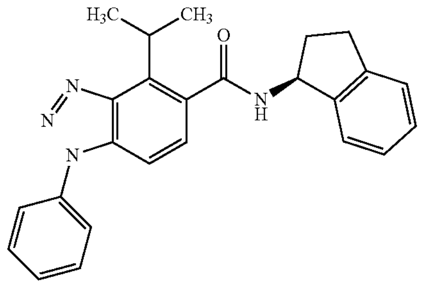 [SMILES: CC(C)c1c(C(=O)N[C@H]2CCc3ccccc32)ccc(Nc2ccccc2)c1N=N]

Example Compound S4-8

1-(3-Chlorophenyl)-N-[(1S)-2,3-dihydro-1H-inden-1-yl]-4-(propan-2-yl)-1H-benzotriazole-5-carboxamide

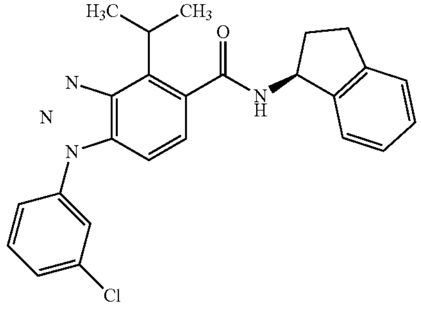

Example Compound S4-9

N-[(1S)-2,3-Dihydro-1H-inden-1-yl]-4-(propan-2-yl)-1-[3-(trifluoromethyl)phenyl]-1H-benzotriazole-5-carboxamide

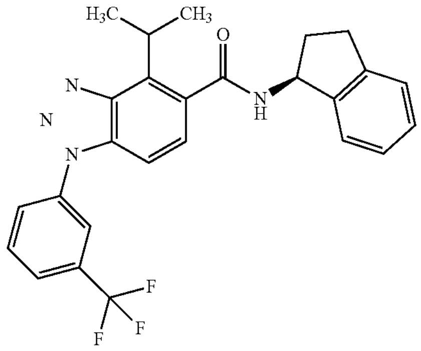

Example Compound S4-10

1-(2-Chlorophenyl)-N-[(1S)-2,3-dihydro-1H-inden-1-yl]-4-(propan-2-yl)-1H-benzotriazole-5-carboxamide

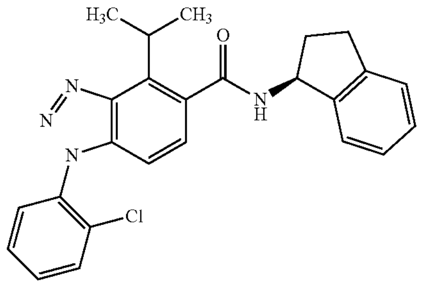 [SMILES: CC(C)c1c(C(=O)N[C@H]2CCc3ccccc32)ccc(Nc2ccccc2Cl)c1N=N]

(Target) Example Compounds (S5)

Example Compound S5-1

3-(3,5-Dichlorophenyl)-N-[(4S)-3,4-dihydro-2H-chromen-4-yl]-7-(dimethylamino)-1-methyl-2-oxo-2,3-dihydro-1H-imidazo[4,5-b]pyridine-6-carboxamide

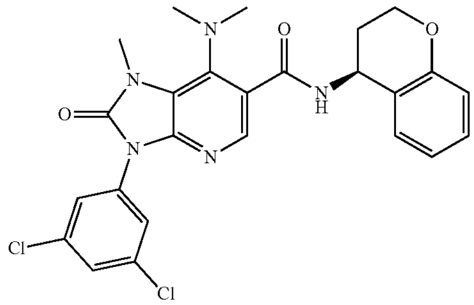 [SMILES: CN(C)c1c(C(=O)N[C@H]2CCOc3ccccc32)cnc2c1n(C)c(=O)n2-c1cc(Cl)cc(Cl)c1]

LC-MS (Method 15): $R_t$=1.04 min; MS (ESIpos): m/z=512 $[M+H]^+$

1H NMR (peaklist): (400 MHz, DMSO-d6) δ[ppm]: −0.008 (3.14), 0.008 (1.66), 2.523 (1.06), 2.807 (16.00), 3.586 (7.10), 4.099 (0.52), 4.107 (0.42), 4.124 (0.62), 4.149 (0.43), 4.767 (0.48), 4.786 (0.47), 5.754 (0.50), 6.743 (0.83), 6.761 (0.90), 6.872 (0.89), 6.890 (0.55), 7.053 (0.80), 7.072 (0.64), 7.120 (0.46), 7.140 (0.72), 7.407 (1.44), 7.703 (0.75), 7.707 (1.30), 7.712 (0.68), 8.055 (2.97), 8.873 (0.76), 8.893 (0.73).

(Target) Example Compounds (S6)

Example Compound S6-1

5-(2,3-Dichlorophenyl)-N-[(4S)-3,4-dihydro-2H-chromen-4-yl]naphthalene-2-carboxamide

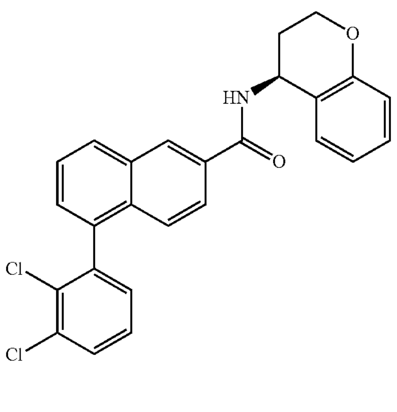 [SMILES: O=C(N[C@H]1CCOc2ccccc21)c1ccc2c(-c3cccc(Cl)c3Cl)cccc2c1]

Example Compound S6-2

1-(2,3-Dichlorophenyl)-N-[(4S)-3,4-dihydro-2H-chromen-4-yl]isoquinoline-6-carboxamide

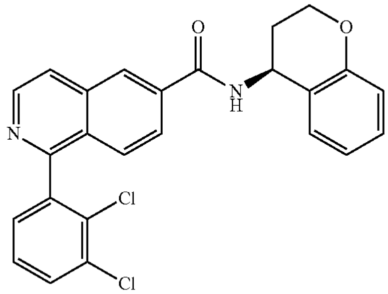 [SMILES: O=C(N[C@H]1CCOc2ccccc21)c1ccc2c(-c3cccc(Cl)c3Cl)nccc2c1]

(Target) Example Compounds (S7)

Example Compound S7-1

8-(3,5-Dichlorophenyl)-N-[(4S)-3,4-dihydro-2H-chromen-4-yl]-7-oxo-7,8-dihydro-1,8-naphthyridine-3-carboxamide

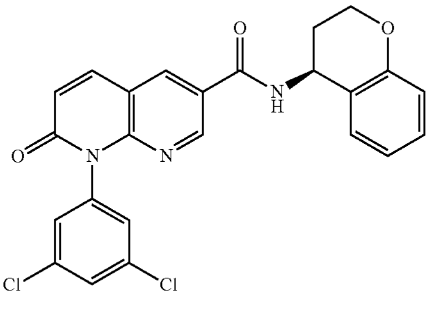 [SMILES: O=C(N[C@H]1CCOc2ccccc21)c1cnc2c(ccc(=O)n2-c2cc(Cl)cc(Cl)c2)c1]

LC-MS (Method 15): $R_t$=1.03 min; MS (ESIpos): m/z=466 $[M+H]^+$ $^1$H-NMR (400 MHz, DMSO-$d_6$): δ [ppm]=9.05 (d, 1H), 8.86 (d, 1H), 8.71 (d, 1H), 8.14 (d, 1H), 7.75 (t, 1H), 7.56 (d, 2H), 7.22-7.14 (m, 2H), 6.90-6.79 (m, 3H), 5.29 (q, 1H), 4.33-4.22 (m, 2H), 2.19-2.00 (m, 2H)

Example Compound S7-2

1-(4-Chlorobenzyl)-N-[(4S)-3,4-dihydro-2H-chromen-4-yl]-5-(dimethylamino)-2-oxo-1,2-dihydro 1,7-naphthyridine-6-carboxamide

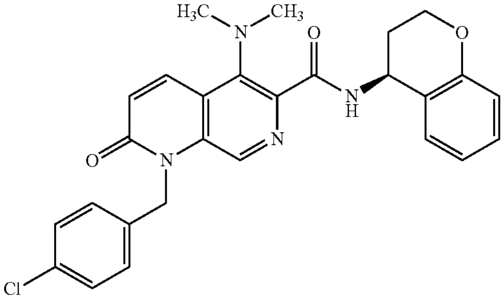 [SMILES: CN(C)c1c(C(=O)N[C@H]2CCOc3ccccc32)ncc2c1ccc(=O)n2Cc1ccc(Cl)cc1]

(Target) Example Compounds (S8)

Example Compound S8a-1

8-(3,5-Dichlorophenyl)-N-[(4S)-3,4-dihydro-2H-chromen-4-yl]-4-(propan-2-yl)-2H-chromene-3-carboxamide

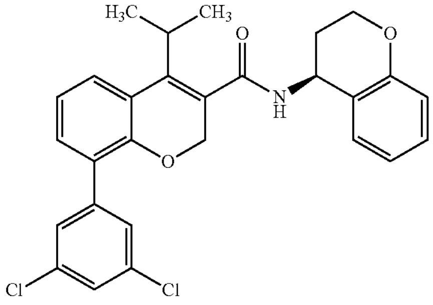 [SMILES: CC(C)C1=C(C(=O)N[C@H]2CCOc3ccccc32)COc2c1cccc2-c1cc(Cl)cc(Cl)c1]

Example Compound S8a-2

8-(3,5-Dichlorophenyl)-N-[(4S)-3,4-dihydro-2H-chromen-4-yl]-2-oxo-4-(propan-2-yl)-2H-chromene-3-carboxamide

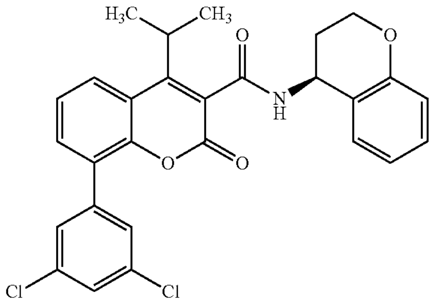 [SMILES: CC(C)c1c(C(=O)N[C@H]2CCOc3ccccc32)c(=O)oc2c(-c3cc(Cl)cc(Cl)c3)cccc12]

To a mixture of crude lithium 8-(3,5-dichlorophenyl)-4-isopropyl-2-oxo-2H-chromene-3-carboxylate (303 mg, 0.79 mmol) in dry N,N-dimethylformamide (10 mL) were added triethylamine (0.6 mL, 4.75 mmol) and 1-[bis(dimethylamino)methylene]-1H-1,2,3-triazolo[4,5-b]pyridinium 3-oxid hexafluorophosphate (663 mg, 1.74 mmol). After stirring for 30 min, (S)-chroman-4-amine hydrochloride (323 mg, 1.74 mmol) was added. The reaction mixture was stirred for 1.5 h and water was added. The resulting precipitate was filtered off, washed with water and dried on air. Purification by flash column chromatography (Method 6; 24 g; heptane, 2%-100% ethyl acetate) afforded 125 mg (0.25 mmol; 31% of theory) of the title compound.

LC-MS (Method 4): $R_t$=4.18 min; m/z=506/508 $(M-H)^-$

1H NMR (400 MHz, DMSO-d6) δ 8.93 (d, J=8.2 Hz, 1H), 8.13 (d, J=8.0 Hz, 1H), 7.72 (m, 2H), 7.63 (d, J=1.9 Hz, 2H), 7.48 (t, J=7.8 Hz, 1H), 7.33 (d, J=7.5 Hz, 1H), 7.19-7.11 (m, 1H), 6.90 (t, J=7.4 Hz, 1H), 6.78 (d, J=8.2 Hz, 1H), 5.18 (q, J=6.3 Hz, 1H), 4.23 (m, 2H), 3.53-3.38 (m, 1H), 2.21-2.09 (m, 1H), 2.02-1.92 (m, 1H), 1.45 (t, J=7.6 Hz, 6H).

Example Compound S8a-3

8-(2,3-Dichlorophenyl)-N-[(4S)-3,4-dihydro-2H-chromen-4-yl]-2-oxo-2H-chromene-3-carboxamide

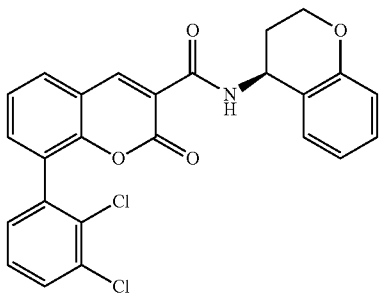 [SMILES: O=C(N[C@H]1CCOc2ccccc21)c1cc2cccc(-c3cccc(Cl)c3Cl)c2oc1=O]

Step 1: Ethyl 8-bromo-2-oxo-2H-chromene-3-carboxylate

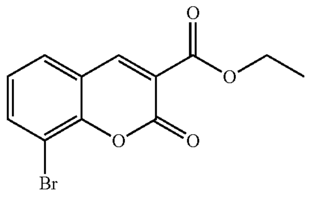 [SMILES: CCOC(=O)c1cc2cccc(Br)c2oc1=O]

To a solution of 3-bromo-2-hydroxybenzaldehyde (1.00 g, 5.0 mmol) in ethanol (15 mL) were added diethyl malonate (1.20 g, 7.5 mmol) and piperidine (85 mg, 1.0 mmol). The resulting mixture was stirred at 80° C. for 6 hours. After cooled to room temperature, the solvent was removed in vacuo and ethyl acetate was added, the resulting mixture was washed with water, dried over anhydrous sodium sulfate and evaporated to dryness. The residue was purified with silica gel column chromatography (petroleum ether/ethyl acetate=3:1) to give 700 mg (34%) of the product as a white solid.

LC-MS (Analytical Method A, 0.01-2.00 min 5-95% B): $R_t$=1.06 min; MS (ESIpos): m/z=297 $(M+H)^+$ Step 2: 8-Bromo-2-oxo-2H-chromene-3-carboxylic acid

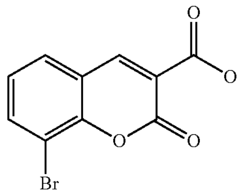 [SMILES: O=C(O)c1cc2cccc(Br)c2oc1=O]

To a solution of ethyl 8-bromo-2-oxo-2H-chromene-3-carboxylate (650 mg, 2.2 mmol) in tetrahydrofuran (13 mL) was added sodium hydroxide (170 mg, 4.4 mmol, in 7 mL of water). The resulting mixture was stirred at room temperature for overnight. Upon completion of the reaction, the solvent was removed in vacuo. Water was added and then diluted hydrochloric acid (1 N) was added to adjust pH to 1, the precipitated solid was collected by filtration and dried to afford 540 mg (92%) of the product as an off-white solid.

LC-MS (Analytical Method A, 0.01-2.00 min 5-95% B): $R_t$=0.76 min; MS (ESIpos): m/z=269 $(M+H)^+$ Step 3: 8-Bromo-N-[(4S)-3,4-dihydro-2H-chromen-4-yl]-2-oxo-2H-chromene-3-carboxamide

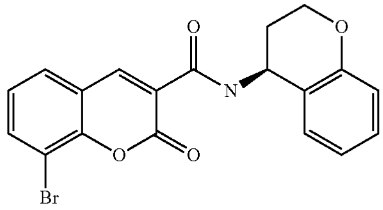 [SMILES: O=C(N[C@H]1CCOc2ccccc21)c1cc2cccc(Br)c2oc1=O]

To a solution of 8-bromo-2-oxo-2H-chromene-3-carboxylic acid (250 mg, 0.93 mmol) in N,N-dimethylformamide (5 mL) were added HATU (530 mg, 1.4 mmol), N,N-diisopropylethylamine (360 mg, 2.8 mmol) and (S)-chroman-4-amine (166 mg, 1.1 mmol), the resulting mixture was stirred at room temperature for 1 hour. Upon completion of the reaction, the water was added and the precipitated solid was collected by filtration, washed with water, dried in vacuo to give 200 mg (50%) of the product as a yellow solid.

LC-MS (Analytical Method E, 0.01-2.00 min 5-95% B): $R_t$=1.20 min; MS (ESIpos): m/z=400 $(M+H)^+$ Step 4: 8-(2,3-Dichlorophenyl)-N-[(4S)-3,4-dihydro-2H-chromen-4-yl]-2-oxo-2H-chromene-3-carboxamide

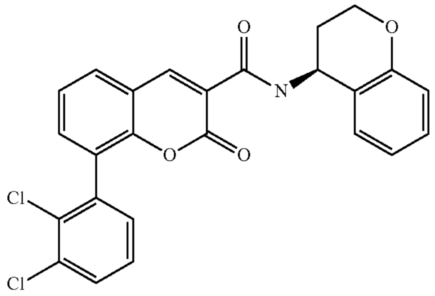 [SMILES: O=C(N[C@H]1CCOc2ccccc21)c1cc2cccc(-c3cccc(Cl)c3Cl)c2oc1=O]

To a solution of (S)-8-bromo-N-(chroman-4-yl)-2-oxo-2H-chromene-3-carboxamide (100 mg, 0.3 mmol) in a mixture solvent of tetrahydrofuran/water (v:v 4:1, 2.5 mL) were added 2,3-dichlorophenylboronic acid (48 mg, 0.3 mmol), tris(dibenzylideneacetone)dipalladium chloroform complex (13 mg, 0.01 mmol), tri-tert-butylphosphine tetrafluoroborate (7 mg, 0.02 mmol) and potassium fluoride (44 mg, 0.8 mmol). The resulting mixture was stirred at 60° C. for overnight under nitrogen atmosphere. After cooled to room temperature, the water was added and the resulting mixture was extracted with ethyl acetate, the combined organic phase was washed with water, dried over anhydrous sodium sulfate and evaporated to dryness. The residue was purified with silica gel column chromatography (petroleum ether/ethyl acetate=3:1) and prep-HPLC [Column: Xbridge Prep C18, 5 um, 19*150 mm; Mobile Phase A: Waters (0.1% FA), Mobile Phase B: Acetonitrile; Gradient: 65% B to 95% B in 8 min;] to give 50.9 mg (43%) of the product as a white solid.

$^1$H-NMR (400 MHz, DMSO-$d_6$): δ [ppm]=2.07-2.08 (m, 1H), 2.17-2.19 (m, 1H), 4.18-4.20 (m, 1H), 4.25-4.28 (m, 1H), 5.22 (q, 1H), 6.79 (d, 1H), 6.89 (t, 1H), 7.18 (t, 1H), 7.24-7.27 (m, 1H), 7.45-7.58 (m, 3H), 7.71 (d, 1H), 7.79 (d, 1H), 8.10 (d, 1H), 8.87 (d, 1H), 8.93 (s, 1H).

LC-MS (Analytical Method C, 0.01-3.00 min 5-95% B): $R_t$=2.05 min; MS (ESIpos): m/z=466 $(M+H)^+$ Example Compound S8a-4

8-(3,5-Dichlorophenyl)-N-[(4S)-3,4-dihydro-2H-chromen-4-yl]-2H-chromene-3-carboxamide

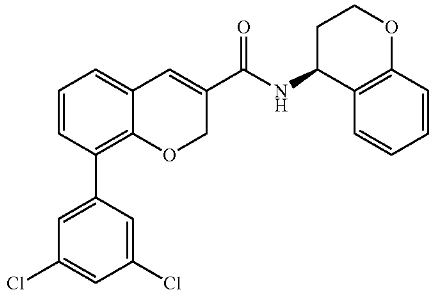 [SMILES: O=C(N[C@H]1CCOc2ccccc21)C1=Cc2cccc(-c3cc(Cl)cc(Cl)c3)c2OC1]

To a solution of (S)-8-bromo-N-(chroman-4-yl)-2H-chromene-3-carboxamide (100 mg, 0.3 mmol) [described for example S8a-5, step 1-4] in a mixture solvent of tetrahydrofuran/water (v:v=4:1, 2.5 mL) were added 3,5-dichlorophenylboronic acid (50 mg, 0.3 mmol), tris(dibenzylideneacetone)dipalladium chloroform complex (13 mg, 0.01 mmol), tri-tert-butylphosphine tetrafluoroborate (8 mg, 0.01 mmol) and potassium fluoride (45 mg, 0.8 mmol). The resulting mixture was stirred at 60° C. for overnight under nitrogen atmosphere. After cooled to room temperature, the solvent was evaporated and the residue was re-dissolved in ethyl acetate. The mixture was washed with water, dried over anhydrous sodium sulfate and evaporated to dryness. The residue was purified with silica gel column chromatography (petroleum ether/ethyl acetate=3:1) and prep-HPLC [Column: Kinetex 5 um EVO C18 OBD, 21.2*150 mm, 5 um; Mobile Phase A: Water (0.1% FA), Mobile Phase B: Acetonitrile; Gradient: 10% B to 50% B in 10 min] to give 53.8 mg (46%) of the product as a white solid. MS (ESIpos): m/z=452 $(M+H)^+$.

$^1$H-NMR (400 MHz, DMSO-$d_6$): δ [ppm]=1.96-2.02 (m, 2H), 4.18-4.31 (m, 2H), 5.00 (s, 2H), 5.17 (q, 1H), 6.80 (d, 1H), 6.89 (t, 1H), 7.07 (t, 1H), 7.15-7.17 (m, 2H), 7.27 (d, 1H), 7.35-7.41 (m, 2H), 7.58-7.61 (m, 3H), 8.64 (d, 1H).

LC-MS (Analytical Method C, 0.01-3.00 min 5-95% B): $R_t$=1.95 min; MS (ESIpos): m/z=452 $(M+H)^+$ Example Compound S8a-5

8-(2,3-Dichlorophenyl)-N-[(4S)-3,4-dihydro-2H-chromen-4-yl]-2H-chromene-3-carboxamide

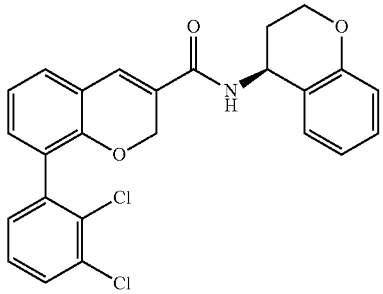 [SMILES: O=C(N[C@H]1CCOc2ccccc21)C1=Cc2cccc(-c3cccc(Cl)c3Cl)c2OC1]

Step 1: Tert-butyl 2-((3-bromo-2-hydroxyphenyl)(hydroxyl)methyl)acrylate

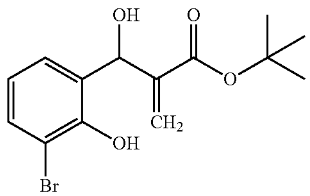 [SMILES: C=C(C(=O)OC(C)(C)C)C(O)c1cccc(Br)c1O]

A mixture of 3-bromo-2-hydroxybenzaldehyde (5.00 g, 24.9 mmol), tert-butyl propenoate (15.94 g, 124.4 mmol) and 1,4-diazabicyclo(2.2.2)octane (0.56 g, 5.0 mmol) were stirred at 65° C. for 2 days. Upon completion of the reaction, the tert-butyl propenoate was removed in vacuo. Water was added and the resulting mixture was extracted with ethyl acetate, the combined organic phase was dried over anhydrous sodium sulfate. The residue was purified with silica gel column chromatography (petroleum ether/ethyl acetate=2:1) to give 3.00 g (37%) of the product as a yellow oil.

LC-MS (Analytical Method A, 0.01-1.80 min 5-95% B): $R_t$=0.94 min; MS (ESIpos): m/z=329 $(M+H)^+$ Step 2: Tert-butyl 8-bromo-2H-chromene-3-carboxylate

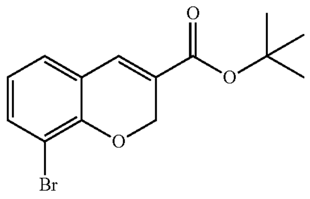 [SMILES: CC(C)(C)OC(=O)C1=Cc2cccc(Br)c2OC1]

To a solution of tert-butyl 2-((3-bromo-2-hydroxyphenyl)(hydroxyl)methyl)acrylate (2.30 g, 7.00 mmol) in a mixture solvent of tetrahydrofuran/water (v:v=1:2, 30 mL) was added potassium hydroxide (392 mg, 7.0 mmol) and the resulting mixture was stirred at reflux for 5 hours. After cooled to room temperature, the solvent was removed in vacuo. Water was added and the resulting mixture was extracted with ethyl acetate and the combined organic phase was dried over anhydrous sodium sulfate. The residue was purified with silica gel column chromatography (petroleum ether/ethyl acetate=10:1). The collected fraction was concentrated to give 400 mg (18%) of the product as colorless oil.

$^1$H-NMR (400 MHz, DMSO-$d_6$): δ [ppm]=1.50 (d, 9H), 5.01 (s, 2H), 6.91 (t, 1H), 7.36 (d, 1H), 7.40 (s, 1H), 7.53 (d, 1H).

Step 3: 8-Bromo-2H-chromene-3-carboxylic acid

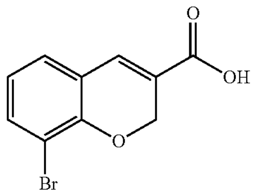 [SMILES: O=C(O)C1=Cc2cccc(Br)c2OC1]

To a solution of tert-butyl 8-bromo-2H-chromene-3-carboxylate (850 mg, 2.7 mmol) in dichloromethane (20 mL) was added trifluoroacetic acid (5 mL) and the resulting mixture was stirred at room temperature for 3 hours. Upon completion of the reaction, the solvent was removed in vacuo. Water was added and saturated sodium bicarbonate solution was added to adjust the pH to 7. The resulting mixture was extracted with dichloromethane; the combined organic phase was dried over anhydrous sodium sulfate and concentrated in vacuo to give 600 mg (85%) of the product as a yellow solid.

LC-MS (Analytical Method A, 0.01-2.00 min 5-95% B): $R_t$=0.90 min; MS (ESIpos): m/z=255 $(M+H)^+$ Step 4: 8-Bromo-N-[(4S)-3,4-dihydro-2H-chromen-4-yl]-2H-chromene-3-carboxamide

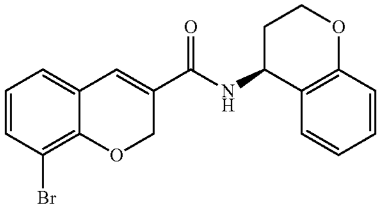 [SMILES: O=C(N[C@H]1CCOc2ccccc21)C1=Cc2cccc(Br)c2OC1]

To a solution of 8-bromo-2H-chromene-3-carboxylic acid (600 mg, 2.4 mmol) in N,N-dimethylformamide (10 mL) were added HATU (1.34 g, 3.53 mmol), N,N-diisopropylethylamine (912 mg, 7.1 mmol) and (S)-chroman-4-amine (421 mg, 2.8 mmol). The resulting mixture was stirred at room temperature for 1 hour. Upon completion of the reaction, the brine solution was added to quench the reaction. The precipitated solid was collected by filtration, washed with water, dried in vacuum to give 500 mg (55%) of the product as a yellow solid.

LC-MS (Analytical Method E, 0.01-2.00 min 5-95% B): $R_t$=1.21 min; MS (ESIpos): m/z=386 $(M+H)^+$ Step 5: 8-(2,3-Dichlorophenyl)-N-[(4S)-3,4-dihydro-2H-chromen-4-yl]-2H-chromene-3-carboxamide

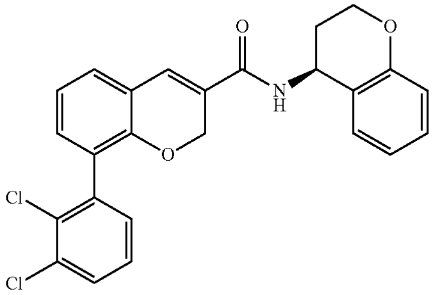 [SMILES: O=C(N[C@H]1CCOc2ccccc21)C1=Cc2cccc(-c3cccc(Cl)c3Cl)c2OC1]

To a solution of (S)-8-bromo-N-(chroman-4-yl)-2H-chromene-3-carboxamide (100 mg, 0.3 mmol) in a mixture solvent of tetrahydrofuran/water (v:v=4:1, 2.5 mL) were added 2,3-dichlorophenylboronic acid (50 mg, 0.3 mmol), tris(dibenzylideneacetone)dipalladium chloroform complex (13 mg, 0.01 mmol), tri-tert-butylphosphine tetrafluoroborate (8 mg, 0.01 mmol) and potassium fluoride (45 mg, 0.8 mmol). The resulting mixture was stirred at 60° C. for overnight under nitrogen atmosphere. After cooled to room temperature, the solvent was evaporated and the residue was re-dissolved in ethyl acetate. The mixture was washed with water, dried over anhydrous sodium sulfate and evaporated to dryness. The residue was purified with silica gel column chromatography (petroleum ether/ethyl acetate=3:1) and prep-HPLC [Column: Kinetex 5 um EVO C18 OBD, 21.2*150 mm, 5 um; Mobile Phase A: Water (0.1% FA), Mobile Phase B: Acetonitrile; Gradient: 10% B to 60% B in 12 min] to give 54.6 mg (46%) of the product as a white solid.

$^1$H-NMR (400 MHz, DMSO-$d_6$): δ [ppm]=1.96-2.08 (m, 2H), 4.22-4.29 (m, 2H), 4.93 (s, 2H), 5.15 (q, 1H), 6.80 (d, 1H), 6.86-6.90 (m, 1H), 7.05 (t, 1H), 7.14-7.18 (m, 3H), 7.28 (d, 1H), 7.33 (d, 1H), 7.40-7.44 (m, 2H), 7.67 (d, 1H), 8.64 (d, 1H).

LC-MS (Analytical Method C, 0.01-3.00 min 5-95% B): $R_t$=1.95 min; MS (ESIpos): m/z=452 $(M+H)^+$ Example Compound S8a-6

8-(3,5-Dichlorophenyl)-N-[(4S)-3,4-dihydro-2H-chromen-4-yl]-4-(morpholin-4-yl)-2-oxo-1,2-dihydroquinoline-3-carboxamide

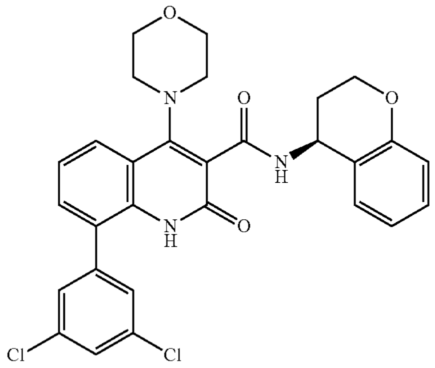 [SMILES: O=C(N[C@H]1CCOc2ccccc21)c1c(N2CCOCC2)c2cccc(-c3cc(Cl)cc(Cl)c3)c2[nH]c1=O]

Example Compound S8b-1

8-(3,5-Dichlorophenyl)-N-[(1S)-2,3-dihydro-1H-inden-1-yl]-2,4-dimethyl-4H-chromene-3-carboxamide

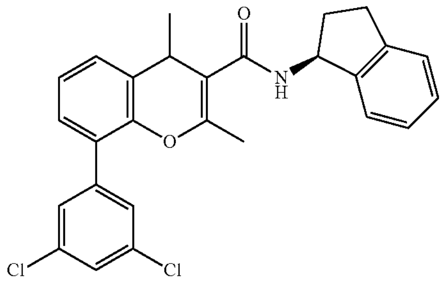 [SMILES: CC1=C(C(=O)N[C@H]2CCc3ccccc32)C(C)c2cccc(-c3cc(Cl)cc(Cl)c3)c2O1]

Step 1: 2-Bromo-6-(1-hydroxyethyl)phenol

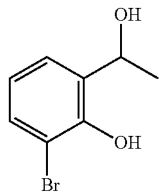

To a cold solution of 3-bromo-2-hydroxybenzaldehyde (30.0 g, 150.0 mmol, 1.0 eq) in anhydrous diethyl ether (300 mL) was added methyl magnesium bromide solution (3M in diethyl ether, 150 mL, 450 mmol, 3.0 eq) dropwise at 0° C. under nitrogen atmosphere. The resulting reaction mixture was allowed to attain ambient temperature for 2 h. The progress of the reaction was monitored by TLC. The reaction mixture was cooled to 0° C. and quenched with 1M HCl. The organic layer was separated and the aqueous layer was extracted with ethyl acetate. The combined organic layers were dried over sodium sulfate and concentrated under reduced pressure to afford the crude product which was purified by flash column chromatography (100-200 Silica gel, 50% EtOAc-Hexane) to afford pure 2-bromo-6-(1-hydroxyethyl)phenol (24.0 g, 74% of theory) as an off white solid.

TLC system: 30% EtOAc in petrol ether

1H-NMR (400 MHz, $CDCl_3$) δ 7.61 (broad, 1H), 7.40-7.37 (m, 1H), 7.05-7.03 (m, 1H), 6.76-6.72 (m, 1H), 5.08-5.05 (m, 1H), 3.00 (broad, 1H), 1.54-1.52 (d, 3H).

$R_f$ value: 0.9

Step 2: Ethyl 8-bromo-2-hydroxy-2,4-dimethylchromane-3-carboxylate

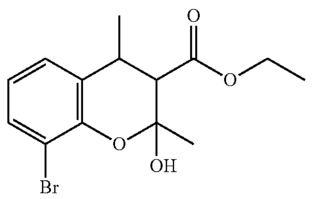 [SMILES: CCOC(=O)C1C(C)c2cccc(Br)c2OC1(C)O]

To a stirred solution of 2-bromo-6-(1-hydroxyethyl)phenol (1.0 g, 4.61 mmol, 1.0 eq) in dichloroethane (15 mL) was added 4 A molecular sieves (4.60 g), anhydrous $FeCl_3$ (0.037 g, 0.23 mmol) followed by ethyl acetoacetate (1.20 g, 9.25 mmol) at room temperature under nitrogen atmosphere and the resulting solution was irradiated under microwave at 60° C. for 1.30 h. The progress of the reaction was monitored by TLC. After completion the reaction mixture was filtered through a pad of Celite and washed thoroughly with dichloromethane. The filtrate was washed with saturated $NaHCO_3$ solution and brine, dried over $Na_2SO_4$ and concentrated to give the crude compound which was purified by flash chromatography (20% EtOAc-hexane) to afford pure ethyl 8-bromo-2-hydroxy-2,4-dimethylchromane-3-carboxylate (1.40 g, 92.3% of theory) as a thick yellow liquid.

TLC system: 50% EtOAc in petrol ether $R_f$ value: 0.3

Step 3: Ethyl 8-bromo-2,4-dimethyl-4H-chromene-3-carboxylate

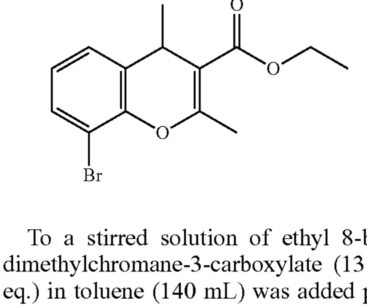

To a stirred solution of ethyl 8-bromo-2-hydroxy-2,4-dimethylchromane-3-carboxylate (13.8 g, 41.9 mmol, 1.0 eq.) in toluene (140 mL) was added p-toluenesulfonic acid (7.2 g, 41.9 mmol, 1.0 eq) and the resulting reaction mixture was refluxed for 1 h. The progress of reaction was monitored by TLC. The reaction mixture was diluted with ethyl acetate and washed successively with saturated $NaHCO_3$ and brine solution. The organic layer was dried over sodium sulfate, concentrated under reduced pressure to afford crude compound which was further purified by flash column chromatography (Silica gel, 50% EtOAc/hexanes) to afford pure ethyl 8-bromo-2,4-dimethyl-4H-chromene-3-carboxylate as an off-white solid (9.0 g, 68% of theory).

TLC system: 50% EtOAc in petroleum ether

1H-NMR (400 MHz, $CDCl_3$) δ 7.61 (broad, 1H), 7.40-7.38 (m, 1H), 7.10-7.08 (m, 1H), 6.96-6.92 (m, 1H), 4.25 (m, 2H), 3.89 (q, 1H), 2.45 (s, 3H), 1.36-1.34 (t, 3H), 1.28-1.26 (d, 3H).

$R_f$ value: 0.8

Step 4: 8-Bromo-2,4-dimethyl-4H-chromene-3-carboxylic acid

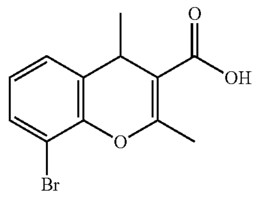 [SMILES: CC1=C(C(=O)O)C(C)c2cccc(Br)c2O1]

To a stirred solution of ethyl 8-bromo-2,4-dimethyl-4H-chromene-3-carboxylate (9.0 g, 29.0 mmol) in EtOH (90 mL) was added $LiOH.H_2O$ (2.3 g, 58 mmol,) in water (40 mL) and the resulting reaction mixture was refluxed for 4 h. The progress of reaction was monitored by TLC. The volatiles were removed under reduced pressure and the obtained crude was poured into cold water and washed with dichloromethane. The aqueous layer was acidified (pH=2) with 2N aq.HCl and extracted with 10% MeOH—$CH_2Cl_2$ (3×50 mL). The combined organic layer was dried over sodium sulfate, concentrated under reduced pressure to afford crude compound which was further purified by trituration with 10% EtOAc/diethylether to afford 8-bromo-2,4-dimethyl-4H-chromene-3-carboxylic acid as an off-white solid (5.25 g, 64.1% of theory). Purity: 99.6%

LC-MS (Method 14): $R_t$=2.20 min;

TLC system: 10% MeOH—$CH_2Cl_2$ $^1$H-NMR (400 MHz, DMSO-d6) δ 7.51-7.49 (m, 1H), 7.31-7.29 (m, 1H), 7.09-7.05 (m, 1H), 3.83 (q, 1H), 2.37 (s, 3H), 1.22-1.20 (d, 3H).

$R_f$ value: 0.1

LC-MS method

Mobile phase-A: 10 mM Ammonium Formate in Water

Mobile phase-B: ACN

Column—Xbridge BEH C18 2.5 μm, 2.1×50 mm

Flow—0.7 mL/min, Temp: 40° C.

Time (min) and % B: 0-5; 3.0-100; 3.5-100; 3.8-5; 4.3-5.

Gas flow 1.6 SLM

Evaporator temperature 40° C.

Step 5: 8-Bromo-N-[(1S)-2,3-dihydro-1H-inden-1-yl]-2,4-dimethyl-4H-chromene-3-carboxamide

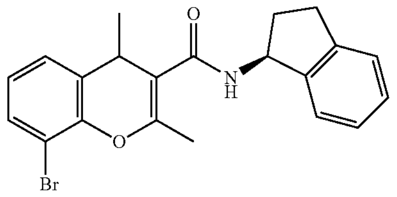 [SMILES: CC1=C(C(=O)N[C@H]2CCc3ccccc32)C(C)c2cccc(Br)c2O1]

To a suspension of 8-bromo-2,4-dimethyl-4H-chromene-3-carboxylic acid (949 mg, 3.35 mmol) in dry toluene (15 mL) was added 2 drops of DMF. Then thionyl chloride (450 mg, 3.78 mmol) was added dropwise within 2 minutes. After stirring for 4 h at 70° C. the mixture was cooled to room temperature, and after adding (1S)-indan-1-amine hydrochloride (460 mg, 3.45 mmol) and N,N-diisopropylethylamine (950 mg, 7.35 mmol) stirring was continued for 18 hours at 40° C.

Solvents were removed under reduced pressure and the residue was partitioned between water (50 mL) and dichloromethane (50 mL). The combined organic layers were dried and removed under reduced pressure, leaving 924 mg (59% of theory) of the title compound.

LC-MS3—Index=1033; m/z=397.1; 399.1 $(M+H)^+$ $^1$H-NMR (400 MHz, DMSO-d6) δ 8.44-8.40 (m, 1H), 7.48-7.45 (m, 1H), 7.29-7.20 (m, 5H), 7.03-6.99 (m, 1H), 5.46-5.42 (m, 1H), 3.86-1.23 (m, 11H).

Step 6: 8-(3,5-Dichlorophenyl)-N-[(1S)-2,3-dihydro-1H-inden-1-yl]-2,4-dimethyl-4H-chromene-3-carboxamide

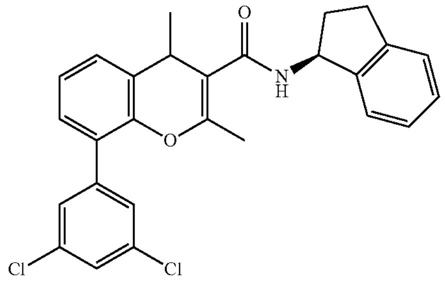 [SMILES: CC1=C(C(=O)N[C@H]2CCc3ccccc32)C(C)c2cccc(-c3cc(Cl)cc(Cl)c3)c2O1]

A mixture of 8-Bromo-N-[(1S)-2,3-dihydro-1H-inden-1-yl]-2,4-dimethyl-4H-chromene-3-carboxamide (120 mg, 0.301 mmol) and bis(triphenylphosphine)dichloropalladium (II) (21 mg, 0.03 mmol) in 1,4-dioxane (10 mL) was stirred at room temperature for 2 h. After the addition of (3,5-dichlorophenyl)boronic acid (100 mg, 0.366 mmol), sodium carbonate (370 mg, 3.49 mmol) and water (1.30 mL) stirring was continued for 18 h at 90° C. The mixture was cooled to room temperature, water was added and the aqueous layer was extracted with dichloromethane (3×20 mL). Solvents were dried and removed under reduced pressure. Purification by flash chromatography (cyclohexane, 80%-20% ethyl acetate) afforded 3.4 mg (2.4% of theory) of the title compound as a brown solid.

LC-MS3—Index=1350; m/z=463.1; 465.1 $(M+H)^+$ $^1$H-NMR (400 MHz, DMSO-d6) δ 8.37-8.33 (m, 1H), 7.61-7.56 (m, 3H), 7.34-7.15 (m, 7H), 5.48-5.42 (m, 1H), 3.91-3.86 (m, 1H), 2.99-2.93 (m, 1H), 2.86-2.78 (m, 1H), 2.46-2.39 (m, 1H), 2.02 (s, 3H), 1.94-1.84 (m, 1H), 1.31-1.29 (m, 3H).

Example Compound S8b-2

2,4-Dimethyl-N-[(1S)-1,2,3,4-tetrahydronaphthalen-1-yl]-8-(2,3,5-trifluorophenyl)-4H-chromene-3-carboxamide

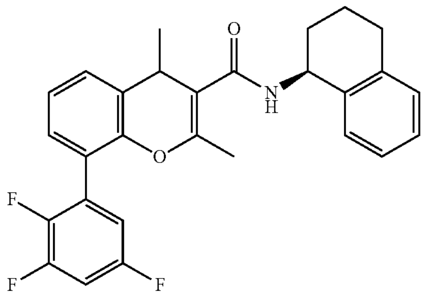 [SMILES: CC1=C(C(=O)N[C@H]2CCCc3ccccc32)C(C)c2cccc(-c3cc(F)cc(F)c3F)c2O1]

Example Compound S8b-2 has been prepared in a similar way as Example Compound S8b-1.

8-Bromo-2,4-dimethyl-N-[(1S)-1,2,3,4-tetrahydronaphthalen-1-yl]-4H-chromene-3-carboxamide

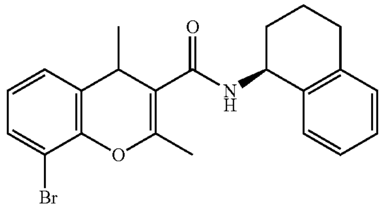 [SMILES: CC1=C(C(=O)N[C@H]2CCCc3ccccc32)C(C)c2cccc(Br)c2O1]

For the preparation of Example Compound S8b-2 the intermediate compound 8-bromo-2,4-dimethyl-N-[(1S)-1,2,3,4-tetrahydronaphthalen-1-yl]-4H-chromene-3-carboxamide has been prepared in a similar way as the intermediate compound 8-bromo-N-[(1S)-2,3-dihydro-1H-inden-1-yl]-2,4-dimethyl-4H-chromene-3-carboxamide (Step 1 in the preparation of Example Compound S8b-1).

LC-MS3—Index=1083; m/z=411.1; 413.1 $(M+H)^+$ $^1$H-NMR (400 MHz, DMSO-d6) δ 8.39-8.37 (m, 1H), 7.46-6.98 (m, 7H), 5.14-5.10 (m, 1H), 3.88-3.83 (m, 1H), 2.76-2.72 (m, 2H), 2.08-2.07 (d, 3H), 1.94-1.91 (m, 2H), 1.76-1.74 (m, 2H), 1.28-1.27 (d, J=6.8 Hz, 3H).

Example Compound S8b-3

N-[(4S)-3,4-Dihydro-2H-chromen-4-yl]-2,4-dimethyl-8-(2,3,5-trifluorophenyl)-4H-chromene-3-carboxamide Step 1: 8-Bromo-N-[(4S)-3,4-dihydro-2H-chromen-4-yl]-2,4-dimethyl-4H-chromene-3-carboxamide

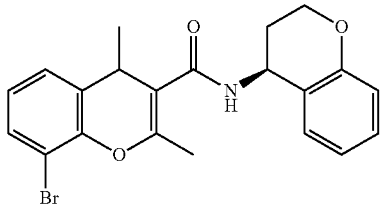 [SMILES: CC1=C(C(=O)N[C@H]2CCOc3ccccc32)C(C)c2cccc(Br)c2O1]

To a suspension of 8-bromo-2,4-dimethyl-4H-chromene-3-carboxylic acid (150 mg, 0.53 mmol) in dry tetrahydrofuran (5 mL) was added 1,1'-carbonyldiimidazole (95 mg, 0.586 mmol). After stirring for 18 h at 60° C. the mixture was cooled to room temperature, and after adding (4S)-3,4-dihydro-2H-chromen-4-amine hydrochloride (95 mg, 0.512 mmol) and N,N-diisopropylethylamine (500 mg, 3.869 mmol) stirring was continued for 18 hours at 60° C.

Solvents were removed under reduced pressure and the residue was partitioned between water (50 mL) and dichloromethane (50 mL). The combined organic layers were dried and removed under reduced pressure, leaving 180 mg (82% of theory) of the crude compound. Purification by flash chromatography (cyclohexane, 80%-20% ethyl acetate) afforded 25 mg (11.4% of theory) of the title compound.

LC-MS3—Index=985

$^{1}$H-NMR (400 MHz, DMSO-d6) δ 8.58-8.56 (m, 1H), 7.47-6.77 (m, 7H), 5.18 (m, 1H), 4.25-4.21 (m, 2H), 3.88-3.86 (m, 1H), 2.10-2.08 (m, 1H), 2.08 (d, 3H), 1.98 (m, 1H), 1.26 (d, 3H).

Step 2: N-[(4S)-3,4-dihydro-2H-chromen-4-yl]-2,4-dimethyl-8-(2,3,5-trifluorophenyl)-4H-chromene-3-carboxamide S8b-3

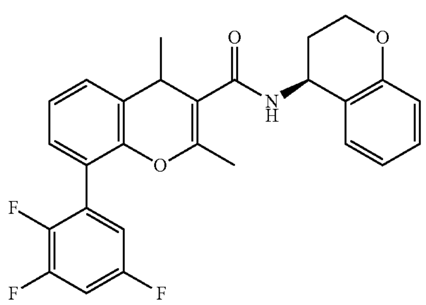 [SMILES: CC1=C(C(=O)N[C@H]2CCOc3ccccc32)C(C)c2cccc(-c3cc(F)cc(F)c3F)c2O1]

A mixture of 8-bromo-N-[(4S)-3,4-dihydro-2H-chromen-4-yl]-2,4-dimethyl-4H-chromene-3-carboxamide (94 mg, 0.227 mmol) and bis(triphenylphosphine)dichloropalladium (II) (44 mg, 0.062 mmol) in 1,4-dioxane (10 mL) was stirred at room temperature for 2 h. After the addition of (2,3,5-trifluorophenyl)boronic acid (300 mg, 1.706 mmol), sodium carbonate (870 mg, 8.21 mmol) and water (3.30 mL) stirring was continued for 18 h at 90° C. The mixture was cooled to room temperature, water was added and the aqueous layer was extracted with dichloromethane (3×20 mL). Solvents were dried and removed under reduced pressure. Purification by flash chromatography (cyclohexane, 80%-20% ethyl acetate) afforded 12 mg (10.5% of theory) of the title compound.

LC-MS7—Index=1091; m/z=466.1 $(M+H)^{+}$

1H-NMR (400 MHz, DMSO-d6) δ 8.51-8.49 (m, 1H), 7.62-6.77 (m, 9H), 5.16-5.11 (m, 1H), 4.23-4.20 (m, 2H), 3.91-3.86 (m, 1H), 2.12-2.08 (m, 1H), 2.00-1.94 (m, 1H), 1.94 (s, 3H), 1.30-1.28 (d, J=6.8 Hz, 3H).

(Target) Example Compounds (S9)

Example S9-1

2-[2-Chloro-3-(trifluoromethyl)phenyl]-N-[(4S)-3,4-dihydro-2H-chromen-4-yl]quinoxaline-6-carboxamide

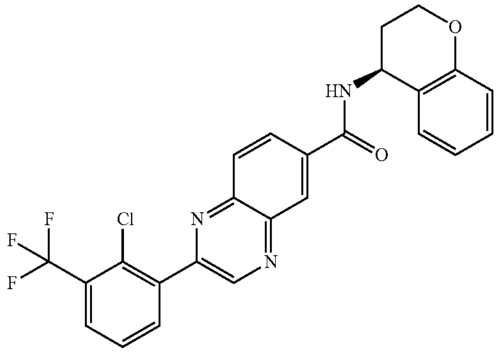 [SMILES: O=C(N[C@H]1CCOc2ccccc21)c1ccc2nc(-c3cccc(C(F)(F)F)c3Cl)cnc2c1]

Example Compound S9-2

2-(2-Chlorophenyl)-N-[(4S)-3,4-dihydro-2H-chromen-4-yl]quinoxaline-6-carboxamide

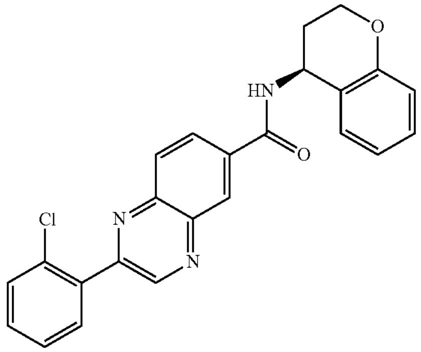 [SMILES: O=C(N[C@H]1CCOc2ccccc21)c1ccc2nc(-c3ccccc3Cl)cnc2c1]

Example Compound S9-3

2-(2-Chlorophenyl)-N-[(1S)-2,3-dihydro-1H-inden-1-yl]quinoxaline-6-carboxamide

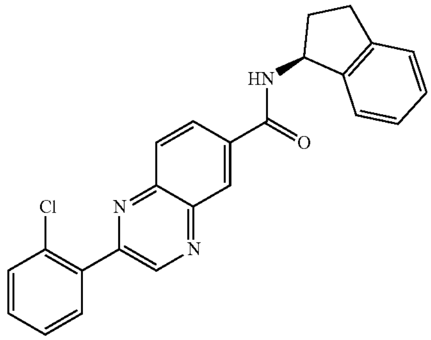 [SMILES: O=C(N[C@H]1CCc2ccccc21)c1ccc2nc(-c3ccccc3Cl)cnc2c1]

Example Compound S9-4

2-(2,3-Dichlorophenyl)-N-[(4S)-3,4-dihydro-2H-chromen-4-yl]quinoxaline-6-carboxamide

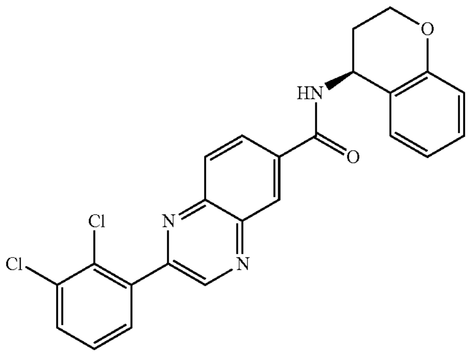 [SMILES: O=C(N[C@H]1CCOc2ccccc21)c1ccc2nc(-c3cccc(Cl)c3Cl)cnc2c1]

Example S9-5

2-(2,3-Dichlorophenyl)-N-[(1S)-2,3-dihydro-1H-inden-1-yl]quinoxaline-6-carboxamide

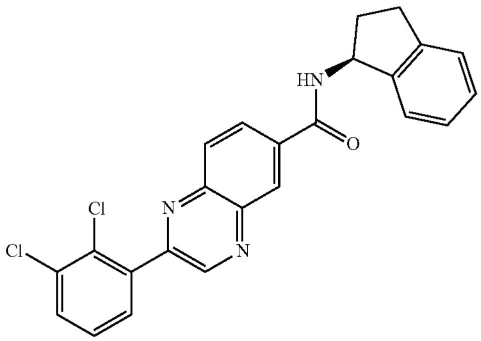 [SMILES: O=C(N[C@H]1CCc2ccccc21)c1ccc2nc(-c3cccc(Cl)c3Cl)cnc2c1]

Example S9-6

2-[2-Chloro-3-(trifluoromethyl)phenyl]-N-[(1S)-2,3-dihydro-1H-inden-1-yl]quinoxaline-6-carboxamide

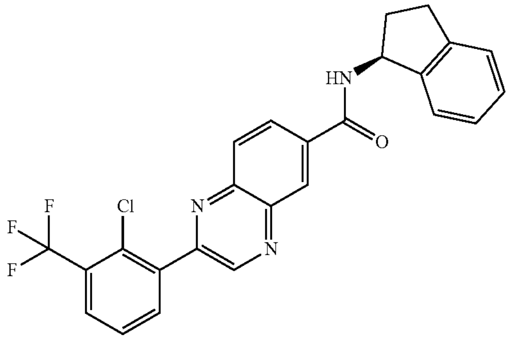 [SMILES: O=C(N[C@H]1CCc2ccccc21)c1ccc2nc(-c3cccc(C(F)(F)F)c3Cl)cnc2c1]

NMR-Peak Lists $^1$H-NMR data of selected examples are written in form of $^1$H-NMR-peak lists. To each signal peak are listed the δ-value in ppm and the signal intensity in round brackets. Between the δ-value-signal intensity pairs are semicolons as delimiters.

The peak list of an example has therefore the form:

$\delta_1$(intensity$_1$); $\delta_2$(intensity$_2$); . . . ; $\delta_i$(intensity$_i$); . . . ; $\delta_n$(intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our H-NMR peak lists and have usually on average a high intensity.

The peaks of stereoisomers of the target compounds and/or peaks of impurities have usually on average a lower intensity than the peaks of target compounds (for example with a purity>90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.#

| Example Compound | Structure | $^1$H NMR Peaklist |
|---|---|---|
| S2-1: | 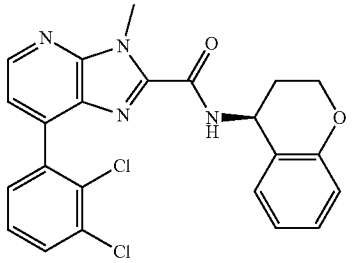 [SMILES: Cn1c(C(=O)N[C@H]2CCOc3ccccc32)nc2c(-c3cccc(Cl)c3Cl)ccnc21] | $^1$H-NMR (400.0 MHz, $d_6$-DMSO): δ = 9.2403 (1.5); 9.2185 (1.5); 8.6120 (3.1); 8.5998 (3.2); 7.7510 (1.5); 7.7462 (1.7); 7.7320 (1.7); 7.7272 (2.0); 7.5336 (0.7); 7.5288 (1.1); 7.5144 (2.7); 7.5097 (2.6); 7.5024 (2.8); 7.4833 (2.7); 7.4642 (0.9); 7.4085 (3.2); 7.3963 (3.2); 7.1739 (1.6); 7.1542 (2.6); 7.1336 (1.7); 7.1150 (1.0); 6.8655 (1.2); 6.8469 (2.1); 6.8284 (1.0); 6.7707 (2.2); 6.7504 (2.0); 5.7536 (0.7); 5.3314 (0.4); 5.3113 (1.0); 5.2960 (1.0); 5.2764 (0.4); 4.3235 (0.4); 4.3157 (0.5); 4.3072 (0.5); 4.2969 (0.9); 4.2878 (0.8); 4.2793 (0.8); 4.2715 (0.6); 4.2045 (0.9); 4.1861 (16.0); 4.1625 (0.6); 4.1555 (0.5); 3.8881 (0.4); 3.3193 (62.9); 2.6708 (0.4); 2.5408 (0.4); 2.5056 (41.8); 2.5015 (59.2); 2.4975 (49.6); 2.3283 (0.3); 2.2294 (0.4); 2.2163 (0.5); 2.2090 (0.5); 2.1952 (0.7); 2.1885 (0.6); 2.1755 (0.4); 2.1111 (0.3); 2.1042 (0.5); 2.0888 (0.7); 2.0781 (0.6); 2.0726 (0.6); 2.0609 (0.5); 1.9884 (0.5); 0.1458 (0.3); 0.0070 (2.7); −0.0003 (64.9) |
| S2-2: | 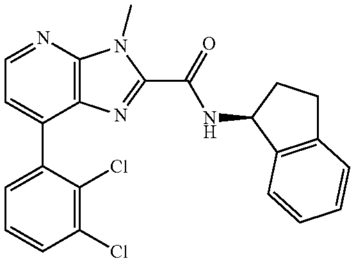 [SMILES: Cn1c(C(=O)N[C@H]2CCc3ccccc32)nc2c(-c3cccc(Cl)c3Cl)ccnc21] | $^1$H-NMR (400.0 MHz, $d_6$-DMSO): δ = 9.1268 (1.4); 9.1054 (1.4); 8.6091 (3.3); 8.5969 (3.4); 7.7570 (1.6); 7.7523 (1.8); 7.7378 (1.9); 7.7331 (2.0); 7.5391 (0.8); 7.5343 (1.1); 7.5198 (2.8); 7.5151 (2.4); 7.5041 (2.7); 7.4849 (2.9); 7.4657 (1.0); 7.4113 (3.4); 7.3992 (3.4); 7.2570 (1.0); 7.2424 (2.8); 7.2274 (2.9); 7.2092 (1.9); 7.1918 (1.1); 7.1841 (1.5); 7.1657 (1.3); 7.1468 (0.4); 5.7536 (2.6); 5.5868 (0.4); 5.5667 (1.3); 5.5460 (1.3); 5.5254 (0.4); 4.1861 (16.0); 3.3188 (70.4); 3.0217 (0.4); 3.0140 (0.4); 2.9999 (0.4); 2.9912 (0.4); 2.9829 (0.6); 2.9745 (0.7); 2.9603 (0.6); 2.9520 (0.6); 2.8651 (0.5); 2.8443 (1.1); 2.8243 (0.8); 2.8044 (0.7); 2.7835 (0.4); 2.6711 (0.5); 2.5237 (1.3); 2.5059 (55.7); 2.5016 (76.8); 2.4973 (59.3); 2.4137 (0.6); 2.4038 (0.7); 2.3937 (0.7); 2.3825 (0.8); 2.3739 (0.7); 2.3620 (0.4); 2.3286 (0.4); 2.3245 (0.4); 2.1521 (0.9); 2.1420 (0.4); 2.1313 (0.8); 2.1208 (0.7); 2.1101 (0.4); 2.1001 (0.7); 1.9885 (0.4); 0.1462 (0.4); 0.0079 (3.1); −0.0002 (87.0); −0.0080 (3.7); −0.1497 (0.4) |
| S2-3: | 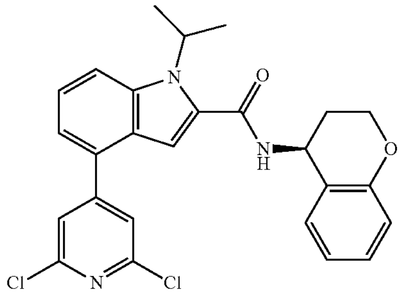 | $^1$H-NMR (400.0 MHz, $d_6$-DMSO): δ = 9.0400 (0.5); 9.0190 (0.6); 8.3022 (0.6); 7.9051 (0.6); 7.8851 (0.6); 7.8014 (5.6); 7.3908 (0.4); 7.3723 (0.9); 7.3527 (1.0); 7.3482 (1.0); 7.3450 (1.1); 7.3300 (0.4); 7.2403 (0.5); 7.2202 (0.6); 7.1883 (0.4); 7.1710 (0.6); 7.1527 (0.4); 7.1494 (0.4); 7.1104 (1.6); 6.9215 (0.4); 6.9191 (0.4); 6.9004 (0.7); 6.8843 (0.3); 6.8816 (0.3); 6.8195 (0.8); 6.8172 (0.7); 6.7991 (0.8); 5.5978 (0.4); 5.2915 (0.3); 5.2732 (0.3); 4.3031 (0.4); 4.2940 (0.4); 4.2853 (0.4); 4.2771 (0.5); 4.2691 (0.4); 4.2592 (0.3); 4.2501 (0.4); 3.3204 (10.0); 2.6702 (0.3); 2.5237 (0.8); 2.5101 (22.0); 2.5058 (45.5); 2.5013 (60.2); 2.4968 (42.4); 2.4924 (19.8); 2.3281 (0.3); 1.6640 (0.4); 1.6570 (0.5); 1.6473 (3.0); 1.6412 (2.9); 1.6299 (2.8); 1.6238 (2.6); 1.3973 (16.0); 1.2343 (0.4); −0.0002 (6.8) |
| S2-4: | 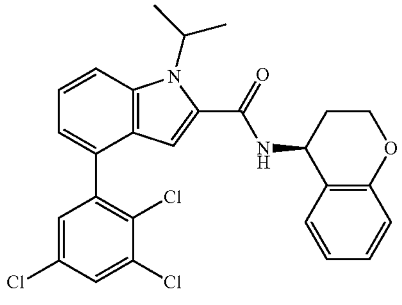 [SMILES: CC(C)n1c(C(=O)N[C@H]2CCOc3ccccc32)cc2c(-c3cc(Cl)cc(Cl)c3Cl)cccc21] | $^1$H-NMR (400.0 MHz, $d_6$-DMSO): δ = 9.1441 (0.3); 9.1216 (0.4); 8.9090 (1.2); 8.8889 (1.3); 7.9118 (3.2); 7.9057 (3.3); 7.8178 (1.6); 7.7972 (1.8); 7.7628 (0.5); 7.7428 (0.5); 7.5075 (1.6); 7.3420 (1.3); 7.3239 (1.7); 7.3208 (1.7); 7.3026 (1.5); 7.2385 (0.4); 7.2214 (0.5); 7.1791 (1.3); 7.1708 (0.9); 7.1615 (2.1); 7.1514 (0.9); 7.1421 (1.4); 7.1304 (0.5); 7.1231 (0.8); 7.0473 (2.3); 7.0295 (2.1); 6.9753 (1.2); 6.9308 (0.3); 6.9129 (0.5); 6.8874 (0.9); 6.8694 (1.6); 6.8508 (0.7); 6.8188 (0.5); 6.8000 (0.4); 6.7834 (1.9); 6.7635 (1.7); 6.6661 (4.0); 5.6681 (0.4); 5.6520 (0.8); 5.6333 (1.0); 5.6167 (0.7); 5.2665 (0.5); 5.2497 (1.0); 5.2310 (0.8); 5.2139 (0.4); 4.2863 (0.3); 4.2768 (0.5); 4.2572 (1.0); 4.2487 (1.0); 4.2394 (0.9); 4.2309 (1.3); 4.2216 (0.9); 4.2124 (0.7); 4.2025 (0.8); 4.1868 (0.4); 3.3202 (114.2); |

-continued
| Example Compound | Structure | $^1$H NMR Peaklist |
| --- | --- | --- |
| | | 2.6700 (2.0); 2.6656 (1.4); 2.5234 (4.8); 2.5098 (133.2); 2.5056 (273.0); 2.5012 (361.5); 2.4967 (260.9); 2.4926 (126.7); 2.3322 (1.6); 2.3280 (2.1); 2.3236 (1.5); 2.1414 (0.4); 2.1054 (0.6); 2.0880 (0.8); 2.0640 (0.7); 2.0464 (0.6); 2.0381 (0.8); 2.0197 (0.5); 1.6442 (3.8); 1.6299 (3.8); 1.6086 (4.5); 1.5909 (3.9); 1.3976 (16.0); 1.3515 (0.4); 1.2367 (0.5); 1.1687 (1.3); 0.9531 (0.7); 0.0078 (1.2); −0.0002 (36.0); −0.0080 (1.4) |
| S2-5: | 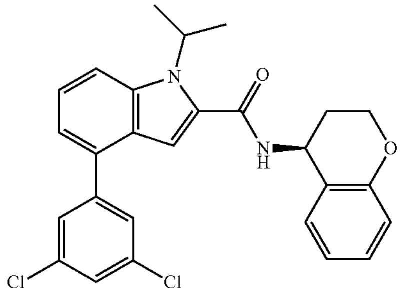 [SMILES: CC(C)n1c(C(=O)N[C@H]2CCOc3ccccc32)cc2c(-c3cc(Cl)cc(Cl)c3)cccc21] | $^1$H-NMR (400.0 MHz, $d_6$-DMSO): δ = 10.4133 (0.5); 9.0332 (1.1); 9.0122 (1.1); 7.8044 (1.4); 7.7834 (1.5); 7.6326 (16.0); 7.3489 (1.1); 7.3303 (1.5); 7.3093 (1.3); 7.2226 (1.1); 7.1994 (2.3); 7.1810 (2.1); 7.1617 (1.1); 7.1432 (0.7); 7.0266 (3.4); 6.9715 (0.4); 6.9106 (0.8); 6.8923 (1.4); 6.8763 (0.6); 6.8062 (1.6); 6.7932 (1.0); 6.7883 (2.1); 5.6177 (0.3); 5.6017 (0.7); 5.5841 (0.9); 5.5661 (0.7); 5.2835 (0.7); 5.2660 (0.7); 5.2473 (0.4); 4.2934 (0.7); 4.2844 (0.7); 4.2759 (0.7); 4.2664 (0.9); 4.2569 (0.7); 4.2470 (0.7); 4.2383 (0.8); 4.2174 (0.3); 3.3210 (124.4); 2.6747 (1.1); 2.6701 (1.5); 2.6660 (1.1); 2.5236 (3.7); 2.5100 (96.0); 2.5057 (198.4); 2.5013 (263.6); 2.4968 (188.9); 2.4926 (90.8); 2.3279 (1.5); 2.3233 (1.1); 2.1423 (0.4); 2.1260 (0.6); 2.1193 (0.5); 2.1002 (0.4); 2.0802 (0.6); 2.0709 (0.6); 2.0618 (0.4); 2.0539 (0.4); 1.6440 (6.4); 1.6404 (6.4); 1.6266 (6.3); 1.6230 (6.0); 1.3976 (9.8); 1.2363 (0.4); 0.0081 (0.8); −0.0002 (25.4); −0.0083 (1.0) |
| S2-6: | 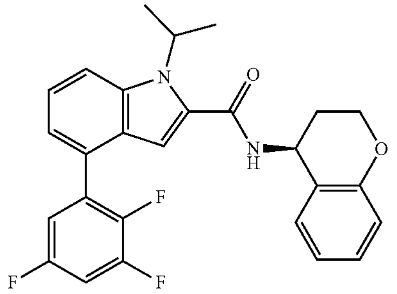 [SMILES: CC(C)n1c(C(=O)N[C@H]2CCOc3ccccc32)cc2c(-c3cc(F)cc(F)c3F)cccc21] | $^1$H-NMR (400.0 MHz, $d_6$-DMSO): δ = 8.9589 (1.1); 8.9380 (1.1); 7.8470 (1.4); 7.8257 (1.5); 7.6053 (0.5); 7.6001 (0.5); 7.5917 (0.5); 7.5789 (0.5); 7.5711 (0.3); 7.3626 (1.1); 7.3442 (1.5); 7.3231 (1.3); 7.2930 (0.4); 7.2803 (0.6); 7.2710 (0.6); 7.2677 (0.6); 7.2582 (0.6); 7.2533 (0.5); 7.2019 (1.2); 7.1821 (1.3); 7.1691 (2.1); 7.1514 (2.3); 7.1345 (0.8); 6.9016 (0.9); 6.8991 (0.9); 6.8803 (3.4); 6.8645 (0.7); 6.7983 (1.6); 6.7780 (1.5); 5.6506 (0.7); 5.6333 (0.9); 5.6160 (0.7); 5.2880 (0.4); 5.2717 (0.7); 5.2544 (0.7); 5.2372 (0.3); 4.2766 (0.8); 4.2670 (0.7); 4.2591 (0.8); 4.2502 (1.0); 4.2427 (0.7); 4.2326 (0.6); 4.2238 (0.8); 3.3222 (116.0); 2.6748 (0.8); 2.6704 (1.0); 2.6658 (0.8); 2.5236 (2.6); 2.5101 (67.3); 2.5058 (138.2); 2.5013 (182.3); 2.4968 (129.0); 2.4925 (60.6); 2.3325 (0.8); 2.3279 (1.0); 2.3235 (0.7); 2.1259 (0.4); 2.1176 (0.5); 2.1089 (0.5); 2.1025 (0.5); 2.0847 (0.4); 2.0756 (0.4); 2.0661 (0.5); 2.0571 (0.6); 2.0492 (0.4); 2.0398 (0.4); 2.0316 (0.3); 1.6466 (8.3); 1.6291 (8.2); 1.3976 (16.0); 0.0081 (0.6); −0.0002 (19.8); −0.0084 (0.7) |
| S2-7: | 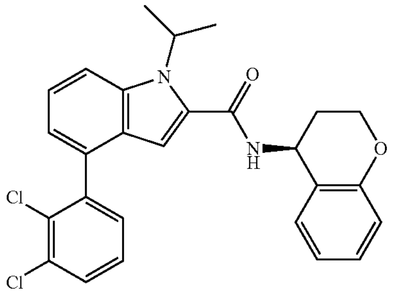 [SMILES: CC(C)n1c(C(=O)N[C@H]2CCOc3ccccc32)cc2c(-c3cccc(Cl)c3Cl)cccc21] | $^1$H-NMR (400.0 MHz, $d_6$-DMSO): δ = 8.9074 (1.9); 8.8866 (2.0); 7.7899 (2.4); 7.7685 (2.7); 7.6966 (2.2); 7.6922 (2.2); 7.6771 (2.5); 7.6728 (2.6); 7.4661 (1.5); 7.4469 (3.9); 7.4276 (2.9); 7.4120 (2.4); 7.4081 (2.6); 7.3929 (1.2); 7.3885 (1.2); 7.3820 (0.4); 7.3334 (1.9); 7.3153 (2.5); 7.2942 (2.0); 7.1692 (2.0); 7.1508 (2.9); 7.1359 (2.1); 7.1164 (1.3); 7.0341 (3.5); 7.0164 (3.2); 6.8811 (1.4); 6.8639 (2.4); 6.8460 (1.1); 6.8441 (1.1); 6.7780 (2.7); 6.7576 (2.5); 6.6551 (5.3); 5.6704 (0.4); 5.6531 (1.1); 5.6354 (1.5); 5.6178 (1.1); 5.6001 (0.4); 5.2599 (0.6); 5.2438 (1.2); 5.2259 (1.2); 5.2089 (0.5); 4.2770 (0.3); 4.2687 (0.5); 4.2500 (1.3); 4.2407 (1.2); 4.2320 (1.3); 4.2236 (1.7); 4.2154 (1.2); 4.2059 (1.1); 4.1973 (1.2); 4.1786 (0.5); 4.1697 (0.3); 3.5676 (0.4); 3.3208 (29.4); 2.6746 (0.6); 2.6700 (0.8); 2.5233 (2.1); 2.5055 (105.7); 2.5011 (138.7); 2.4968 (99.4); 2.3328 (0.5); 2.3278 (0.8); 2.3239 (0.6); 2.1077 (0.4); 2.0961 (0.7); 2.0879 (0.8); 2.0802 (0.9); 2.0731 (0.8); 2.0557 (0.8); 2.0464 (0.6); 2.0368 (0.9); 2.0281 (1.0); 2.0196 (0.8); |

-continued
| Example Compound | Structure | $^1$H NMR Peaklist |
|---|---|---|
| | | 2.0113 (0.6); 2.0027 (0.5); 1.9926 (0.4); 1.6489 (8.9); 1.6316 (8.8); 1.5911 (0.3); 1.3973 (16.0); 1.3554 (0.5); 1.2351 (0.7); 1.1693 (0.5); 0.0079 (0.5); −0.0002 (13.3) |
| S3-1: | 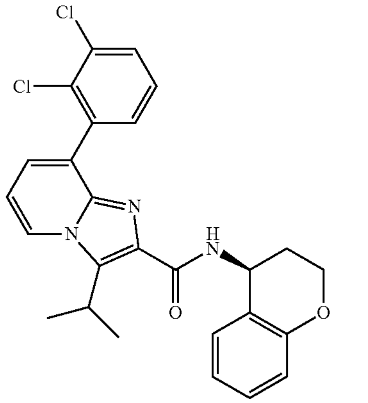 [SMILES: CC(C)c1c(C(=O)N[C@H]2CCOc3ccccc32)nc2c(-c3cccc(Cl)c3Cl)cccn12] | $^1$H-NMR (400.0 MHz, $d_6$-DMSO): δ = 8.6869 (3.2); 8.6692 (3.3); 8.2169 (2.5); 8.1952 (2.6); 8.1393 (0.5); 7.6869 (2.9); 7.6832 (2.8); 7.6669 (3.5); 7.6634 (3.1); 7.5220 (2.4); 7.5184 (2.1); 7.5028 (4.1); 7.4999 (3.1); 7.4849 (0.4); 7.4673 (0.6); 7.4433 (3.6); 7.4361 (1.1); 7.4238 (4.8); 7.4041 (1.8); 7.3846 (0.4); 7.2929 (3.4); 7.2758 (4.0); 7.1373 (4.8); 7.1187 (6.5); 7.1009 (2.0); 7.0927 (2.6); 7.0752 (4.2); 7.0577 (2.0); 6.8539 (1.9); 6.8346 (3.2); 6.8167 (1.5); 6.7608 (3.3); 6.7398 (2.9); 5.2717 (0.7); 5.2523 (1.5); 5.2365 (1.6); 5.2168 (0.7); 4.3938 (0.5); 4.3754 (1.4); 4.3574 (1.9); 4.3393 (1.4); 4.3216 (0.5); 4.2523 (0.3); 4.2425 (0.5); 4.2246 (1.5); 4.2092 (2.8); 4.1999 (2.7); 4.1876 (1.4); 4.1800 (1.6); 4.1600 (0.5); 4.1521 (0.4); 3.3199 (81.2); 2.6716 (0.6); 2.5414 (25.3); 2.5064 (81.6); 2.5023 (100.7); 2.4986 (72.3); 2.3290 (0.6); 2.1700 (0.3); 2.1599 (0.5); 2.1459 (0.8); 2.1364 (0.7); 2.1258 (1.3); 2.1166 (1.1); 2.1060 (0.7); 2.0949 (0.7); 2.0906 (0.7); 2.0737 (14.0); 2.0537 (0.9); 2.0423 (0.6); 2.0330 (0.6); 1.4890 (16.0); 1.4710 (15.9); 0.0000 (0.4) |
| S6-1: | 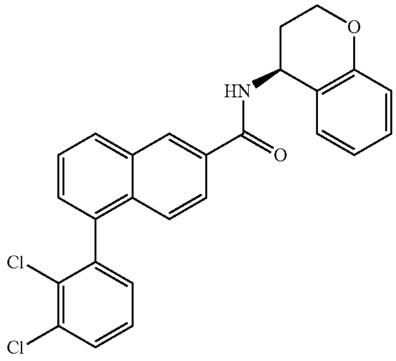 [SMILES: O=C(N[C@H]1CCOc2ccccc21)c1ccc2c(-c3cccc(Cl)c3Cl)cccc2c1] | $^1$H-NMR (400.0 MHz, $d_6$-DMSO): δ = 9.0682 (1.1); 9.0476 (1.2); 8.6231 (1.2); 8.6179 (1.6); 8.6127 (1.2); 8.1196 (1.1); 8.0996 (1.2); 7.9790 (0.6); 7.9739 (1.1); 7.9688 (0.8); 7.9572 (0.7); 7.9519 (1.1); 7.9468 (0.7); 7.8155 (1.4); 7.8118 (1.5); 7.7954 (1.6); 7.7917 (1.6); 7.7002 (1.1); 7.6822 (1.5); 7.6619 (1.3); 7.5587 (1.0); 7.5393 (2.2); 7.5263 (1.7); 7.5241 (1.9); 7.5197 (1.5); 7.5090 (1.4); 7.5066 (1.4); 7.4467 (1.5); 7.4432 (1.6); 7.4277 (1.1); 7.4241 (1.1); 7.3942 (1.7); 7.3723 (1.6); 7.2327 (1.0); 7.2138 (1.1); 7.1901 (0.6); 7.1713 (1.2); 7.1518 (0.7); 6.9053 (0.7); 6.8866 (1.3); 6.8680 (0.6); 6.8277 (1.7); 6.8074 (1.5); 5.3536 (0.7); 5.3357 (0.7); 4.3335 (0.6); 4.3242 (0.5); 4.3154 (0.5); 4.2928 (0.5); 4.2844 (0.6); 4.2753 (0.6); 4.2659 (0.8); 4.2468 (0.3); 3.3201 (11.1); 2.6705 (0.3); 2.5239 (0.8); 2.5103 (21.1); 2.5060 (43.6); 2.5016 (57.8); 2.4971 (41.5); 2.4928 (20.0); 2.3282 (0.3); 2.1668 (0.4); 2.1583 (0.5); 2.1496 (0.6); 2.1369 (0.6); 2.1261 (0.6); 2.1218 (0.6); 2.1124 (0.6); 2.1049 (0.5); 2.0963 (0.4); 1.3971 (16.0); 0.0079 (0.6); −0.0001 (19.5); −0.0083 (0.7) |
| S6-2: | 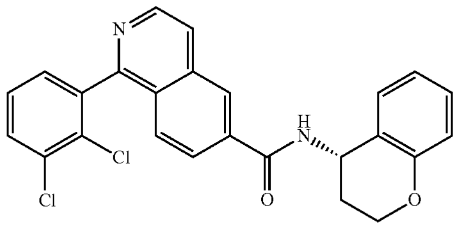 [SMILES: O=C(N[C@H]1CCOc2ccccc21)c1ccc2c(-c3cccc(Cl)c3Cl)nccc2c1] | $^1$H-NMR (400.0 MHz, $d_6$-DMSO): δ = 9.2135 (6.6); 9.1931 (6.7); 8.6812 (13.1); 8.6670 (14.2); 8.6216 (11.0); 8.0797 (4.0); 8.0751 (6.7); 8.0706 (4.0); 8.0577 (4.5); 8.0531 (7.7); 8.0431 (7.4); 8.0285 (6.8); 7.8719 (7.6); 7.8679 (7.9); 7.8520 (9.1); 7.8480 (8.9); 7.5983 (14.8); 7.5788 (16.0); 7.5599 (8.1); 7.5275 (8.6); 7.5247 (9.2); 7.5085 (5.0); 7.5057 (4.7); 7.2433 (5.6); 7.2241 (6.3); 7.1973 (3.2); 7.1788 (6.5); 7.1588 (4.0); 6.9111 (4.2); 6.9077 (3.0); 6.8924 (7.2); 6.8770 (2.4); 6.8738 (3.4); 6.8704 (2.3); 6.8329 (9.3); 6.8126 (8.4); 5.3608 (1.8); 5.3446 (4.2); 5.3268 (4.1); 5.3106 (1.8); 4.3488 (1.4); 4.3459 (1.4); 4.3265 (3.5); 4.3203 (3.1); 4.3078 (3.2); 4.2974 (4.0); 4.2874 (3.7); 4.2784 (3.5); 4.2692 (4.1); 4.2603 (1.4); 4.2503 (1.7); 4.2420 (1.2); 4.0564 (0.9); 4.0386 (2.8); 4.0208 (2.9); 4.0030 (1.0); 3.3223 (113.0); 2.6756 (0.8); 2.6712 (1.1); 2.6667 (0.8); 2.5245 (3.1); 2.5110 (64.3); 2.5067 (128.8); 2.5022 (167.7); 2.4977 (120.5); 2.4934 (58.3); 2.3334 (0.7); 2.3289 (1.0); 2.3244 (0.8); 2.2105 (0.6); 2.2025 (1.0); 2.1892 (1.3); 2.1765 (2.2); 2.1679 (2.6); 2.1570 (2.8); 2.1352 (2.3); 2.1266 (1.8); 2.1173 (2.5); 2.1095 (2.8); 2.1042 |

-continued
| Example Compound | Structure | $^1$H NMR Peaklist |
|---|---|---|
| | | (2.6); 2.0953 (2.1); 2.0868 (1.8); 2.0778 (1.4); 2.0702 (1.0); 2.0606 (0.8); 1.9893 (12.3); 1.3964 (0.4); 1.2339 (0.5); 1.1927 (3.4); 1.1749 (6.6); 1.1571 (3.2); 0.0079 (1.0); −0.0002 (28.3); −0.0086 (0.9) |
| S7-2: | 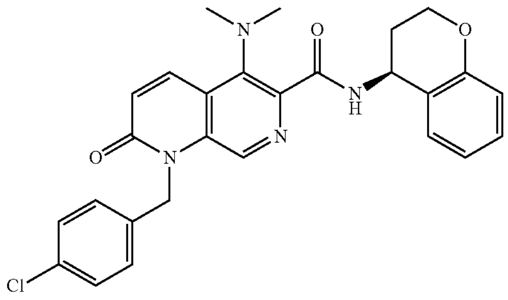 [SMILES: CN(C)c1c(C(=O)N[C@H]2CCOc3ccccc32)ncc2c1ccc(=O)n2Cc1ccc(Cl)cc1] | $^1$H-NMR (400.0 MHz, $d_6$-DMSO): δ = 8.8470 (0.8); 8.8257 (0.8); 8.4621 (2.4); 8.2428 (1.3); 8.2182 (1.4); 7.3897 (1.9); 7.3686 (2.9); 7.2802 (2.4); 7.2589 (1.7); 7.2423 (0.8); 7.2233 (0.8); 7.1620 (0.4); 7.1581 (0.4); 7.1411 (0.8); 7.1232 (0.5); 7.1193 (0.5); 7.0003 (1.8); 6.9756 (1.7); 6.8949 (0.6); 6.8763 (1.0); 6.8600 (0.4); 6.8577 (0.5); 6.7757 (1.1); 6.7570 (1.0); 5.7559 (3.5); 5.5976 (0.6); 5.5500 (0.7); 5.2294 (0.5); 5.2092 (0.5); 4.2430 (0.8); 4.2297 (1.5); 4.2168 (0.9); 3.3209 (18.8); 2.8748 (16.0); 2.5239 (0.4); 2.5101 (12.4); 2.5059 (26.3); 2.5014 (35.6); 2.4970 (26.2); 2.4926 (13.1); 2.1074 (0.5); 2.0939 (0.4); 2.0211 (0.4); 2.0060 (0.4); 1.9887 (1.4); 1.1748 (0.6); 1.1571 (0.3); 0.0078 (0.8); −0.0002 (23.9); −0.0081 (1.0) |
| S8a-6: | 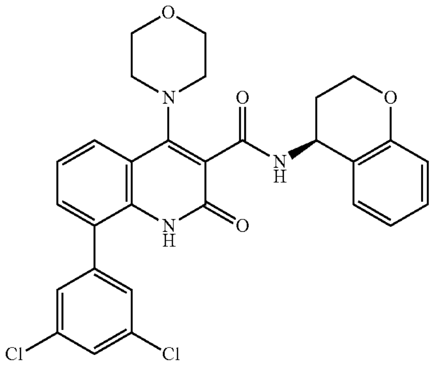 [SMILES: O=C(N[C@H]1CCOc2ccccc21)c1c(N2CCOCC2)c2cccc(-c3cc(Cl)cc(Cl)c3)c2[nH]c1=O] | $^1$H-NMR (601.6 MHz, $d_6$-DMSO): δ = 10.5818 (3.4); 8.7594 (1.9); 8.7461 (1.6); 7.9335 (1.7); 7.9198 (1.7); 7.6584 (3.2); 7.5450 (1.8); 7.5327 (1.8); 7.4270 (1.9); 7.4145 (2.3); 7.4035 (5.9); 7.2936 (1.4); 7.2805 (2.0); 7.2676 (1.0); 7.1439 (1.0); 7.1322 (1.8); 7.1182 (1.1); 6.8639 (1.3); 6.8515 (2.3); 6.8402 (1.2); 6.7622 (2.5); 6.7488 (2.3); 5.2354 (0.6); 5.2238 (1.2); 5.2125 (1.1); 5.2008 (0.6); 4.2651 (2.0); 4.2552 (3.4); 4.2465 (2.1); 4.0472 (1.2); 4.0354 (3.7); 4.0236 (3.7); 4.0117 (1.3); 3.8364 (0.8); 3.8238 (2.2); 3.8141 (4.0); 3.8085 (4.2); 3.7986 (2.3); 3.7855 (0.9); 3.7805 (0.6); 3.3028 (49.9); 3.2289 (1.0); 3.2174 (1.8); 3.2078 (2.0); 3.1724 (1.8); 3.1633 (1.7); 3.1501 (1.0); 2.6123 (0.7); 2.5176 (1.5); 2.5144 (1.6); 2.5025 (85.2); 2.4999 (119.4) 2.4973 (96.8); 2.3846 (0.8); 2.1712 (0.4); 2.1638 (0.8); 2.1548 (0.8); 2.1407 (0.9); 2.1313 (0.8); 2.0183 (0.7); 2.0109 (0.9); 1.9989 (0.8); 1.9870 (16.0); 1.3983 (0.7); 1.1869 (3.9); 1.1750 (8.0); 1.1631 (4.1); −0.0002 (34.6) |
| S9-1: | 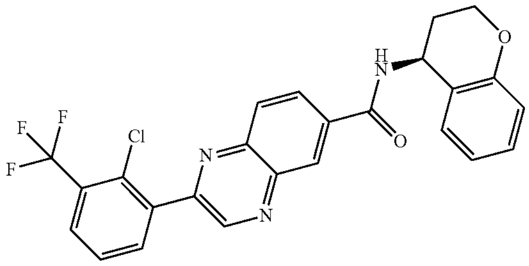 [SMILES: O=C(N[C@H]1CCOc2ccccc21)c1ccc2nc(-c3cccc(C(F)(F)F)c3Cl)cnc2c1] | $^1$H-NMR (400.0 MHz, $d_6$-DMSO): δ = 9.3519 (0.4); 9.3300 (1.2); 9.3222 (2.3); 9.3180 (4.7); 9.3088 (1.0); 8.7646 (0.8); 8.7601 (0.9); 8.7536 (1.8); 8.7492 (1.8); 8.4311 (0.9); 8.4264 (1.2); 8.4092 (1.2); 8.4045 (1.7); 8.2865 (1.9); 8.2640 (1.9); 8.2406 (0.6); 8.1043 (1.0); 8.1009 (1.0); 8.0847 (1.4); 8.0663 (1.3); 8.0466 (1.1); 7.8144 (0.9); 7.7951 (1.6); 7.7756 (0.7); 7.2733 (0.4); 7.2598 (1.0); 7.2430 (1.0); 7.1984 (0.5); 7.1940 (0.6); 7.1772 (1.0); 7.1600 (0.6); 7.1566 (0.5); 6.9104 (1.0); 6.8921 (1.3); 6.8763 (0.6); 6.8737 (0.6); 6.8432 (0.6); 6.8327 (1.3); 6.8306 (1.3); 6.8252 (0.6); 6.8122 (1.2); 5.3790 (0.5); 5.3632 (0.8); 5.3457 (0.6); 4.3611 (0.3); 4.3557 (0.4); 4.3417 (0.7); 4.3327 (0.6); 4.3227 (0.6); 4.3140 (0.5); 4.2985 (0.5); 4.2906 (0.6); 4.2827 (0.6); 4.2722 (0.6); 3.3195 (49.0); 2.6710 (0.4); 2.5109 (22.2); 2.5067 (45.7); 2.5022 (61.0); 2.4977 (44.6); 2.4934 (22.2); 2.3288 (0.4); 2.2053 (0.3); 2.1930 (0.5); 2.1852 (0.6); 2.1735 (0.6); 2.1646 (0.6); 2.1543 (0.6); 2.1467 (0.6); 2.1374 (0.6); 2.1292 (0.6); 2.1200 (0.5); 2.1114 (0.4); 1.9888 (0.7); 1.3975 (16.0); 1.1757 (0.4); 0.1458 (0.3); 0.0079 (3.2); −0.0002 (77.7); −0.0085 (3.3); −0.1498 (0.4) |

-continued
| Example Compound | Structure | $^1$H NMR Peaklist |
| --- | --- | --- |
| S9-2: | 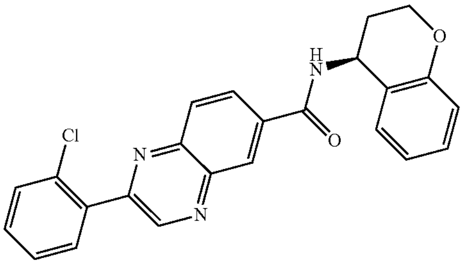 [SMILES: O=C(N[C@H]1CCOc2ccccc21)c1ccc2nc(-c3ccccc3Cl)cnc2c1] | $^1$H-NMR (400.0 MHz, $d_6$-DMSO): δ = 9.3400 (3.5); 9.3196 (3.7); 9.3033 (16.0); 9.2961 (1.8); 8.7464 (7.2); 8.7420 (7.4); 8.4101 (3.4); 8.4054 (3.5); 8.3884 (4.4); 8.3835 (4.7); 8.3143 (0.4); 8.2615 (0.7); 8.2480 (7.5); 8.2262 (5.9); 7.8200 (3.4); 7.8150 (3.0); 7.8023 (4.3); 7.7967 (4.3); 7.7817 (0.5); 7.7760 (0.4); 7.7170 (3.2); 7.7126 (3.8); 7.6971 (4.5); 7.6941 (5.4); 7.6772 (0.3); 7.6394 (1.4); 7.6343 (1.8); 7.6209 (4.1); 7.6157 (4.0); 7.6038 (5.9); 7.5993 (5.1); 7.5966 (4.0); 7.5860 (4.1); 7.5823 (3.7); 7.5676 (1.3); 7.5638 (1.0); 7.2718 (3.5); 7.2531 (3.8); 7.2092 (1.7); 7.2061 (1.7); 7.1883 (3.6); 7.1710 (2.4); 7.1674 (2.1); 6.9270 (2.6); 6.9244 (2.6); 6.9082 (4.4); 6.9061 (4.4); 6.8898 (2.2); 6.8871 (2.1); 6.8441 (5.0); 6.8235 (4.6); 5.3960 (1.0); 5.3794 (2.3); 5.3619 (2.4); 5.3457 (1.2); 4.3829 (0.7); 4.3747 (1.0); 4.3646 (0.9); 4.3552 (2.4); 4.3466 (2.0); 4.3369 (2.0); 4.3283 (1.6); 4.3102 (1.5); 4.3016 (1.9); 4.2925 (1.9); 4.2836 (2.4); 4.2742 (1.0); 4.2648 (1.1); 4.2563 (0.8); 3.3192 (126.8); 2.6755 (1.0); 2.6711 (1.3); 2.6666 (1.0); 2.5241 (3.6); 2.5064 (172.7); 2.5020 (223.4); 2.4975 (161.5); 2.3332 (1.0); 2.3289 (1.3); 2.3249 (0.9); 2.2368 (0.3); 2.2283 (0.5); 2.2150 (0.7); 2.2034 (1.3); 2.1937 (1.5); 2.1846 (1.8); 2.1713 (2.2); 2.1626 (2.0); 2.1550 (2.0); 2.1460 (2.0); 2.1376 (1.5); 2.1292 (1.4); 2.1206 (0.9); 2.1116 (0.7); 2.1028 (0.5); 2.0940 (0.4); 2.0740 (1.0); 0.1461 (1.2); 0.0077 (11.1); −0.0001 (266.0); −0.0082 (12.1); −0.1495 (1.3) |
| S9-3: | 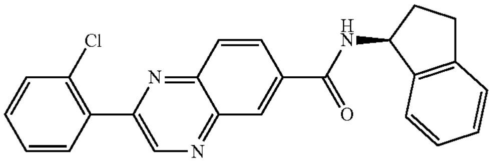 [SMILES: O=C(N[C@H]1CCc2ccccc21)c1ccc2nc(-c3ccccc3Cl)cnc2c1] | $^1$H-NMR (400.0 MHz, $d_6$-DMSO): δ = 9.3031 (12.8); 9.2944 (16.0); 9.2487 (2.4); 9.2289 (4.6); 9.2092 (2.6); 8.7437 (5.3); 8.7385 (10.2); 8.7335 (6.2); 8.4137 (2.9); 8.4087 (5.8); 8.4038 (3.4); 8.3919 (3.7); 8.3869 (7.7); 8.3820 (4.6); 8.3142 (0.5); 8.2619 (6.8); 8.2481 (6.0); 8.2401 (5.4); 8.2262 (4.6); 7.8204 (2.7); 7.8157 (2.3); 7.8136 (2.2); 7.8029 (6.7); 7.7976 (5.1); 7.7859 (3.9); 7.7796 (3.8); 7.7163 (4.0); 7.7132 (4.2); 7.7110 (3.9); 7.6982 (4.7); 7.6935 (6.4); 7.6790 (0.4); 7.6399 (1.2); 7.6346 (2.7); 7.6290 (2.0); 7.6215 (3.8); 7.6160 (7.2); 7.6104 (4.3); 7.6033 (7.7); 7.5973 (8.0); 7.5913 (3.6); 7.5869 (4.4); 7.5848 (5.2); 7.5811 (4.1); 7.5685 (1.3); 7.5666 (1.5); 7.5625 (1.0); 7.3268 (3.1); 7.3079 (5.6); 7.3054 (5.6); 7.2975 (3.6); 7.2879 (3.8); 7.2716 (1.2); 7.2688 (1.4); 7.2618 (1.5); 7.2581 (1.8); 7.2537 (3.0); 7.2508 (2.7); 7.2439 (3.6); 7.2367 (4.5); 7.2314 (3.9); 7.2262 (3.9); 7.2233 (4.0); 7.2194 (4.4); 7.2061 (2.6); 7.2025 (2.6); 7.1883 (0.8); 5.6858 (0.7); 5.6658 (2.3); 5.6504 (2.9); 5.6312 (2.6); 5.6117 (0.8); 3.3219 (108.6); 3.0861 (0.6); 3.0775 (1.2); 3.0662 (1.0); 3.0553 (1.5); 3.0466 (1.8); 3.0381 (2.2); 3.0276 (1.7); 3.0158 (2.1); 3.0072 (1.2); 2.9392 (0.8); 2.9279 (1.0); 2.9183 (1.8); 2.9076 (2.1); 2.8982 (1.5); 2.8872 (1.6); 2.8795 (1.2); 2.8685 (1.2); 2.8586 (0.7); 2.8479 (0.7); 2.6761 (1.0); 2.6716 (1.4); 2.6670 (1.1); 2.6623 (0.6); 2.5673 (0.7); 2.5590 (0.9); 2.5549 (1.0); 2.5470 (1.9); 2.5353 (2.7); 2.5250 (5.2); 2.5200 (6.8); 2.5115 (83.7); 2.5070 (178.7); 2.5024 (241.0); 2.4978 (172.4); 2.4933 (82.0); 2.3383 (0.4); 2.3337 (1.0); 2.3292 (1.4); 2.3247 (1.0); 2.1265 (0.6); 2.1125 (0.8); 2.1048 (1.6); 2.0908 (2.0); 2.0840 (1.9); 2.0741 (12.4); 2.0596 (1.9); 2.0527 (1.6); 2.0390 (1.6); 2.0311 (0.6); 2.0172 (0.5); 1.2329 (0.5); 0.1459 (1.4); 0.0080 (12.4); −0.0002 (361.1); −0.0085 (12.8); −0.1497 (1.4) |

-continued
| Example Compound | Structure | $^1$H NMR Peaklist |
| --- | --- | --- |
| S9-4 | 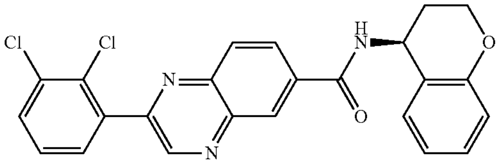 [SMILES: O=C(N[C@H]1CCOc2ccccc21)c1ccc2nc(-c3cccc(Cl)c3Cl)cnc2c1] | : $^1$H-NMR (400.0 MHz, $d_6$-DMSO): δ = 9.7154 (1.2); 9.7068 (1.2); 9.3479 (2.3); 9.3276 (4.6); 9.3087 (12.8); 9.3009 (13.2); 8.7719 (0.6); 8.7672 (0.7); 8.7534 (4.4); 8.7488 (4.7); 8.7402 (5.0); 8.7356 (5.0); 8.7125 (0.6); 8.7076 (0.6); 8.4368 (0.7); 8.4183 (5.2); 8.4135 (4.9); 8.3965 (6.2); 8.3916 (6.4); 8.3678 (0.6); 8.3631 (0.6); 8.3589 (0.6); 8.3538 (0.6); 8.3494 (0.4); 8.3371 (0.5); 8.3321 (0.5); 8.3134 (0.6); 8.2722 (5.4); 8.2500 (9.0); 8.2276 (4.2); 8.2037 (0.4); 8.0765 (0.3); 7.8903 (2.9); 7.8863 (3.6); 7.8835 (3.6); 7.8796 (3.6); 7.8701 (3.5); 7.8662 (4.1); 7.8635 (4.2); 7.8595 (3.9); 7.7665 (2.6); 7.7627 (2.8); 7.7460 (4.9); 7.7433 (4.8); 7.7263 (4.1); 7.7224 (3.7); 7.6732 (0.9); 7.6703 (0.9); 7.6650 (1.0); 7.6620 (1.1); 7.6573 (0.8); 7.6215 (4.0); 7.6192 (4.5); 7.6016 (6.2); 7.5996 (6.8); 7.5822 (2.8); 7.5798 (3.1); 7.2711 (2.8); 7.2613 (2.9); 7.2518 (3.2); 7.2451 (2.8); 7.2060 (1.4); 7.1987 (1.5); 7.1887 (2.9); 7.1776 (2.7); 7.1678 (1.9); 7.1604 (1.7); 7.1565 (1.5); 6.9242 (2.1); 6.9139 (2.0); 6.9088 (3.4); 6.9056 (3.7); 6.8953 (3.2); 6.8925 (3.6); 6.8871 (2.0); 6.8769 (1.6); 6.8741 (1.6); 6.8421 (3.9); 6.8328 (3.7); 6.8305 (3.6); 6.8239 (3.5); 6.8216 (3.5); 6.8124 (3.2); 6.6386 (0.7); 5.3949 (0.6); 5.3785 (2.2); 5.3617 (3.1); 5.3446 (2.2); 5.3285 (0.7); 4.3818 (0.6); 4.3738 (1.0); 4.3618 (1.3); 4.3543 (2.2); 4.3421 (2.5); 4.3357 (2.4); 4.3267 (1.9); 4.3137 (1.6); 4.2994 (2.1); 4.2912 (2.4); 4.2827 (2.7); 4.2722 (2.1); 4.2639 (1.3); 4.2538 (1.1); 4.2452 (0.6); 4.0564 (1.2); 4.0387 (3.6); 4.0209 (3.6); 4.0031 (1.2); 3.3192 (266.9); 2.9424 (0.4); 2.8913 (1.0); 2.7318 (0.8); 2.6758 (1.2); 2.6711 (1.6); 2.6668 (1.2); 2.5244 (4.9); 2.5111 (98.9); 2.5067 (205.6); 2.5022 (275.8); 2.4976 (199.5); 2.4932 (96.0); 2.3336 (1.2); 2.3289 (1.5); 2.3243 (1.2); 2.2042 (1.3); 2.1843 (2.2); 2.1716 (2.6); 2.1632 (2.3); 2.1546 (2.4); 2.1463 (2.4); 2.1375 (2.3); 2.1289 (2.3); 2.1203 (1.7); 2.1118 (1.4); 2.1030(1.0); 2.0950 (0.8); 2.0863 (0.4); 1.9888 (16.0); 1.2333 (0.3); 1.1933 (4.2); 1.1756 (8.4); 1.1578 (4.1); 0.0079 (1.1); −0.0002 (30.8); −0.0084 (1.2) |
| S9-5: | 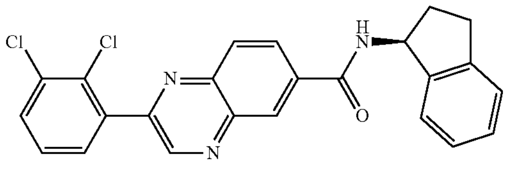 [SMILES: O=C(N[C@H]1CCc2ccccc21)c1ccc2nc(-c3cccc(Cl)c3Cl)cnc2c1] | $^1$H-NMR (400.0 MHz, $d_6$-DMSO): δ = 9.7144 (1.1); 9.7057 (1.5); 9.3092 (10.7); 9.3003 (11.8); 9.2585 (2.3); 9.2364 (3.2); 9.2129 (2.3); 8.7601 (0.8); 8.7519 (4.6); 8.7473 (4.6); 8.7341 (4.7); 8.7296 (4.8); 8.7084 (0.5); 8.7036 (0.5); 8.4358 (0.6); 8.4228 (5.3); 8.4180 (4.9); 8.4009 (6.0); 8.3961 (6.2); 8.3706 (0.6); 8.3657 (0.5); 8.3596 (0.7); 8.3549 (0.6); 8.3449 (0.4); 8.3378 (0.7); 8.3332 (0.7); 8.2727 (5.2); 8.2505 (9.0); 8.2283 (4.3); 8.2041 (0.6); 7.9536 (0.6); 7.8905 (2.9); 7.8858 (4.4); 7.8812 (3.4); 7.8704 (3.4); 7.8656 (5.1); 7.8611 (3.8); 7.7675 (2.6); 7.7637 (2.8); 7.7484 (5.3); 7.7453 (5.0); 7.7305 (3.8); 7.7267 (3.5); 7.6736 (0.8); 7.6706 (0.9); 7.6673 (1.3); 7.6641 (1.1); 7.6586 (0.8); 7.6539 (0.8); 7.6223 (6.6); 7.6026 (10.0); 7.5830 (4.6); 7.3329 (2.3); 7.3154 (5.4); 7.3046 (5.2); 7.2877 (3.3); 7.2691 (1.6); 7.2516 (3.2); 7.2438 (3.2); 7.2375 (4.4); 7.2322 (4.3); 7.2262 (3.6); 7.2192 (4.2); 7.2020 (2.6); 7.1877 (0.8); 5.6865 (0.7); 5.6667 (2.3); 5.6481 (3.3); 5.6294 (2.4); 5.6103 (0.7); 4.0570 (1.2); 4.0392 (3.6); 4.0213 (3.6); 4.0036 (1.2); 3.3224 (156.0); 3.0860 (0.6); 3.0772 (1.1); 3.0663 (1.2); 3.0547 (1.3); 3.0463 (1.7); 3.0380 (1.8); 3.0265 (2.0); 3.0155 (1.8); 3.0058 (1.0); 2.9391 (0.8); 2.9185 (1.8); 2.9069 (1.9); 2.8977 (1.6); 2.8917 (5.3); 2.8678 (1.1); 2.8474 (0.6); 2.7326 (3.7); 2.6766 (0.6); 2.6721 (0.9); 2.6675 (0.6); 2.6631 (0.4); 2.5684 (0.6); 2.5600 (0.8); 2.5544 (0.9); 2.5484 (1.5); 2.5401 (1.8); 2.5352 (2.0); 2.5258 (3.7); 2.5120 (51.0); 2.5076 (107.4); 2.5031 (144.3); 2.4985 (104.0); 2.4941 (50.1); 2.4756 (0.8); 2.3343 (0.6); 2.3298 (0.8); |

-continued

| Example Compound | Structure | $^1$H NMR Peaklist |
|---|---|---|
| | | 2.3252 (0.6); 2.1270 (0.5); 2.1052 (1.5); 2.0949 (0.9); 2.0879 (1.8); 2.0851 (1.8); 2.0786 (1.3); 2.0738 (1.6); 2.0679 (1.9); 2.0566 (1.7); 2.0536 (1.6); 2.0467 (1.0); 2.0363 (1.3); 2.0145 (0.4); 1.9895 (16.0); 1.3967 (10.8); 1.2312 (0.4); 1.1937 (4.2); 1.1759 (8.3); 1.1581 (4.1); 0.0080 (0.7); −0.0002 (21.2); −0.0084 (0.7) |
| S9-6: | 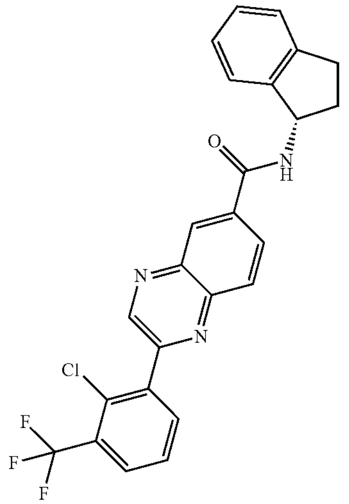 [SMILES: O=C(N[C@H]1CCc2ccccc21)c1ccc2nc(-c3cccc(C(F)(F)F)c3Cl)cnc2c1] | $^1$H-NMR (400.0 MHz, $d_6$-DMSO): δ = 9.7819 (0.3); 9.3225 (6.6); 9.3173 (16.0); 9.2614 (1.5); 9.2340 (3.7); 9.2132 (3.4); 8.7610 (2.7); 8.7566 (3.0); 8.7447 (6.7); 8.7404 (7.2); 8.4338 (3.6); 8.4293 (4.6); 8.4120 (4.7); 8.4074 (6.2); 8.3132 (1.7); 8.2874 (7.4); 8.2651 (7.3); 8.2412 (2.3); 8.1076 (4.3); 8.0872 (6.3); 8.0684 (5.1); 8.0502 (4.1); 7.8169 (3.7); 7.7977 (6.6); 7.7786 (2.9); 7.3193 (4.4); 7.3049 (7.7); 7.2871 (4.8); 7.2705 (1.0); 7.2572 (2.8); 7.2396 (4.7); 7.2217 (5.5); 7.2022 (3.6); 7.1868 (1.1); 5.6846 (0.5); 5.6672 (2.0); 5.6477 (3.9); 5.6284 (3.2); 5.6087 (1.0); 4.0563 (0.5); 4.0383 (1.8); 4.0206 (1.8); 4.0026 (0.6); 3.3195 (625.7); 3.0755 (1.2); 3.0664 (1.3); 3.0349 (1.9); 3.0262 (2.2); 3.0141 (1.8); 3.0055 (1.5); 2.9404 (0.6); 2.9218 (1.4); 2.9062 (2.6); 2.8870 (2.2); 2.8680 (1.6); 2.8460 (0.9); 2.7321 (0.4); 2.6748 (3.7); 2.6704 (5.0); 2.6663 (3.7); 2.5058 (658.9); 2.5014 (862.0); 2.4970 (634.4); 2.3324 (3.9); 2.3282 (5.1); 2.1252 (0.4); 2.1052 (1.2); 2.0851 (2.5); 2.0737 (1.4); 2.0639 (2.3); 2.0534 (2.3); 2.0431 (1.0); 2.0326 (1.9); 2.0114 (0.7); 1.9883 (8.4); 1.1929 (2.1); 1.1751 (4.3); 1.1571 (2.0); 1.0455 (0.4); 1.0308 (0.4); 0.0080 (2.2); −0.0001 (63.3); −0.1498 (0.4) |

EXPERIMENTAL SECTION—BIOLOGICAL ASSAYS

Examples were tested in selected biological assays one or more times. When tested more than once, data are reported as either average values or as median values, wherein

- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

In Vitro Assay 1: *C. elegans* Slo-1a—Action at a Recombinant *C. elegans* Cell Line Generation of a Stable *C. elegans* CHO Cell Line A CHO cell line was obtained from ATCC, code ATCC CRL-9096. For transfection with plasmid DNA to express *C. elegans* Slo-1a (accession number AAL28102) CHO cells were passaged to 40% confluence before adding the transfection solution to the cell culture. The transfection solution included 300 μL OptiMEM (Life Technologies, Nr.: 31985), 2 μL (=6 μg) of plasmid DNA containing the *C. elegans* Slo 1a gene and 9 μL FugeneHD (Promega, Nr.: E2311), and was added to the cells prior to incubation for 48 hours at 37° C., 5% $CO_2$. The transfection medium was exchanged for the selection medium which contains additional G418 (2 mg/ml, Invitrogen, Nr.: 10131) and the cells were seeded into 384 well plates (300 cells/well). After a few weeks, the remaining surviving cells were tested with a voltage sensitive dye (Membrane Potential Assay Kit, Molecular Devices Nr.: R8034) for K+ channel expression. Positive cell clones were purified by the limited dilution technique. For this the clone with the highest and most robust signal in the voltage sensitive dye assay was further subcloned (incubated) in 384 well plates (0.7 cells/well) in order to obtain clonal purity. This generated a final stable CHO cell line expressing the *C. elegans* Slo-1a.

Cell Culture Conditions

Cells were cultured at 37° C. and 5% $CO_2$ in MEMalpha with Gutamax I (Invitrogen, Nr.: 32571), supplemented with 10% (v/v) heat inactivated fetal bovine serum (Invitrogen, Nr.: 10500), G418 (1 mg/ml, Invitrogen, Nr.: 10131). Cells were detached using Accutase (Sigma, Nr.: A6964).

Membrane Potential Measurements

Laboratory compound testing was performed on 384-well microtiter plates (MTPs, Greiner, Nr.: 781092). 8000 cells/well were plated onto 384-well MTPs and cultured for 20 to 24 hours at 37° C. and 5% $CO_2$. After removal of the cell culture medium, the cells were washed once with tyrode (150 mM NaCl, 0.3 mM KCl, 2 mM $CaCl_2$, 1 mM $MgCl_2$, 0.8 mM $NaH_2PO_4$, 5 mM Glucose, 28 mM Hepes, pH 7.4) and then loaded with the voltage sensitive dye of the Membrane Potential Assay Kit diluted in tyrode for 1 h at room temperature.

After starting the measurement of fluorescence using a FLIPR Tetra (Molecular Devices, Exc. 510-545 nm, Emm. 565-625 nm), test compounds were added followed by the addition of KCl tyrode (final assay concentration: 70 mM KCl, 2 mM $CaCl_2$, 1 mM $MgCl_2$, 0.8 mM $NaH_2PO_4$, 5 mM Glucose, 28 mM Hepes, pH 7.4, including the voltage sensitive dye). The measurement was completed after 7 minutes.

Statistics

The data were evaluated by using the ActivityBase XLfit software (IDBS) for curve fitting and calculation of the half-maximal effective concentration ($EC_{50}$) and are reported as negative decadic logarithm ($pE_{50}$).

For the following Example Compounds, $pE_{50}$ are listed in Table 1.

TABLE 1

| Example Compound | $pE_{50}$ |
|---|---|
| S1-1 | 8.60 |
| S1-2 | 8.40 |
| S1-3 | 9.20 |
| S1-4 | 7.30 |
| S1-5 | 7.60 |
| S1-6 | 7.50 |
| S1-7 | 8.00 |
| S1-8 | 5.50 |
| S1-9 | 6.60 |
| S1-10 | 6.40 |
| S1-11 | 7.50 |
| S1-12 | 6.80 |
| S1-13 | 7.80 |
| S1-14 | 6.10 |
| S1-15 | 6.10 |
| S1-16 | 7.60 |
| S1-17 | 7.30 |
| S1-18 | 6.90 |
| S2-1 | 7.50 |
| S2-2 | 6.30 |
| S2-3 | 7.00 |
| S2-4 | 7.80 |
| S2-5 | 7.60 |
| S2-6 | 7.80 |
| S2-7 | 7.70 |
| S3-1 | 6.60 |
| S4-1 | 5.95 |
| S4-2 | 5.70 |
| S4-3 | 6.80 |
| S4-4 | 6.30 |
| S4-5 | 6.40 |
| S4-6 | 6.60 |
| S4-7 | 5.70 |
| S4-8 | 5.00 |
| S4-9 | 5.80 |
| S4-10 | 5.50 |
| S5-1 | 7.00 |
| S6-1 | 7.10 |
| S6-2 | 6.10 |
| S7-1 | 6.70 |
| S7-2 | 6.00 |
| S8a-1 | 8.50 |
| S8a-2 | 8.90 |
| S8a-3 | 7.30 |
| S8a-4 | 7.70 |
| S8a-5 | 8.30 |
| S8a-6 | 7.40 |
| S8b-1 | nd |
| S8b-2 | <4.30 |
| S9-1 | 7.70 |
| S9-2 | 6.20 |
| S9-3 | 7.00 |
| S9-4 | 7.70 |
| S9-5 | 7.50 |
| S9-6 | 7.50 |

* nd = not determined

In Vitro Assay 2: *Dirofilaria immitis* Microfilariae (DIROIM L1)

≥250 *Dirofilaria immitis* microfilariae, which were freshly purified from blood, were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Efficacy was determined as the reduction of motility in comparison to the negative control. Based on the evaluation of a wide concentration range, concentration-response curves as well as $EC_{50}$-values were calculated.

For the following Example Compound, $EC_{50}$ are listed in Table 2.

TABLE 2

| Example Compound | $EC_{50}$ ppm |
|---|---|
| S1-1 | 0.08 |
| S1-2 | 0.03 |
| S1-3 | 0.01 |
| S1-4 | 0.77 |
| S1-5 | 0.25 |
| S1-6 | 0.25 |
| S1-7 | 0.11 |
| S1-8 | 0.63 |
| S1-9 | 0.27 |
| S1-10 | 0.37 |
| S1-11 | 0.04 |
| S1-12 | 0.10 |
| S1-13 | 0.08 |
| S1-14 | 2.00 |
| S1-15 | >2.00 |
| S1-16 | 0.18 |
| S1-17 | 0.52 |
| S1-18 | 0.27 |
| S2-1 | 0.63 |
| S2-2 | 0.37 |
| S2-3 | >2.00 |
| S2-4 | 0.02 |
| S2-5 | 0.06 |
| S2-6 | 8.60E−3 |
| S2-7 | 0.01 |
| S3-1 | 0.63 |
| S4-1 | 0.41 |
| S4-2 | >2.00 |
| S4-3 | 1.82 |
| S4-4 | >2.00 |
| S4-5 | >2.00 |
| S4-6 | >2.00 |
| S4-7 | >2.00 |
| S4-8 | >2.00 |
| S4-9 | >2.00 |
| S4-10 | >2.00 |
| S5-1 | 0.38 |
| S6-1 | 0.63 |
| S6-2 | >2.00 |
| S7-1 | 1.95 |
| S7-2 | >2.00 |
| S8a-1 | <3.20E−3 |
| S8a-2 | <3.20E−3 |
| S8a-3 | 0.25 |
| S8a-4 | >2.00 |
| S8a-5 | 0.09 |
| S8a-6 | 0.64 |
| S8b-1 | 1.47 |
| S8b-2 | 0.08 |
| S9-1 | 0.52 |
| S9-2 | 1.95 |
| S9-3 | 0.61 |
| S9-4 | 0.32 |
| S9-5 | 0.37 |
| S9-6 | 0.44 |

In Vitro Assay 3: *Dirofilaria immitis* (DIROIM L4)

10 *Dirofilaria immitis* third-stage larvae, which were freshly isolated from their vector (intermediate host), were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Within these 72 h of incubation the majority of larvae in negative control moult to fourth-stage larvae. Efficacy was determined as the reduction of motility in comparison to the negative control. Based on the evaluation of a wide concentration range, concentration-response curves as well as $EC_{50}$-values were calculated.

For the following Example Compound, $EC_{50}$ are listed in Table 3.

TABLE 3

| Example Compound | $EC_{50}$ ppm |
|---|---|
| S1-1 | nd |
| S1-2 | >0.08 |
| S1-3 | 0.03 |
| S1-4 | nd |
| S1-5 | nd |
| S1-6 | nd |
| S1-7 | nd |
| S1-8 | nd |
| S1-9 | nd |
| S1-10 | nd |
| S1-11 | >0.08 |
| S1-12 | nd |
| S1-13 | nd |
| S1-14 | nd |
| S1-15 | nd |
| S1-16 | nd |
| S1-17 | nd |
| S1-18 | nd |
| S2-1 | nd |
| S2-2 | nd |
| S2-3 | nd |
| S2-4 | nd |
| S2-5 | nd |
| S2-6 | 0.08 |
| S2-7 | nd |
| S3-1 | nd |
| S4-1 | nd |
| S4-2 | nd |
| S4-3 | nd |
| S4-4 | nd |
| S4-5 | nd |
| S4-6 | nd |
| S4-7 | nd |
| S4-8 | nd |
| S4-9 | nd |
| S4-10 | nd |
| S5-1 | nd |
| S6-1 | nd |
| S6-2 | nd |
| S7-1 | nd |
| S7-2 | nd |
| S8a-1 | 0.04 |
| S8a-2 | 0.18 |
| S8a-3 | nd |
| S8a-4 | nd |
| S8a-5 | 0.04 |
| S8a-6 | nd |
| S8b-1 | >0.40 |
| S8b-2 | 1.26 |
| S9-1 | nd |
| S9-2 | nd |
| S9-3 | nd |
| S9-4 | nd |
| S9-5 | nd |
| S9-6 | nd |

* nd = not determined

The invention claimed is:

1. A compound of formula (I)

(I)

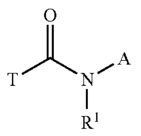

wherein:

A is A1 or A2,

A1

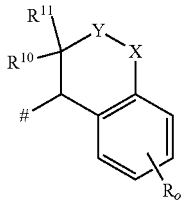

A2

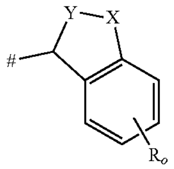

o is 0, 1, 2, 3 or 4;

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms;

X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$— and —$SO_2$—O—;

T is selected from the group consisting of $T^1$, $T^2$, $T^3$, $T^4$, $T^5$, $T^6$, $T^7$, $T^{8a}$, and $T^{8b}$:

$T^1$

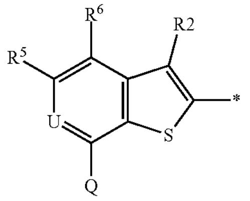

,

-continued

T2

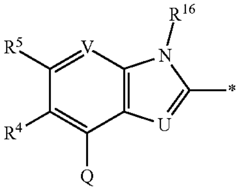

,

T3

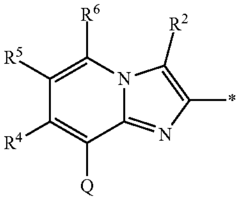

,

T4

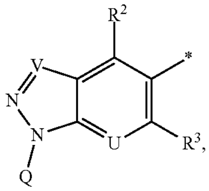

T5

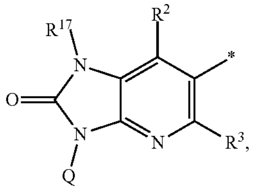

T6

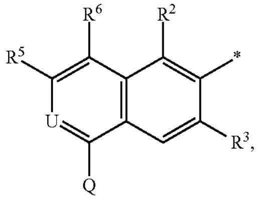

T7

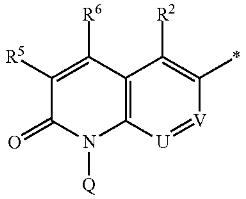

,

T8a

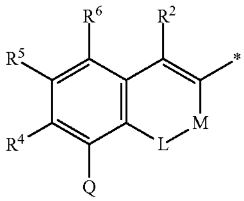

, and

-continued

T8b

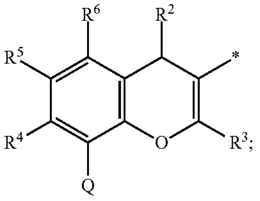

L is selected from the group consisting of O and $NR^9$;

M is selected from the group consisting of C═O and $CR^7R^8$;

U is selected from the group consisting of $CR^7$ and N;

V is selected from the group consisting of $CR^7$ and N;

$R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$—$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;

—$NR^{12}R^{13}$;

—$OR^{14}$;

—$SR^{15}$, —S(O)$R^{15}$, —$SO_2R^{15}$;

$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$—$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and 4- to 10-membered heterocycloalkyl;

$R^3$ is selected from the group consisting of hydrogen, halogen or $C_1$-$C_4$-alkyl;

$R^4$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S—$C_1$-$C_4$-halogenoalkyl having 1 to 5 halogen atoms —S(O)—$C_1$-$C_4$-alkyl, —$SO_2$—$C_1$-$C_4$-alkyl;

$R^5$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl;

$R^6$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-halogenoalkoxy having 1 to 5 halogen atoms, $C_1$-$C_4$-alkyl-C(O)—, —$NH_2$, —NH($C_1$-$C_4$-alkyl), —N($C_1$-$C_4$-alkyl)$_2$, —S—$C_1$-$C_4$-alkyl, —S—$C_1$-$C_4$-halogenoalkyl having 1 to 5 halogen atoms, —S(O)—$C_1$-$C_4$-alkyl, —$SO_2$—$C_1$-$C_4$-alkyl;

$R^7$ is selected from the group consisting of hydrogen, —OH, halogen, $C_1$-$C_4$-alkyl and $C_1$-$C_4$-alkoxy;

$R^8$ is selected from the group consisting of hydrogen, —OH, halogen, $C_1$-$C_4$-alkyl and $C_1$-$C_4$-alkoxy;

or $R^7$ and $R^8$ form, together with the carbon atom to which they are attached, a 3- to 6-membered ring selected from the group consisting of $C_3$-$C_6$-cycloalkyl and 3- to 6-membered heterocycloalkyl;

$R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy;

$R^{10}$ is selected from the group consisting of hydrogen, —OH, $C_1$-$C_4$-alkyl and $C_1$-$C_4$-alkoxy;

$R^{11}$ is selected from the group consisting of hydrogen, $C_1$-$C_4$-alkyl and $C_1$-$C_4$-alkoxy;

or $R^{10}$ and $R^{11}$ form, together with the carbon atom to which they are attached, a 3- to 6-membered ring selected from the group consisting of $C_3$-$C_6$-cycloalkyl and 3- to 6-membered heterocycloalkyl, $R^{12}$ and $R^{13}$ are independently selected from the group consisting of hydrogen, —OH, —$NH_2$, —NH($C_1$-$C_4$-alkyl), —N($C_1$-$C_4$-alkyl)$_2$, —NH(—C(O)—$C_1$-$C_4$-alkyl), —N($C_1$-$C_4$-alkyl)(—C(O)—$C_1$-$C_4$-alkyl), $C_1$-$C_4$-alkoxy, $C_1$-$C_4$-alkoxy-C(O)—;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(═O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)-$C_1$—$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, benzo-$C_5$-$C_6$-cycloalkyl, each of which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{14}$ is selected from the group consisting of —$NH_2$, —NH($C_1$-$C_4$-alkyl), —N($C_1$-$C_4$-alkyl)$_2$;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alky)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{16}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

$R^{17}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

Q is selected from the group consisting of 6- to 10-membered aryl and 5- to 10-membered heteroaryl, each of which is substituted by 1, 2, 3, 4 or 5 substituents selected from the group consisting of halogen, SFs, cyano, —CHO, oxo, $C_1$-$C_4$-alkyl, $C_1$-$C_4$-hydroxyalkyl, $C_1$-$C_4$-halogenoalkyl having 1 to 5 halogen atoms, —OH, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$_$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms;

wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH;

and/or a stereoisomer, tautomer, N-oxide, hydrate, solvate, and/or a salt thereof, and/or a mixture thereof.

2. The compound of claim 1, wherein:

A is A1 or A2,

A1

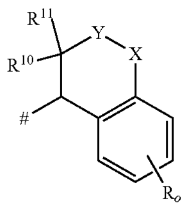

A2

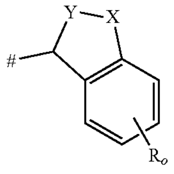

is 0, 1,2,3 or 4;

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms;

X, Y are independently selected from the group consisting of $CR^7R^8$, O, S, and N—$R^9$, wherein at least one of X and Y is $CR^7R^8$, or X, Y form together a ring member selected from the group consisting of —C(O)—O—, —C(O)—$NR^9$—, —S(O)—$NR^9$—, —$SO_2$—$NR^9$—and —$SO_2$—O—;

T is selected from the group consisting of $T^1$, $T^2$, $T^3$, $T^4$, $T^5$, $T^6$, $T^7$, $T^{8a}$, and $T^{8b}$:

-continued

T1

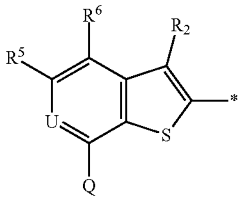

,

T2

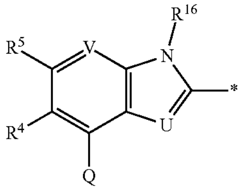

,

T3

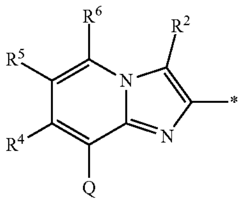

,

T4

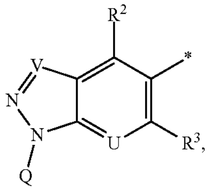

T5

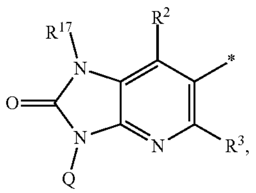

T6

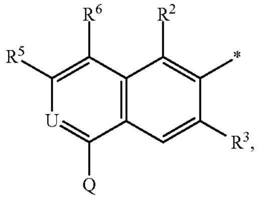

T7

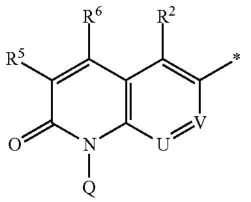

,

T8a

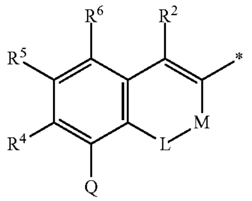

, and

T8b

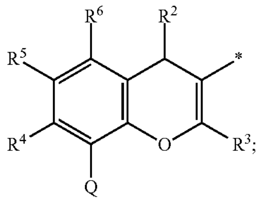

L is selected from the group consisting of O and $NR^9$;

M is selected from the group consisting of C═O and $CR^7R^8$;

U is selected from the group consisting of $CR^7$ and N;

V is selected from the group consisting of $CR^7$ and N;

$R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;

—$NR^{12}R^{13}$;

—$OR^{14}$;

—$SR^{15}$, —S(O)$R^{15}$, —$SO_2R^{15}$;

$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and 4- to 10-membered heterocycloalkyl;

$R^3$ is selected from the group consisting of hydrogen, halogen or $C_1$-$C_4$-alkyl;

$R^4$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^5$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy;

$R^6$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^7$ is selected from the group consisting of hydrogen, —OH, halogen, $C_1$-$C_4$-alkyl and $C_1$-$C_4$-alkoxy;

$R^8$ is selected from the group consisting of hydrogen, —OH, halogen, $C_1$-$C_4$-alkyl and $C_1$-$C_4$-alkoxy;

$R^9$ is selected from the group consisting of hydrogen, $C_1$-$C_4$-alkyl, $C_1$-$C_4$-halogenoalkyl having 1 to 5 halogen atoms and $C_1$-$C_4$-alkoxy;

$R^{10}$ is selected from the group consisting of hydrogen, —OH, $C_1$-$C_4$-alkyl and $C_1$-$C_4$-alkoxy;

$R^{11}$ is selected from the group consisting of hydrogen, $C_1$-$C_4$-alkyl and $C_1$-$C_4$-alkoxy;

$R^{12}$ and $R^{13}$ are independently selected from the group consisting of hydrogen, —OH, —$NH_2$, —NH($C_1$-$C_4$-alkyl), —N($C_1$-$C_4$-alkyl)$_2$, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, benzo-$C_5$-$C_6$-cycloalkyl, each of which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{14}$ is selected from the group consisting of —$NH_2$, —NH($C_1$-$C_4$-alkyl), —N($C_1$-$C_4$-alkyl)$_2$;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{15}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{16}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

$R^{17}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

Q is selected from the group consisting of 6-membered aryl and 5- to 6-membered heteroaryl, each of which is substituted by 1, 2, 3, 4 or 5 substituents selected from the group consisting of halogen, $SF_5$, cyano, —CHO, oxo, $C_1$-$C_4$-alkyl, $C_1$-$C_4$-hydroxyalkyl, $C_1$-$C_4$-halogenoalkyl having 1 to 5 halogen atoms, —OH, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms;

wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH;

and/or a stereoisomer, tautomer, N-oxide, hydrate, solvate, and/or a salt thereof, and/or a mixture thereof.

3. The compound of claim 1, wherein:

A is A1 or A2;

A1

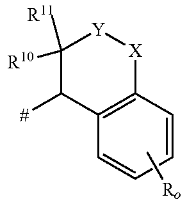

A2

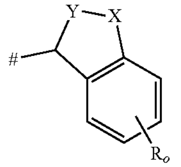

o is 0, 1 or 2;

R is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy;

X, Y are independently selected from the group consisting of $CR^7R^8$, O, S, and N—$R^9$, wherein at least one of X and Y is $CR^7R^8$;

T is selected from the group consisting of $T^1$, $T^2$, $T^3$, $T^4$, $T^5$, $T^6$, $T^7$, $T^{8a}$, and $T^{8b}$:

$T^1$

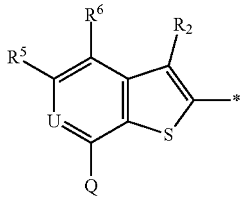

, $T^2$

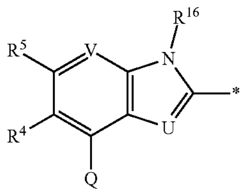

, $T^3$

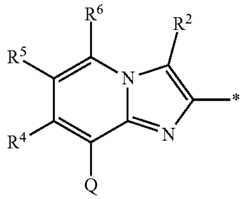

,

-continued

T4

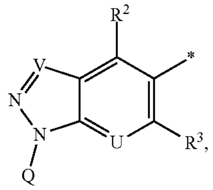

T5

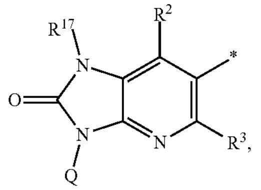

T6

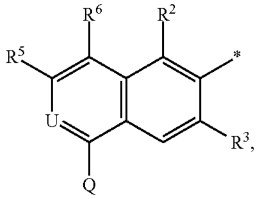

T7

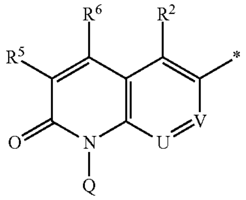

,

T8a

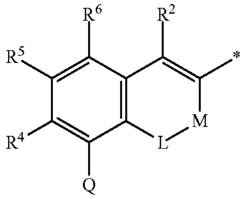

, and

T8b

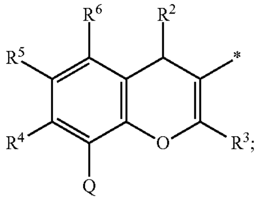

L is selected from the group consisting of O and $NR^9$;

M is selected from the group consisting of C=O and $CR^7R^8$;

U is selected from the group consisting of $CR^7$ and N;

V is selected from the group consisting of $CR^7$ and N;

$R^1$ is selected from the group consisting of hydrogen, $C_1$-$C_4$-alkyl, $C_1$-$C_4$-halogenoalkyl having 1 to 5 halogen atoms, $C_1$-$C_4$-alkoxy;

$R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$;

—$NR^{12}R^{13}$;

—$OR^{14}$;

—$R^{15}$, —S(O)$R^{15}$, —$SO_2R^{15}$;

$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and 4- to 10-membered heterocycloalkyl;

$R^3$ is selected from the group consisting of hydrogen, halogen or $C_1$-$C_4$-alkyl;

$R^4$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^5$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy;

$R^6$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^7$ is selected from the group consisting of hydrogen, halogen, $C_1$-$C_4$-alkyl;

$R^8$ is selected from the group consisting of hydrogen, halogen, $C_1$-$C_4$-alkyl;

$R^9$ is selected from the group consisting of hydrogen, $C_1$-$C_4$-alkyl;

$R^{10}$ is selected from the group consisting of hydrogen, —OH, $C_1$-$C_4$-alkyl and $C_1$-$C_4$-alkoxy;

$R^{11}$ is selected from the group consisting of hydrogen;

$R^{12}$ and $R^{13}$ are independently selected from the group consisting of hydrogen;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(═O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

phenyl, benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms;

$R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{15}$ is selected from the group consisting of $C_1$-$C_4$-alkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{16}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

$R^{17}$ is selected from the group consisting of hydrogen, $C_1$-$C_4$-alkyl, $C_1$-$C_4$-halogenoalkyl having 1 to 5 halogen atoms and $C_1$-$C_4$-alkoxy;

Q is selected from the group consisting of 6-membered aryl and 5- to 6-membered heteroaryl, each of which is substituted by 1, 2, 3, 4 or 5 substituents selected from the group consisting of halogen, cyano, $C_1$-$C_4$-alkyl, $C_1$-$C_4$-hydroxyalkyl, $C_1$-$C_4$-halogenoalkyl having 1 to 5 halogen atoms, —OH, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, 4- to 6-membered heterocyclyl, which is optionally substituted with 1 or 2 substituents selected from the group consisting of fluorine, chlorine, bromine, methyl and cyano;

wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH;

and/or a stereoisomer, tautomer, N-oxide, hydrate, solvate, and/or a salt thereof, and/or a mixture thereof.

4. The compound of claim 1, wherein:

A is A1 or A2;

A1

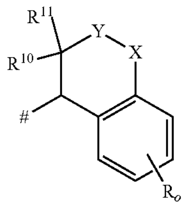

A2

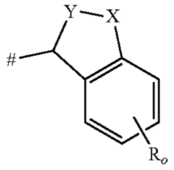

is 0 or 1;

R is selected from the group consisting of hydrogen, halogen, $C_1$-$C_4$-alkyl, $C_1$-$C_4$-halogenoalkyl having 1 to 5 halogen atoms, $C_1$-$C_4$-alkoxy;

X is selected from the group consisting of $CR^7R^8$, O, S, and N—$R^9$,

Y is $CR^7R^8$;

T is selected from the group consisting of $T^1$, $T^2$, $T^3$, $T^4$, $T^5$, $T^6$, $T^7$, $T^{8a}$, and $T^{8b}$:

$T^1$

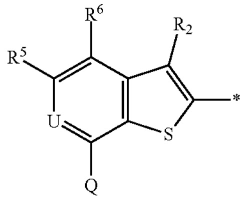

,

-continued

T²

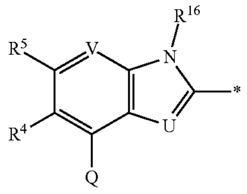

,

T³

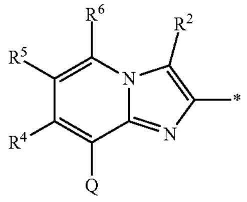

,

T⁴

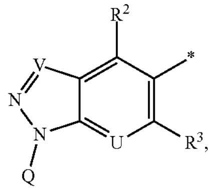

T⁵

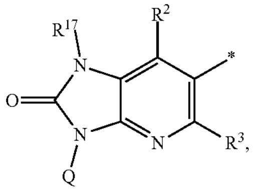

T⁶

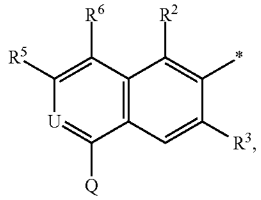

T⁷

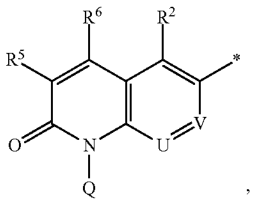

,

T^8a

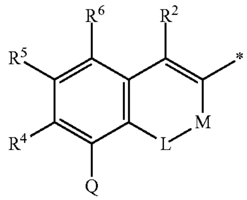

, and

-continued

T^8b

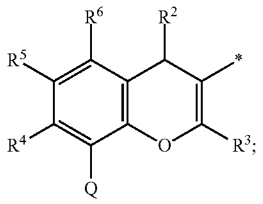

L is selected from the group consisting of O and $NR^9$;

M is selected from the group consisting of C═O and $CR^7R^8$;

U is selected from the group consisting of $CR^7$ and N;

V is selected from the group consisting of $CR^7$ and N;

$R^1$ is selected from the group consisting of hydrogen and $C_1$-$C_4$-alkyl;

$R^2$ is selected from the group consisting of hydrogen, halogen;

—$NR^{12}R^{13}$;

—$OR^{14}$;

—$R^{15}$, —$S(O)R^{15}$, —$SO_2R^{15}$;

$C_1$-$C_6$-alkyl or $C_3$-$C_6$-cycloalkyl, each of which is optionally substituted by 1, 2, 3, 4 or 5 substituents independently selected from the group consisting of halogen, cyano, $C_1$-$C_4$-alkyl;

a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, —OH, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms;

$R^3$ is selected from the group consisting of hydrogen, halogen or $C_1$-$C_4$-alkyl;

$R^4$ is selected from the group consisting of hydrogen, halogen, $C_1$-$C_4$-alkyl, $C_1$-$C_4$-halogenoalkyl having 1 to 5 halogen atoms;

$R^5$ is selected from the group consisting of hydrogen, halogen, $C_1$-$C_4$-alkyl, $C_1$-$C_4$-halogenoalkyl having 1 to 5 halogen atoms;

$R^6$ is selected from the group consisting of hydrogen, halogen, $C_1$-$C_4$-alkyl, $C_1$-$C_4$-halogenoalkyl having 1 to 5 halogen atoms;

$R^7$ is selected from the group consisting of hydrogen, halogen, $C_1$-$C_4$-alkyl;

$R^8$ is selected from the group consisting of hydrogen, halogen, $C_1$-$C_4$-alkyl;

$R^9$ is selected from the group consisting of hydrogen, $C_1$-$C_4$-alkyl;

$R^{10}$ is selected from the group consisting of hydrogen, $C_1$-$C_4$-alkyl;

$R^{11}$ is selected from the group consisting of hydrogen;

$R^{12}$ and $R^{13}$ are independently selected from the group consisting of hydrogen;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl;

heterocyclyl-$C_1$-$C_4$-alkyl, wherein the heterocyclyl substituent is selected from the group consisting of 4- to 10-membered heterocycloalkyl, which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

phenyl, which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{14}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{15}$ is selected from the group consisting of $C_1$-$C_4$-alkyl, phenyl-$C_1$-$C_4$-alkyl, each of which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{16}$ is selected from the group consisting of hydrogen, $C_1$-$C_4$-alkyl, $C_1$-$C_4$-halogenoalkyl having 1 to 5 halogen atoms;

$R^{17}$ is selected from the group consisting of hydrogen, $C_1$-$C_4$-alkyl, $C_1$-$C_4$-halogenoalkyl having 1 to 5 halogen atoms;

Q is selected from the group consisting of 6-membered aryl and 5- to 6-membered heteroaryl, each of which is substituted by 1, 2, 3, 4 or 5 substituents selected from the group consisting of halogen, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

wherein when Y is O, S or N—$R^9$, none of $R^7$, $R^8$, $R^{10}$ and $R^{11}$ is —OH, and wherein when X is O, S or N—$R^9$, none of $R^7$ and $R^8$ is —OH;

and/or a stereoisomer, tautomer, N-oxide, hydrate, solvate, and/or a salt thereof, and/or a mixture thereof.

5. The compound of claim 1, wherein:

Q is a substituted phenyl ring of formula (Q1)

(Q1)

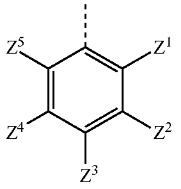

in which:

$Z^1$, $Z^2$, $Z^3$, $Z^4$, and $Z^5$ are independently selected from the group consisting of hydrogen, halogen, SFs, cyano, —CHO, —$C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or $Z^1$ and $Z^2$ form, together with the carbon atoms that they are connected to, a 5-or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, $SF_5$, cyano, CHO, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-alkoxy-C(O)—, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or $Z^2$ and $Z^3$ form, together with the carbon atoms that they are connected to, a 5-or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, $SF_5$, cyano, CHO, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH—$SO_2$—($C_1$-$C_4$-alkyl), —N($SO_2$—[$C_1$-$C_4$-alkyl])($C_1$-$C_4$-alkyl), ($C_1$_$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or Q is a pyridine ring of formula (Q2)

(Q2)

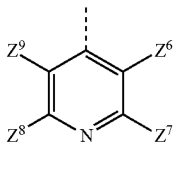

in which:

$Z^6$, $Z^7$, $Z^8$ and $Z^9$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, $NH_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, or Q is a pyrimidine ring of formula (Q3)

(Q3)

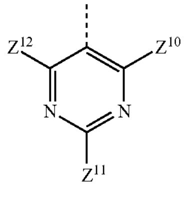

in which:

$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyridine ring of formula (Q4)

(Q4)

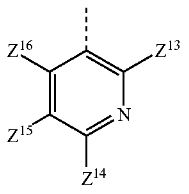

in which:

$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a pyridine ring of formula (Q5)

(Q5)

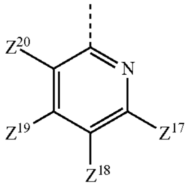

in which:

$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, or Q is a 5-membered aromatic heterocycle of formula (Q6)

(Q6)

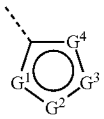

in which:

$G^1$-$G^4$ are independently selected from the group consisting of N, O, S, C—$Z^{21}$ and N—$Z^{22}$, wherein not more than one of $G^1$-$G^4$ is O, not more than one of $G^1$-$G^4$ is S, not more than one of $G^1$-$G^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of formula (Q7)

(Q7)

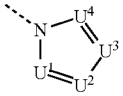

in which:

$U^1$—$U^4$ are independently selected from the group consisting of N and C—$Z^{23}$, wherein not more than three of $U^1$—$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and/or a stereoisomer, tautomer, N-oxide, hydrate, solvate, and/or a salt thereof, and/or a mixture thereof.

6. The compound of claim 1, wherein:

A is selected from the group consisting of

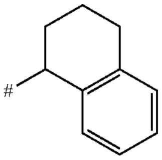 , 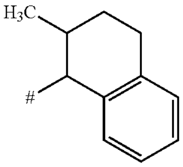 ,

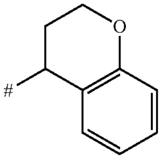 , 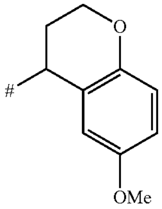 ,

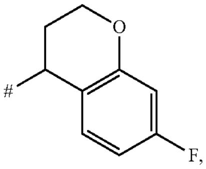 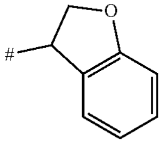 ,

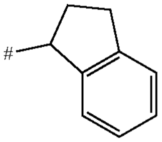 , 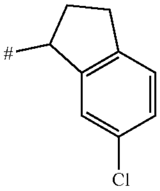 ,

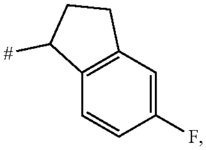 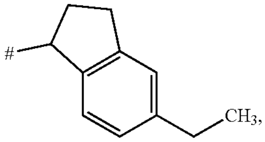

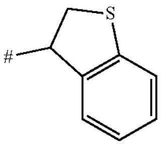 , 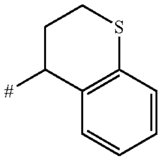 ,

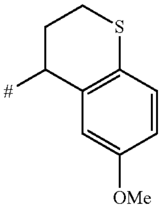 , 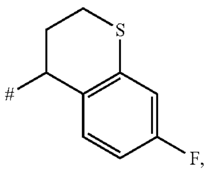

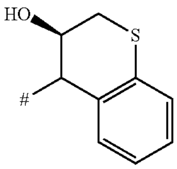 , 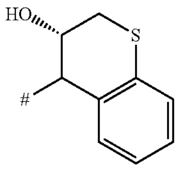 ,

-continued

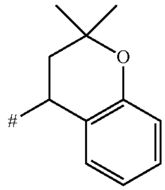
,
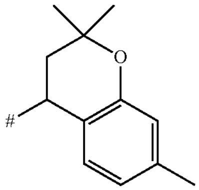
,
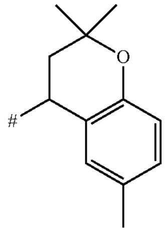
,
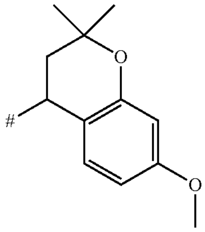
,
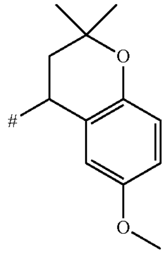
,
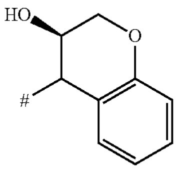
,
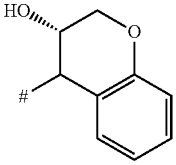
, and
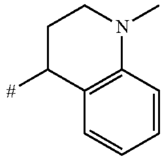
;

T is selected from the group consisting of $T^1$, $T^2$, $T^3$, $T^4$, $T^5$, $T^6$, $T^7$, $T^{8a}$, and $T^{8b}$:

$T^1$

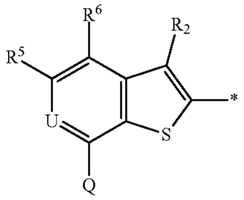
, $T^2$

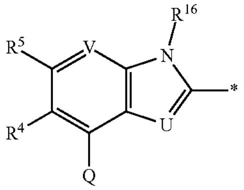
, $T^3$

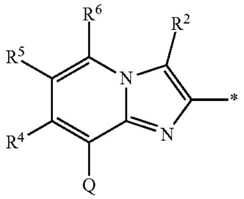
,

-continued $T^4$

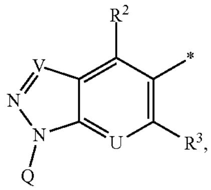

$T^5$

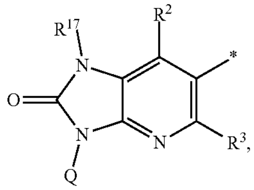

$T^6$

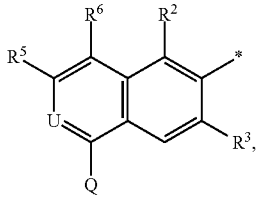

$T^7$

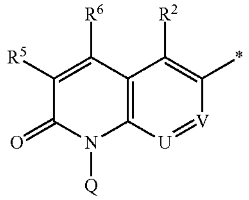
, $T^{8a}$

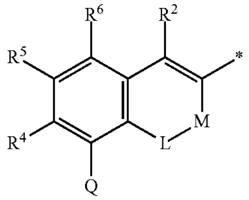
, and $T^{8b}$

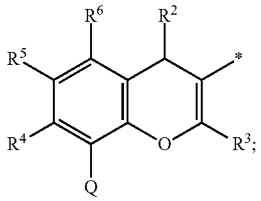

L is selected from the group consisting of O and $NR^9$;

M is selected from the group consisting of C═O and $CR^7R^8$;

U is selected from the group consisting of $CR^7$ and N;

V is selected from the group consisting of $CR^7$ and N;

$R^1$ is selected from the group consisting of hydrogen or methyl;

$R^2$ is selected from the group consisting of hydrogen, chlorine, fluorine, bromine;

—$NR^{12}R^{13}$;

—$OR^{14}$;

methyl, ethyl, propyl, isopropyl, cyclopropyl, cyclohexyl, each of which is optionally substituted by 1 of 2 substituents independently selected from the group consisting of fluorine, chlorine, cyano, methyl, ethyl, propyl, and isopropyl;

a monocyclic or a bicyclic heterocycle selected from the group consisting of azetidine, pyrrolidine, pyrazolidine, imidazolidine, 1,2,4-triazolidine, piperidine, piperazine, tetrahydropyridine, dihydro-2H-pyrane, tetrahydropyrane, 1,2-oxazolidine, 1,2-oxazine, morpholine, thiomorpholine, 3,4-dihydroisoquinoline, 2,3-dihydro-indole, 1,3-dihydro-isoindole, 3,9-dioxa-7-azabicyclo[3.3.1]nonane, 6-oxa-3-azabicyclo[3.1.1]heptane, 8-oxa-3-azabicyclo[3.2.1]octane, imidazole, pyrazole, 1,2,4-triazole, 1,2,3-triazole, 4-oxa-7-azaspiro[2.5]octane, each of which is optionally substituted by 1, 2, 3 or 4 substituents independently selected from the group consisting of fluorine, chlorine, —OH, methyl, trifluoromethyl, methoxymethyl, trifluoromethoxymethyl;

$R^3$ is selected from the group consisting of hydrogen, chlorine or methyl;

$R^4$ is selected from the group consisting of hydrogen, fluorine, chlorine, methyl, methoxy, trifluoromethyl, trifluoromethoxy;

$R^5$ is selected from the group consisting of hydrogen, fluorine, chlorine, methyl, trifluoromethyl;

$R^6$ is selected from the group consisting of hydrogen, fluorine, chlorine, methyl, methoxy, trifluoromethyl, trifluoromethoxy;

$R^{12}$ and $R^{13}$ are independently selected from the group consisting of hydrogen and methyl;

$R^{14}$ is methyl;

$R^{16}$ is selected from the group consisting of hydrogen, methyl, ethyl, propyl, isopropyl, trifluoromethyl;

$R^{17}$ is selected from the group consisting of hydrogen, methyl, ethyl, propyl, isopropyl, trifluoromethyl;

Q is a phenyl ring of formula (Q1)

(Q1)

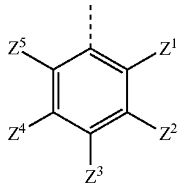

wherein:

$Z^1$ to $Z^5$ are independently selected from the group consisting of hydrogen, fluorine, chlorine, methyl and trifluoromethyl;

or

Q is a pyridine ring of formula (Q2)

(Q2)

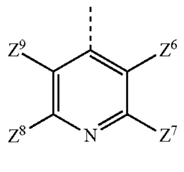

wherein:

$Z^6$ to $Z^9$ are independently selected from the group consisting of hydrogen, fluorine, chlorine, methyl and trifluoromethyl;

and/or a stereoisomer, tautomer, N-oxide, hydrate, solvate, and/or a salt thereof, and/or a mixture thereof.

7. The compound of claim 1, wherein:

Q is a phenyl ring of formula (Q1)

(Q1)

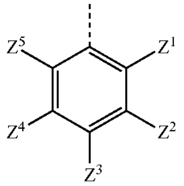

wherein:

$Z^1$, $Z^3$ and $Z^5$ are independently selected from the group consisting of hydrogen, fluorine and chlorine;

$Z^2$ and $Z^4$ are independently selected from the group consisting of hydrogen, fluorine, chlorine and trifluoromethyl;

or

Q is a pyridine ring of formula (Q2)

(Q2)

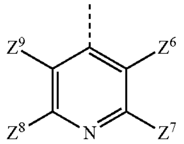

wherein:

$Z^6$ to $Z^9$ are independently selected from the group consisting of hydrogen, fluorine and chlorine; and/or a stereoisomer, tautomer, N-oxide, hydrate, solvate, and/or a salt thereof, and/or a mixture thereof.

8. The compound of claim 1, wherein:

A is selected from the group consisting of

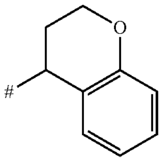 , 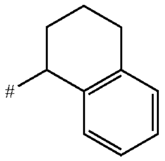 , 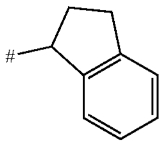 , and/or a stereoisomer, tautomer, N-oxide, hydrate, solvate, and/or a salt thereof, and/or a mixture thereof.

9. The compound of claim 1, wherein:

A is selected from the group consisting of

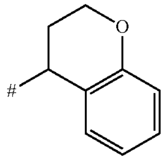 , 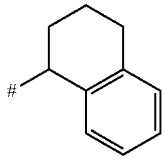 , 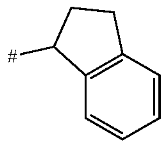 ,

T is selected from the group consisting of $T^1$, $T^2$, $T^3$, $T^4$, $T^5$, $T^6$, $T^7$, $T^{8a}$, and $T^{8b}$:

$T^1$

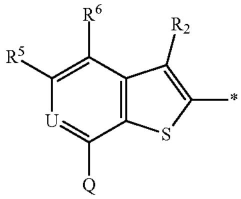

, $T^2$

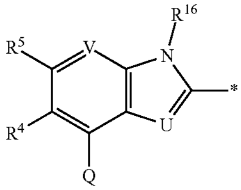

, $T^3$

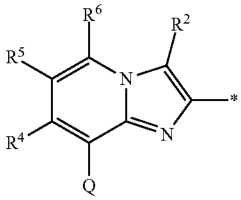

, $T^4$

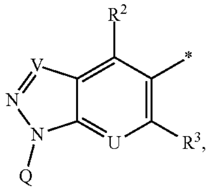

$T^5$

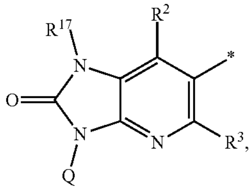

$T^6$

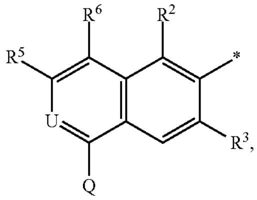

$T^7$

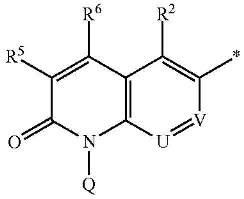

,

-continued $T^{8a}$

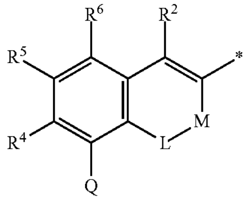

, and $T^{8b}$

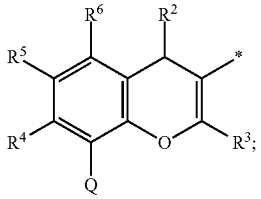

L is selected from the group consisting of O and $NR^9$;

M is selected from the group consisting of C═O and $CR^7R^8$;

U is selected from the group consisting of $CR^7$ and N;

V is selected from the group consisting of $CR^7$ and N;

$R^1$ is hydrogen;

$R^2$ is selected from the group consisting of hydrogen, chlorine, —$NR^{12}R^{13}$, —$OR^{14}$; methyl, isopropyl, and morpholine;

$R^3$ is hydrogen or methyl;

$R^4$ is hydrogen or fluorine;

$R^5$ is hydrogen or methyl;

$R^6$ is hydrogen or fluorine;

$R^{12}$ and $R^{13}$ are independently selected from the group consisting of hydrogen and methyl;

$R^{14}$ is methyl;

$R^{16}$ is methyl or isopropyl;

$R^{17}$ is methyl;

Q is a phenyl ring of formula (Q1)

(Q1)

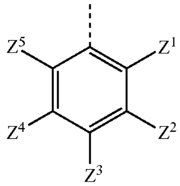

wherein:

$Z^1$, $Z^3$ and $Z^5$ are independently selected from the group consisting of hydrogen, fluorine and chlorine;

$Z^2$ and $Z^4$ are independently selected from the group consisting of hydrogen, fluorine, chlorine and trifluoromethyl;

or

Q is a pyridine ring of formula (Q2)

(Q2)

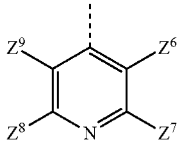

wherein:

$Z^6$ to $Z^9$ are independently selected from the group consisting of hydrogen and chlorine;

and/or a stereoisomer, tautomer, N-oxide, hydrate, solvate, and/or a salt thereof, and/or a mixture thereof.

10. The compound of claim 1, wherein:

A is selected from the group consisting of

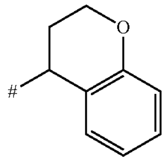

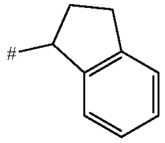

and/or a stereoisomer, tautomer, N-oxide, hydrate, solvate, and/or a salt thereof, and/or a mixture thereof.

11. A method of preparing a compound of claim 1, said method comprising allowing an intermediate compound of formula Int-I-T1, Int-I-T2, Int-I-T3, Int-I-T4, Int-I-T5, Int-I-T6, Int-I-T7, Int-I-T8a, or Int-I-T8b:

Int-I-T1

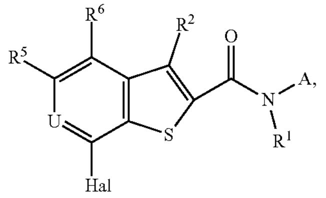

Int-I-T2

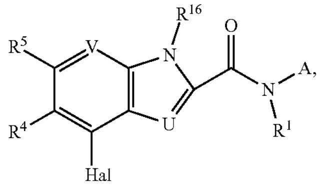

Int-I-T3

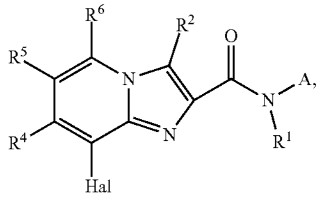

Int-I-T4

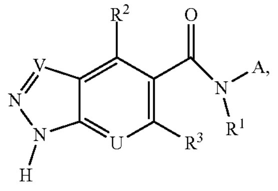

Int-I-T5

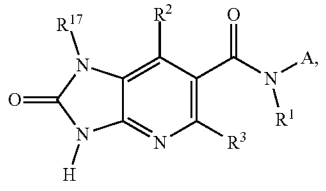

-continued

Int-I-T6

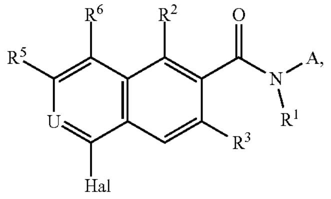

Int-I-T7

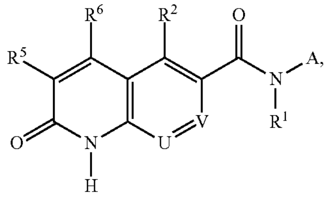

Int-I-T8a

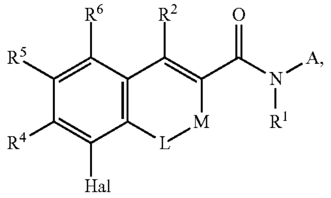

Int-I-T8b

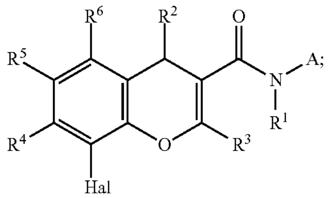

wherein L, M, U, V, A, $R^1$, $R^2$, $R^3$, $R^4$, $R^5$, $R^6$, $R^{16}$ and $R^{17}$ are as defined for the compound of claim 1, and wherein Hal is halogen, to react with a compound of formula 1H $Q\text{-}B(OR)_2$ 1H, wherein Q is as defined for the compound of claim 1, and wherein each R may be individually H or Me or both R are pinacolate, thereby giving a compound of formula (I):

(I)

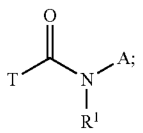

wherein T, L, M, U, V, A, $R^1$, $R^2$, $R^3$, $R^4$, $R^5$, $R^6$, and Q are as defined in claim 1, or allowing an intermediate compound of formula Int-II-T1, Int-II-T2, Int-II-T3, Int-II-T4, Int-II-T5, Int-II-T6, Int-II-T7, Int-II-T8a, or Int-II-T8b:

Int-II-T1

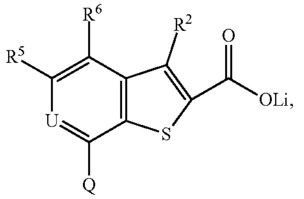

Int-II-T2

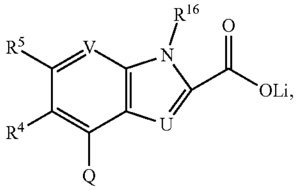

Int-II-T3

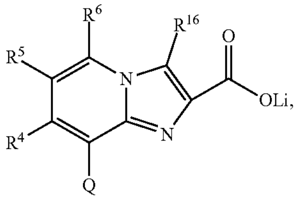

Int-II-T4

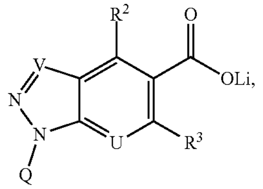

Int-II-T5

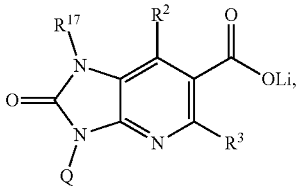

Int-II-T6

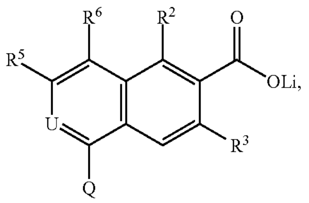

Int-II-T7

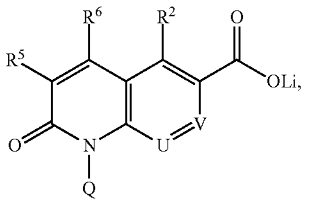

-continued

Int-II-T8a

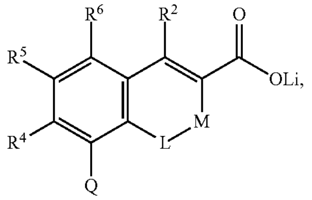

Int-II-T8b

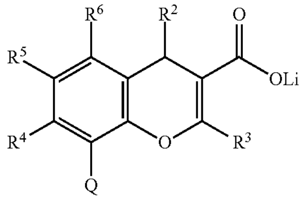

to react with a compound of formula 1V:

1V

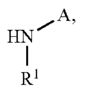

thereby giving a compound of formula (I):

(I)

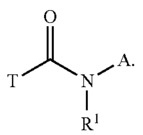

12. A pharmaceutical composition comprising a compound of claim 1 and one or more pharmaceutically acceptable excipients.

13. A method for controlling helminth infection in humans and/or animals comprising administering an anthelminthically effective amount of at least one compound of claim 1 or a pharmaceutical composition thereof to a human or an animal in need thereof.

14. The method of claim 11, wherein Hal is selected from the group consisting of chlorine, bromine, and iodine.

* * * * *